US008329886B2

(12) United States Patent
Bardroff et al.

(10) Patent No.: US 8,329,886 B2
(45) Date of Patent: Dec. 11, 2012

(54) NUCLEIC ACID MOLECULES ENCODING ANTI-AMYLOID BETA ANTIBODIES

(75) Inventors: Michael Bardroff, München (DE); Bernd Bohrmann, Freiburg (DE); Manfred Brockhaus, Bettingen (CH); Walter Huber, Kaiseraugst (CH); Titus Kretzschmar, Hurlach (DE); Hansruedi Loetscher, Möhlin (CH); Corinna Löhning, Stockdorf (DE); Christer Nordstedt, Sodertalje (SE); Christine Rothe, Dachau (DE)

(73) Assignees: Hoffman-La Roche Inc., Nutley, NJ (US); Morphosys AG, Martinsried (DE)

( * ) Notice: Subject to any disclaimer, the term of this patent is extended or adjusted under 35 U.S.C. 154(b) by 0 days.

(21) Appl. No.: 13/472,781

(22) Filed: May 16, 2012

(65) Prior Publication Data
US 2012/0225478 A1 Sep. 6, 2012

Related U.S. Application Data

(62) Division of application No. 12/462,119, filed on Jul. 28, 2009, now Pat. No. 8,216,577, which is a division of application No. 10/505,313, filed as application No. PCT/EP03/01759 on Feb. 20, 2003, now Pat. No. 7,794,719.

(30) Foreign Application Priority Data

Feb. 20, 2002 (EP) ..................................... 02003844

(51) Int. Cl.
C07H 21/00 (2006.01)
(52) U.S. Cl. ............. 536/23.53; 435/70.21; 435/252.33; 435/326
(58) Field of Classification Search ........................ None
See application file for complete search history.

(56) References Cited

U.S. PATENT DOCUMENTS

| 5,195,317 | A | 3/1993 | Nobue et al. |
| 5,688,651 | A | 11/1997 | Solomon |
| 5,955,317 | A | 9/1999 | Suzuki et al. |
| 7,794,719 | B2 | 9/2010 | Bardroff et al. |
| 8,216,577 | B2 | 7/2012 | Bardroff et al. |
| 2004/0082762 | A1 | 4/2004 | Basi et al. |
| 2009/0252724 | A1 | 10/2009 | Loetscher et al. |

FOREIGN PATENT DOCUMENTS

| EP | 0 683 234 | 11/1995 |
| EP | 1 125 905 | 8/2001 |
| JP | Hei 03/502455 | 6/1991 |
| WO | WO 94/17197 | 8/1994 |
| WO | WO 96/20218 | 7/1996 |
| WO | WO 97/08320 | 3/1997 |
| WO | WO 99/27944 | 6/1999 |
| WO | WO 00/72880 | 12/2000 |
| WO | WO 01/15655 | 3/2001 |
| WO | WO 0114424 A2 * | 3/2001 |
| WO | WO 01/39796 | 6/2001 |
| WO | WO 02/10354 | 2/2002 |
| WO | WO 02/46237 | 6/2002 |
| WO | WO 02/064734 | 8/2002 |
| WO | WO 02/096937 | 12/2002 |

OTHER PUBLICATIONS

O'Nuallain et al., "Conformational Abs Recognizing a Generic Amyloid Fibril Epitope," PNAS, vol. 99, No. 3, pp. 1485-1490 (2002).
Ghoshal et al., "Tau-66: Evidence for a Novel Tau Conformation in Alzheimer's Disease," Journal of Neurochemistry, vol. 77, pp. 1372-1385 (2001).
Knappik et al., "Fully Synthetic Human Combinatorial Antibody Libraries (HuCAL) Based on Modular Consensus Frameworks and CDRs Randomized with Trinucleotides," J. Mol. Biol., vol. 296, pp. 57-86 (2000).
Solomon et al., "Vaccination for the Prevention and Treatment of Alzheimer's Disease," Drugs of Today, vol. 36, No. 9, pp. 655-663 (2000).
Cribbs et al., "Adjuvant-Dependent Modulation of Th1 and Th2 Responses to Immunization with .beta.-Amyloid," International Immunology, vol. 15, No. 4, pp. 505-514 (2003).
Cheong et al., "Affinity enhancement of bispecific antibody against two different epitopes in the same antigen," Biochemical and Biophysical Research Communications, vol. 173, pp. 795-800 (1990).
Frenkel et al., "High affinity binding of monoclonal antibodies to the sequential epitope EFRH of .beta.-amyloid peptide is essential for modulation of fibrillar aggregation," Journal of Neuroimmunology, vol. 95, pp. 136-142 (1999).
Frenkel et al., "Immunization against Alzheimer's .beta.-amyloid plaques via EFRH phage administration," Proc. Natl. Acad. Sci., vol. 99, pp. 11455-11459 (2000).
Solomon et al., "Disaggregation of Alzheimer .beta.-amyloid by site-directed mAb," Proc. Natl. Acad. Sci., vol. 94, pp. 4109-4112 (1997).
Solomon et al., "Monoclonal antibodies inhibit in vitro fibrillar aggregation of the Alzheimer .beta.-amyloid. peptide," Proc. Natl. Acad. Sci., vol. 93, pp. 452-455 (1996).
Schier et al., "Isolation of Picomolar Affinity Anti-c-erbB-2 Single-chain Fv by Molecular Evolution of the Complementarity Determining Regions in the Center of the Antibody Binding Site," J. Mol. Biol., vol. 263, 551-567 (1996).

(Continued)

Primary Examiner — Gregory S Emch
(74) Attorney, Agent, or Firm — Bryan Cave LLP

(57) ABSTRACT

The present invention relates to antibody molecules capable of specifically recognizing two regions of the β-A4 peptide, wherein the first region comprises the amino acid sequence AEFRHDSGY as shown in SEQ ID NO: 1 or a fragment thereof and wherein the second region comprises the amino acid sequence VHHQKLVFFAEDVG as shown in SEQ ID NO: 2 or a fragment thereof. Furthermore, nucleic acid molecules encoding the inventive antibody molecules and vectors and hosts comprising said nucleic acid molecules are disclosed. In addition, the present invention provides for compositions, preferably pharmaceutical or diagnostic compositions, comprising the compounds of the invention as well as for specific uses of the antibody molecules, nucleic acid molecules, vectors or hosts of the invention.

33 Claims, 53 Drawing Sheets

OTHER PUBLICATIONS

Kay et al., "An M13 Phage library displaying random 38-amino-acid peptides as a source of novel sequences with affinity to selected targets," Gene, vol. 128, pp. 59-65 (1993).

Frenkel et al., "N-terminal EFRH sequence of Alzheimer's .beta.-amyloid peptide represents the epitope of its anti-aggregating antibodies," Journal of Neuroimmunology, vol. 88, pp. 85-90 (1998).

Solomon et al., "Activity of monoclonal antibodies in prevention of in vitro aggregation of their antigens," Stability and Stabilization of Biocatalysts, pp. 183-188 (1998).

Rudikoff et al., "Single amino acid substitution altering antigen-binding specificity," Proc. Natl. Acad. Sci. USA, vol. 79, pp. 1979-1983 (1982).

Paul, Fundamental Immunology, 3rd Edition, pp. 292-295 (1993).

Frenkel et al., "Immunization against Alzheimer's .beta.-amyloid plaques via EFRH phage administration," Proc. Natl. Acad. Sci., vol. 97, pp. 11455-11459 (2000).

English translation of Notice of Grounds for Rejection in Japanese Patent Application No. 2009-053951, dispatched Aug. 11, 2011.

English translation of the Summary of Invention Section of Japanese Patent Publication No. Hei 03-502455, Jun. 1991.

Frenkel et al., "Modulation of Alzheimer's .beta.-amyloid neurotoxicity by site-directed single-chain antibody", J. Neuroimmunology, vol. 106, pp. 23-31 (2000).

Kuby, Immunology, Third Edition, pp. 131-134 (1997).

Alberts et al., 1994. Molecular Biology of the Cell, $3^{rd}$ Edition, pp. 1216-1220.

* cited by examiner

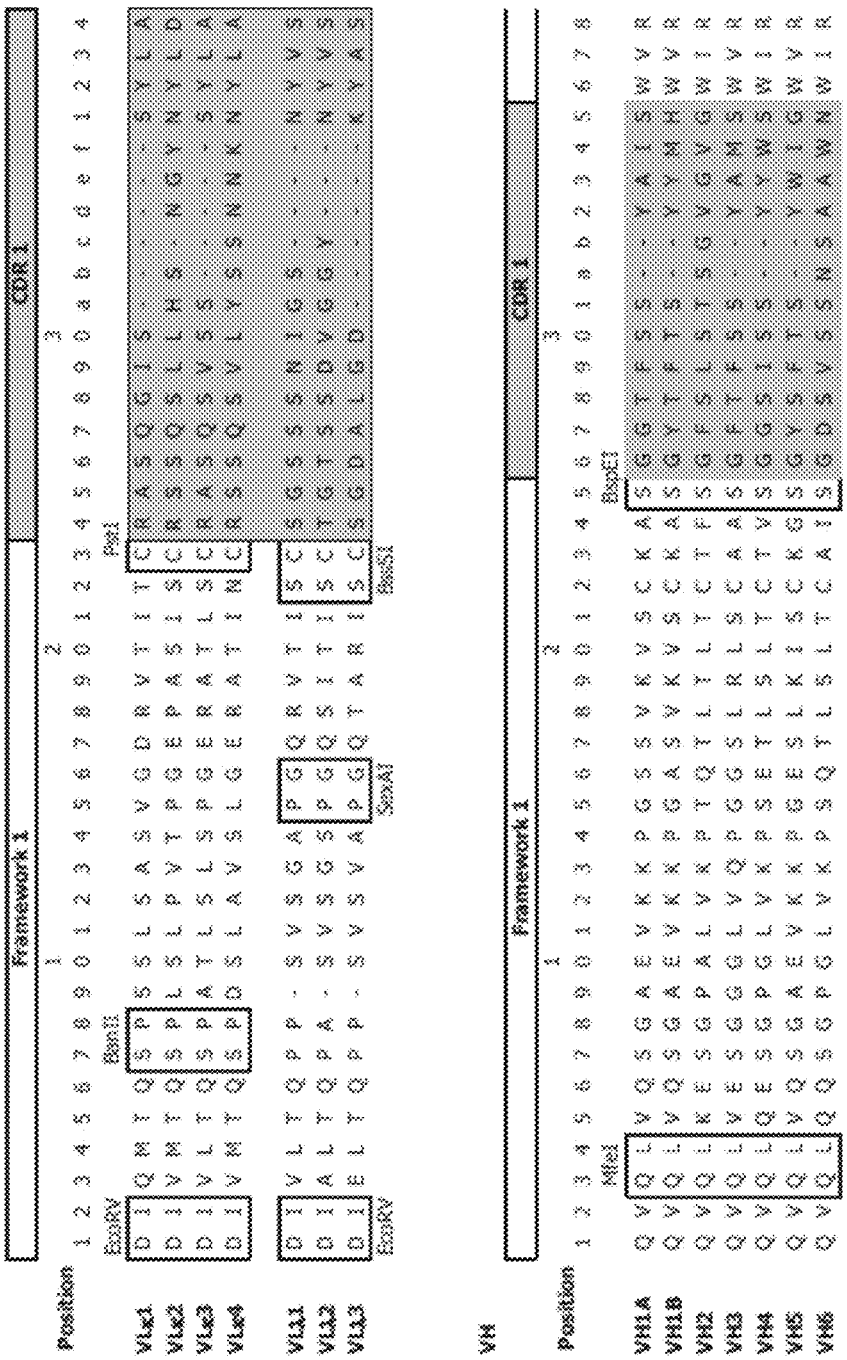

Fig. 1b

Sequence Summary of HuCAL-Fab1 Library

Fig. 1b continued

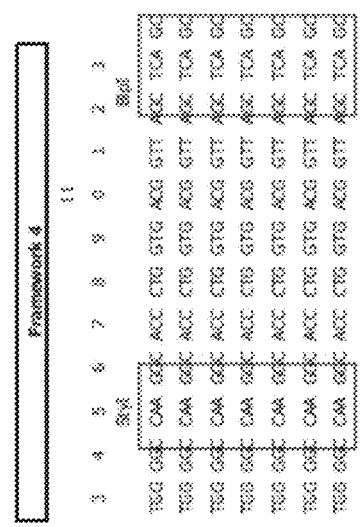

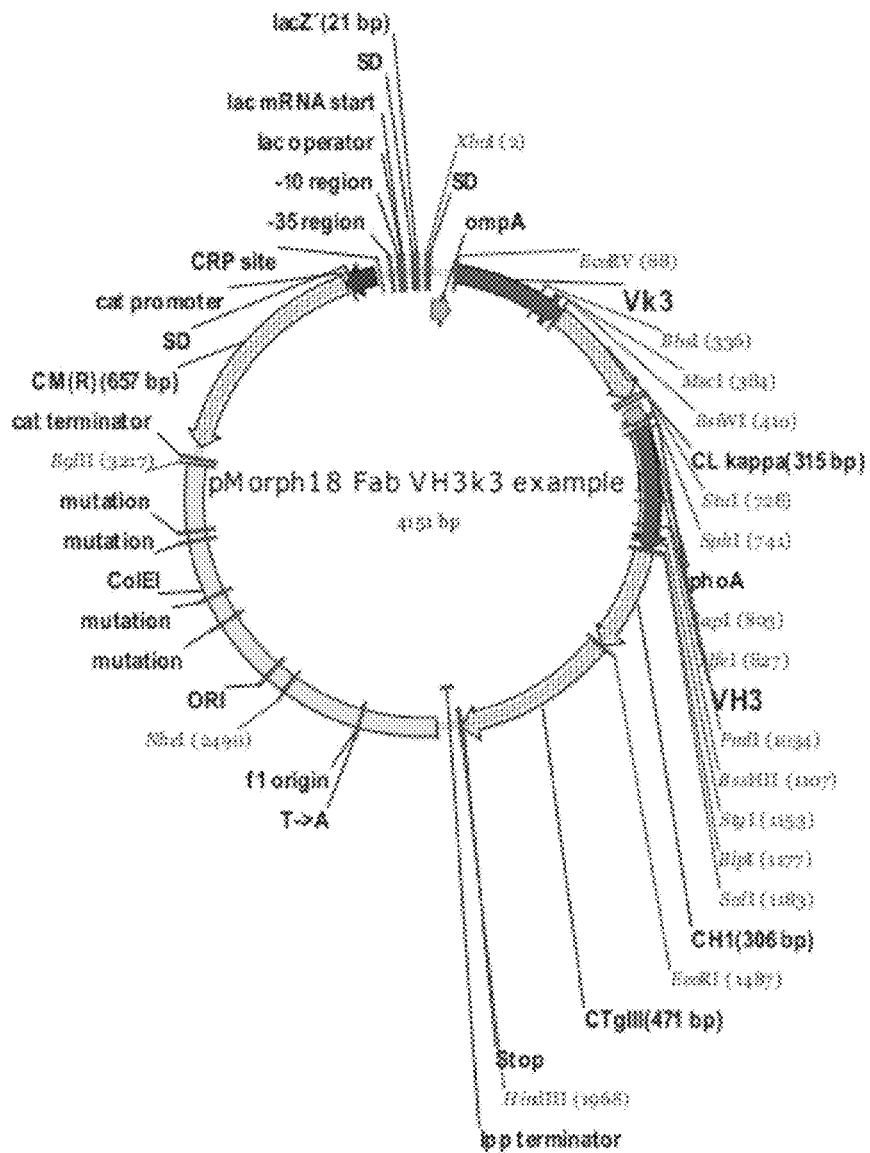

The page is a figure showing an annotated DNA/protein sequence that is too low-resolution to transcribe reliably.

Fig. 2 Continued

[Figure: DNA sequence listing with translated amino acids, continued from previous page. Sequence is too low-resolution to transcribe reliably. Annotations visible include: CTgIII (repeated), Stop, lpp terminator, HindIII, RBS, f1 origin.]

Fig. 2 Continued

The page content is too degraded/faded to reliably transcribe the nucleotide sequences. Legible annotations include:

- f1 origin (labels at positions 2251, 2301, 2351, 2401, 2451)
- NheI (restriction site label near 2451)
- ColEI (labels starting around 2501 and continuing)
- ORI (near 2551)
- mutation (labels near 2701, 2751, 2801)

Fig. 2 Continued

[Figure: DNA sequence listing from positions 2651 to 3500, with annotations including ColE1, mutation, BglII, cat terminator, and CM(R) regions. Text is too degraded/low-resolution for reliable OCR.]

Fig. 2 Continued

```
                         CM(R)
3501   ATTCTGAATA AACCCTTTAG GAAATAGGC CAGTTTTCA CCTAACACG
       TAAGACTTAT TTGGGAAATC CTTTATCCG GTCAAAAGT GGATTGTGC
       ----------------------------------------
                         CM(R)
3551   CCACATCTTG CGAATATATG TGTAGAAACT GCCGGAAATC GTCGTGGTAT
       GGTGTAGAAC GCTTATATAC ACATCTTTGA CGGCCTTTAG CAGCACCATA
       ----------------------------------------
                         CM(R)
3601   TCACTCCAGA GCGATGAAAA CGTTTCAGTT TGCTCATGGA AAACGGTGTA
       AGTGAGGTCT CGCTACTTTT GCAAAGTCAA ACGAGTACCT TTTGCCACAT
       ----------------------------------------
                         CM(R)
3651   ACAGGGTGA ACACTATCCC ATATCACCAG CTCACCGTCT TTCATTGCCA
       TGTCCCACT TGTGATAGGG TATAGTGGTC GAGTGGCAGA AAGTAACGGT
       ----------------------------------------
                         CM(R)
3701   TACGAACTC CGGTGACA TTCATCAGGC GGCAAGAT GTGATAAAG
       ATGCTTGAG GCCACTGT AAGTAGTCCG CCGTTCTA CACTTATTTC
       ----------------------------------------
                         CM(R)
3751   GCCGGATAAA ACTTGTGCTT ATTTTCTTT ACGTCTTTA AAAGGCCGT
       CGGCCTATTT TGAACACGAA TAAAAGAAA TGCAGAAAT TTTTCCGGCA
       ----------------------------------------
                         CM(R)
3801   AAATCCAGC TGAACGGTCT GGTTATAGGT ACATTGAGCA ACTGACTGAA
       TTTAGGTCG ACTTGCCAGA CCAATATCCA TGTAACTCGT TGACTGACTT
       ----------------------------------------
                         CM(R)
3851   ATGCCTCAA ATGTTCTTTA CGATGCCATT GGGATATATC AACGGTGGTA
       TACGGAGTTT TACAAGAAAT GCTACGGTAA CCCTATATAG TTGCCACCAT
       ----------------------------------------
                         CM(R)
3901   TATCACTGA TTTTTTTCTC CATTTTAGCT TCCTTAGCTC CTGAAAATCT
       ATAGTGACT AAAAAAGAG GTAAAATCGA AGGAATCGAG GACTTTTAGA
       ----------------------------------------
               CM(R)                             SD
                                          ---------------
                                             cat promoter
3951   CGATAACTCA AAAAATACGC CCGGTAGTGA TCTTATTTCA TTATGGTGAA
       GCTATTGAGT TTTTTATGCG GGCCATCACT AGAATAAAGT AATACCACTT
       ----------------------------------------
              cat promoter
                                 CRP site
                                ----------------
4001   AGTTGGAACC TCACCGACG TGTATGTGA GTTAGCTCAC TCATTAGGCA
       TCAACCTTGG AGTGGCTGC ACATACACT CAATCGAGTG AGTAATCCGT
       ----------------
       cat promoter
                                               lac mRNA
                                                start
                                                   ~
                                               lac operator
                                               --------
                -35 region           -10 region
                --------             --------
4051   CCCCAGGCTT TACACTTTAT GCTTCCGGCT CGTATGTTGT GTGGAATTGT
       GGGGTCCGAA ATGTGAAATA CGAAGGCCGA GCATACAACA CACCTTAACA
            lac operator          SD            lacI'
4101   GAGCGGATAA CAATTTCACA CAGGAAACAG CTATGACCAT GATTACGGAT
```

Fig. 2 Continued

```
     CTCGCCTATT GTTAAAGTGT GTCCTTTGTC GATACTGGTA CTAATGCTTA
     lacZ'
4151  T
      A
```

Fig. 3 Continued

```
        EcoRV                                          SexAI
        ----                                          ----------
  1  ATCGTGCTGA  CCCAGCCGCC  TTCAGTGAGT  GGCGCACCAG  GTCAGCGTGT
     TAGCACGACT  GGGTCGGCGG  AAGTCACTCA  CCGCGTGGTC  CAGTCGCACA

51  GACCATCTCG  TGTAGCGGCA  GCAGCAGCAA  CATTGGCAGC  AACTATGTGA
     CTGGTAGAGC  ACATCGCCGT  CGTCGTCGTT  GTAACCGTCG  TTGATACACT

XmaI
                           ----------
              KpnI         SmaI
            --------     ----------
            Acc65I         AvaI
            --------     ----------
101  GCTGGTACCA  GCAGTTGCCC  GGGACGGCGC  CGAAACTGCT  GATTATGAT
     CGACCATGGT  CGTCAACGGG  CCCTGCCGCG  GCTTTGACGA  CTAATACTA

Bsu36I                              BamHI
                     ----------                         ----------
151  AACAACCAGC  GTCCTCAGG   CGTGCCGGAT  CGTTTTAGCG  GATCCAAAAG
     TTGTTGGTCG  CAGGGAGTCC  GCACGGCCTA  GCAAAATCGC  CTAGGTTTTC

BpuAI
                                                      ----------
                                                        BbsI
                                                      ----------
201  CGGCACCAGC  GCGAGCCTTG  CGATTACGGG  CCTGCAAAGC  GAAGACGAAG
     GCCGTGGTCG  CGCTCGGAAC  GCTAATGCCC  GGACGTTTCG  CTTCTGCTTC

Bsu36I
                            ----------
251  CGGATTATTA  TTGCCAGAGC  TATGACATGC  CTCAGGCTGT  GTTTGGCGGC
     GCCTAATAAT  AACGGTCTCG  ATACTGTACG  GAGTCCGACA  CAAACCGCCG

MscI                      DraIII
                            ----------                ----------
301  GGCACGAAGT  TTAACCGTTC  TTGGCCAGCC  GAAAGCCGCA  CCGAGTGTGA
     CCGTGCTTCA  AATTGGCAAG  AACCGGTCGG  CTTTCGGCGT  GGCTCACACT

351  CGCTGTTTCC  GCCGAGCAGC  GAAGAATTGC  AGGCGAACAA  AGCGACCCTG
     GCGACAAAGG  CGGCTCGTCG  CTTCTTAACG  TCCGCTTGTT  TCGCTGGGAC

401  GTGTGCCTGA  TTAGCGACTT  TTATCCGGGA  GCCGTGACAG  TGGCCTGGAA
```

Fig. 3 Continued

```
        CACACGGACT AATCGCTGAA AATAGGCCCT CGGCACTGTC ACCGGACCTT
  451   GGCAGATAGC AGCCCCGTCA AGGCGGGAGT GGAGACCACC ACACCCTCCA
        CCGTCTATCG TCGGGGCAGT TCCGCCCTCA CCTCTGGTGG TGTGGGAGGT

501   AACAAAGCAA CAACAAGTAC GCGGCCAGCA GCTATCGAG  CCTGACGCCT
        TTGTTTCGTT GTTGTTCATG CGCCGGTCGT CGATAGACTC GGACTGCGGA

551   GAGCAGTGGA AGTCCCACAG AAGCTACAGC TGCCAGGTCA CGCATGAGGG
        CTCGTCACCT TCAGGGTGTC TTCGATGTCG ACGGTCCAGT GCGTACTCCC

StuI           SphI
                                              ~~~~~~         ~~~~~~
  601   GAGCACCGTG GAAAAAACCG TTGCGCTGAC TGAGGCCTGA TAAGCATGCG
        CTCGTGGCAC CTTTTTTGGC AACGCGACTG ACTCCGGACT ATTCGTACGC

651   TAGGAGAAAA TAAAATGAAA CAAAGCACTA TTGCACTGGC ACTCTTACCG
        ATCCTCTTTT ATTTTACTTT GTTTCGTGAT AACGTGACCG TGAGAATGGC

MfeI
                                       ~~~~~~
  701   TTGCTCTTCA CCCCTGTTAC CAAAGCCCAG GTGCAATTGA AGAAAGCGG
        AACGAGAAGT GGGGACAATG GTTTCGGGTC CACGTTAACT TCTTTCGCC

BspEI
                                                            ~
  751   CCCGGTCCTG GTGAAACCGA CCCAAACCCT GACCCTGACC TGTACCTTTT
        GGGCCGGGAC CACTTTGGCT GGGTTTGGGA CTGGGACTGG ACATGGAAAA

BspEI
        ~~~~~~
  801   CCGGATTTAG CCTGTCCACG TCTGGCGTTG GCGTGGGCTG GATTCGCCAG
        GGCCTAAATC GGACAGGTGC AGACCGCAAC CGCACCCGAC CTAAGCGGTC

XhoI
                   ~~~~~~
                   AvaI
                   ~~~~~~
  851   CCGGCTGGGA AAGCCCTCGA GTGGCTGGCT CTGATTGATT GGGATGATGA
        GGCCGACCCT TTCGGGAGCT CACCGACCGA GACTAACTAA CCCTACTACT

901   TAAGTATTAT AGCACCAGCC TGAAAACGCG TCTGACCATT AGCAAAGATA
        ATTCATAATA TCGTGGTCGG ACTTTTGCGC AGACTGGTAA TCGTTTCTAT
```

Fig. 3 Continued

```
     BstBI
     ~~~~~~
     SfuI
     ~~~~~~
     NspV
     ~~~~~~
 951 CTTCGAAAAA TCAGGTGGTG CTGACTATGA CCAACATGGA CCCCGTGGAT
     GAAGCTTTTT AGTCCACCAC GACTGATACT GGTTGTACCT GGGGCACCTA

BssHII
                     ~~~~~~~~
1001 ACGGCCACCT ATTATTGCGC GCGTTCTCCT CGTTATCGTG GTGCTTTTGA
     TGCCGGTGGA TAATAACGCG CGCAAGAGGA GCAATAGCAC CACGAAAACT

BlpI
                                              ~~~~~~~~
              StyI                            CelII
              ~~~~~~~~                        ~~~~~~~~
1051 TTATTGGGGC CAAGGCACCC TGGTGACGGT TAGCTCAGCG TCGACCAAAG
     AATAACCCCG GTTCCGTGGG ACCACTGCCA ATCGAGTCGC AGCTGGTTTC

1101 GTCCAAGCGT GTTTCCGTTG GCTCCGAGCA GCAAAAGTAC CAGCGGCGGC
     CAGGTTCGCA CAAAGGCAAC CGAGGCTCGT CGTTTTCGTG GTCGCCGCCG

1151 ACGGCTGCCC TGGCTGCCTG GTTAAAGAT TATTTCCCGG AACCAGTCAC
     TGCCGACGGG ACCGACGGA CCAATTTCTA ATAAAGGGCC TTGGTCAGTG

1201 CGTGAGCTGG AACAGCGGGG CGCTGACCAG CGGCGTGCAT ACCTTTCCGG
     GCACTCGACC TTGTCGCCCC GCGACTGGTC GCCGCACGTA TGGAAAGGCC

1251 CGGTGCTGCA AAGCAGCGGC CTGTATAGCC TGAGCAGCGT TGTGACCGTG
     GCCACGACGT TTCGTCGCCG GACATATCGG ACTCGTCGCA ACACTGGCAC

1301 CCGAGCAGCA GCTTAGGCAC TCAGACCTAT ATTTGCAACG TGAACCATAA
     GGCTCGTCGT CGAATCCGTG AGTCTGGATA TAAACGTTGC ACTTGGTATT

EcoRI
                                                      ~~~~~~~~
1351 ACCGAGCAAC ACCAAAGTGG ATAAAAAAGT GGAACCGAAA AGCGAATTCG
     TGGCTCGTTG TGGTTTCACC TATTTTTTCA CCTTGGCTTT TCGCTTAAGC

BssHII
                                ~~~~~~~~
1401 ACTATAAAGA TGACGATGAC AAAGGCGCGC CGTGGAGCCA CCCGCAGTTT
```

Fig. 3 Continued

```
      TGATATTTCT ACTGCTACTG TTCCGCGCG GCACCTCGGT GGGCGTCAAA

HindIII
               ------
1451  GAAAAATGAT AAGCTTGACC TGTGAAGTTA AAAATGGCGC AGATTGTGCG
      CTTTTTACTA TTCGAACTGG ACACTTCAAT TTTTACCGCG TCTAACACGC
                           OGIII3 100.0%
                           =========================

1501  ACATTTTTTT TGTCTGCCGT TTAATTAAAG GGGGGGGGGG GCCGGCCTGG
      TGTAAAAAAA ACAGACGGCA AATTAATTTC CCCCCCCCCC CGGCCGGACC

1551  GGGGGGGTGT ACATAAAATT GTAAACGTTA ATATTTTGTT AAAATTCGCG
      CCCCCCCACA TGTACTTTAA CATTTGCAAT TATAAAACAA TTTTAAGCGC

1601  TTAAATTTTT GTAAATCAG CTCATTTTTT AACCAATAGG CCGAAATCGG
      AATTTAAAAA CAATTTAGTC GAGTAAAAAA TTGGTTATCC GGCTTTAGCC

1651  CAAAATCCCT TATAAATCAA AAGAATAGAC CGAGATAGGG TTGAGTGTTG
      GTTTTAGGGA ATATTTAGTT TTCTTATCTG GCTCTATCCC AACTCACAAC

1701  TTCCAGTTTG GAACAAGAGT CCACTATTAA AGAACGTGGA CTCCAACGTC
      AAGGTCAAAC CTTGTTCTCA GGTGATAATT TCTTGCACCT GAGGTTGCAG

1751  AAAGGGCGAA AAACCGTCTA TCAGGGCGAT GGCCCACTAC GAGAACCATC
      TTTCCCGCTT TTTGGCAGAT AGTCCCGCTA CCGGGTGATG CTCTTGGTAG

1801  ACCCTAATCA AGTTTTTTGG GGTCGAGGTG CCGTAAAGCA CTAAATCGGA
      TGGGATTAGT TCAAAAAACC CCAGCTCCAC GGCATTTCGT GATTTAGCCT

1851  ACCCTAAAGG GAGCCCCCGA TTTAGAGCTT GACGGGGAAA GCCGGCGAAC
      TGGGATTTCC CTCGGGGGCT AAATCTCGAA CTGCCCCTTT CGGCCGCTTG

1901  GTGGCGAGAA AGGAAGGGAA GAAAGCGAAA GGAGCGGGCG CTAGGGCGCT
      CACCGCTCTT TCCTTCCCTT CTTTCGCTTT CCTCGCCCGC GATCCCGCGA

1951  GGCAAGTGTA GCGGTCACGC TGCGCGTAAC CACCACACCC GCCGCGCTTA
      CCGTTCACAT CGCCAGTGCG ACGCGCATTG GTGGTGTGGG CGGCGCGAAT

2001  ATGCGCCGCT ACAGGGCGCG TGCTAGACTA GTGTTTAAAC CGGACCGGGG
      TACGCGGCGA TGTCCCGCGC ACGATCTGAT CACAAATTTG GCCTGGCCCC

2051  GGGGCTTAA GTGGCTGCA AAACAAAACG GCCTCCTGTC AGGAAGCCGC
      CCCCCGAATT CACCGACGT TTTGTTTTGC CGGAGGACAG TCCTTCGGCG
```

Fig. 3 Continued

```
2101  TTTTATCGGG TAGCCTCACT GCCCGCTTTC CAGTCGGGAA ACCTGTCGTG
      AAAATAGCCC ATCGGAGTGA CGGGCGAAAG GTCAGCCCTT TGGACAGCAC

2151  CCAGCTGCAT CAGTGAATCG GCCAACGCGC GGGGAGAGGC GGTTTGCGTA
      GGTCGACGTA GTCACTTAGC CGGTTGCGCG CCCCTCTCCG CCAAACGCAT

2201  TTGGCAGCCA GGGTGGTTTT TCTTTTCACC AGTGAGACGG GCAACAGCTG
      AACCGTCGGT CCCACCAAAA AGAAAAGTGG TCACTCTGCC CGTTGTCGAC

2251  ATTGCCCTTC ACCGCCTGGC CCTGAGAGAG TTGCAGCAAG CGGTCCACGC
      TAACGGGAAG TGGCGGACCG GGACTCTCTC AACGTCGTTC GCCAGGTGCG

2301  TGGTTTGCCC CAGCAGGCGA AAATCCTGTT TGATGGTGGT CAGCGGCGGG
      ACCAAACGGG GTCGTCCGCT TTTAGGACAA ACTACCACCA GTCGCCGCCC

2351  ATATAACATG AGCTGTCCTC GGTATCGTCG TATCCACTA CCGAGATGTC
      TATATTGTAC TCGACAGGAG CCATAGCAGC ATAGGTGAT GGCTCTACAG

2401  CGCACCAACG GGCAGCCCGG ACTCGGTAAT GGCACGCATT GCGCCCAGCG
      GCGTGGTTGC CCGTCGGGCC TGAGCCATTA CCGTGCGTAA CGCGGGTCGC

2451  CCATCTGATC GTTGGCAACC AGCATCGCAG TGGGAACGAT GCCCTCATTC
      GGTAGACTAG CAACCGTTGG TCGTAGCGTC ACCCTTGCTA CGGGAGTAAG

2501  AGCATTTGCA TGGTTTGTTG AAAACGGGAC ATGGCACTCC AGTCGCCTTC
      TCGTAAACGT ACCAAACAAC TTTTGCCCTG TACCGTGAGG TCAGCGGAAG

2551  CCGTTCCGCT ATCGGCTGAA TTTGATTGCG AGTGAGATAT TATGCCAGC
      GGCAAGGCGA TAGCCGACTT AAACTAACGC TCACTCTATA AATACGGTCG

2601  CAGCCAGACG CAGACGCGCC GAGACAGAAC TTAATGGGCC AGCTAACAGC
      GTCGGTCTGC GTCTGCGCGG CTCTGTCTTG AATTACCCGG TCGATTGTCG

2651  GCGATTTGCT GGTGGCCCAA TGCGACCAGA TGCTCCACGC CCAGTCGCGT
      CGCTAAACGA CCACCGGGTT ACGCTGGTCT ACGAGGTGCG GGTCAGCGCA

2701  ACCGTCCTCA TGGAGAAAAA TAATACTGTT GATGGTGTC TGGTCAGAGA
      TGGCAGGAGT ACCTCTTTTT ATTATGACAA CTACCACAG ACCAGTCTCT

2751  CATCAAGAAA TAACGCCGGA ACATTAGTGC AGGCAGCTTC CACAGCAATA
      GTAGTTCTTT ATTGCGGCCT TGTAATCACG TCCGTCGAAG GTGTCGTTAT

2801  GCATCCTGGT CATCCAGCGG ATAGTTAATA ATCAGCCCAC TGACACGTTG
```

Fig. 3 Continued

```
          CGTAGGACCA GTAGGTCGCC TATCAATTAT TAGTCGGGTG ACTGTGCAAC
                  ApaLI
                  ------
    2851  CGCGAGAAGA TTGTGCACCG CCGCTTTACA GGCTTCGACG CCGCTTCGTT
          GCGCTCTTCT AACACGTGGC GGCGAAATGT CCGAAGCTGC GGCGAAGCAA

2901  CTACCATCGA CACGACCACG CTGGCACCCA GTTGATCGGC GCGAGATTTA
          GATGGTAGCT GTGCTGGTGC GACCGTGGGT CAACTAGCCG CGCTCTAAAT

2951  ATCGCCGCGA CAATTTGCGA CGGCGCGTGC AGGGCCAGAC TGGAGGTGGC
          TAGCGGCGCT GTTAAACGCT GCCGCGCACG TCCCGGTCTG ACCTCCACCG

3001  AACGCCAATC AGCAACGACT GTTTGCCCGC CAGTTGTTGT GCCACGCGGT
          TTGCGGTTAG TCGTTGCTGA CAAACGGGCG GTCAACAACA CGGTGCGCCA

3051  TAGGAATGTA ATTCAGCTCC GCCATCGCCG CTTCCACTTT TTCCCGCGTT
          ATCCTTACAT TAAGTCGAGG CGGTAGCGGC GAAGGTGAAA AAGGGCGCAA

3101  TTCGCAGAAA CGTGGCTGGC CTGGTTCACC ACGCGGGAAA CGGTCTGATA
          AAGCGTCTTT GCACCGACCG GACCAAGTGG TGCGCCCTTT GCCAGACTAT

3151  AGAGACACCG GCATACTCTG CGACATCGTA TAACGTTACT GGTTTCACAT
          TCTCTGTGGC CGTATGAGAC GCTGTAGCAT ATTGCAATGA CCAAAGTGTA

3201  TCACCACCCT GAATTGACTC TCTTCCGGGC GCTATCATGC CATACCGCGA
          AGTGGTGGGA CTTAACTGAG AGAAGGCCCG CGATAGTACG GTATGGCGCT

3251  AAGGTTTTGC GCCATTCGAT GCTAGCCATG TGAGCAAAAG GCCAGCAAAA
          TTCCAAAACG CGGTAAGCTA CGATCGGTAC ACTCGTTTTC CGGTCGTTTT

3301  GGCCAGGAAC CGTAAAAAGG CCGCGTTGCT GGCGTTTTTC CATAGGCTCC
          CCGGTCCTTG GCATTTTTCC GGCGCAACGA CCGCAAAAAG GTATCCGAGG

3351  GCCCCCCTGA CGAGCATCAC AAAAATCGAC GCTCAAGTCA GAGGTGGCGA
          CGGGGGGACT GCTCGTAGTG TTTTTAGCTG CGAGTTCAGT CTCCACCGCT

3401  AACCCGACAG GACTATAAAG ATACCAGGCG TTTCCCCCTG GAAGCTCCCT
          TTGGGCTGTC CTGATATTTC TATGGTCCGC AAAGGGGAC CTTCGAGGGA

3451  CGTGCGCTCT CCTGTTCCGA CCCTGCCGCT TACCGGATAC CTGTCCGCCT
          GCACGCGAGA GGACAAGGCT GGGACGGCGA ATGGCCTATG GACAGGCGGA

3501  TTCTCCCTTC GGGAAGCGTG GCGCTTTCTC ATAGCTCACG CTGTAGGTAT
```

Fig. 3 Continued

```
          AAGAGGGAAG  CCCTTCGCAC  CGCGAAAGAG  TATCGAGTGC  GACATCCATA
                                                          ApaLI
                                                          ------
     3551 CTCAGTTCGG  TGTAGGTCGT  TCGCTCCAAG  CTGGGCTGTG  TGCACGAACC
          GAGTCAAGCC  ACATCCAGCA  AGCGAGGTTC  GACCCGACAC  ACGTGCTTGG

3601 CCCCGTTCAG  CCCGACCGCT  GCGCCTTATC  CGGTAACTAT  CGTCTTGAGT
          GGGGCAAGTC  GGGCTGGCGA  CGCGGAATAG  GCCATTGATA  GCAGAACTCA

3651 CCAACCCGGT  AAGACACGAC  TTATCGCCAC  TGGCAGCAGC  CACTGGTAAC
          GGTTGGGCCA  TTCTGTGCTG  AATAGCGGTG  ACCGTCGTCG  GTGACCATTG

3701 AGGATTAGCA  GAGCGAGGTA  TGTAGGCGGT  GCTACAGAGT  TCTTGAAGTG
          TCCTAATCGT  CTCGCTCCAT  ACATCCGCCA  CGATGTCTCA  AGAACTTCAC

3751 GTGGCCTAAC  TACGGCTACA  CTAGAAGAAC  AGTATTTGGT  ATCTGCGCTC
          CACCGGATTG  ATGCCGATGT  GATCTTCTTG  TCATAAACCA  TAGACGCGAG

3801 TGCTGTAGCC  AGTTACCTTC  GGAAAAAGAG  TTGGTAGCTC  TTGATCCGGC
          ACGACATCGG  TCAATGGAAG  CCTTTTTCTC  AACCATCGAG  AACTAGGCCG

3851 AAACAAACCA  CCGCTGGTAG  CGGTGGTTTT  TTTGTTTGCA  AGCAGCAGAT
          TTTGTTTGGT  GGCGACCATC  GCCACCAAAA  AAACAAACGT  TCGTCGTCTA

3901 TACGCGCAGA  AAAAAAGGAT  CTCAAGAAGA  TCCTTTGATC  TTTTCTACGG
          ATGCGCGTCT  TTTTTTCCTA  GAGTTCTTCT  AGGAAACTAG  AAAAGATGCC

3951 GGTCTGACGC  TCAGTGGAAC  GAAAACTCAC  GTTAAGGGAT  TTTGGTCAGA
          CCAGACTGCG  AGTCACCTTG  CTTTTGAGTG  CAATTCCCTA  AAACCAGTCT

4001 TCTAGCACCA  GGCGTTTAAG  GGCACCAATA  ACTGCCTTAA  AAAAATTACG
          AGATCGTGGT  CCGCAAATTC  CCGTGGTTAT  TGACGGAATT  TTTTTAATGC

4051 CCCCGCCCTG  CCACTCATCG  CAGTACTGTT  GTAATTCATT  AAGCATTCTG
          GGGGCGGGAC  GGTGAGTAGC  GTCATGACAA  CATTAAGTAA  TTCGTAAGAC

4101 CCGACATGGA  AGCCATCACA  AACGGCATGA  TGAACCTGAA  TCGCCAGCGG
          GGCTGTACCT  TCGGTAGTGT  TTGCCGTACT  ACTTGGACTT  AGCGGTCGCC

4151 CATCAGCACC  TTGTCGCCTT  GCGTATAATA  TTTGCCCATA  GTGAAAACGG
          GTAGTCGTGG  AACAGCGGAA  CGCATATTAT  AAACGGGTAT  CACTTTTGCC

4201 GGCGAAGAA   GTTGTCCATA  TTGGCTACGT  TTAAATCAAA  ACTGGTGAAA
```

Fig. 3 Continued

```
     CCCGCTTCTT CAACAGGTAT AACCGATGCA AATTAGTTT TGACCACTTT
4251 CTCACCCAGG GATTGGCTGA GACGAAAAAC ATATTCTCAA TAAACCCTTT
     GAGTGGGTCC CTAACCGACT CTGCTTTTTG TATAAGAGTT ATTTGGGAAA

4301 AGGGAAATAG GCCAGGTTTT CACCGTAACA CGCCACATCT TGCGAATATA
     TCCCTTTATC CGGTCCAAAA GTGGCATTGT GCGGTGTAGA ACGCTTATAT

4351 TGTGTAGAAA CTGCCGGAAA TCGTCGTGGT ATTCACTCCA GAGCGATGAA
     ACACATCTTT GACGGCCTTT AGCAGCACCA TAAGTGAGGT CTCGCTACTT

4401 AACGTTTCAG TTTGCTCATG GAAAACGGTG TAACAAGGGT GAACACTATC
     TTGCAAAGTC AAACGAGTAC CTTTTGCCAC ATTGTTCCCA CTTGTGATAG

4451 CCATATCACC AGCTCACCGT CTTTCATTGC CATACGGAAC TCCGGGTGAG
     GGTATAGTGG TCGAGTGGCA GAAAGTAACG GTATGCCTTG AGGCCCACTC

4501 CATTCATCAG GCGGGCAAGA ATGTGAATAA AGGCCGGATA AAACTTGTGC
     GTAAGTAGTC CGCCCGTTCT TACACTTATT TCCGGCCTAT TTTGAACACG

4551 TTATTTTCT TTACGGTCTT TAAAAAGGCC GTAATATCCA GCTGAACGGT
     AATAAAAGA AATGCCAGAA ATTTTTCCGG CATTATAGGT CGACTTGCCA

4601 CTGGTTATAG GTACATTGAG CAACTGACTG AAATGCCTCA AAATGTTCTT
     GACCAATATC CATGTAACTC GTTGACTGAC TTTACGGAGT TTTACAAGAA

4651 TACGATGCCA TTGGGATATA TCAACGGTGG TATATCCAGT GATTTTTTC
     ATGCTACGGT AACCCTATAT AGTTGCCACC ATATAGGTCA CTAAAAAAG

4701 TCCATTTTAG CTTCCTTAGC TCCTGAAAAT CTCGATAACT CAAAAAATAC
     AGGTAAAATC GAAGGAATCG AGGACTTTTA GAGCTATTGA GTTTTTTATG

4751 GCCCGGTAGT GATCTTATTT CATTATGGTG AAAGTTGGAA CCTCACCCGA
     CGGGCCATCA CTAGAATAAA GTAATACCAC TTTCAACCTT GGAGTGGGCT

4801 CGTCTAATGT GAGTTAGCTC ACTCATTAGG CACCCCAGGC TTTACACTTT
     GCAGATTACA CTCAATCGAG TGAGTAATCC GTGGGGTCCG AAATGTGAAA

4851 ATGCTTCCGG CTCGTATGTT GTGTGGAATT GTGAGCGGAT AACAATTTCA
     TACGAAGGCC GAGCATACAA CACACCTTAA CACTCGCCTA TTGTTAAAGT

M13 Reverse primer 100.0%              XbaI
         ―――――――――――――――――――――――――                ------
4901 CACAGGAAAC AGCTATGACC ATGATTACGA ATTCTAGAT AACGAGGGCA
```

Fig. 3 Continued

```
      GTGTCCTTTG TCGATACTGG TACTAATGCT TAAAGATCTA TTGCTCCCGT

4951  AAAAATGAAA AAGACAGCTA TCGCGATTGC AGTGGCACTG GCTGGTTTCG
      TTTTTACTTT TTCTGTCGAT AGCGCTAACG TCACCGTGAC CGACCAAAGC

EcoRV
                    ----
5001  CTACCGTAGC GCAGGCCGAT
      GATGGCATCG CGTCCGGCTA
```

Fig. 4a

Sequence of MS-Roche#3, #7 and #8

VL

| Position | | | | | | | | | | 1 | | | | | | | | | | 2 | | | | | | | | | | 3 | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| | EcoRV | | | | | | BsiXI | | | | | | | | | | | | | | | | | | | | | | | | PstI | | | | | | | | |
| VLκ3 | D | I | V | L | T | Q | S | P | A | T | L | S | L | S | P | G | E | R | A | T | L | S | C | | | | | | | | | | | | | | | | |
| MS-Roche #3 | D | I | V | L | T | Q | S | P | A | T | L | S | L | S | P | G | E | R | A | T | L | S | C | | | | | | | | | | | | | | | | |
| MS-Roche #7 | D | I | V | L | T | Q | S | P | A | T | L | S | L | S | P | G | E | R | A | T | L | S | C | | | | | | | | | | | | | | | | |
| MS-Roche #8 | D | I | V | L | T | Q | S | P | A | T | L | S | L | S | P | G | E | R | A | T | L | S | C | | | | | | | | | | | | | | | | |

Framework 1

VH

| Position | | | | | | | | | | 1 | | | | | | | | | | 2 | | | | | | | | | | 3 | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| | MfeI | | | | | | | | | | | | | | | | | | | | | | | | | | | | | BspEI | | | | | | | | |
| VH3 | Q | V | Q | L | V | E | S | G | G | G | L | V | Q | P | G | G | S | L | R | L | S | C | A | A | S | G | | | | | | | | | | | | |
| MS-Roche #3 | Q | V | Q | L | V | E | S | G | G | G | L | V | Q | P | G | G | S | L | R | L | S | C | A | A | S | G | | | | | | | | | | | | |
| MS-Roche #7 | Q | V | Q | L | V | E | S | G | G | G | L | V | Q | P | G | G | S | L | R | L | S | C | A | A | S | G | | | | | | | | | | | | |
| MS-Roche #8 | Q | V | Q | L | V | E | S | G | G | G | L | V | Q | P | G | G | S | L | R | L | S | C | A | A | S | G | | | | | | | | | | | | |

Framework 1

Sequence of MS-Roche#3, #7 and #8

VL

Framework 1

| Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| | EcoRV | | | | | | BsrtI | | | | | | | | | | | | | | | | |
| VLa3 | GAT | ATC | GTG | CTG | ACC | CAG | AGC | CCG | GGC | ACC | CTG | AGC | CTG | TCT | CCG | GGC | GAA | CGT | GCG | ACC | CTG |
| MS-Roche #3 | GAT | ATC | GTG | CTG | ACC | CAG | AGC | CCG | GGC | ACC | CTG | AGC | CTG | TCT | CCG | GGC | GAA | CGT | GCG | ACC | CTG |
| MS-Roche #7 | GAT | ATC | GTG | CTG | ACC | CAG | AGC | CCG | GGC | ACC | CTG | AGC | CTG | TCT | CCG | GGC | GAA | CGT | GCG | ACC | CTG |
| MS-Roche #8 | GAT | ATC | GTG | CTG | ACC | CAG | AGC | CCG | GGC | ACC | CTG | AGC | CTG | TCT | CCG | GGC | GAA | CGT | GCG | ACC | CTG |

VH

Framework 1

| Position | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| | | | | NcoI | | | | | | | | | | | | | | | | | |
| VH3 | CAG | GTG | CAA | TTG | GTG | GAA | AGC | GGC | GGC | GGC | CTG | GTG | CAA | CCG | GGC | GGC | AGC | CTG | CGT | CTG | AGC |
| MS-Roche #3 | CAG | GTG | CAA | TTG | GTG | GAA | AGC | GGC | GGC | GGC | CTG | GTG | CAA | CCG | GGC | GGC | AGC | CTG | CGT | CTG | AGC |
| MS-Roche #7 | CAG | GTG | CAA | TTG | GTG | GAA | AGC | GGC | GGC | GGC | CTG | GTG | CAA | CCG | GGC | GGC | AGC | CTG | CGT | CTG | AGC |
| MS-Roche #8 | CAG | GTG | CAA | TTG | GTG | GAA | AGC | GGC | GGC | GGC | CTG | GTG | CAA | CCG | GGC | GGC | AGC | CTG | CGT | CTG | AGC |

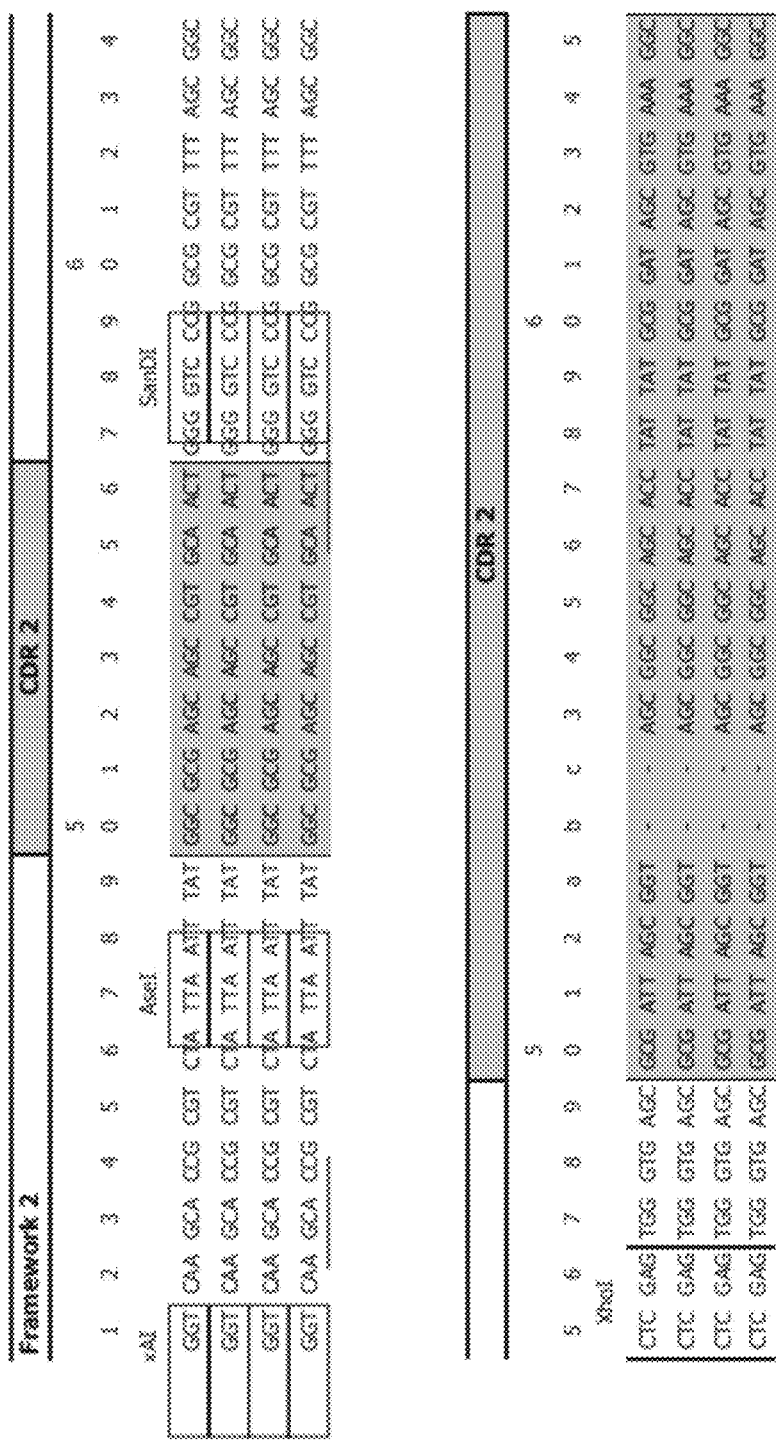

Fig. 4b continued

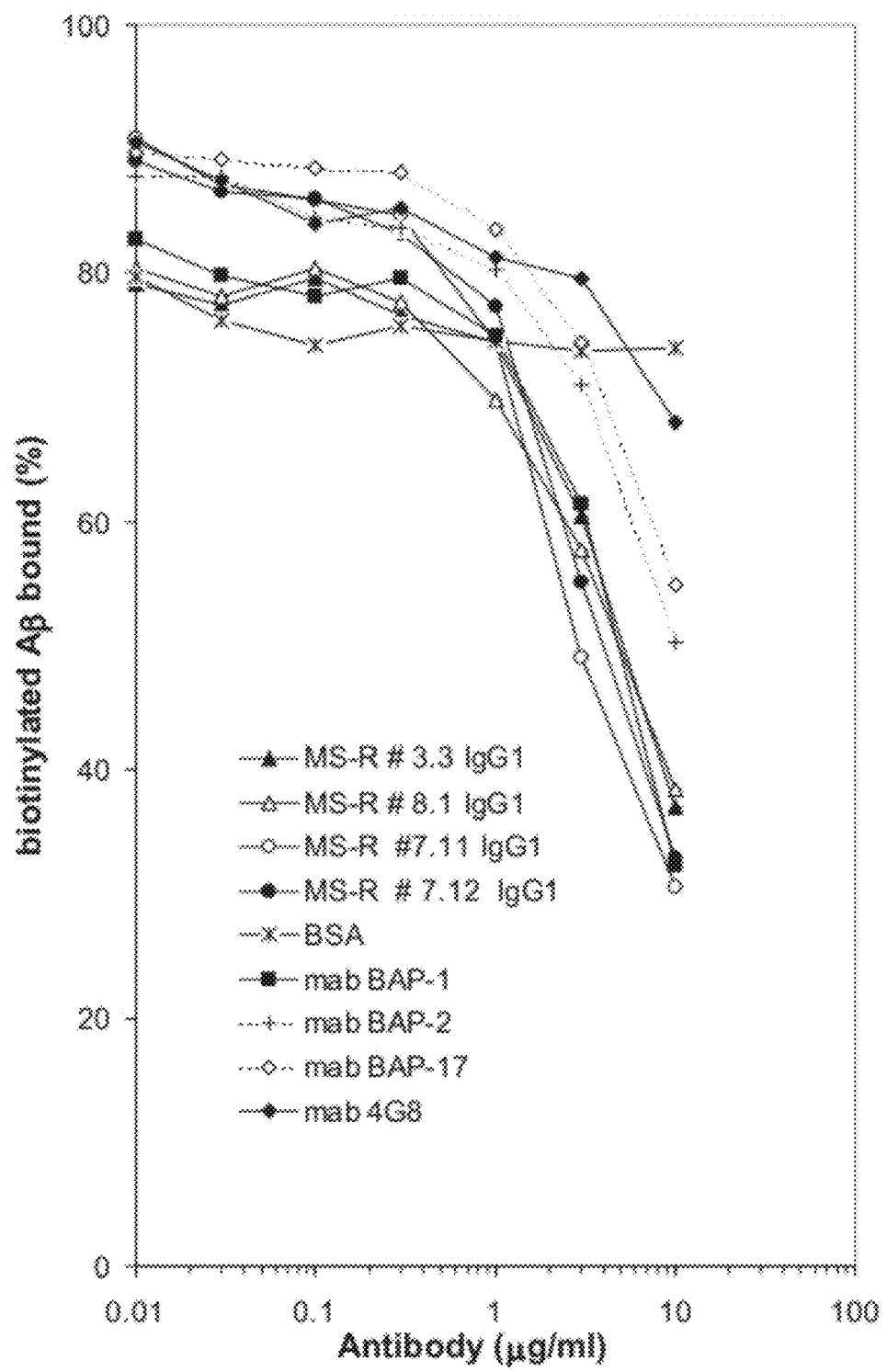

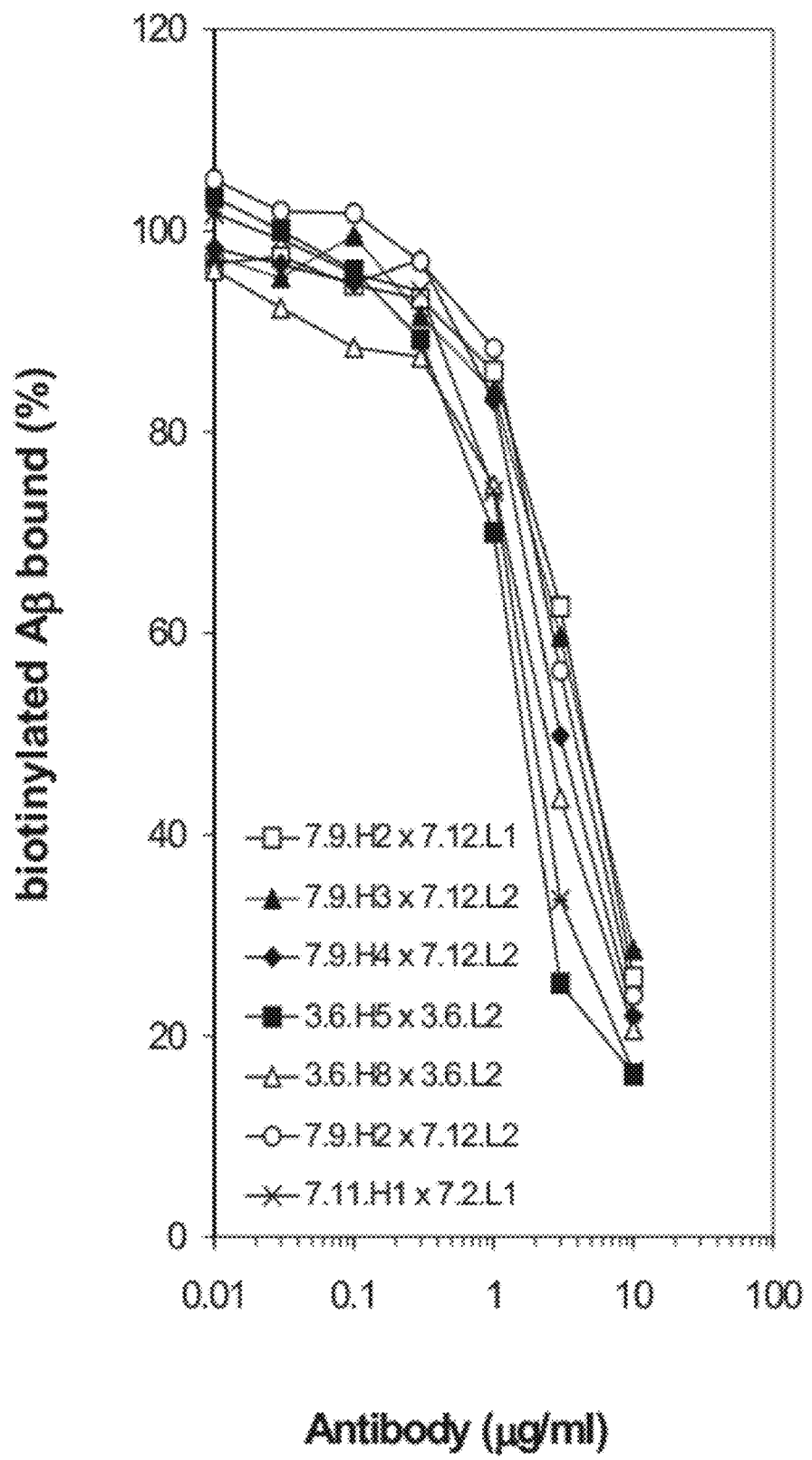

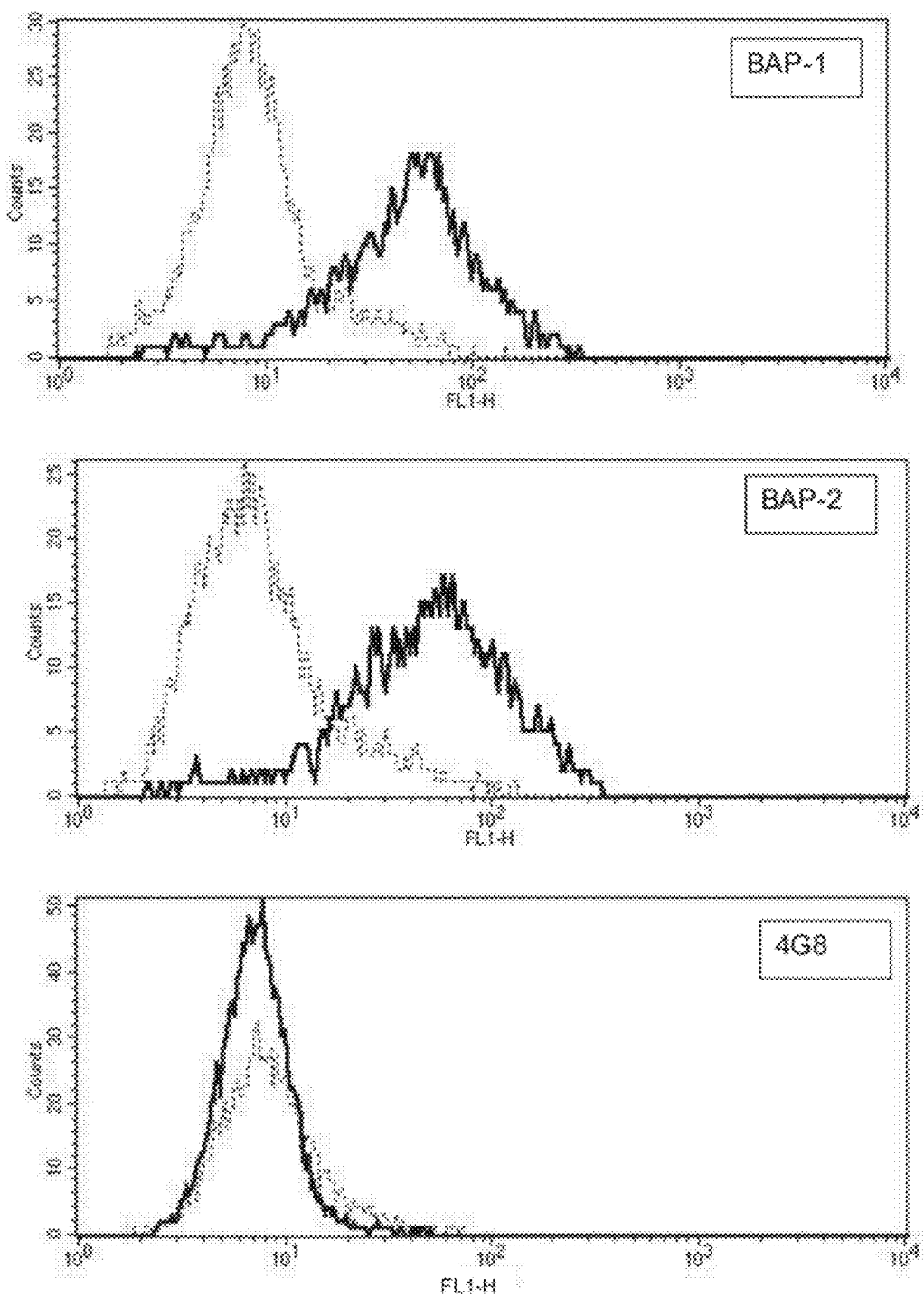

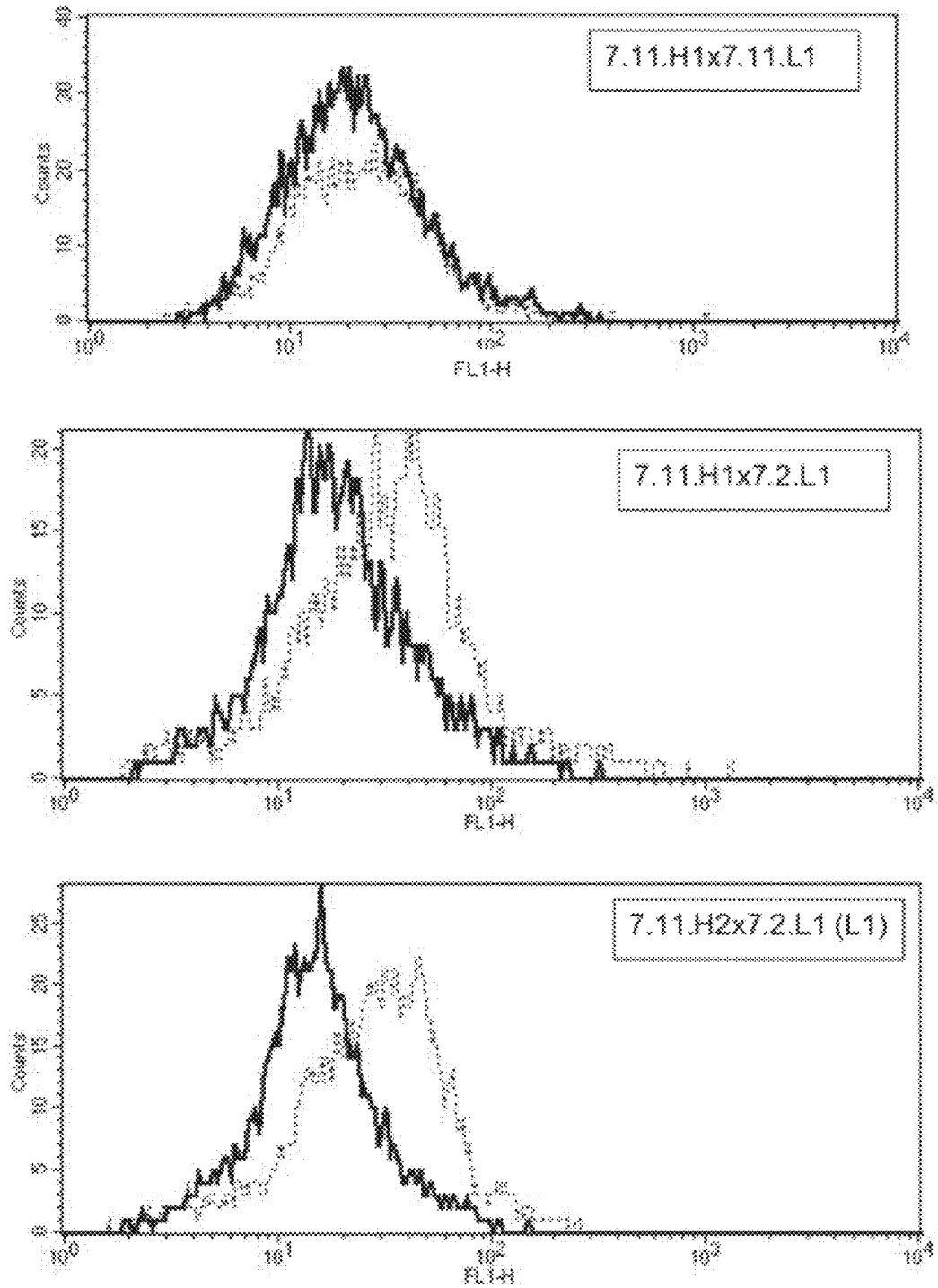

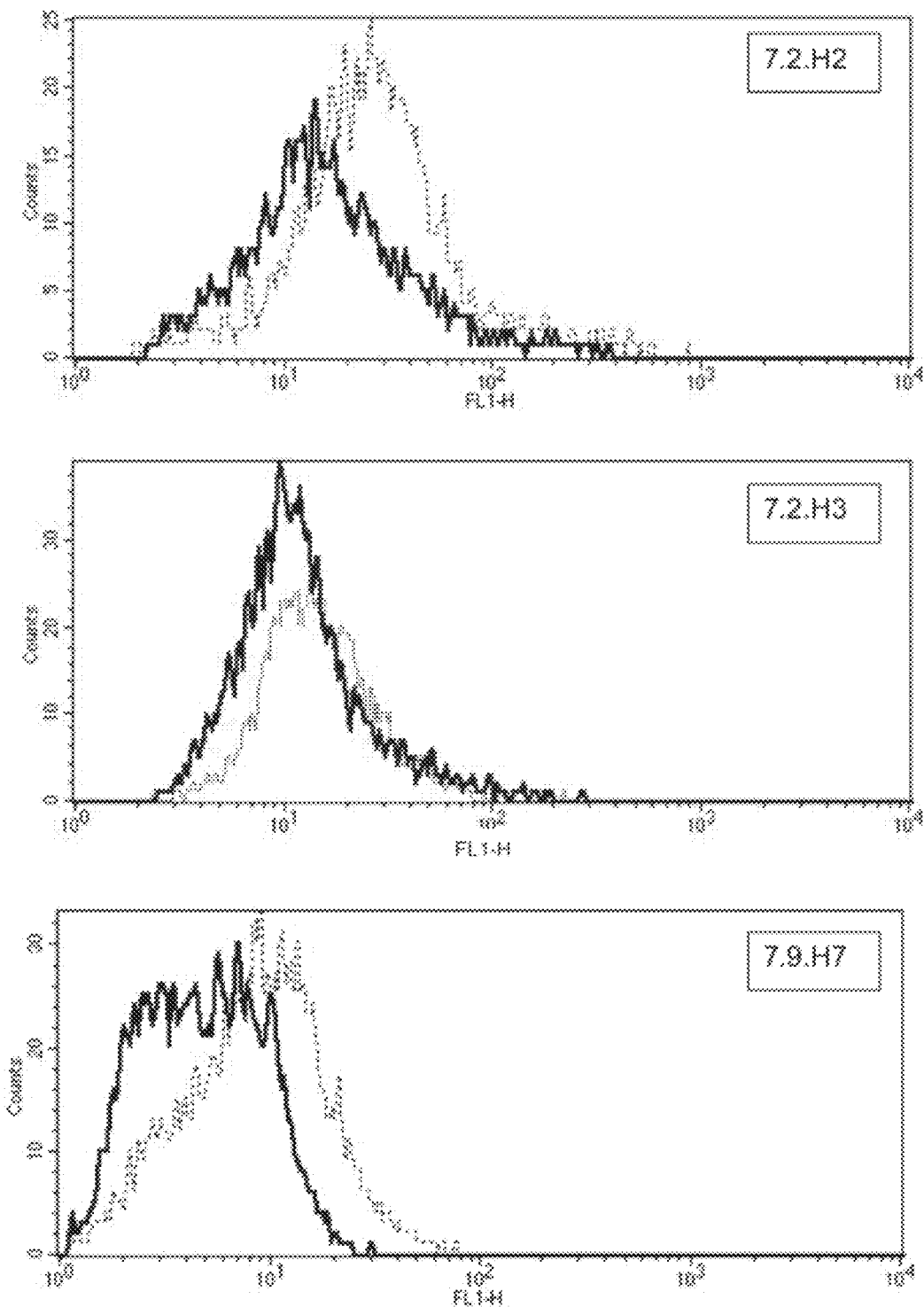
Figure 15, cont.

NUCLEIC ACID MOLECULES ENCODING ANTI-AMYLOID BETA ANTIBODIES

CROSS-REFERENCE TO RELATED APPLICATIONS

This application is a divisional of and claims benefit to U.S. patent application Ser. No. 12/462,119, filed on Jul. 28, 2009 now U.S. Pat. No. 8,216,577. The '119 application is a divisional of and claims benefit to U.S. patent application Ser. No. 10/505,313, filed Aug. 20, 2004, now issued as U.S. Pat. No. 7,794,719. The '313 application is the national stage of PCT/EP2003/001759, filed Feb. 20, 2003.

INCORPORATION BY REFERENCE OF SEQUENCE LISTING

This application contains references to amino acids and/or nucleic acid sequences that have been filed concurrently herewith as sequence listing text file "0235444div_sequence.txt", file size of 217 KB, created on Apr. 25, 2012. The aforementioned sequence listing is hereby incorporated by reference in its entirety pursuant to 37 C.F.R. §1.52(e)(5).

FIELD OF THE INVENTION

The present invention relates to antibody molecules capable of specifically recognizing two regions of the β-A4 peptide, wherein the first region comprises the amino acid sequence AEFRHDSGY as shown in SEQ ID NO: 1 or a fragment thereof and wherein the second region comprises the amino acid sequence VHHQKLVFFAEDVG as shown in SEQ ID NO: 2 or a fragment thereof. Furthermore, nucleic acid molecules encoding the inventive antibody molecules and vectors and hosts comprising said nucleic acid molecules are disclosed. In addition, the present invention provides for compositions, preferably pharmaceutical or diagnostic compositions, comprising the compounds of the invention as well as for specific uses of the antibody molecules, nucleic acid molecules, vectors or hosts of the invention.

BACKGROUND OF THE INVENTION

Several documents are cited throughout the text of this specification. Each of the documents cited herein (including any manufacturers specifications, instructions, etc.) are hereby incorporated by reference.

About 70% of all cases of dementia are due to Alzheimer's disease which is associated with selective damage of brain regions and neural circuits critical for cognition. Alzheimer's disease is characterized by neurofibrillary tangles in particular in pyramidal neurons of the hippocampus and numerous amyloid plaques containing mostly a dense core of amyloid deposits and defused halos.

The extracellular neuritic plaques contain large amounts of a pre-dominantly fibrillar peptide termed "amyloid β", "A-beta", "Aβ4", "β-A4" or "Aβ"; see Selkoe (1994), Ann. Rev. Cell Biol. 10, 373-403, Koo (1999), PNAS Vol. 96, pp. 9989-9990, U.S. Pat. No. 4,666,829 or Glenner (1984), BBRC 12, 1131. This amyloid β is derived from "Alzheimer precursor protein/β-amyloid precursor protein" (APP). APPs are integral membrane glycoproteins (see Sisodia (1992), PNAS Vol. 89, pp. 6075) and are endoproteolytically cleaved within the Aβ sequence by a plasma membrane protease, α-secretase (see Sisodia (1992), loc. cit.). Furthermore, further secretase activity, in particular β-secretase and γ-secretase activity leads to the extracellular release of amyloid-β (Aβ) comprising either 39 amino acids (Aβ39), 40 amino acids (Aβ40), 42 amino acids (Aβ42) or 43 amino acids (Aβ43); see Sinha (1999), PNAS 96, 11094-1053; Price (1998), Science 282, 1078 to 1083; WO 00/72880 or Hardy (1997), TINS 20, 154.

It is of note that Aβ has several naturally occurring forms, whereby the human forms are referred to as the above mentioned Aβ39, Aβ40, Aβ41, Aβ42 and Aβ43. The most prominent form, Aβ42, has the amino acid sequence (starting from the N-terminus): DAEFRHDSGYEVHHQKLVFFAEDVG-SNKGAIIGLMVGGVVIA (SEQ ID NO: 27). In Aβ41, Aβ40, Aβ39, the C-terminal amino acids A, IA and VIA are missing, respectively. In the Aβ43-form an additional threonine residue is comprised at the C-terminus of the above depicted sequence (SEQ ID NO: 27).

The time required to nucleate Aβ40 fibrils was shown to be significantly longer than that to nucleate Aβ42 fibrils; see Koo, loc. cit. and Harper (1997), Ann. Rev. Biochem. 66, 385-407. As reviewed in Wagner (1999), J. Clin. Invest. 104, 1239-1332, the Aβ42 is more frequently found associated with neuritic plaques and is considered to be more fibrillogenic in vitro. It was also suggested that Aβ42 serves as a "seed" in the nucleation-dependent polymerization of ordered non-crystalline Aβ peptides; Jarrett (1993), Cell 93, 1055-1058.

It has to be stressed that modified APP processing and/or the generation of extracellular plaques containing proteinaceous depositions are not only known from Alzheimer's pathology but also from subjects suffering from other neurological and/or neurodegenerative disorders. These disorders comprise, inter alia, Down's syndrome, Hereditary cerebral hemorrhage with amyloidosis Dutch type, Parkinson's disease, ALS (amyotrophic lateral sclerosis), Creutzfeld Jacob disease, HIV-related dementia and motor neuropathy.

In order to prevent, treat and/or ameliorate disorders and/or diseases related to the pathological deposition of amyloid plaques, means and methods have to be developed which either interfere with β-amyloid plaque formation, which are capable of preventing Aβ aggregation and/or are useful in de-polymerization of already formed amyloid deposits or amyloid-β aggregates.

Accordingly, and considering the severe defects of modified and/or pathological amyloid biology, means and methods for treating amyloid related disorders are highly desirable. In particular, efficient drugs which either interfere with pathological amyloid aggregation or which are capable of de-polymerization of aggregated Aβ are desired. Furthermore, diagnostic means are desirable to detect, inter alia, amyloid plaques.

Thus, the technical problem of the present invention is to comply with the needs described herein above.

BRIEF SUMMARY OF THE INVENTION

Accordingly, the present invention relates to an antibody molecule capable of specifically recognizing two regions of the β-A4/Aβ4 peptide, wherein the first region comprises the amino acid sequence AEFRHDSGY (SEQ ID NO: 1) or a fragment thereof and wherein the second region comprises the amino acid sequence VHHQKLVFFAEDVG (SEQ ID NO: 2) or a fragment thereof.

In context of the present invention, the term "antibody molecule" relates to full immunoglobulin molecules, preferably IgMs, IgDs, IgEs, IgAs or IgGs, more preferably IgG1, IgG2a, IgG2b, IgG3 or IgG4 as well as to parts of such immunoglobulin molecules, like Fab-fragments or $V_L$-, $V_H$- or CDR-regions. Furthermore, the term relates to modified and/or altered antibody molecules, like chimeric and humanized antibodies. The term also relates to modified or altered monoclonal or polyclonal antibodies as well as to recombinantly or synthetically generated/synthesized antibodies. The term also relates to intact antibodies as well as to antibody fragments/parts thereof, like, separated light and heavy chains, Fab, Fab/c, Fv, Fab', F(ab')$_2$. The term "antibody molecule" also comprises antibody derivatives, the bifunctional antibodies and antibody constructs, like single chain Fvs (scFv), bispecific scFvs or antibody-fusion proteins. Further details on the term "antibody molecule" of the invention are provided herein below.

The term "specifically recognizing" means in accordance with this invention that the antibody molecule is capable of specifically interacting with and/or binding to at least two amino acids of each of the two regions of β-A4 as defined herein. Said term relates to the specificity of the antibody molecule, i.e. to its ability to discriminate between the specific regions of the β-A4 peptide as defined herein and another, not related region of the β-A4 peptide or another, not APP-related protein/peptide/(unrelated) tests-peptide. Accordingly, specificity can be determined experimentally by methods known in the art and methods as disclosed and described herein. Such methods comprise, but are not limited to Western blots, ELISA-, RIA-, ECL-, IRMA-tests and peptide scans. Such methods also comprise the determination of $K_D$-values as, inter alia, illustrated in the appended examples. The peptide scan (pepspot assay) is routinely employed to map linear epitopes in a polypeptide antigen. The primary sequence of the polypeptide is synthesized successively on activated cellulose with peptides overlapping one another. The recognition of certain peptides by the antibody to be tested for its ability to detect or recognize a specific antigen/epitope is scored by routine colour development (secondary antibody with horseradish peroxidase and 4-chloronaphthol and hydrogenperoxide), by a chemoluminescence reaction or similar means known in the art. In the case of, inter alia, chemoluminescence reactions, the reaction can be quantified. If the antibody reacts with a certain set of overlapping peptides one can deduce the minimum sequence of amino acids that are necessary for reaction; see illustrative Example 6 and appended Table 2.

The same assay can reveal two distant clusters of reactive peptides, which indicate the recognition of a discontinuous, i.e. conformational epitope in the antigenic polypeptide (Geysen (1986), Mol. Immunol. 23, 709-715).

In addition to the pepspot assay, standard ELISA assay can be carried out. As demonstrated in the appended examples small hexapeptides may be coupled to a protein and coated to an immunoplate and reacted with antibodies to be tested. The scoring may be carried out by standard colour development (e.g. secondary antibody with horseradish peroxidase and tetramethyl benzidine with hydrogenperoxide). The reaction in certain wells is scored by the optical density, for example at 450 nm. Typical background (=negative reaction) may be 0.1 OD, typical positive reaction may be 1 OD. This means the difference (ratio) positive/negative can be more than 10 fold. Further details are given in the appended examples. Additional, quantitative methods for determining the specificity and the ability of "specifically recognizing" the herein defined two regions of the β-A4 peptide are given herein below.

The term "two regions of the β-A4 peptide" relates to two regions as defined by their amino acid sequences shown in SEQ ID NOs: 1 and 2, relating to the N-terminal amino acids 2 to 10 and to the central amino acids 12 to 25 of β-A4 peptide. The term "β-A4 peptide" in context of this invention relates to the herein above described Aβ39, Aβ41, Aβ43, preferably to Aβ40 and Aβ42. Aβ42 is also depicted in appended SEQ ID NO: 27. It is of note that the term "two regions of the β-A4 peptide" also relates to an "epitope" and/or an "antigenic determinant" which comprises the herein defined two regions of the β-A4 peptide or parts thereof. In accordance with this invention, said two regions of the β-A4 peptide are separated (on the level of the amino acid sequence) in the primary structure of the β-A4 peptide by at least one amino acid, preferably by at least two amino acids, more preferably by at least three amino acids, more preferably by at least four amino acids, more preferably by at least five amino acids, more preferably at least six amino acids, more preferably at least nine amino acids and most preferably at least twelve amino acids. As shown herein and as documented in the appended examples, the inventive antibodies/antibody molecules detect/interact with and/or bind to two regions of the β-A4 peptide as defined herein, whereby said two regions are separated (on the primary structure level of the amino acid sequence) by at least one amino acid and wherein the sequence separating said two regions/"epitope" may comprise more then ten amino acids, preferably 14 amino acids, more preferably 15 amino acids or 16 amino acids. For example, MSR-3 Fab (as an inventive antibody molecule) recognizes detects/interacts with two regions on the β-A4 peptide, wherein said first region comprises amino acids 3 and 4 (EF) and said second regions comprises amino acids 18 to 23 (VFFAED, SEQ ID NO: 421). Accordingly, the separating sequence between the region/epitopes to be detected/recognized has a length of 13 amino acids on the primary amino acid sequence structure. Similarly, MSR #3.4H7 IgG1, an optimized and matured antibody molecules derived from MSR-3 and comprised in an IgG1-framework, detects/interacts with/binds to two epitopes/regions of β-A4 which comprise in the first region positions 1 to 4 (DAEF) and in the second region positions 19 to 24 (FFAEDV, SEQ ID NO: 423) of β-A4 as defined herein. Accordingly, MSR #3.4H7 IgG1 recognizes/detects/interacts with/binds to two epitopes/regions which are, on the primary amino acid sequence level, separated by 14 amino acids. As detailed in the appended examples, affinity maturation and conversion of monovalent inventive Fab fragments to full-length IgG1 antibodies may result in a certain broadening of the epitopes/regions detected in pepspot, ELISA assays and the like. Therefore, the antibody molecules of the invention are capable of simultaneously and independently recognizing two regions of the β-A4 peptide/Aβ4 wherein said regions comprise the amino acid sequence as shown in SEQ ID NO: 1 (or parts thereof) and the amino acid sequence as shown in SEQ ID NO: 2 (or (a) part(s) thereof). Due to the potential broadening of epitopes as detailed herein it is, however, also envisaged that amino acids in close proximity to the sequences of SEQ ID NO: 1 and 2 are detected/recognized, i.e. that additional amino acids are part of the two regions to be detected/recognized. Accordingly, it is also envisaged that, e.g. the first amino acid of Aβ (1-42) as defined herein, namely D (Aspartic acid) in part of one epitope to be detected/recognized or that amino acids located after the region of Aβ (1-42) as defined in SEQ ID NO: 2 are detected/recognized. Said additional amino acid may, e.g., be the amino acid on position 26 of SEQ ID NO: 27 (βA4/Aβ (1-42)), namely S (Serine).

The term may also relate to a conformational epitope, a structural epitope or a discountinuous epitope consisting of said two regions or parts thereof; see also Geysen (1986), loc. cit. In context of this invention, a conformational epitope is defined by two or more discrete amino acid sequences separated in the primary sequence which come together on the surface when the polypeptide folds to the native protein (Sela, (1969) Science 166, 1365 and Layer, (1990) Cell 61, 553-6). The antibody molecules of the present invention are envisaged to specifically bind to/interact with a conformational/structural epitope(s) composed of and/or comprising the two regions of β-A4 described herein or parts thereof as disclosed herein below. The "antibody molecules" of the present invention are thought to comprise a simultaneous and independent dual specificity to (a) an amino acid stretch comprising amino acids 2 to 10 (or (a) part(s) thereof) of β-A4 and (b) an amino acid stretch comprising amino acids 12 to 25 (or (a) part(s) thereof) of β-A4 (SEQ ID NO. 27). Fragments or parts of these stretches comprise at least two, more preferably at least three amino acids. Preferred fragments or parts are in the first region/stretch of SEQ ID NO: 27 the amino acid sequences AEFRHD (SEQ ID NO: 415), EF, EFR, FR, EFRHDSG (SEQ ID NO: 416), EFRHD (SEQ ID NO: 417) or HDSG (SEQ ID NO: 418), and in the second region/stretch of SEQ ID NO: 27 the amino acid sequences HHQKL (SEQ ID NO: 419), LV, LVFFAE (SEQ ID NO: 420), VFFAED (SEQ ID NO: 421), VFFA (SEQ ID NO: 422) or FFAEDV (SEQ ID NO: 423). As mentioned above, said fragments may also comprise additional amino acids or may be parts of the fragments defined herein. Specific examples are DAE, DAEF, FRH or RHDSG.

DETAILED DESCRIPTION OF THE INVENTION

A number of antibodies specifically recognizing Aβ peptides have been described in the art. These antibodies have mainly been obtained by immunizing animals with Aβ1-40 or Aβ1-42 or fragments thereof using standard technologies. According to published data monoclonal antibodies that were generated by immunization with the complete Aβ peptide (1-40 or 1-42) recognize exclusively an epitope close to the N-terminus of Aβ. Further, examples are the antibodies BAP-1 and BAP-2 (Brockhaus, unpublished) which were generated by immunization of mice with Aβ1-40 and which recognize the amino acids 4-6 in the context of larger Aβ peptides; see appended Example 7, Table 2 and Example 12, Table 7. Antibodies that recognize the middle part of Aβ derive from immunizations with smaller peptides. For example, the antibody 4G8 was generated by immunization with the Aβ peptide 1-24 and recognizes exclusively the sequence 17-24 (Kim, (1988) Neuroscience Research Communications 2, 121-130). Many other monoclonal antibodies have been generated by immunizing mice with Aβ-derived fragments, and antibodies recognizing the C-terminal end of Aβ1-40 and Aβ1-42 are widely used to distinguish and quantitate the corresponding Aβ peptides in biological fluids and tissues by ELISA, Western blot and immunohistochemistry analysis (Ida et al, (1996) J. Biol. Chem. 271, 22908-22914; Johnson-Wood et al., (1997), Proc. Natl. Acad. Sci. USA (1994), 1550-1555; Suzuki et al., (1994), Science 264, 1336-1340; Brockhaus (1998), Neuro Rep. 9, 1481-1486). BAP-17 is a mouse monoclonal antibody which has been generated by immunizing mice with Aβ fragment 35-40. It specifically recognizes the C-terminal end of Aβ1-40 (Brockhaus (1998) Neuroreport 9, 1481-1486).

It is believed that the immunization with T-cell dependent antigens (often poor immunogens) requires a proteolytic cleavage of the antigen in the endosomes of antigen presenting cells. The in vivo selection of high affinity antibodies after immunization is driven by the contact of helper T cells to antigen presenting cells. The antigen presenting cells only present short peptides and not polypeptides of large size. Accordingly, these cells have a complicated (but well known) machinery to endocytose antigen(s), degrade the antigen(s) in endosomes, combine selected peptides with suitable MHC class II molecules, and to export the peptide-MHC complex to the cell surface. This is where the antigen specific recognition by T cells occurs, with the aim to provide help to maturing B cells. The B cells which receive most T cell help have the best chance to develop into antibody secreting cells and to proliferate. This shows that antigen processing by proteolysis is an important step for the generation of an high affinity antibody response in vivo and may explain the dominance of the N-terminal Aβ epitope in prior art monoclonal and polyclonal antibodies derived by immunization.

In contrast, the selection of antibodies/antibody molecules of the present invention is driven by the physical adherence of Fab expressing phages to the antigen. There is no degradation of the antigen involved in this in vitro selection process. The phages which express the Fab with the highest affinity towards the antigen are selected and propagated. A synthetic library as employed in the appended examples to select for specific antibody molecules according to this invention is particularly suited for avoiding any bias for single, continuous epitopes that is often found in libraries derived from immunized B cells.

It is of note that the prior art has not described antibody molecules recognizing two, independent regions of Aβ4 which specifically recognizes (a) discontinuous/structural/conformational epitope(s) and/or which are capable of simultaneously and independently recognizing two regions/epitopes of Aβ4. Vaccination of transgenic mice overexpressing mutant human $APP_{V717F}$ (PDAPP mice) with Aβ1-42 resulted in an almost complete prevention of amyloid deposition in the brain when treatment was initiated in young animals, i.e. before the onset of neuropathologies, whereas in older animals a reduction of already formed plaques was observed suggesting antibody-mediated clearance of plaques (Schenk et al., (1999), Nature 400, 173-177). The antibodies generated by this immunization procedure were reactive against the N-terminus of Aβ4 covering an epitope around amino acids 3-7 (Schenk et al., (1999), loc. cit.; WO 00/72880). Active immunization with Aβ1-42 also reduced behavioural impairment and memory loss in different transgenic models for Alzheimer's Disease (Janus et al., (2000) Nature 408, 979-982; Morgan et al., (2000) Nature 408, 982-985). Subsequent studies with peripherally administered antibodies, i.e. passive immunization, have confirmed that antibodies can enter the central nervous system, decorate plaques and induce clearance of preexisting amyloid plaques in APP transgenic mice (PDAPP mice) (Bard et al., (2000) Nat. Med. 6, 916-919; WO 00/72880). In these studies, the monoclonal antibodies with the most potent in vivo and ex vivo efficacy (triggering of phagocytosis in exogenous microglial cells) were those which recognized Aβ4 N-terminal epitopes 1-5 (mab 3D6, IgG2b) or 3-6 (mab 10D5, IgG1). Likewise, polyclonal antibodies isolated from mice, rabbits or monkeys after immunization with Aβ1-42 displayed a similar N-terminal epitope specificity and were also efficacious in triggering phagocytosis and in vivo plaque clearing. In contrast, C-terminal specific antibodies binding to Aβ1-40 or Aβ1-42 with high affinity did not induce phagocytosis in the ex vivo assay and were not efficacious in vivo (WO 00/72880). Monoclonal antibody m266 (WO 00/72880) was raised against Aβ13-28 (central domain of Aβ) and epitope mapping confirmed the antibody specificity to cover amino acids 16-24 in the Aβ sequence. This antibody does not bind well to aggregated Aβ and amyloid deposits and merely reacts with soluble (monomeric) Aβ, i.e. properties which are similar to another well-known and commercially available monoclonal antibody (4G8; Kim, (1988) Neuroscience Research Communications 2, 121-130; commercially available from Signet Laboratories Inc. Dedham, Mass. USA) which recognizes the same epitope.

In vivo, the m266 antibody was recently found to markedly reduce Aβ deposition in PDAPP mice after peripheral administration (DeMattos, (2001) Proc. Natl. Acad. Sci. USA 98, 8850-8855). However, and in contrast to N-terminal specific antibodies, m266 did not decorate amyloid plaques in vivo, and it was therefore hyothesized that the brain Aβ burden was reduced by an antibody-induced shift in equilibrium between CNS and plasma Aβ resulting in the accumulation of brain-derived Aβ in the periphery, firmly complexed to m266 (DeMattos, (2001) loc. cit.).

The antibodies/antibody molecules of the present invention, by simultaneously (for example in a structural/conformational epitope formed by the N-terminal and central region of βA4 as described herein) and independently (for example in pepspot assays as documented in the appended experimental part) binding to the N-terminal and central epitopes, combine the properties of an N-terminal-specific antibody and a central epitope-specific antibody in a single molecule. Antibodies with the dual epitope specificity, as described in the present invention, are considered to be more efficacious in vivo, in particular in medical and diagnostic settings for, e.g., reducing amyloid plaque burden or amyloidogenesis or for the detection of amyloid deposits and plaques. It is well known that in the process of Aβ4 aggregation and amyloid deposition conformational changes occur, and while the central epitope is easily accessible in soluble Aβ4 it appears to be hidden and less reactive in aggregated or fibrillar Aβ4. The fact that the central/middle epitope-specific antibody m266 is efficacious in vivo indicates that neutralization of soluble Aβ4 may also be a critical parameter. The antibodies/antibody molecules of the present invention, due to the dual epitope specificity, can bind to both fibrillar and soluble Aβ4 with similar efficacy, thus allowing interaction with amyloid plaques as well as neutralization of soluble Aβ4. The term "simultaneously and independently binding to the N-terminal and central/middle epitopes of β-A4" as employed herein in context of the inventive antibody molecules relates to the fact that the antibodies/antibody molecules described herein may detect and/or bind to both epitopes simultaneously, i.e. at the same time (for example on conformational/structural epitopes formed by the N-terminal epitope (or (a) part(s) thereof) and central epitopes (or (a) part(s) thereof) of βA4 as defined herein) and that the same antibody molecules, however, are also capable of detecting/binding to each of the defined epitopes in an independent fashion, as inter alia, demonstrated in the pepspot analysis shown in the examples.

Clearance of amyloid plaques in vivo in PDAPP mice after direct application of the antibodies to the brain is not dependent on the IgG subtype and may also involve a mechanism which is not Fc-mediated, i.e. no involvement of activated microglia in plaque clearance (Bacskai, (2001), Abstract Society for Neuroscience 31$^{st}$ Annual Meeting, Nov. 10-15, 2001, San Diego). This observation is in contrast to what has been postulated in an earlier study by Bard (2000), loc. cit.

In another study antibodies raised against Aβ1-28 and Aβ1-16 peptides were found to be effective in disaggregating Aβ fibrils in vitro, whereas an antibody specific for Aβ13-28 was much less active in this assay (Solomon, (1997) Proc. Natl. Acad. Sci. USA 94, 4109-4112). Prevention of Aβ aggregation by an anti-Aβ1-28 antibody (AMY-33) has also been reported (Solomon, (1996) Proc. Natl. Acad. Sci. USA 93, 452-455). In the same study, antibody 6F/3D which has been raised against Aβ fragment 8-17 slightly interfered with $Zn^{2+}$-induced Aβ aggregation but had no effect on the self aggregation induced by other aggregation-inducing agents.

The efficacy of the various antibodies in these in vitro assays correlates with the accessibility of their epitopes in Aβ4 aggregates. The N-terminus is exposed and N-terminal specific antibodies clearly induce de-polymerization, whereas the central region and the C-terminus are hidden and not easily accessible and thus antibodies against these epitope are much less effective.

Investigations with respect to epitope accessibilty for antibodies have shown that in aggregated Aβ the N-terminal epitope is exposed and reacts with the BAP-1 antibody, whereas the middle or central epitope indeed remains cryptic, i.e. no binding of the 4G8 antibody was observed. However, in monomeric Aβ both epitopes are overt and are equally recognized by both prior art antibodies.

In contrast, in the present invention, it was surprisingly found that the herein described antibody molecules recognize two discontinuous amino acid sequences, e.g. a conformational/structural epitope on the Aβ peptide. Two "discontinuous amino acid sequences" in accordance with this invention means that said two amino acid sequences forming the N-terminal and central/middle epitopes, respectively, are separated on β-A4 in its primary structure by at least two amino acids which are not part of either epitope.

The binding area of an antibody Fab (=paratope) occupies a molecular surface of approximately 30×30 Å in size (Layer, Cell 61 (1990), 553-556). This is enough to contact 15 to 22 amino acid residues which may be present on several surface loops. The discontinuous epitope recognized by the inventive antibody molecules resembles a conformation in which the N-terminal (residues 2 to 10 or parts thereof) and middle Aβ peptide sequences (residues 12 to 25 or parts thereof) are in close proximity. Only within this conformation, the maximum number of antigen-antibody contacts and the lowest free energy state are obtained.

Based on energetic calculations it has been suggested that a smaller subset of 5-6 residues, which are not arranged in a linear sequence but are scattered over the epitope surface, contributes most of the binding energy while surrounding residues may merely constitute a complementary array (layer (1990) loc. cit.).

The inventive antibodies/antibody molecules are capable of binding to aggregated Aβ and strongly react with amyloid plaques in the brain of AD patients (as documented in the appended examples). In addition, they are capable of de-polymerizing/disintegrating amyloid aggregates.

Without being bound by theory, the conformational/structural epitope (composed by the two regions of Aβ4 or (a) part(s) of said regions as described herein) is believed to be partially exposed in aggregated Aβ. However, it is known that major part of the middle/second epitope/region alone is not freely accessible in these Aβ aggregates (based on the poor reactivities of middle epitope-specific antibodies 4G8 and m266). On the other hand, and in view of the considerations mentioned above, it is likely that one or several residues of the middle region are components of the conformational epitope and, in conjunction with the residues from the N-terminal region, are accessible to the antibodies of the present invention, thereby significantly contributing to the binding energy of the antibody-Aβ4 interaction. The reactivity of the inventive antibody molecules with the conformational epitope in aggregated Aβ is therefore unique and clearly distinct from α-Aβ4 antibodies described in the prior art. Yet, as pointed out herein above, a further unique feature of the inventive antibodies/antibody molecules is their capacity to simultaneously and independently binding to/recognizing two separate epitopes on β-A4, as defined herein and in the appended examples.

In a preferred embodiment of the invention, the inventive antibody molecule is an antibody molecule wherein the least two regions of the β-A4 to be specifically recognized by said antibody form a conformational/structural epitope or a discontinuous epitope; see Geysen (1986), loc. cit.; Ghoshal (2001), J. Neurochem. 77, 1372-1385; Hochleitner (2000), J. Imm. 164, 4156-4161; Laver (1990), loc. cit. The term "discontinuous epitope" means in context of the invention non-linear epitopes that are assembled from residues from distant portions of the polypeptide chain. These residues come together on the surface when the polypeptide chain folds into a three-dimensional structure to constitute a conformational/structural epitope. The present invention provides for preferred, unexpected epitopes within β-A4, which result in the inventive generation of specific antibody molecules, capable of specifically interacting with these epitopes. These inventive antibodies/antibody molecules provide the basis for increased efficacy, and a reduced potential for side effects. As pointed out above, the inventive antibodies, however, were also capable of independently interacting with each of the defined two regions/epitopes of β-A4, for example in Pepspot assays as documented in the appended examples.

The present invention, accordingly, provides for unique tools which may be employed to de-polymerize aggregated Aβ-fibrils in vivo and in vitro and/or which are capable of stabilizing and/or neutralizing a conformational epitope of monomeric Aβ and thereby capable of preventing the pathological Aβ aggregation.

It is furthermore envisaged that the inventive antibodies bind to Aβ deposits at the rim of amyloid plaques in, inter alia, Alzheimer's brain and efficiently dissolve the pathological protofibrils and fibrils.

In a preferred embodiment, the antibody molecule of the invention recognizes at least two consecutive amino acids within the two regions of Aβ4 defined herein, more preferably said antibody molecule recognizes in the first region an amino acid sequence comprising the amino acids: AEFRHD (SEQ ID NO: 415), EF, EFR, FR, EFRHDSG (SEQ ID NO: 416), EFRHD (SEQ ID NO: 417) or HDSG (SEQ ID NO: 418), and in the second region an amino acid sequence comprising the amino acids: HHQKL (SEQ ID NO: 419), LV, LVFFAE (SEQ ID NO: 420), VFFAED (SEQ ID NO: 421), VFFA (SEQ ID NO: 422) or FFAEDV (SEQ ID NO: 423). Further fragments or broadened parts comprise: DAE, DAEF, FRH or RHDSG.

It is particularly preferred that the antibody molecule of the invention comprises a variable $V_H$-region as encoded by a nucleic acid molecule as shown in SEQ ID NO: 3, 5 or 7 or a variable $V_H$-region as shown in the amino acid sequences depicted in SEQ ID NOs: 4, 6 or 8. The sequences as shown in SEQ ID NOs: 3 and 4 depict the coding region and the amino acid sequence, respectively, of the $V_H$-region of the inventive, parental antibody MSR-3 (MS-Roche 3), the sequences in SEQ ID NOs: 5 and 6 depict the coding region and the amino acid sequence, respectively, of the $V_H$-region of the inventive, parental antibody MSR-7 (MS-Roche 7) and SEQ ID NOs: 7 and 8 depict the coding region and the amino acid sequence, respectively, of the $V_H$-region of the inventive, parental antibody MSR-8 (MS-Roche 8). Accordingly, the invention also provides for antibody molecules which comprise a variable $V_L$-region as encoded by a nucleic acid molecule as shown in a SEQ ID NO selected from the group consisting of SEQ ID NO: 9, 11 or 13 or a variable $V_L$-region as shown in the amino acid sequences depicted in SEQ ID NOs: 10, 12 or 14. SEQ ID NOs: 9 and 10 correspond to the $V_L$-region of MSR-3, SEQ ID NOs: 11 and 12 correspond to the $V_L$-region of MSR-7 and SEQ ID NOs: 13 and 14 correspond to the $V_L$-region of MSR-8. As illustrated in the appended examples, the parental antibodies MSR-3, -7 and -8, are employed to further generate optimized antibody molecules with even better properties and/or binding affinities. Some of the corresponding and possible strategies are exemplified and shown in the appended examples.

The optimization strategy as illustrated in the appended examples lead to a plurality of inventive, optimized antibodies. These optimized antibodies share with their parental antibodies the CDR-3 domain of the $V_H$-region. Whereas the original framework region (as shown in appended FIG. 1) remains the same, in the matured/optimized antibody molecules, CDR1, CDR2 and/or $V_L$ CDR3-regions are changed. Illustrative, modified sequence motives for optimized antibody molecules are shown in appended table 1. Accordingly, within the scope of the present invention are also optimized antibody molecules which are derived from the herein disclosed MSR-3, -7 and -8 and which are capable of specifically reacting with/specifically recognizing the two regions of the β-A4 peptide as defined herein. In particular, CDR-regions, preferably CDR1 s, more preferably CDR1s and CDR2s, most preferably CDR1 s, CDR2s and CDR3s as defined herein may be employed to generate further inventive antibodies/antibody molecules, inter alia, by CDR-grafting methods known in the art; see Jones (1986), Nature 321, 522-515 or Riechmann (1988), Nature 332, 323-327. Most preferably the inventive antibodies/antibody molecules as well as antibody fragments or derivatives are derived from the parental antibodies as disclosed herein and share, as disclosed above, the CDR-3 domain of the $V_H$-region with at least one of said parental antibodies. As illustrated below, it is also envisaged that cross-cloned antibodies are generated which are to be considered as optimized/maturated antibodies/antibody molecules of the present invention. Accordingly, preferred antibody molecules may also comprise or may also be derived from antibodies/antibody molecules which are characterized by $V_H$-regions as shown in any of SEQ ID NOs: 32 to 45 or $V_L$-regions as shown in SEQ ID NOs: 46 to 59 or which may comprise a CDR-3 region as defined in any of SEQ ID NOs: 60 to 87. In a particular preferred embodiment, the optimized antibody molecule of the present invention comprises $V_H$-regions and $V_L$-regions as depicted in SEQ ID NOs: 88/89 and 90/91, respectively, or parts thereof. Apart thereof may be (a) CDR-region(s), preferably (a) CDR3-region(s). A particularly preferred antibody molecule of the optimized type comprises a H-CDR3 as characterized in SEQ ID NOs: 92 or 93 and/or a L-CDR3 as characterized in SEQ ID NOs: 94 or 95. It is preferred that the antibodies/antibody molecules of the invention are characterized by their specific reactivity with β-A4 and/or peptides derived from said β-A4. For example, optical densities in ELISA-tests, as illustrated in the appended examples, may be established and the ratio of optical densities may be employed to define the specific reactivity of the parental or the optimized antibodies. Accordingly, a preferred antibody of the invention is an antibody which reacts in an ELISA-test with β-A4 to arrive at an optical density measured at 450 nm that is 10 times higher than the optical density measured without β-A4, i.e. 10 times over background. Preferably the measurement of the optical density is performed a few minutes (e.g. 1, 2, 3, 4, 5, 6, or 7 minutes) after initiation of the color developing reaction in order to optimize signal to background ratio.

In a particular preferred embodiment, the inventive antibody molecule comprises at least one CDR3 of an $V_L$-region as encoded by a nucleic acid molecule as shown in SEQ ID NOs: 15, 17 or 19 or at least one CDR3 amino acid sequence of an $V_L$-region as shown in SEQ ID NOs: 16, 18 or 20 and/or said antibody molecule comprises at least one CDR3 of an $V_H$-region as encoded by a nucleic acid molecule as shown in SEQ ID NOs: 21, 23 or 25 or at least one CDR3 amino acid sequence of an $V_H$-region as shown in SEQ ID NOs: 22, 24 or 26. Most preferred are antibodies comprising at least one CDR3 of an $V_H$-region as defined herein. The CDR-3 domains mentioned herein above relate to the inventive, illustrative parental antibody molecules MSR-3, -7, or -8. However, as illustrated in the appended tables 1, 8 or 10, matured and/or optimized antibody molecules obtainable by the methods disclosed in the appended examples may comprise modified $V_H$-, $V_L$-, CDR1, CDR2 and CDR3 regions. Accordingly, the antibody molecule of the invention is preferably selected from the group consisting of MSR-3, -7 and -8 or an affinity-matured version of MSR-3, -7 or -8. Affinity-matured as well as cross-cloned versions of MSR-3, -7 and -8 comprise, inter alia, antibody molecules comprising CDR1, CDR2 and/or CDR3 regions as shown in table 1 or 8 or characterized in any of SEQ ID NOs: 15 to 20, 21 to 26, 60 to 74, 75 to 87, 92 and 93 or 94 and 95 as well as in SEQ ID NOs: 354 to 413. Most preferably, the antibody of the invention comprises at least one CDR, preferably a CDR1, more preferably a CDR2, most preferably a CDR3 as shown in the appended table 1, 8 or as documented in appended table 10.

It is of note that affinity-maturation techniques are known in the art, described in the appended examples and, inter alia, in Knappik (2000), J. Mol. Biol. 296, 55; Krebs (2000), J. Imm. Meth. 254, 67-84; WO 01/87337; WO 01/87338; U.S. Pat. No. 6,300,064; EP 96 92 92 78.8 and further references cited herein below.

In a more preferred embodiment of the invention, the antibody molecule is a full antibody (immunoglobulin, like an IgG1, an IgG2, an IgG2b, an IgG3, an IgG4, an IgA, an IgM, an IgD or an IgE), an F(ab)-, Fabc-, Fv-, Fab'-, F(ab')₂—fragment, a single-chain antibody, a chimeric antibody, a CDR-grafted antibody, a bivalent antibody-construct, an antibody-fusion protein, a cross-cloned antibody or a synthetic antibody. Also envisaged are genetic variants of immunoglobulin genes. Genetic variants of, e.g., immunoglobulin heavy G chain subclass 1 (IgG1) may comprise the G1m(17) or G1m(3) allotypic markers in the CH1 domain, or the G1m(1) or the G1m(non-1) allotypic marker in the CH3 domain. The antibody molecule of the invention also comprises modified or mutant antibodies, like mutant IgG with enhanced or attenuated Fc-receptor binding or complement activation. It is also envisaged that the antibodies of the invention are produced by conventional means, e.g. the production of specific monoclonal antibodies generated by immunization of mammals, preferably mice, with peptides comprising the two regions of βA4 as defined herein, e.g. the N-terminal and central region/epitope comprising (a) amino acids 2 to 10 (or (a) part(s) thereof) of β-A4 and (b) an amino acid stretch comprising amino acids 12 to 25 (or (a) part(s) thereof) of β-A4 (SEQ ID NO. 27). Accordingly, the person skilled in the art may generate monoclonal antibodies against such a peptide and may screen the obtained antibodies for the capacity to simultaneously and independently binding to/reacting with the N-terminal and central region/epitope of βA4 as defined herein. Corresponding screening methods are disclosed in the appended examples.

As illustrated in the appended examples, the inventive antibodies/antibody molecules can readily and preferably be recombinantly constructed and expressed. Preferably, the antibody molecule of the invention comprises at least one, more preferably at least two, preferably at least three, more preferably at least four, more preferably at least five and most preferably six CDRs of the herein defined MSR-3, MSR-7 or MSR-8 parental antibodies or of affinity-matured/optimized antibodies derived from said parental antibodies. It is of note that also more than six CDRs may be comprised in recombinantly produced antibodies of the invention. The person skilled in the art can readily employ the information given in the appended examples to deduce corresponding CDRs of the parental as well as the affinity optimized antibodies. Examples of optimized antibodies which have been obtained by maturation/optimization of the parental antibodies are, inter alia, shown in appended table 1. An maturated/optimized antibody molecule of the invention is, e.g. MSR 7.9H7 which is also characterized by sequences appended herein, which comprise SEQ ID NOs: 88 to 95 and which depict the $V_H$-region of MSR 7.9H7 (SEQ ID NOs: 88 and 89), the $V_L$-region of MSR 7.9H7 (SEQ ID NOs: 90 and 91), the H-CDR3 of MSR 7.9H7 (SEQ ID NOs: 92 and 93) as well as the L-CDR3 of MSR 7.9H7 (SEQ ID NOs: 94 and 95). Illustrative antibody molecule 7.9H7 is derived from parental antibody MSR7 and is a particular preferred inventive example of an optimized/matured antibody molecule of the present invention. This antibody molecule may be further modified in accordance with this invention, for example in form of cross-cloning, see herein below and appended examples.

As documented in the appended examples, the antibodies of the invention also comprise cross-cloned antibodies, i.e. antibodies comprising different antibody regions (e.g. CDR-regions) from one or more parental or affinity-optimized antibody(ies) as described herein. These cross-cloned antibodies may be antibodies in several, different frameworks, whereby the most preferred framework is an IgG-framework, even more preferred in an IgG1-, IgG2a or an IgG2b-framework. It is particularly preferred that said antibody framework is a mammalian, most preferably a human framework. The domains on the light and heavy chains have the same general structure and each domain comprises four framework regions, whose sequences are relatively conserved, joined by three hypervariable domains known as complementarity determining regions (CDR1-3).

As used herein, a "human framework region" relates to a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. It is of note that not only cross-cloned antibodies described herein may be presented in a preferred (human) antibody framework, but also antibody molecules comprising CDRs from, inter alia, the parental antibodies MSR-3, -7 or -8 as described herein or of matured antibodies derived from said parental antibodies, may be introduced in an immunoglobulin framework. Preferred frameworks are IgG1, IgG2a and IgG2b. Most preferred are human frameworks and human IgG1 frameworks.

As shown in the appended examples, it is, inter alia possible, to transfer, by genetic engineering known in the art whole light chains from an optimized donor clone to an optimized recipient clone. Example for an optimized donor clone is, e.g. L-CDR1 (L1) and an example for an optimized recipient clone is H-CDR2 (H2). Epitope specificity may be conserved by combining clones which possess the same H-CDR-3 regions. Further details are given in illustrative Example 13.

Preferred cross-cloned antibody molecules of the invention are selected from the group consisting of MS-R #3.3H1× 3.4L9, MS-R #3.4H1×3.4L9, MS-R #3.4H3×3.4L7, MS-R #3.4H3×3.4L9, MS-R #3.4H7×3.4L9, MS-R #3.4H7×3.4L7, MS-R #3.6H5×3.6.L1, MS-R #3.6H5×3.6.L2, MS-R #3.6.H8×3.6.L2, MS-R #7.2H2×7.2L1, MS-R #7.4H2× 7.2L1, MS-R #7.4H2×7.12L2, MS-R #7.9H2×7.2L1(L1), MS-R #7.9H2×7.12L1, MS-R #7.9H2×7.12L2, MS-R #7.9H2×7.12L2(L1+2), MS-R #7.9H4×7.12.L2, MS-R #7.11H1×7.2L1, MS-R #7.11H1×7.11L1, MS-R #7.11H2× 7.2L1(L1), MS-R #7.11H2×7.9L1 (L1), MS-R #7.11H2× 7.12L1 or MS-R #8.1H1×8.2L1.

The generation of cross-cloned antibodies is also illustrated in the appended examples. The above mentioned preferred cross-cloned antibodies/antibody molecules are optimized/matured antibody molecules derived from parental antibodies disclosed herein, in particular from MSR-3 and MSR-7. in addition, further characterizing CDR-sequences and V-regions of the cross-cloned antibody molecules/antibodies are given in appended SEQ ID NOs: 32, 33, 46 and 47 (MSR 3.6H5×3.6.L2; $V_H$-, $V_L$-region); 34, 35, 48 and 49 (MSR 3.6H8×3.6.L2; $V_H$-, $V_L$-regions); 36, 37, 50 and 51 (MSR 7.4H2×7.2.L1; $V_H$-, $V_L$-regions); 38, 39, 52 and 53 (MSR 7.9H2×7.12.L2; $V_H$-, $V_L$-regions); 40, 41, 54 and 55 (MSR # 7.9H4×7.12.L2; $V_H$-, $V_L$-regions); 42, 43, 56 and 57 (MSR #7.11H1×7.11.L1; $V_H$-, $V_L$-regions); and 44, 45, 58 and 59 (MSR # 7.11H1×7.2.L1; $V_H$-, $V_L$-regions). Corresponding CDR3 regions of these particular preferred cross-cloned antibody molecules are depicted in SEQ ID NOs: 60 to 87. For further MSR antibody molecules, $V_H$-, $V_L$-, CDR-regions can be deduced from appended Tables 8 or 10 and from the appended sequence listing, in particular SEQ ID NOS: 32 to 95 for MS-R antibodies/antibody molecules #3.6H5×3.6.L2, #3.6H8×3.6.L2, #7.4H2×7.2L1, #7.9H2× 7.12L2, #7.9H4×7.12L2, #7.11H1×7.11L1, #7.11H1×7.2L1 and #7.9H7 or SEQ ID NOS: 294 to 413 for MSR—R antibodies/antibody molecules MS-R #3.3H1×3.4L9, #3.4H1× 3.4L9, #3.4H3×3.4L7, #3.4H3×3.4L9, #3.4H7×3.4L9, #3.4H7×3.4L7, #3.6H5×3.6L1, #7.2H2×7.2L1, #7.4H2× 7.12L2, #7.9H2×7.2L1, #7.9H2×7.12L1, #7.11H2×7.2L1, #7.11H2×7.9L1, #7.11H2×7.12L1 or #8.1H1×8.2L1. Accordingly, besides $V_H$-regions defined above, preferred antibody molecules of the invention may comprise $V_H$-regions as defined in any one of SEQ ID NOs: 294 to 323. Similarly, SEQ ID NOs: 324 to 353 depict preferred $V_L$-regions which, besides to $V_L$-regions defined above which may be comprised in the inventive antibody molecules. Corresponding CDR-3 regions are defined above, as well as in additional sequences shown in SEQ ID NOs: 354 to 413.

Inventive antibody molecules can easily be produced in sufficient quantities, inter alia, by recombinant methods known in the art, see, e.g. Bentley, Hybridoma 17 (1998), 559-567; Racher, Appl. Microbiol. Biotechnol. 40 (1994), 851-856; Samuelsson, Eur. J. Immunol. 26 (1996), 3029-3034.

Theoretically, in soluble β-A4 (monomeric/oligomeric) both the N-terminal and the middle epitopes are accessible for antibody interaction and antibody molecules of the present invention may either bind to the N-terminal or middle epitope separately, but under these conditions maximum affinity will not be obtained. However, it is more likely that an optimal contact to the antibody paratope will be attained by simultaneous binding to both epitopes, i.e. similar to the interaction with aggregated β-A4. Thus, antibodies of the present invention are unique anti-Aβ antibodies in that they bind to aggregated β-A4 (via interaction with the N-terminal and middle epitope), and at the same time are also able to stabilize and neutralize the conformational epitope in soluble β-A4. These antibodies are distinct to prior art antibodies.

Most preferred are antibody molecules of the invention which have an affinity to Aβ or defined fragments thereof with a $K_D$ value lower than 2000 nM, preferably lower than 100 nM, more preferably lower than 10 nM, most preferably lower than 1 nM. The measurement of such affinity/affinities may be carried out by methods illustrated in the examples and known in the art. Such methods comprise, but are not limited to BIACORE™-assays (www.biacore.com; Malmquist (1999), Biochem. Soc. Trans 27, 335-340) and solid phase assays using labeled antibodies or labeled Aβ.

Preferably, the antibody molecule of the invention is capable of decorating/reacting with/binding to amyloid plaques in in vitro (post-mortem) brain sections from patients suffering from amyloid-related disorders, like Alzheimer's disease. Yet, it is also preferred that the inventive antibody/antibody molecules prevent Aβ-aggregation in vivo as well as in in vitro assays, as illustrated in the appended examples. Similarly, the antibody molecules of the present invention are preferred to de-polymerize Aβ-aggregate in vivo and/or in in vitro assays shown in the examples. This capacity of the inventive antibodies/antibody molecules is, inter alia, to be employed in medical settings, in particular in pharmaceutical compositions described herein below.

The invention also provides for a nucleic acid molecule encoding an inventive antibody molecule as defined herein.

Said nucleic acid molecule may be a naturally nucleic acid molecule as well as a recombinant nucleic acid molecule. The nucleic acid molecule of the invention may, therefore, be of natural origin, synthetic or semi-synthetic. It may comprise DNA, RNA as well as PNA and it may be a hybrid thereof.

It is evident to the person skilled in the art that regulatory sequences may be added to the nucleic acid molecule of the invention. For example, promoters, transcriptional enhancers and/or sequences which allow for induced expression of the polynucleotide of the invention may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62), or a dexamethasone-inducible gene expression system as described, e.g. by Crook (1989) EMBO J. 8, 513-519.

Furthermore, it is envisaged for further purposes that nucleic acid molecule may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. In this respect, it is also to be understood that the polynucleotide of the invention can be used for "gene targeting" or "gene therapeutic" approaches. In another embodiment said nucleic acid molecules are labeled. Methods for the detection of nucleic acids are well known in the art, e.g., Southern and Northern blotting, PCR or primer extension. This embodiment may be useful for screening methods for verifying successful introduction of the inventive nucleic acid molecules during gene therapy approaches.

The nucleic acid molecule(s) of the invention may be a recombinantly produced chimeric nucleic acid molecule comprising any of the aforementioned nucleic acid molecules either alone or in combination. Preferably, the nucleic acid molecule of the invention is part of a vector.

The present invention therefore also relates to a vector comprising the nucleic acid molecule of the present invention.

The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

Furthermore, the vector of the present invention may, in addition to the nucleic acid sequences of the invention, comprise expression control elements, allowing proper expression of the coding regions in suitable hosts. Such control elements are known to the artisan and may include a promoter, a splice cassette, translation initiation codon, translation and insertion site for introducing an insert into the vector. Preferably, the nucleic acid molecule of the invention is operatively linked to said expression control sequences allowing expression in eukaryotic or prokaryotic cells.

Control elements ensuring expression in eukaryotic and prokaryotic cells are well known to those skilled in the art. As mentioned herein above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous Sarcoma Virus), human elongation factor 1α-promoter, the glucocorticoid-inducible MMTV-promoter (Moloney Mouse Tumor Virus), metallothionein- or tetracyclin-inducible promoters, or enhancers, like CMV enhancer or SV40-enhancer. For expression in neural cells, it is envisaged that neurofilament-, PGDF-, NSE-, PrP-, or thy-1-promoters can be employed. Said promoters are known in the art and, inter alia, described in Charron (1995), J. Biol. Chem. 270, 25739-25745. For the expression in prokaryotic cells, a multitude of promoters including, for example, the tac-lac-promoter or the trp promoter, has been described. Besides elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-vitrogene), pSPORT1 (GIBCO BRL), pX (Pagano (1992) Science 255, 1144-1147), yeast two-hybrid vectors, such as pEG202 and dpJG4-5 (Gyuris (1995) Cell 75, 791-803), or prokaryotic expression vectors, such as lambda gt11 or pGEX (Amersham-Pharmacia). Beside the nucleic acid molecules of the present invention, the vector may further comprise nucleic acid sequences encoding for secretion signals. Such sequences are well known to the person skilled in the art. Furthermore, depending on the expression system used leader sequences capable of directing the peptides of the invention to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusionprotein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the antibody molecules or fragments thereof of the invention may follow. The invention also relates, accordingly, to hosts/host cells which comprise a vector as defined herein. Such hosts may be useful for in processes for obtaining antibodies/antibody molecules of the invention as well as in medical/pharmaceutical settings. Said host cells may also comprise transduced or transfected neuronal cells, like neuronal stem cells, preferably adult neuronal stem cells. Such host cells may be useful in transplantation therapies.

Furthermore, the vector of the present invention may also be an expression, a gene transfer or gene targeting vector. Gene therapy, which is based on introducing therapeutic genes into cells by ex-vivo or in-vivo techniques is one of the most important applications of gene transfer. Transgenic mice expressing a neutralizing antibody directed against nerve growth factor have been generated using the "neuroantibody" technique; Capsoni, Proc. Natl. Acad. Sci. USA 97 (2000), 6826-6831 and Biocca, Embo J. 9 (1990), 101-108. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. Nos. 5,580,859; 5,589,466; 4,394,448 or Schaper, Current Opinion in Biotechnology 7 (1996), 635-640, and references cited therein. In particular, said vectors and/or gene delivery systems are also described in gene therapy approaches in neurological tissue/cells (see, inter alia Blomer, J. Virology 71 (1997) 6641-6649) or in the hypothalamus (see, inter alia, Geddes, Front Neuroendocrinol. (1999), 296-316 or Geddes, Nat. Med. 3 (1997), 1402-1404). Further suitable gene therapy constructs for use in neurological cells/tissues are known in the art, for example in Meier (1999), J. Neuropathol. Exp. Neurol. 58, 1099-1110. The nucleic acid molecules and vectors of the invention may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention. The introduction and gene therapeutic approach should, preferably, lead to the expression of a functional antibody molecule of the invention, whereby said expressed antibody molecule is particularly useful in the treatment, amelioration and/or prevention of neurological disorders related to abnormal amyloid synthesis, assembly and/or aggregation, like, Alzheimer's disease and the like.

Accordingly, the nucleic acid molecule of the present invention and/or the above described vectors/hosts of the present invention may be particularly useful as pharmaceutical compositions. Said pharmaceutical compositions may be employed in gene therapy approaches. In this context, it is envisaged that the nucleic acid molecules and/or vectors of the present invention may be employed to modulate, alter and/or modify the (cellular) expression and/or concentration of the antibody molecules of the invention or of (a) fragment(s) thereof.

For gene therapy applications, nucleic acids encoding the peptide(s) of the invention or fragments thereof may be cloned into a gene delivering system, such as a virus and the virus used for infection and conferring disease ameliorating or curing effects in the infected cells or organism.

The present invention also relates to a host cell transfected or transformed with the vector of the invention or a non-human host carrying the vector of the present invention, i.e. to a host cell or host which is genetically modified with a nucleic acid molecule according to the invention or with a vector comprising such a nucleic acid molecule. The term "genetically modified" means that the host cell or host comprises in addition to its natural genome a nucleic acid molecule or vector according to the invention which was introduced into the cell or host or into one of its predecessors/parents. The nucleic acid molecule or vector may be present in the genetically modified host cell or host either as an independent molecule outside the genome, preferably as a molecule which is capable of replication, or it may be stably integrated into the genome of the host cell or host.

The host cell of the present invention may be any prokaryotic or eukaryotic cell. Suitable prokaryotic cells are those generally used for cloning like *E. coli* or *Bacillus subtilis*. Furthermore, eukaryotic cells comprise, for example, fungal or animal cells. Examples for suitable fungal cells are yeast cells, preferably those of the genus *Saccharomyces* and most preferably those of the species *Saccharomyces cerevisiae*. Suitable animal cells are, for instance, insect cells, vertebrate cells, preferably mammalian cells, such as e.g. HEK293, NSO, CHO, MDCK, U2-OSHela, NIH3T3, MOLT-4, Jurkat, PC-12, PC-3, IMR, NT2N, Sk-n-sh, CaSki, C33A. These host cells, e.g. CHO-cells, may provide post-translational modifications to the antibody molecules of the invention, including leader peptide removal, folding and assembly of H (heavy) and L (light) chains, glycosylation of the molecule at correct sides and secretion of the functional molecule. Further suitable cell lines known in the art are obtainable from cell line depositories, like the American Type Culture Collection (ATCC). In accordance with the present invention, it is furthermore envisaged that primary cells/cell cultures may function as host cells. Said cells are in particular derived from insects (like insects of the species *Drosophila* or *Blatta*) or mammals (like human, swine, mouse or rat). Said host cells may also comprise cells from and/or derived from cell lines like neuroblastoma cell lines. The above mentioned primary cells are well known in the art and comprise, inter alia, primary astrocytes, (mixed) spinal cultures or hippocampal cultures.

In a more preferred embodiment the host cell which is transformed with the vector of the invention is a neuronal cell, a neuronal stem cell (e.g. an adult neuronal stem cell), a brain cell or a cell (line) derived therefrom. However, also a CHO-cell comprising the nucleic acid molecule of the present invetion may be particularly useful as host. Such cells may provide for correct secondary modifications on the expressed molecules, i.e. the antibody molecules of the present invention. These modifications comprise, inter alia, glycosylations and phosphorylations.

Hosts may be non-human mammals, most preferably mice, rats, sheep, calves, dogs, monkeys or apes. Said mammals may be indispensable for developing a cure, preferably a cure for neurological and/or neurodegenerative disorders mentioned herein. Furthermore, the hosts of the present invention may be particularly useful in producing the antibody molecules (or fragments thereof) of the invention. It is envisaged that said antibody molecules (or fragments thereof) be isolated from said host. It is, inter alia, envisaged that the nucleic acid molecules and or vectors described herein are incorporated in sequences for transgenic expression. The introduction of the inventive nucleic acid molecules as transgenes into non-human hosts and their subsequent expression may be employed for the production of the inventive antibodies. For example, the expression of such (a) transgene(s) in the milk of the transgenic animal provide for means of obtaining the inventive antibody molecules in quantitative amounts; see inter alia, U.S. Pat. Nos. 5,741,957, 5,304,489 or 5,849,992. Useful transgenes in this respect comprise the nucleic acid molecules of the invention, for example, coding sequences for the light and heavy chains of the antibody molecules described herein, operatively linked to promotor and/or enhancer structures from a mammary gland specific gene, like casein or beta-lactoglobulin.

The invention also provides for a method for the preparation of an antibody molecule of the invention comprising culturing the host cell described herein above under conditions that allow synthesis of said antibody molecule and recovering said antibody molecule from said culture.

The invention also relates to a composition comprising an antibody molecule of the invention or produced by the method described herein above, a nucleic acid molecule encoding the antibody molecule of the invention, a vector comprising said nucleic acid molecule or a host-cell as defined herein above and optionally, further molecules, either alone or in combination, like e.g. molecules which are capable of interfering with the formation of amyloid plaques or which are capable of depolymerizing already formed amyloid-plaques. The term "composition" as employed herein comprises at least one compound of the invention. Preferably, such a composition is a pharmaceutical or a diagnostic composition.

The composition may be in solid or liquid form and may be, inter alia, in a form of (a) powder(s), (a) tablet(s), (a) solution(s) or (an) aerosol(s). Said composition may comprise on or more antibodies/antibody molecules of the invention or nucleic acid molecules, vector or hosts of the invention. It is also envisaged that said composition comprises at least two, preferably three, more preferably four, most preferably five antibody molecules of the invention or nucleic acid molecule(s) encoding said antibody molecule(s). Said composition may also comprise optimized, inventive antibodies/antibody molecules obtainable by the methods described herein below and in the appended examples.

It is preferred that said pharmaceutical composition, optionally comprises a pharmaceutically acceptable carrier and/or diluent. The herein disclosed pharmaceutical composition may be particularly useful for the treatment of neurological and/or neurodegenerative disorders. Said disorders comprise, but are not limited to Alzheimer's disease, amyothrophic lateral sclerosis (ALS), hereditary cerebral hemorrhage with amyloidosis Dutch type, Down's syndrome, HIV-dementia, Parkinson's disease and neuronal disorders related to aging. The pharmaceutical composition of the invention is, inter alia, envisaged as potent inhibitors of amyloid plaque formation or as a potent stimulator for the de-polymerization of amyloid plaques. Therefore, the present invention provides for pharmaceutical compositions comprising the compounds of the invention to be used for the treatment of diseases/disorders associated with pathological APP proteolysis and/or amyloid plaque formation.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in a brain artery or directly into brain tissue. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg/kg body weight per dose; however, doses below or above this exemplary range are envisioned, especially considering the aforementioned factors. If the regimen is a continuous infusion, it should also be in the range of 1 µg to 10 mg units per kilogram of body weight per minute.

Progress can be monitored by periodic assessment. The compositions of the invention may be administered locally or systemically. It is of note that peripherally administered antibodies can enter the central nervous system, see, inter alia, Bard (2000), Nature Med. 6, 916-919. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. Said agents may be drugs acting on the central nervous system, like, neuroprotective factors, cholinesterase inhibitors, agonists of M1 muscarinic receptor, hormones, antioxidants, inhibitors of inflammation etc. It is particularly preferred that said pharmaceutical composition comprises further agents like, e.g. neurotransmitters and/or substitution molecules for neurotransmitters, vitamin E, or alpha-lipoic acid.

The pharmaceutical compositions, as well as the methods of the invention or the uses of the invention described infra can be used for the treatment of all kinds of diseases hitherto unknown or being related to or dependent on pathological APP aggregation or pathological APP processing. They may be particularly useful for the treatment of Alzheimer's disease and other diseases where extracellular deposits of amyloid-β, appear to play a role. They may be desirably employed in humans, although animal treatment is also encompassed by the methods, uses and compositions described herein.

In a preferred embodiment of the invention, the composition of the present invention as disclosed herein above is a diagnostic composition further comprising, optionally, suitable means for detection. The diagnostic composition comprises at least one of the aforementioned compounds of the invention.

Said diagnostic composition may comprise the compounds of the invention, in particular and preferably the antibody molecules of the present invention, in soluble form/liquid phase but it is also envisaged that said compounds are bound to/attached to and/or linked to a solid support.

Solid supports may be used in combination with the diagnostic composition as defined herein or the compounds of the present invention may be directly bound to said solid supports. Such supports are well known in the art and comprise, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The compound(s) of the invention, in particular the antibodies of the present invention, may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Appropriate labels and methods for labeling have been identified above and are furthermore mentioned herein below. Suitable methods for fixing/immobilizing said compound(s) of the invention are well known and include, but are not limited to ionic, hydrophobic, covalent interactions and the like.

It is particularly preferred that the diagnostic composition of the invention is employed for the detection and/or quantification of APP and/or APP-processing products, like amyloid-β or for the detection and/or quantification of pathological and/or (genetically) modified APP-cleavage sides.

As illustrated in the appended examples, the compounds of the present invention, in particular the inventive antibody molecules are particularly useful as diagnostic reagents in the detection of genuine human amyloid plaques in brain sections of Alzheimer's Disease patients by indirect immunofluorescence.

It is preferred that said compounds of the present invention to be employed in a diagnostic composition are detectably labeled. A variety of techniques are available for labeling biomolecules, are well known to the person skilled in the art and are considered to be within the scope of the present invention. Such techniques are, e.g., described in Tijssen, "Practice and theory of enzyme immuno assays", Burden, R H and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology" Academic Press, London (1987), or in the series "Methods in Enzymology", Academic Press, Inc.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}P$ or $^{125}I$), biotin, digoxygenin, colloidal metals, chemi- or bioluminescent compounds (like dioxetanes, luminol or acridiniums). Labeling procedures, like covalent coupling of enzymes or biotinyl groups, iodinations, phosphorylations, biotinylations, etc. are well known in the art.

Detection methods comprise, but are not limited to, autoradiography, fluorescence microscopy, direct and indirect enzymatic reactions, etc. Commonly used detection assays comprise radioisotopic or non-radioisotopic methods. These comprise, inter alia, Westernblotting, overlay-assays, RIA (Radioimmuno Assay) and IRMA (Immune Radioimmunometric Assay), EIA (Enzyme Immuno Assay), ELISA (Enzyme Linked Immuno Sorbent Assay), FIA (Fluorescent Immuno Assay), and CLIA (Chemioluminescent Immune Assay).

Furthermore, the present invention provides for the use of an antibody molecule of invention, or an antibody molecule produced by the method of the invention, of a nucleic acid molecule, vector of or a host of the invention for the preparation of a pharmaceutical or a diagnostic composition for the prevention, treatment and/or diagnosis of a disease associated with amyloidogenesis and/or amyloid-plaque formation. It is further preferred that the compounds described herein, in particular the antibody molecules of the invention, be employed in the prevention and/or treatment of neuropathologies associated with modified or abnormal APP-processing and/or amyloidogenesis. The antibody molecules, e.g in format of (engineered) immunoglobulins, like antibodies in a IgG framework, in particular in an IgG1-framework, or in the format of chimeric antibodies, bispecific antibodies, single chain Fvs (scFvs) or bispecific scFvs and the like are to employed in the preparation of the pharmaceutical compositions provided herein. Yet, the antibody molecules are also useful in diagnostic settings as documented in the appended examples, since the antibody molecules of the invention specifically interact with/detect Aβ4 and/or amyloid deposits/plaques.

Therefore an inventive use of the compounds of the present invention is the use for the preparation of a pharmaceutical composition for a neurological disorder which calls for amelioration, for example by disintegration of β-amyloid plaques, by amyloid (plaque) clearance or by passive immunization against β-amyloid plaque formation. As illustrated in the appended examples, the inventive antibody molecules are particularly useful in preventing Aβ aggregation and in depolymerization of already formed amyloid aggregates. Accordingly, the inventive antibodies are to be employed in the reduction of pathological amyloid deposits/plaques, in the clearance of amyloid plaques/plaque precursors as well as in neuronal protection. It is in particular envisaged that the antibody molecules of the invention be employed in the in vivo prevention of amyloid plaques as well as in in vivo clearance of pre-existing amyloid plaques/deposits. Furthermore, the antibody molecules of the invention may be employed in passive immunization approaches against Aβ4. Clearance of Aβ4/Aβ4 deposits may, inter alia, be achieved by the medical use of antibodies of the present invention which comprise an Fc-part. Said Fc-part of an antibody may be particularly useful in Fc-receptor mediated immune responses, e.g. the attraction of macrophages (phagocytic cells and/or microglia) and/or helper cells. For the mediation of Fc-part-related immunoresponses, the antibody molecule of the invention is preferably in an (human) IgG1-framework. As discussed herein, the preferred subject to be treated with the inventive antibody molecules, the nucleic acid molecules encoding the same or parts thereof, the vectors of the invention or the host cells of this invention is a human subject. Other frameworks, like IgG2a- or IgG2b-frameworks for the inventive antibody molecules are also envisaged. Immunoglobulin frameworks in IgG2a and IgG2b format are particular envisaged in mouse settings, for example in scientific uses of the inventive antibody molecules, e.g. in tests on transgenic mice expressing (human) wildtype or mutated APP, APP-fragments and/or Aβ4.

The above recited diseases associated with amyloidogenesis and/or amyloid-plaque formation comprise, but are not limited to dementia, Alzheimer's disease, motor neuropathy, Parkinson's disease, ALS (amyotrophic lateral sclerosis), scrapie, HIV-related dementia as well as Creutzfeld-Jakob disease, hereditary cerebral hemorrhage, with amyloidis Dutch type, Down's syndrome and neuronal disorders related to aging. The antibody molecules of the invention and the compositions provided herein may also be useful in the amelioration and or prevention of inflammatory processes relating to amyloidogenesis and/or amyloid plaque formation.

Accordingly, the present invention also provides for a method for treating, preventing and/or delaying neurological and/or neurodegenerative disorders comprising the step of administering to a subject suffering from said neurological and/or neurodegenerative disorder and/or to a subject susceptible to said neurological and/or neurodegenerative disorder an effective amount of a antibody molecule of the invention, a nucleic acid molecule of invention and/or a composition as defined herein above.

In yet another embodiment, the present invention provides for a kit comprising at least one antibody molecule, at least one nucleic acid molecule, at least one vector or at least one host cell of the invention. Advantageously, the kit of the present invention further comprises, optionally (a) buffer(s), storage solutions and/or remaining reagents or materials required for the conduct of medical, scientific or diagnostic assays and purposes. Furthermore, parts of the kit of the invention can be packaged individually in vials or bottles or in combination in containers or multicontainer units.

The kit of the present invention may be advantageously used, inter alia, for carrying out the method of the invention and could be employed in a variety of applications referred herein, e.g., as diagnostic kits, as research tools or medical tools. Additionally, the kit of the invention may contain means for detection suitable for scientific, medical and/or diagnostic purposes. The manufacture of the kits follows preferably standard procedures which are known to the person skilled in the art.

The invention also provides for a method for the optimization of an antibody molecule as defined herein above comprising the steps of (a) constructing a library of diversified Fab antibody fragments derived from an antibody comprising at least one CDR3 of an $V_H$-region as encoded by a nucleic acid molecule as shown in SEQ ID NOs: 21, 23 or 25 or at least one CDR3 amino acid sequence of an $V_H$-region as shown in SEQ ID NOs: 22, 24 or 26;

(b) testing the resulting Fab optimization library by panning against Aβ/Aβ4;

(c) identifying optimized clones; and (d) expressing of selected, optimized clones.

Optimization of the antibodies/antibody molecules of the invention is also documented in the appended examples and may comprise the selection for, e.g. higher affinity for one or both regions/epitopes of β-A4 as defined herein or selection for improved expression and the like. In one embodiment, said selection for to higher affinity for one or both regions/epitopes of β-A4 comprises the selection for high affinity to (a) an amino acid stretch comprising amino acids 2 to 10 (or (a) part(s) thereof) of β-A4 and/or (b) an amino acid stretch comprising amino acids 12 to 25 (or (a) part(s) thereof) of β-A4 (SEQ ID NO. 27).

The person skilled in the art can readily carry out the inventive method employing the teachings of the present invention. Optimization protocols for antibodies are known in the art. These optimization protocols comprise, inter alia, CDR walking mutagenesis as disclosed and illustrated herein and described in Yang (1995), J. Mol. Biol. 25, 392-403; Schier (1996), J. Mol. Biol. 263, 551-567; Barbas (1996), Trends. Biotech 14, 230-34 or Wu (1998), PNAS 95, 6037-6042; Schier (1996), Human Antibodies Hybridomas 7, 97; Moore (1997), J. Mol. Biol. 272, 336.

"Panning"-techniques are also known in the art, see, e.g. Kay (1993), Gene 128, 59-65. Furthermore, publications like Borrebaeck (1995), "Antibody Engineering", Oxford University, 229-266; McCafferty (1996), "Antibody Engineering", Oxford University Press; Kay (1996), A Laboratory Manual, Academic Press provide for optimization protocols which may be modified in accordance with this invention.

The optimization method may further comprise a step (ca), whereby the optimized clones are further optimized by cassette mutagenesis, as illustrated in the appended examples.

The method for the optimization of an antibody molecule described herein is further illustrated in the appended examples as affinity maturation of parental antibodies/antibody molecules capable of specifically recognizing two regions of the beta-A4 peptide/Abeta4/Aβ/Aβ4/βA4.

Preferably, said Aβ/Aβ4 (also designated as βA4 in context of this invention) in step (b) of the method described herein above is aggregated Aβ/Aβ4. Said panning may be carried out (as described in the appended examples) with increased stringency of binding. Stringency may be increased, inter alia, by reducing the Aβ/Aβ4 concentration or by elevating the (assay) temperature. The testing of the optimized library by panning is known to the skilled artisan and described in Kay (1993), loc. cit. Preferably, the identification in step (c) is carried out by ranking according to the lowest $K_D$-values.

Most preferably said identification in step (c) is carried out by koff-ranking. Koff-ranking is known to the skilled artisan and described in Schier (1996), loc. cit.; Schier (1996), J. Mol. Biol. 255, 28-43 or Duenas (1996), Mol. Immunol. 33, 279-286. Furthermore, koff-ranking is illustrated in the appended examples. The off-rate constant may be measured as described in the appended examples.

As mentioned herein above, the identified clones may, for further evaluation, be expressed. The expression may be carried out by known methods, inter alia, illustrated in the appended examples. The expression may, inter alia, lead to expressed Fab-fragments, scFvs, bispecific immunoglobulins, bispecific antibody molecules, Fab- and/or Fv fusion proteins, or full antibodies, like IgGs, in particular IgG1.

Optimized antibodies, in particular optimized Fabs or optimized IgGs, preferably IgG1s, may be tested by methods as illustrated in the appended examples. Such methods comprise, but are not limited to, the testing of binding affinities, the determination of $K_D$ values, pepspot anaylysis, ELISA-assays, RIA-assays, CLIA-assays, (immuno-) histological studies (for example staining of amyloid plaques), de-polymerization assays or antibody-dependent β-A4 phagocytoses.

In a further embodiment of the present invention, a method is provided wherein optimized antibodies are generated by cross-cloning. This method is also illustrated in the appended examples and comprises the step of combining independently optimized CDR-regions, for example, by combining independently optimized H-CDR2 and L-CDR2 from matured clones with H-CDR3, preferably the same H-CDR3.

In a preferred embodiment, the invention relates to a method for the preparation of a pharmaceutical composition comprising the steps of
(a) optimization of an antibody according to the method described herein and illustrated in the appended examples; and
(b) formulating the optimized antibody/antibody molecule with an physiologically acceptable carrier, as described herein above.

Accordingly, the invention also provides for a pharmaceutical composition prepared by the method disclosed herein and comprising further optimized antibody molecules capable of specifically recognizing two regions of the beta-A4 petide/Abeta4/Aβ/A4β/βA4, as described herein above.

Exemplified Sequences as Recited Herein:

```
SEQ ID NO: 1
AEFRHDSGY
First region of β-A4 peptide, "N-terminal region/epitope"

SEQ ID NO: 2
VHHQKLVFFAEDVG
Second region of β-A4 peptide, "Central/middle region/epitope"

SEQ ID NO: 3
VH-region of MS-Roche#3 (nucleic acid sequence)
                                                                    (SEQ ID NO: 3)
CAGGTGCAATTGGTGGAAAGCGGCGGCGGCCTGGTGCAACCGGGCGGCAGCCTGC

GTCTGAGCTGCGCGGCCTCCGGATTTACCTTTAGCAGCTATGCGATGAGCTGGGTGC

GCCAAGCCCCTGGGAAGGGTCTCGAGTGGGTGAGCGCGATTAGCGGTAGCGGCGGC

AGCACCTATTATGCGGATAGCGTGAAAGGCCGTTTTACCATTTCACGTGATAATTCGA

AAAACACCCTGTATCTGCAAATGAACAGCCTGCGTGCGGAAGATACGGCCGTGTATTA

TTGCGCGCGTCTTACTCATTATGCTCGTTATTATCGTTATTTTGATGTTTGGGGCCAAG

GCACCCTGGTGACGGTTAGCTCAGC
```

SEQ ID NO: 4
VH-region of MS-Roche#3 (amino acid sequence)
(SEQ ID NO: 4)

QVQLVESGGGLVQPGGSLRLSCAASGFTFSSYAMSWVRQAPGKGLEWVSAISGSGGST

YYADSVKGRFTISRDNSKNTLYLQMNSLRAEDTAVYYCARLTHYARYYRYFDVWGQGTL

VTVSS

SEQ ID NO: 5
VH-region of MS-Roche#7 (nucleic acid sequence)
(SEQ ID NO: 5)

CAGGTGCAATTGGTGGAAAGCGGCGGCGGCCTGGTGCAACCGGGCGGCAGCCTGC

GTCTGAGCTGCGCGGCCTCCGGATTTACCTTTAGCAGCTATGCGATGAGCTGGGTGC

GCCAAGCCCCTGGGAAGGGTCTCGAGTGGGTGAGCGCGATTAGCGGTAGCGGCGG

AGCACCTATTATGCGGATAGCGTGAAAGGCCGTTTACCATTTCACGTGATAATTCGAA

AAACACCCTGTATCTGCAAATGAACAGCCTGCGTGCGGAAGATACGGCCGTGTATTAT

TGCGCGCGTGGTAAGGGTAATACTCATAAGCCTTATGGTTATGTTCGTTATTTTGATGT

TTGGGGCCAAGGCACCCTGGTGACGGTTAGCTCAGC

SEQ ID NO: 6
VH-region of MS-Roche#7 (amino acid sequence)
(SEQ ID NO: 6)

QVQLVESGGGLVQPGGSLRLSCAASGFTFSSYAMSWVRQAPGKGLEWVSAISGSGGST

YYADSVKGRFTISRDNSKNTLYLQMNSLRAEDTAVYYCARGKGNTHKPYGYVRYFDVWG

QGTLVTVSS

SEQ ID NO: 7
VH-region of MS-Roche#8 (nucleic acid sequence)
(SEQ ID NO: 7)

CAGGTGCAATTGGTGGAAAGCGGCGGCGGCCTGGTGCAACCGGGCGGCAGCCTGC

GTCTGAGCTGCGCGGCCTCCGGATTTACCTTTAGCAGCTATGCGATGAGCTGGGTGC

GCCAAGCCCCTGGGAAGGGTCTCGAGTGGGTGAGCGCGATTAGCGGTAGCGGCGG

AGCACCTATTATGCGGATAGCGTGAAAGGCCGTTTTACCATTTCACGTGATAATTCGA

AAACACCCTGTATCTGCAAATGAACAGCCTGCGTGCGGAAGATACGGCCGTGTATTA

TTGCGCGCGTCTTCTTTCTCGTGGTTATAATGGTTATTATCATAAGTTTGATGTTTGGG

GCCAAGGCACCCTGGTGACGGTTAGCTCAGC

SEQ ID NO: 8
VH-region of MS-Roche#8 (amino acid sequence)
(SEQ ID NO: 8)

QVQLVESGGGLVQPGGSLRLSCAASGFTFSSYAMSWVRQAPGKGLEWVSAISGSGGST

YYADSVKGRFTISRDNSKNTLYLQMNSLRAEDTAVYYCARLLSRGYNGYYHKFDVWGQG

TLVTVSS

SEQ ID NO: 9
VL-region of MS-Roche#3 (nucleic acid sequence)
(SEQ ID NO: 9)

GATATCGTGCTGACCCAGAGCCCGGCGACCCTGAGCCTGTCTCCGGGCGAACGTGC

GACCCTGAGCTGCAGAGCGAGCCAGAGCGTGAGCAGCAGCTATCTGGCGTGGTACC

AGCAGAAACCAGGTCAAGCACCGCGTCTATTAATTTATGGCGCGAGCAGCCGTGCAA

CTGGGGTCCCGGCGCGTTTTAGCGGCTCTGGATCCGGACACGGATTTTACCCTGACCA

TTAGCAGCCTGGAACCTGAAGACTTTGCGGTTTATTATTGCCAGCAGGTTTATAATCCT

CCTGTTACCTTTGGCCAGGGTACGAAAGTTGAAATTAAACGTACG

SEQ ID NO: 10
VL-region of MS-Roche #3 (amino acid sequence)
(SEQ ID NO: 10)
DIVLTQSPATLSLSPGERATLSCRASQSVSSSYLAWYQQKPGQAPRLLIYGASSRATGVPA

RFSGSGSGTDFTLTISSLEPEDFAVYYCQQVYNPPVTFGQGTKVEIKRT

SEQ ID NO: 11
VL-region of MS-Roche#7 (nucleic acid sequence)
(SEQ ID NO. 11)
GATATCGTGCTGACCCAGAGCCCGGCGACCCTGAGCCTGTCTCCGGGCGAACGTGC

GACCCTGAGCTGCAGAGCGAGCCAGAGCGTGAGCAGCAGCTATCTGGCGTGGTACC

AGCAGAAACCAGGTCAAGCACCGCGTCTATTAATTTATGGCGCGAGCAGCCGTGCAA

CTGGGGTCCCGGCGCGTTTTAGCGGCTCTGGATCCGGCACGGATTTTACCCTGACCA

TTAGCAGCCTGGAACCTGAAGACTTTGCGACTTATTATTGCTTTCAGCTTTATTCTGAT

CCTTTTACCTTTGGCCAGGGTACGAAAGTTGAAATTAAACGTACG

SEQ ID NO: 12
VL-region of MS-Roche#7 (amino acid sequence)
(SEQ ID NO: 12)
DIVLTQSPATLSLSPGERATLSCRASQSVSSSYLAWYQQKPGQAPRLLIYGASSRATGVPA

RFSGSGSGTDFTLTISSLEPEDFATYYCFQLYSDPFTFGQGTKVEIKRT

SEQ ID NO: 13
VL-region of MS-Roche#8 (nucleic acid sequence)
(SEQ ID NO: 13)
GATATCGTGCTGACCCAGAGCCCGGCGACCCTGAGCCTGTCTCCGGGCGAACGTGC

GACCCTGAGCTGCAGAGCGAGCCAGAGCGTGAGCAGCAGCTATCTGGCGTGGTACC

AGCAGAAACCAGGTCAAGCACCGCGTCTATTAATTTATGGCGCGAGCAGCCGTGCAA

CTGGGGTCCCGGCGCGTTTTAGCGGCTCTGGATCCGGCACGGATTTTACCCTGACCA

TTAGCAGCCTGGAACCTGAAGACTTTGCGACTTATTATTGCCAGCAGCTTTCTTCTTTT

CCTCCTACCTTTGGCCAGGGTACGAAAGTTGAAATTAAACGTACG

SEQ ID NO: 14
VL-region of MS-Roche#8 (amino acid sequence)
(SEQ ID NO: 14)
DIVLTQSPATLSLSPGERATLSCRASQSVSSSYLAWYQQKPGQAPRLLIYGASSRATGVPA

RFSGSGSGTDFTLTISSLEPEDFATYYCQQLSSFPPTFGQGTKVEIKRT

SEQ ID NO: 15
CDR3 of $V_L$-region of MSR-3 (nucleic acid sequence)
(SEQ ID NO: 15)
|CAGCAGGTTTATAATCCTCCTGTT|

SEQ ID NO: 16
CDR3 of $V_L$-region of MSR-3 (amino acid sequence)
(SEQ ID NO: 16)
QQVYNPPV SEQ ID NO: 17
CDR3 of $V_L$-region of MSR-7 (nucleic acid sequence)
(SEQ ID NO: 17)
|TTTCAGCTTTATTCTGATCCTTTT|

SEQ ID NO: 18
CDR3 of $V_L$-region of MSR-7 (amino acid sequence)
(SEQ ID NO. 18)
FQLYSDPF SEQ ID NO: 19
CDR3 of $V_L$-region of MSR-8 (nucleic acid sequence)
(SEQ ID NO. 19)
CAG CAG CTT TCT TCT TTT CCT CCT SEQ ID NO: 20
CDR3 of $V_L$-region of MSR-8 (amino acid sequence)

-continued

SEQ ID NO: 20
QQLSSFPP

SEQ ID NO: 21
CDR of V$_H$-region of MSR-3 (nucleic acid sequence)
(SEQ ID NO: 21)
CTTACTCATTATGCTCGTTATTATCGTTATTTTGATGTT SEQ ID NO: 22
CDR of V$_H$-region of MSR-3 (amino acid sequence)
(SEQ ID NO: 22)
LTHYARYYRYFDV SEQ ID NO: 23
CDR of V$_H$-region of MSR-7 (nucleic acid sequence)
(SEQ ID NO: 23)
GGTAAG GGT AAT ACT CAT AAG CCT TAT GGT TAT GTT CGT TAT TTT GAT GTT SEQ ID NO: 24
CDR of V$_H$-region of MSR-7 (amino acid sequence)
(SEQ ID NO: 24)
GKGNTHKPYGYVRYFDV SEQ ID NO: 25
CDR of V$_H$-region of MSR-8 (nucleic acid sequence)
(SEQ ID NO. 25)
CTT CTT TCT CGT GGT TAT AAT GGT TAT TAT CAT AAG TTT GAT GTT SEQ ID NO: 26
CDR of V$_H$-region of MSR-8 (amino acid sequence)
(SEQ ID NO: 26)
LLSRGYNGYYHKFDV SEQ ID NO: 27 Aβ4 (amino acids 1 to 42)
(SEQ ID NO: 27)
DAEFRHDSGYEVHHQKLVFFAEDVGSNKGAIIGLMVGGVVIA SEQ ID NO: 28 primer
(SEQ ID NO: 28)
5'-GTGGTGGTTCCGATATC-3'

SEQ ID NO: 29 primer
(SEQ ID NO: 29)
5'- AGCGTCACACTCGGTGCGGCTTTCGGCTGGCCAAGAACGGTTA-3'

SEQ ID NO: 30 primer
(SEQ ID NO: 30)
5'-CAGGAAACAGCTATGAC-3'

SEQ ID NO: 31 primer
(SEQ ID NO: 31)
5'-TACCGTTGCTCTTCACCCC-3'

SEQ ID NO: 32 VH of MS-Roche#3.6H5 × 3.6L2; DNA; artificial sequence
(SEQ ID NO: 32)
CAATTGGTGGAAAGCGGCGGCGGCCTGGTGCAACCGGGCGGCAGCCTGCGTCTGAG

CTGCGCGGCCTCCGGATTTACCTTTAGCAGCTATGCGATGAGCTGGGTGCGCCAAGC

CCCTGGGAAGGGTCTCGAGTGGGTGAGCGCTATTTCTGAGTCTGGTAAGACTAAGTA

TTATGCTGATTCTGTTAAGGGTCGTTTTACCATTTCACGTGATAATTCGAAAAACACCC

TGTATCTGCAAATGAACAGCCTGCGTGCGGAAGATACGGCCGTGTATTATTGCGCGC

GTCTTACTCATTATGCTCGTTATTATCGTTATTTTGATGTTTGGGGCCAAGGCACCCTG

GTGACGGTTAGCTCA

SEQ ID NO. 33: prot VH region of MS-Roche#3.6H5 × 3.6L2; protein/1; artificial sequence
(SEQ ID NO: 33)
QLVESGGGLVQPGGSLRLSCAASGFTFSSYAMSWVRQAPGKGLEWVSAISESGKTKYYA

DSVKGRFTISRDNSKNTLYLQMNSLRAEDTAVYYCARLTHYARYYRYFDVWGQGTLVTVS

S

SEQ ID NO: 34 VH region of MS-Roche#3.6H8 × 3.6L2; DNA; artificial sequence
(SEQ ID NO: 34)
CAATTGGTGGAAAGCGGCGGCGGCCTGGTGCAACCGGGCGGCAGCCTGCGTCTGAG -continued

CTGCGCGGCCTCCGGATTTACCTTTAGCAGCTATGCGATGAGCTGGGTGCGCCAAGC

CCCTGGGAAGGGTCTCGAGTGGGTGAGCGCTATTTCTGAGTATTCTAAGTTTAAGTAT

TATGCTGATTCTGTTAAGGGTCGTTTTACCATTTCACGTGATAATTCGAAAAACACCCT

GTATCTGCAAATGAACAGCCTGCGTGCGGAAGATACGGCCGTGTATTATTGCGCGCG

TCTTACTCATTATGCTCGTTATTATCGTTATTTTGATGTTTGGGGCCAAGGCACCCTGG

TGACGGTTAGCTCA

SEQ ID NO: 35 prot VH region of MS-Roche#3.6H8 × 3.6L2; protein/1; artificial sequence
(SEQ ID NO: 35)
QLVESGGGLVQPGGSLRLSCAASGFTFSSYAMSWVRQAPGKGLEWVSAISEYSKFKYYA

DSVKGRFTISRDNSKNTLYLQMNSLRAEDTAVYYCARLTHYARYYRYFDVWGQGTLVTVS

S

SEQ ID NO: 36 VH region of MS-Roche#7.4H2 × 7.2L1; DNA; artificial sequence
(SEQ ID NO: 36)
CAATTGGTGGAAAGCGGCGGCGGCCTGGTGCAACCGGGCGGCAGCCTGCGTCTGAG

CTGCGCGGCCTCCGGATTTACCTTTAGCAGCTATGCGATGAGCTGGGTGCGCCAAGC

CCCTGGGAAGGGTCTCGAGTGGGTGAGCGCTATTAATTATAATGGTGCTCGTATTTAT

TATGCTGATTCTGTTAAGGGTCGTTTTACCATTTCACGTGATAATTCGAAAAACACCCT

GTATCTGCAAATGAACAGCCTGCGTGCGGAAGATACGGCCGTGTATTATTGCGCGCG

TGGTAAGGGTAATACTCATAAGCCTTATGGTTATGTTCGTTATTTTGATGTTTGGGGCC

AAGGCACCCTGGTGACGGTTAGCTCA

SEQ ID NO: 37 prot VH region of MS-Roche#7.4H2 × 7.2L1; protein/1; artificial sequence
(SEQ ID NO: 37)
QLVESGGGLVQPGGSLRLSCAASGFTFSSYAMSWVRQAPGKGLEWVSAINYNGARIYYA

DSVKGRFTISRDNSKNTLYLQMNSLRAEDTAVYYCARGKGNTHKPYGYVRYFDVWGQGT

LVTVSS

SEQ ID NO: 38 VH region of MS-Roche#7.9H2 × 7.12 L2; DNA; artificial sequence
(SEQ ID NO: 38)
CAATTGGTGGAAAGCGGCGGCGGCCTGGTGCAACCGGGCGGCAGCCTGCGTCTGAG

CTGCGCGGCCTCCGGATTTACCTTTAGCAGCTATGCGATGAGCTGGGTGCGCCAAGC

CCCTGGGAAGGGTCTCGAGTGGGTGAGCGCTATTAATGCTGATGGTAATCGTAAGTA

TTATGCTGATTCTGTTAAGGGTCGTTTTACCATTTCACGTGATAATTCGAAAAACACCC

TGTATCTGCAAATGAACAGCCTGCGTGCGGAAGATACGGCCGTGTATTATTGCGCGC

GTGGTAAGGGTAATACTCATAAGCCTTATGGTTATGTTCGTTATTTTGATGTTTGGGGC

CAAGGCACCCTGGTGACGGTTAGCTCA

SEQ ID NO: 39 prot VH region of MS-Roche#7.9H2 × 7.12L2; protein/1; artificial sequence
(SEQ ID NO: 39)
QLVESGGGLVQPGGSLRLSCAASGFTFSSYAMSWVRQAPGKGLEWVSAINADGNRKYY

ADSVKGRFTISRDNSKNTLYLQMNSLRAEDTAVYYCARGKGNTHKPYGYVRYFDVWGQG

TLVTVSS

SEQ ID NO: 40 VH region of MS-Roche#7.9H4 × 7.12L2; DNA; artificial sequence
(SEQ ID NO: 40)
CAATTGGTGGAAAGCGGCGGCGGCCTGGTGCAACCGGGCGGCAGCCTGCGTCTGAG

CTGCGCGGCCTCCGGATTTACCTTTAGCAGCTATGCGATGAGCTGGGTGCGCCAAGC

CCCTGGGAAGGGTCTCGAGTGGGTGAGCGCTATTAATGCTGTTGGTATGAAGAAGTT

TTATGCTGATTCTGTTAAGGGTCGTTTTACCATTTCACGTGATAATTCGAAAAACACCC

TGTATCTGCAAATGAACAGCCTGCGTGCGGAAGATACGGCCGTGTATTATTGCGCGC

GTGGTAAGGGTAATACTCATAAGCCTTATGGTTATGTTCGTTATTTTGATGTTTGGGGC

CAAGGCACCCTGGTGACGGTTAGCTCA

SEQ ID NO: 41 prot VH region of MS-Roche#7.9H4 x 7.12L2; protein/1; artificial sequence
(SEQ ID NO: 41)
QLVESGGGLVQPGGSLRLSCAASGFTFSSYAMSWVRQAPGKGLEWVSAINAVGMKKFY

ADSVKGRFTISRDNSKNTLYLQMNSLRAEDTAVYYCARGKGNTHKPYGYVRYFDVWGQG

TLVTVSS

SEQ ID NO: 42 VH region of MS-Roche#7.11H1 x 7.11L1; DNA; artificial sequence
(SEQ ID NO: 42)
CAATTGGTGGAAAGCGGCGGCGGCCTGGTGCAACCGGGCGGCAGCCTGCGTCTGAG

CTGCGCGGCCTCCGGATTTACCTTTAGCAGCTATGCGATGAGCTGGGTGCGCCAAGC

CCCTGGGAAGGGTCTCGAGTGGGTGAGCGGTATTAATGCTGCTGGTTTTCGTACTTAT

TATGCTGATTCTGTTAAGGGTCGTTTTACCATTTCACGTGATAATTCGAAAAACACCCT

GTATCTGCAAATGAACAGCCTGCGTGCGGAAGATACGGCCGTGTATTATTGCGCGCG

TGGTAAGGGTAATACTCATAAGCCTTATGGTTATGTTCGTTATTTTGATGTTTGGGGCC

AAGGCACCCTGGTGACGGTTAGCTCA

SEQ ID NO. 43 prot VH region of MS-Roche#7.11H1 x 7.11L1; protein/1; artificial
sequence
(SEQ ID NO: 43)
QLVESGGGLVQPGGSLRLSCAASGFTFSSYAMSWVRQAPGKGLEWVSGINAAGFRTYY

ADSVKGRFTISRDNSKNTLYLQMNSLRAEDTAVYYCARGKGNTHKPYGYVRYFDVWGQG

TLVTVSS

SEQ ID NO: 44 VH region of MS-Roche#7.11H1 x 7.2L1; DNA; artificial sequence
(SEQ ID NO: 44)
CAATTGGTGGAAAGCGGCGGCGGCCTGGTGCAACCGGGCGGCAGCCTGCGTCTGAG

CTGCGCGGCCTCCGGATTTACCTTTAGCAGCTATGCGATGAGCTGGGTGCGCCAAGC

CCCTGGGAAGGGTCTCGAGTGGGTGAGCGGTATTAATGCTGCTGGTTTTCGTACTTAT

TATGCTGATTCTGTTAAGGGTCGTTTTACCATTTCACGTGATAATTCGAAAAACACCCT

GTATCTGCAAATGAACAGCCTGCGTGCGGAAGATACGGCCGTGTATTATTGCGCGCG

TGGTAAGGGTAATACTCATAAGCCTTATGGTTATGTTCGTTATTTTGATGTTTGGGGCC

AAGGCACCCTGGTGACGGTTAGCTCA

SEQ ID NO: 45 prot VH region of MS-Roche#7.11H1 x 7.2L1; protein/1; artificial sequence
(SEQ ID NO: 45)
QLVESGGGLVQPGGSLRLSCAASGFTFSSYAMSWVRQAPGKGLEWVSGINAAGFRTYY

ADSVKGRFTISRDNSKNTLYLQMNSLRAEDTAVYYCARGKGNTHKPYGYVRYFDVWGQG

TLVTVSS

SEQ ID NO: 46 VL region of MS-Roche#3.6H5 x 3.6L2; DNA; artificial sequence
(SEQ ID NO: 46)
GATATCGTGCTGACCCAGAGCCCGGCGACCCTGAGCCTGTCTCCGGGCGAACGTGC

GACCCTGAGCTGCAGAGCGAGCCAGTTTCTTTCTCGTTATTATCTGGCGTGGTACCAG

CAGAAACCAGGTCAAGCACCGCGTCTATTAATTTATGGCGCGAGCAGCCGTGCAACT

GGGGTCCCGGCGCGTTTTAGCGGCTCTGGATCCGGCACGGATTTTACCCTGACCATT

AGCAGCCTGGAACCTGAAGACTTTGCGGTTTATTATTGCCAGCAGACTTATAATTATCC

TCCTACCTTTGGCCAGGGTACGAAAGTTGAAATTAAACGTACG

SEQ ID NO:47 prot VL region of MS-Roche#3.6H5 x 3.6L2; protein/1; artificial sequence
(SEQ ID NO: 47)
DIVLTQSPATLSLSPGERATLSCRASQFLSRYYLAWYQQKPGQAPRLLIYGASSRATGVPA

RFSGSGSGTDFTLTISSLEPEDFAVYYCQQTYNYPPTFGQGTKVEIKRT

SEQ ID NO: 48 VL region of MS-Roche#3.6H8 x 3.6L2; DNA; artificial sequence

-continued

SEQ ID NO: 48
```
GATATCGTGCTGACCCAGAGCCCGGCGACCCTGAGCCTGTCTCCGGGCGAACGTGC

GACCCTGAGCTGCAGAGCGAGCCAGTTTCTTTCTCGTTATTATCTGGCGTGGTACCAG

CAGAAACCAGGTCAAGCACCGCGTCTATTAATTTATGGCGCGAGCAGCCGTGCAACT

GGGGTCCCGGCGCGTTTTAGCGGCTCTGGATCCGGCACGGATTTTACCCTGACCATT

AGCAGCCTGGAACCTGAAGACTTTGCGGTTTATTATTGCCAGCAGACTTATAATTATCC

TCCTACCTTTGGCCAGGGTACGAAAGTTGAAATTAAACGTACG
```

SEQ ID NO: 49 prot VL region of MS-Roche#3.6H8 × 3.6L2; protein/1; artificial sequence
```
DIVLTQSPATLSLSPGERATLSCRASQFLSRYYLAWYQQKPGQAPRLLIYGASSRATGVPA

RFSGSGSGTDFTLTISSLEPEDFAVYYCQQTYNYPPTFGQGTKVEIKRT
```

SEQ ID NO: 50 VL region of MS-Roche#7.4H2 × 7.2L1; DNA; artificial sequence
```
GATATCGTGCTGACCCAGAGCCCGGCGACCCTGAGCCTGTCTCCGGGCGAACGTGC

GACCCTGAGCTGCAGAGCGAGCCAGTATGTTGATCGTACTTATCTGGCGTGGTACCA

GCAGAAACCAGGTCAAGCACCGCGTCTATTAATTTATGGCGCGAGCAGCCGTGCAAC

TGGGGTCCCGGCGCGTTTTAGCGGCTCTGGATCCGGCACGGATTTTACCCTGACCAT

TAGCAGCCTGGAACCTGAAGACTTTGCGACTTATTATTGCCAGCAGATTTATTCTTTTC

CTCATACCTTTGGCCAGGGTACGAAAGTTGAAATTAAACGTACG
```

SEQ ID NO: 51 prot VL region of MS-Roche#7.4H2 × 7.2L1; protein/1; artificial sequence
```
DIVLTQSPATLSLSPGERATLSCRASQYVDRTYLAWYQQKPGQAPRLLIYGASSRATGVP

ARFSGSGSGTDFTLTISSLEPEDFATYYCQQIYSFPHTFGQGTKVEIKRT
```

SEQ ID NO: 52 VL region of MS-Roche#7.9H2 × 7.12 L2; DNA; artificial sequence
```
GATATCGTGCTGACCCAGAGCCCGGCGACCCTGAGCCTGTCTCCGGGCGAACGTGC

GACCCTGAGCTGCAGAGCGAGCCAGCGTTTTTTTTATAAGTATCTGGCGTGGTACCAG

CAGAAACCAGGTCAAGCACCGCGTCTATTAATTTCTGGTTCTTCTAACCGTGCAACTG

GGGTCCCGGCGCGTTTTAGCGGCTCTGGATCCGGCACGGATTTTACCCTGACCATTA

GCAGCCTGGAACCTGAAGACTTTGCGGTTTATTATTGCCTTCAGCTTTATAATATTCCT

AATACCTTTGGCCAGGGTACGAAAGTTGAAATTAAACGTACG
```

SEQ ID NO: 53 prot VL region of MS-Roche#7.9H2 × 7.12 L2; protein/1; artificial sequence
```
DIVLTQSPATLSLSPGERATLSCRASQRFFYKYLAWYQQKPGQAPRLLISGSSNRATGVP

ARFSGSGSGTDFTLTISSLEPEDFAVYYCLQLYNIPNTFGQGTKVEIKRT
```

SEQ ID NO: 54 VL region of MS-Roche#7.9H4 × 7.12L2; DNA; artificial sequence
```
GATATCGTGCTGACCCAGAGCCCGGCGACCCTGAGCCTGTCTCCGGGCGAACGTGC

GACCCTGAGCTGCAGAGCGAGCCAGCGTTTTTTTTATAAGTATCTGGCGTGGTACCAG

CAGAAACCAGGTCAAGCACCGCGTCTATTAATTTCTGGTTCTTCTAACCGTGCAACTG

GGGTCCCGGCGCGTTTTAGCGGCTCTGGATCCGGCACGGATTTTACCCTGACCATTA

GCAGCCTGGAACCTGAAGACTTTGCGGTTTATTATTGCCTTCAGCTTTATAATATTCCT

AATACCTTTGGCCAGGGTACGAAAGTTGAAATTAAACGTACG
```

SEQ ID NO: 55 prot VL region of MS-Roche#7.9H4 × 7.12L2; protein/1; artificial sequence
```
DIVLTQSPATLSLSPGERATLSCRASQRFFYKYLAWYQQKPGQAPRLLISGSSNRATGVP

ARFSGSGSGTDFTLTISSLEPEDFAVYYCLQLYNIPNTFGQGTKVEIKRT
```

SEQ ID NO: 56 VL region of MS-Roche#7.11H1 × 7.11L1; DNA; artificial sequence

-continued

SEQ ID NO: 56 (continued)

```
GATATCGTGCTGACCCAGAGCCCGGCGACCCTGAGCCTGTCTCCGGGCGAACGTGC

GACCCTGAGCTGCAGAGCGAGCCAGCGTATTCTTCGTATTTATCTGGCGTGGTACCA

GCAGAAACCAGGTCAAGCACCGCGTCTATTAATTTATGGCGCGAGCAGCCGTGCAAC

TGGGGTCCCGGCGCGTTTTAGCGGCTCTGGATCCGGCACGGATTTTACCCTGACCAT

TAGCAGCCTGGAACCTGAAGACTTTGCGACTTATTATTGCCAGCAGGTTTATTCTCCTC

CTCATACCTTTGGCCAGGGTACGAAAGTTGAAATTAAACGTACG
```

SEQ ID NO: 57 prot VL region of MS-Roche#7.11H1 x 7.11L1; protein/1; artificial sequence
(SEQ ID NO: 57)

```
DIVLTQSPATLSLSPGERATLSCRASQRILRIYLAWYQQKPGQAPRLLIYGASSRATGVPAR

FSGSGSGTDFTLTISSLEPEDFATYYCQQVYSPPHTFGQGTKVEIKRT
```

SEQ ID NO: 58 VL region of MS-Roche#7.11H1 x 7.2L1; DNA; artificial sequence
(SEQ ID NO: 58)

```
GATATCGTGCTGACCCAGAGCCCGGCGACCCTGAGCCTGTCTCCGGGCGAACGTGC

GACCCTGAGCTGCAGAGCGAGCCAGTATGTTGATCGTACTTATCTGGCGTGGTACCA

GCAGAAACCAGGTCAAGCACCGCGTCTATTAATTTATGGCGCGAGCAGCCGTGCAAC

TGGGGTCCCGGCGCGTTTTAGCGGCTCTGGATCCGGCACGGATTTTACCCTGACCAT

TAGCAGCCTGGAACCTGAAGACTTTGCGACTTATTATTGCCAGCAGATTTATTCTTTTC

CTCATACCTTTGGCCAGGGTACGAAAGTTGAAATTAAACGTACG
```

SEQ ID NO: 59 prot VL region of MS-Roche#7.11H1 x 7.2L1; protein/1; artificial sequence
(SEQ ID NO: 59)

```
DIVLTQSPATLSLSPGERATLSCRASQYVDRTYLAWYQQKPGQAPRLLIYGASSRATGVP

ARFSGSGSGTDFTLTISSLEPEDFATYYCQQIYSFPHTFGQGTKVEIKRT
```

SEQ ID NO: 60 HCDR3 region of MS-Roche#3.6H5 x 3.6L2; DNA; artificial sequence
(SEQ ID NO: 60)

```
CTTACTCATTATGCTCGTTATTATCGTTATTTTGATGTT
```

SEQ ID NO: 61 prot HCDR3 region of MS-Roche#3.6H5 x 3.6L2; protein/1; artificial sequence
(SEQ ID NO: 61)

```
LTHYARYYRYFDV
```

SEQ ID NO: 62 HCDR3 region of MS-Roche#3.6H8 x 3.6L2; DNA; artificial sequence
(SEQ ID NO: 62)

```
CTTACTCATTATGCTCGTTATTATCGTTATTTTGATGTT
```

SEQ ID NO: 63 prot HCDR3 region of MS-Roche#3.6H8 x 3.6L2; protein/1; artificial sequence
(SEQ ID NO: 63)

```
LTHYARYYRYFDV
```

SEQ ID NO: 64 HCDR3 region of MS-Roche#7.4H2 x 7.2L1; DNA; artificial sequence
(SEQ ID NO: 64)

```
GGTAAGGGTAATACTCATAAGCCTTATGGTTATGTTCGTTATTTTGATGTT
```

SEQ ID NO: 65 prot HCDR3 region of MS-Roche#7.4H2 x 7.2L1; protein/1; artificial sequence
(SEQ ID NO: 65)

```
GKGNTHKPYGYVRYFDV
```

SEQ ID NO: 66 HCDR3 region of MS-Roche#7.9H2 x 7.12 L2; DNA; artificial sequence
(SEQ ID NO: 66)

```
GGTAAGGGTAATACTCATAAGCCTTATGGTTATGTTCGTTATTTTGATGTT
```

SEQ ID NO: 67 prot HCDR3 region of#MS-Roche 7.9H2 x 7.12 L2; protein/1; artificial sequence
(SEQ ID NO: 67)

```
GKGNTHKPYGYVRYFDV
```

SEQ ID NO: 68 HCDR3 region of MS-Roche#7.9H4 x 7.12L2; DNA; artificial sequence
(SEQ ID NO: 68)

```
GGTAAGGGTAATACTCATAAGCCTTATGGTTATGTTCGTTATTTTGATGTT
```

SEQ ID NO: 69 prot HCDR3 region of MS-Roche#7.9H4 x 7.12L2; protein/1; artificial sequence -continued

GKGNTHKPYGYVRYFDV
(SEQ ID NO: 69)

SEQ ID NO: 70 HCDR3 region of MS-Roche#7.11H1 x 7.11L1; DNA; artificial sequence
(SEQ ID NO: 70)
GGTAAGGGTAATACTCATAAGCCTTATGGTTATGTTCGTTATTTTGATGTT SEQ ID NO: 71 prot HCDR3 region of MS-Roche#7.11H1 x 7.11L1; protein/1; artificial sequence
(SEQ ID NO: 71)
GKGNTHKPYGYVRYFDV SEQ ID NO: 72 HCDR3 region of MS-Roche#7.11H1 x 7.2L1; DNA; artificial sequence
(SEQ ID NO: 72)
GGTAAGGGTAATACTCATAAGCCTTATGGTTATGTTCGTTATTTTGATGTT SEQ ID NO: 73 prot HCDR3 region of MS-Roche#7.11H1 x 7.2L1; protein/1; artificial sequence
(SEQ ID NO: 73)
GKGNTHKPYGYVRYFDV SEQ ID NO: 74 LCDR3 region of MS-Roche#3.6H5 x 3.6L2; DNA; artificial sequence
(SEQ ID NO: 74)
CAGCAGACTTATAATTATCCTCCT SEQ ID NO: 75 prot LCDR3 region of MS-Roche#3.6H5 x 3.6L2; protein/1; artificial sequence
(SEQ ID NO: 75)
QQTYNYPP SEQ ID NO: 76 LCDR3 region of MS-Roche#3.6H8 x 3.6L2; DNA; artificial sequence
(SEQ ID NO: 76)
CAGCAGACTTATAATTATCCTCCT SEQ ID NO: 77 prot LCDR3 region of MS-Roche#3.6H8 x 3.6L2; protein/1; artificial sequence
(SEQ ID NO: 77)
QQTYNYPP SEQ ID NO: 78 LCDR3 region of MS-Roche#7.4H2 x 7.2L1; DNA; artificial sequence
(SEQ ID NO: 78)
CAGCAGATTTATTCTTTTCCTCAT SEQ ID NO: 79 prot LCDR3 region of MS-Roche#7.4H2 x 7.2L1; protein/1; artificial sequence
(SEQ ID NO: 79)
QQIYSFPH SEQ ID NO: 80 LCDR3 region of MS-Roche#7.9H2 x 7.12 L2; DNA; artificial sequence
(SEQ ID NO: 80)
CTTCAGCTTTATAATATTCCTAAT SEQ ID NO: 81 prot LCDR3 region of MS-Roche#7.9H2 x 7.12 L2; protein/1; artificial sequence
(SEQ ID NO: 81)
LQLYNIPN SEQ ID NO: 82 LCDR3 region of MS-Roche#7.9H4 x 7.12L2; DNA; artificial sequence
(SEQ ID NO: 82)
CTTCAGCTTTATAATATTCCTAAT SEQ ID NO: 83 prot LCDR3 region of MS-Roche#7.9H4 x 7.12L2; protein/1; artificial sequence
(SEQ ID NO: 83)
LQLYNIPN SEQ ID NO: 84 LCDR3 region of MS-Roche#7.11H1 x 7.11L1; DNA; artificial sequence
(SEQ ID NO: 84)
CAGCAGGTTTATTCTCCTCCTCAT SEQ ID NO: 85 prot LCDR3 region of MS-Roche#7.11H1 x 7.11L1; protein/1; artificial sequence
(SEQ ID NO: 85)
QQVYSPPH SEQ ID NO: 86 LCDR3 region of MS-Roche#7.11H1 x 7.2L1; DNA; artificial sequence
(SEQ ID NO: 86)
CAGCAGATTTATTCTTTTCCTCAT SEQ ID NO: 87 prot LCDR3 region of MS-Roche#7.11H1 x 7.2L1; protein/1; artificial sequence

QQIYSFPH (SEQ ID NO: 87)

SEQ ID NO: 88 VH region of MS-Roche#7.9H7; DNA; artificial sequence
(SEQ ID NO: 88)

Caggtgcaattggtggaaagcggcggcggcctggtgcaaccgggcggcagcctgcgtctgagctgcgcggcctccggattt acctttagcagctatgcgatgagctgggtgcgccaagcccctgggaaggg tctcgagtgggtgagcgctattaatgcttctggta ctcgtacttattatgctgattctgttaagggtcgttttaccatttcacgtgataattcgaaaaacaccctgtatctgcaaatgaacagc ctgcgtgcggaagatacggccgtgtattattgcgcgcgtggtaagggtaatactcataagccttatggttatgttcgttatttt gatgtt tggggccaaggcaccctggtgacggttagctca SEQ ID NO: 89 prot VH region of MS-Roche#7.9H7; protein/1; artificial sequence
(SEQ ID NO: 89)

QVQLVESGGGLVQPGGSLRLSCAASGFTFSSYAMSWVRQAPGKGLEWVSAINASGTRT

YYADSVKGRFTISRDNSKNTLYLQMNSLRAEDTAVYYCARGKGNTHKPYGYVRYFDVWG

QGTLVTVSS

SEQ ID NO: 90 VL region of MS-Roche#7.9H7; DNA; artificial sequence
(SEQ ID NO: 90)

Gatatcgtgctgacccagagcccggcgaccctgagcctgtctccgggcgaacgtgcgaccctgagctgcagagcgagcca gagcgtgagcagcagctatctggcgtggtaccagcagaaaccaggtcaagcaccgcgtctattaatttatggcgcgagcagc cgtgcaactggggtcccggcgcgttttagcggctctggatccggcacggattttaccctgaccattagcagcctggaacctgaa gactttgcgacttattattgccttcagatttataatatgcctattacctttggccagggtacgaaagttgaaattaaacgtacg SEQ ID NO: 91 prot VL region of MS-Roche#7.9H7; protein/1; artificial sequence
(SEQ ID NO: 91)

DIVLTQSPATLSLSPGERATLSCRASQSVSSSYLAWYQQKPGQAPRLLIYGASSRATGVP

ARFSGSGSGTDFTLTISSLEPEDFATYYCLQIYNMPITFGQGTKVEIKRT

SEQ ID NO: 92 HCDR3 region of MS-Roche#7.9H7; DNA; artificial sequence
(SEQ ID NO: 92)

Ggtaagggtaatactcataagccttatggttatgttcgttatttt gatgtt

SEQ ID NO: 93 prot HCDR3 region of MS-Roche#7.9H7; protein/1; artificial sequence
(SEQ ID NO: 93)

GKGNTHKPYGYVRYFDV

SEQ ID NO: 94 LCDR3 region of MS-Roche#7.9H7; DNA; artificial sequence
(SEQ ID NO: 94)

Cttcagatttataatatgcctatt

SEQ ID NO: 95 prot LCDR3 region of MS-Roche#7.9H7; protein/1; artificial sequence
(SEQ ID NO: 95)

LQIYNMPI

Further illustrative sequences are depicted in the appended sequence listing and are also shown in the appended tables, in particular tables 1, 8 and 10.

BRIEF DESCRIPTION OF THE DRAWINGS

The Figures show.

Scale: 8.5 mm=150 µm.

Figure 8:
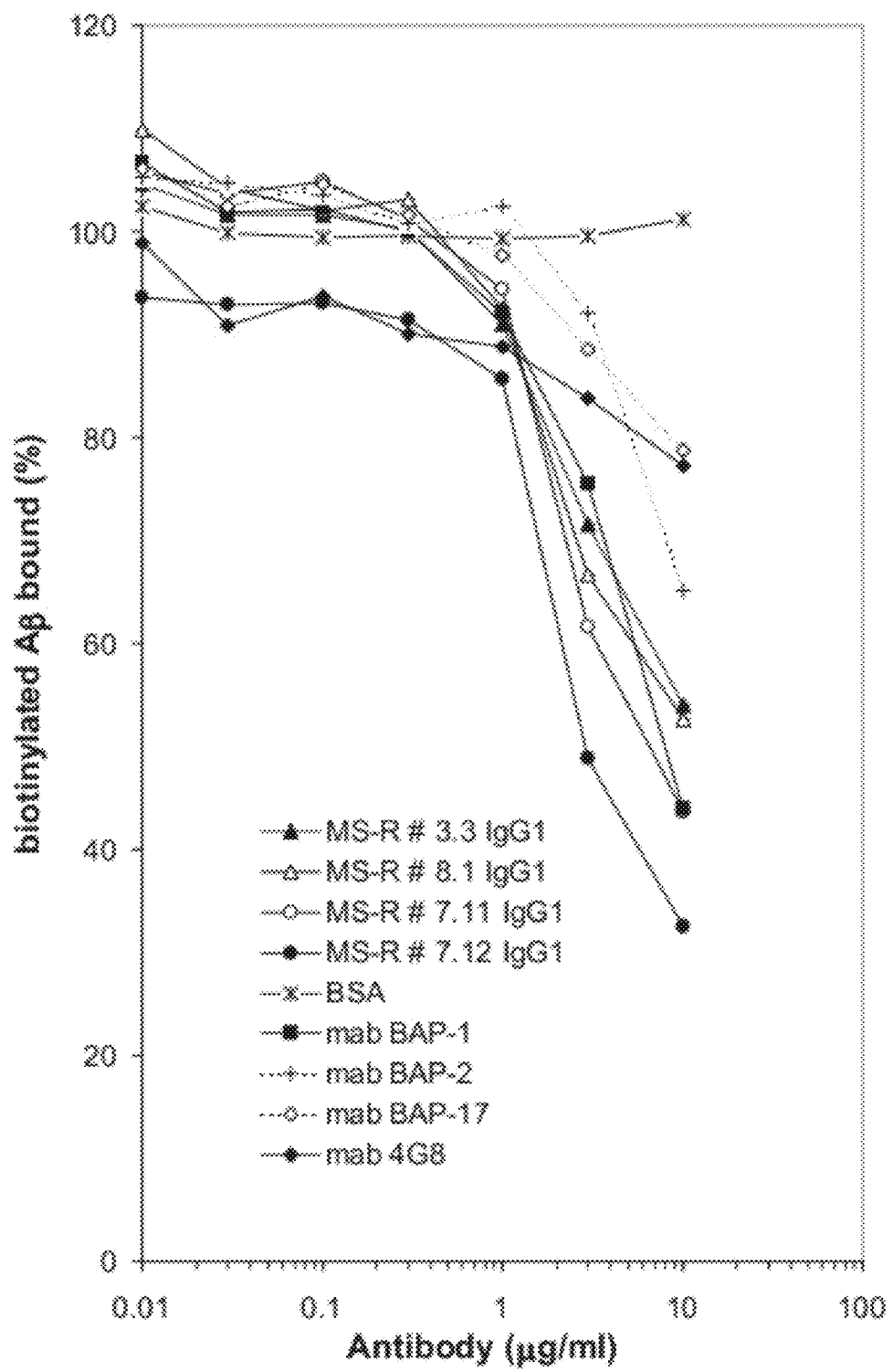

FIG. 8: Polymerization Assay. Anti-Aβ antibodies prevent incorporation of biotinylated Aβ into preformed Aβ aggregates.

Figure 9B:
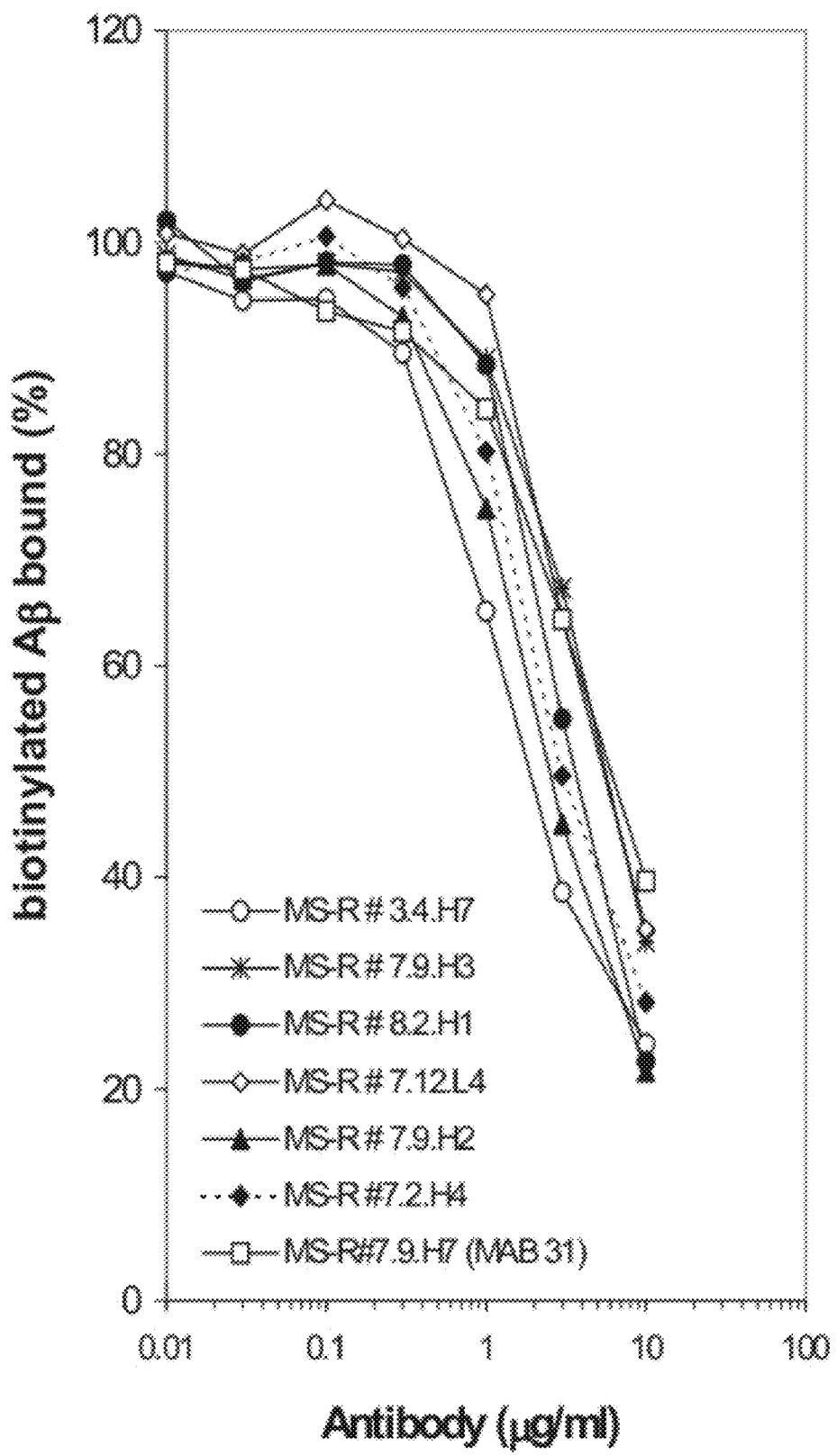
Figure 9D:
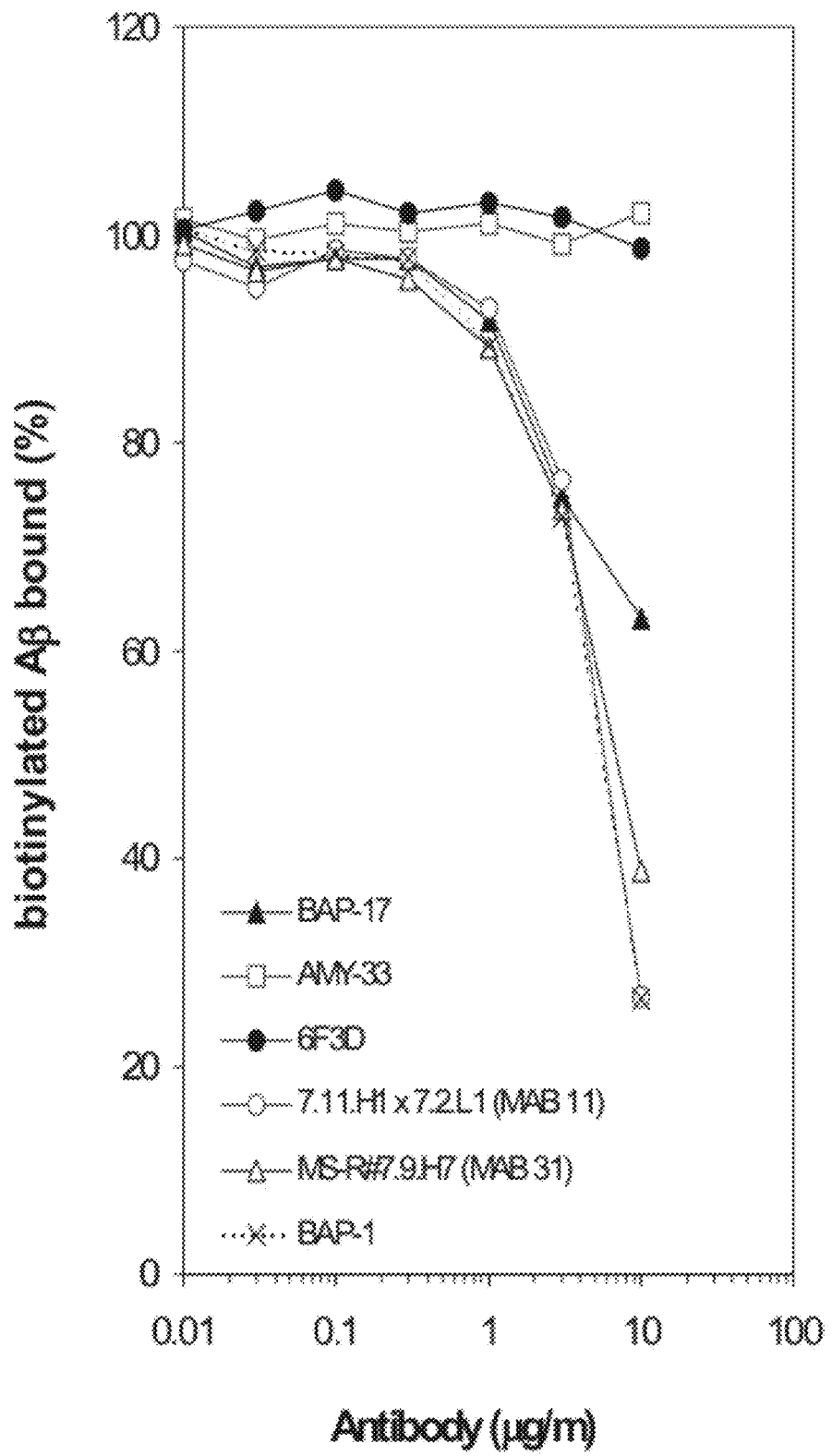

FIG. 9: De-polymerization Assay. Anti-Aβ antibodies induce release of biotinylated Aβ from aggregated Aβ.

Figure 10:
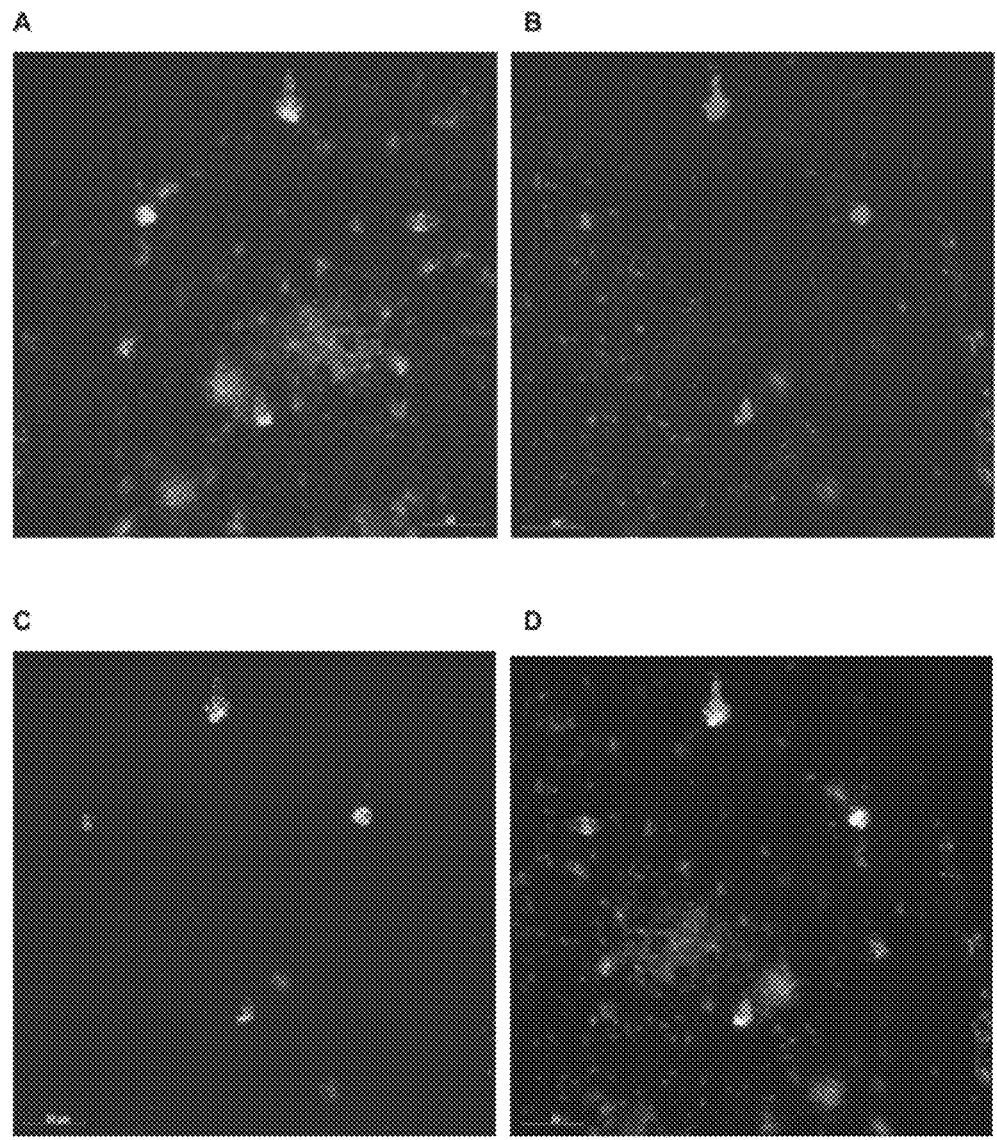

FIG. 10: In vivo decoration of amyloid plaques in an APP/PS2 double transgenic mouse after intravenous injection of 1 mg MS-Roche IgG #7.9.H2×7.12.L2. After three days the mouse was perfused with phosphate-buffered saline and sacrificed. The presence of human IgG bound to amyloid plaques was revealed by confocal microscopy after labelling cryostat sections from the frontal cortex with a goat anti-human IgG-Cy3 conjugate (panel B). The same section was counterstained with an anti-Abeta mouse monoclonal antibody (BAP-2-Alexa488 conjugate, panel A) to visualize the position of amyloid plaques. Individual red (panel B) and green (panel A) channels, merged image (panel D) and colocalized (pancel C) signals are shown.

Scale: 1 cm=50 µm

Figure 11:
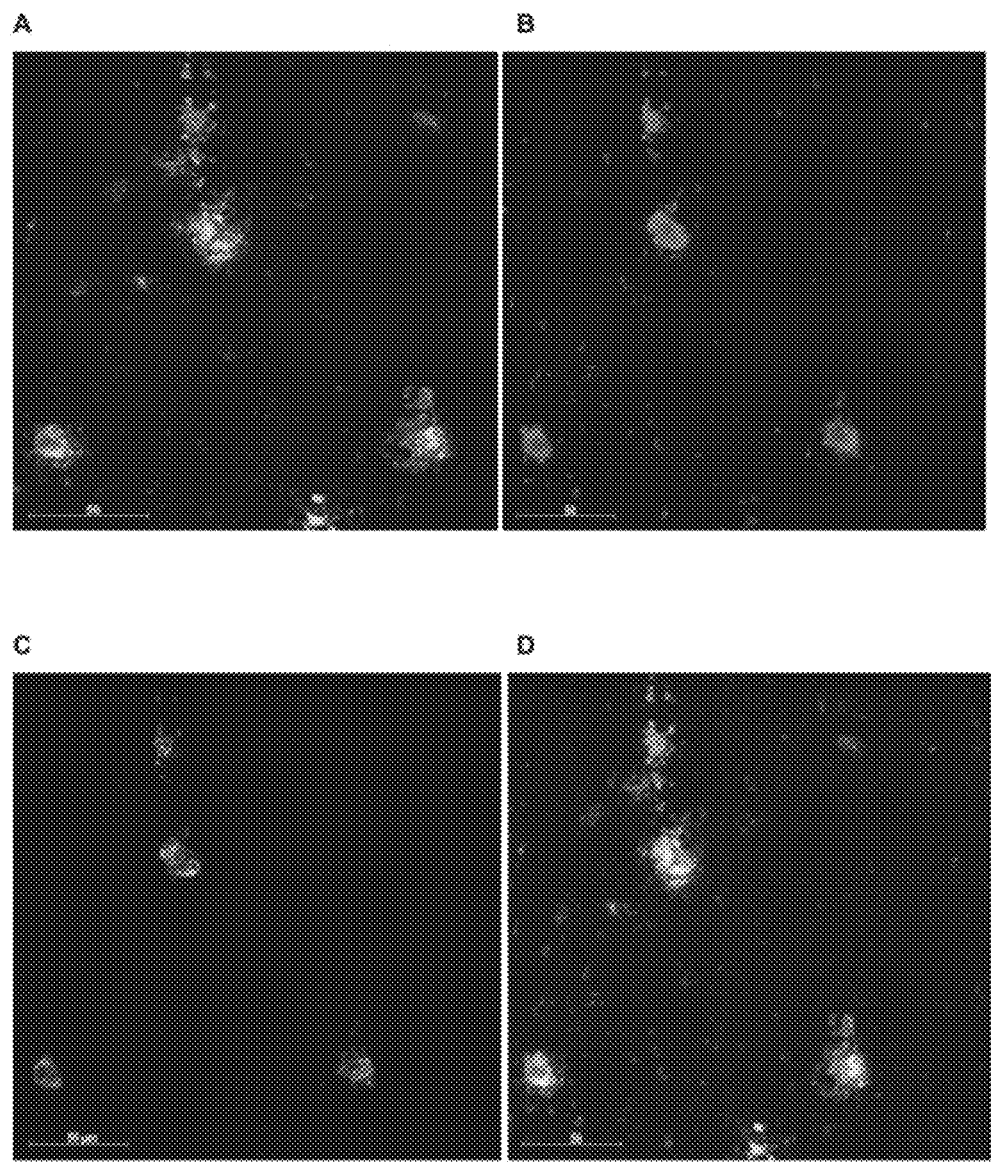

FIG. 11: In vivo decoration of amyloid plaques in an APP/PS2 double transgenic mouse after intravenous injection of 1 mg MS-Roche IgG #7.9.H4×7.12.L2. Experimental conditions and staining procedure were identical to those described in the legend of FIG. 10.

Scale: 1.6 cm=50 µm

Figure 12:
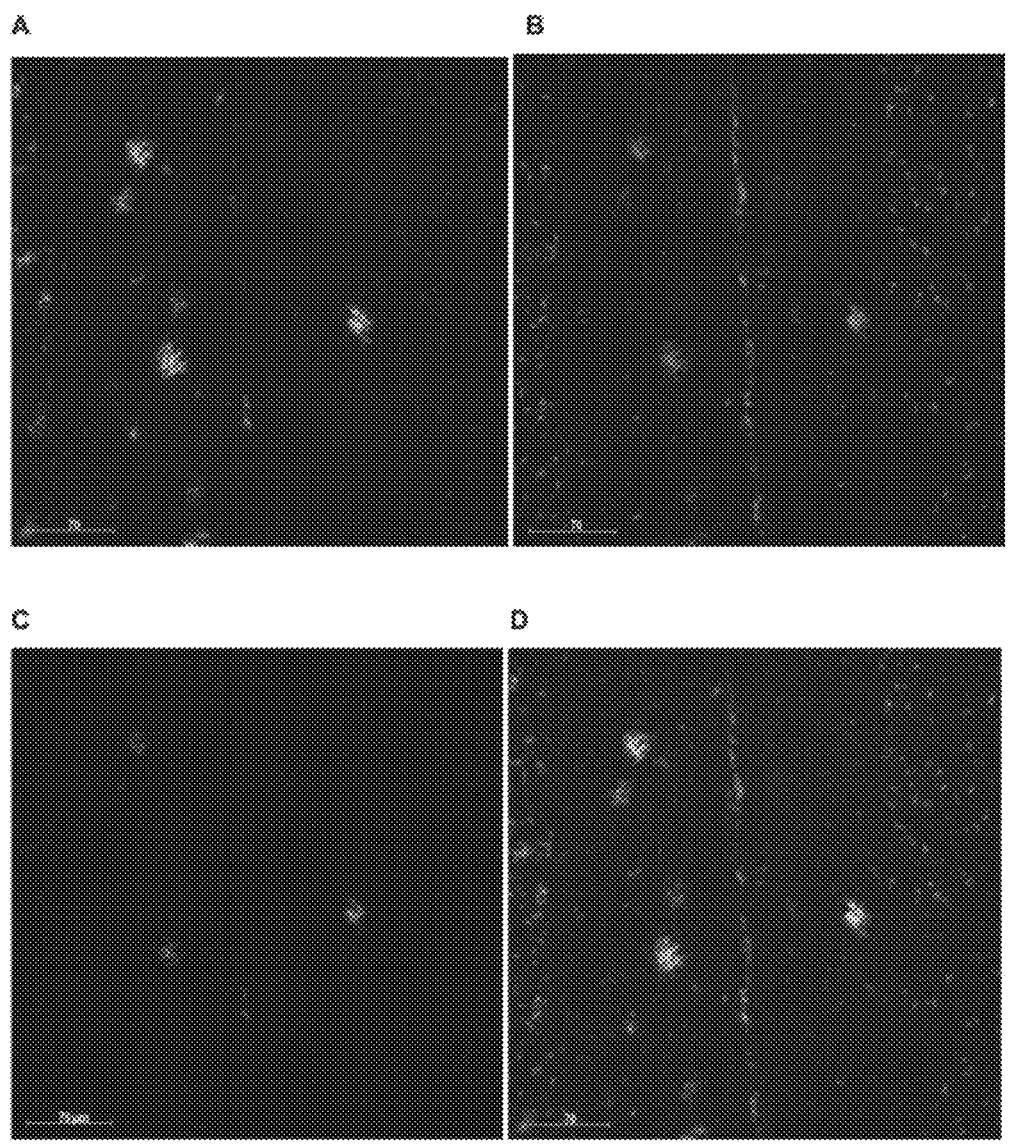

FIG. 12: In vivo decoration of amyloid plaques in an APP/PS2 double transgenic mouse after intravenous injection of 1 mg MS-Roche IgG #7.11.H1×7.2.L1 (MAB 11). Experimental conditions and staining procedure were identical to those described in the legend of FIG. 10.

Scale: 1.4 cm=70 µm

Figure 13:
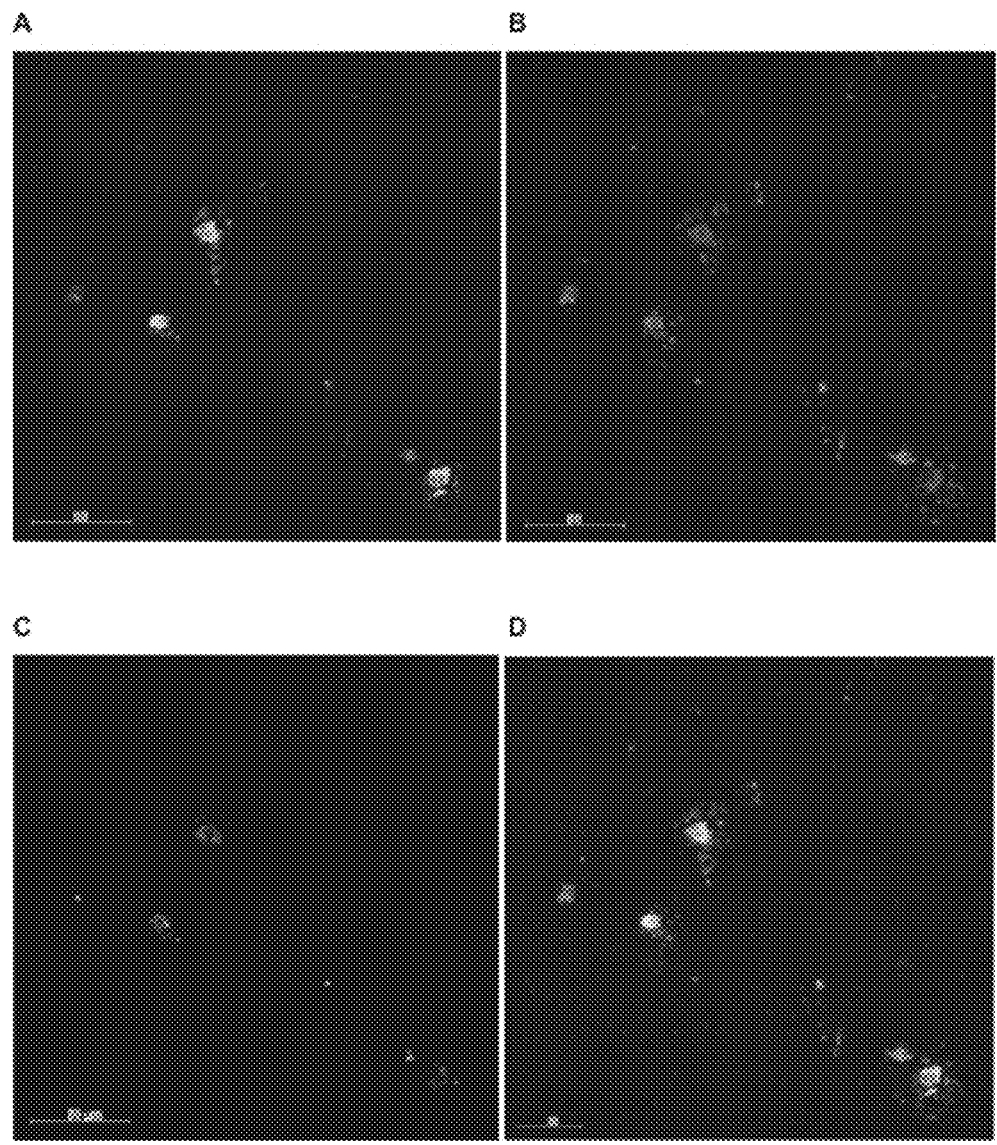

FIG. 13: In vivo decoration of amyloid plaques in an APP/PS2 double transgenic mouse after intravenous injection of 2 mg MS-Roche IgG #7.9.H7 (MAB 31) at day 0, 3, and 6. After nine days the mouse was perfused with phosphate-buffered saline and sacrificed. The presence of human IgG bound to amyloid plaques was revealed by confocal microscopy after labelling cryostat sections from the frontal cortex with a goat anti-human IgG-Cy3 conjugate (panel B). The same section was counterstained with an anti-Abeta mouse monoclonal antibody (BAP-2-Alexa488 conjugate, panel A) to visualize the position of amyloid plaques. Individual red (panel B) and green (panel A) channels, merged image (panel D) and colocalized (panel C) signals and are shown.

Scale: 1.6 cm=80 µm (panels A, B, C); 1.0 cm=50 µm (panel D)

Figure 14:
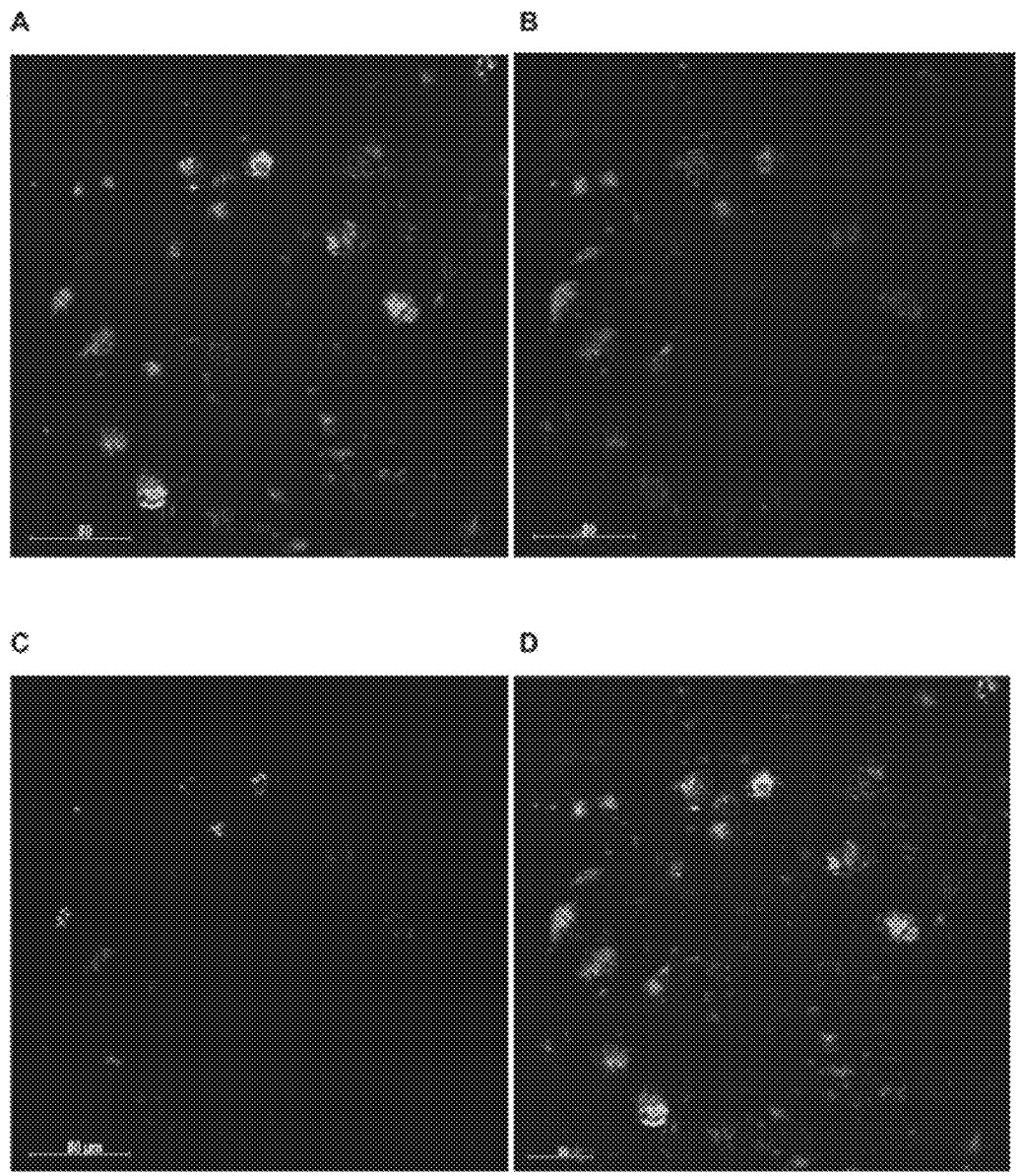

FIG. 14: In vivo decoration of amyloid plaques in an APP/PS2 double transgenic mouse after intravenous injection of 2 mg MS-Roche IgG #7.11.H1×7.2.L1 (MAB 11) at day 0, 3 and 6. Experimental conditions and staining procedure were identical to those described in the legend of FIG. 13.

Scale: 1.6 cm=80 µm

Figure 15:
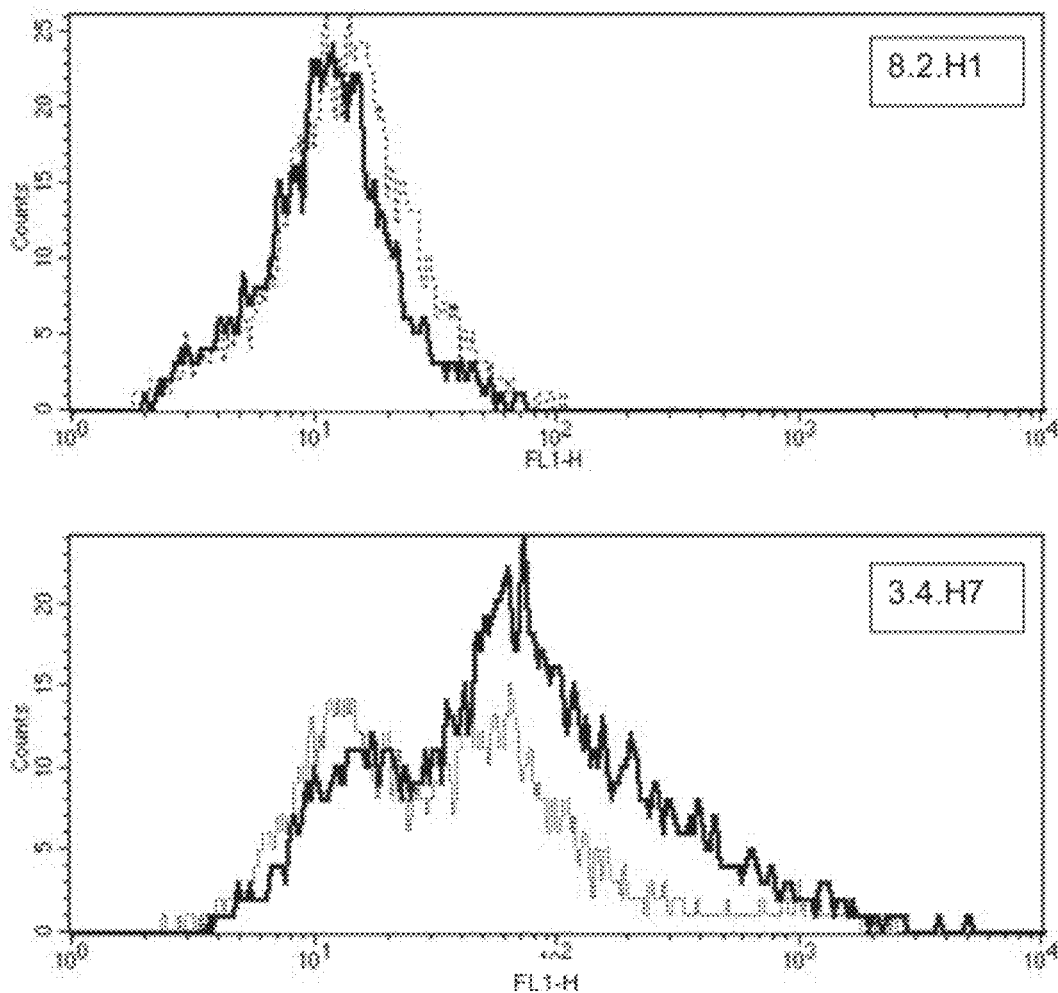

FIG. 15: Binding analysis of anti-Aβ antibodies to cell surface APP. Antibody binding to human APP-transfected HEK293 cells and non-transfected control cells was analyzed by flow cytometry.

The examples illustrate the invention.

EXAMPLES

Example 1

Construction and Screening of a Human Combinatorial Antibody Library (HuCAL®-Fab 1)

Cloning of HuCAL®-Fab 1

Figure 1A:
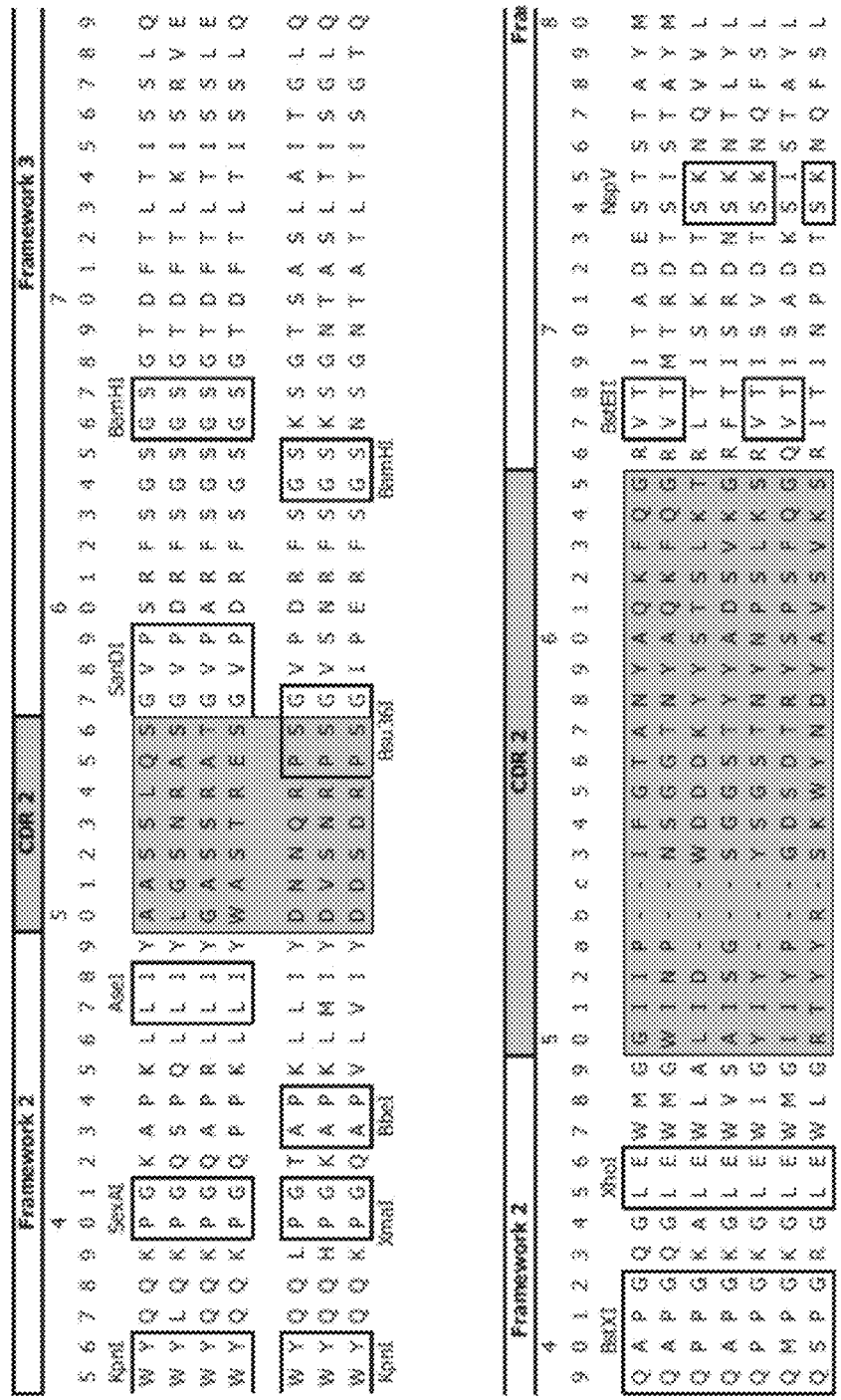
FIG. 1 Sequence summary of HuCAL®-Fab1 Library
The numbering is according to VBASE except the gap in VLλ position 9. In VBASE the gap is set at position 10 (Chothia et al., 1992). In the sequence summary all CDR3 residues which were kept constant are indicated. Corresponding sequences employed for the HuCAL-Fab1 library can be found in the appended sequence listing.
A: amino acid sequence
B: DNA sequence
FIG. 2 Fab display vector pMORPH®18_Fab
Vector map and DNA sequence including restriction sites
FIG. 3 Fab expression vector pMORPH®x9_Fab
Vector map and DNA sequence including restriction sites FIG. 4 Sequences of the parental Fab fragments MS-Roche-3, MS-Roche-7 and MS-Roche 8
A: amino acid sequence
B: DNA sequence
Figure 1A:
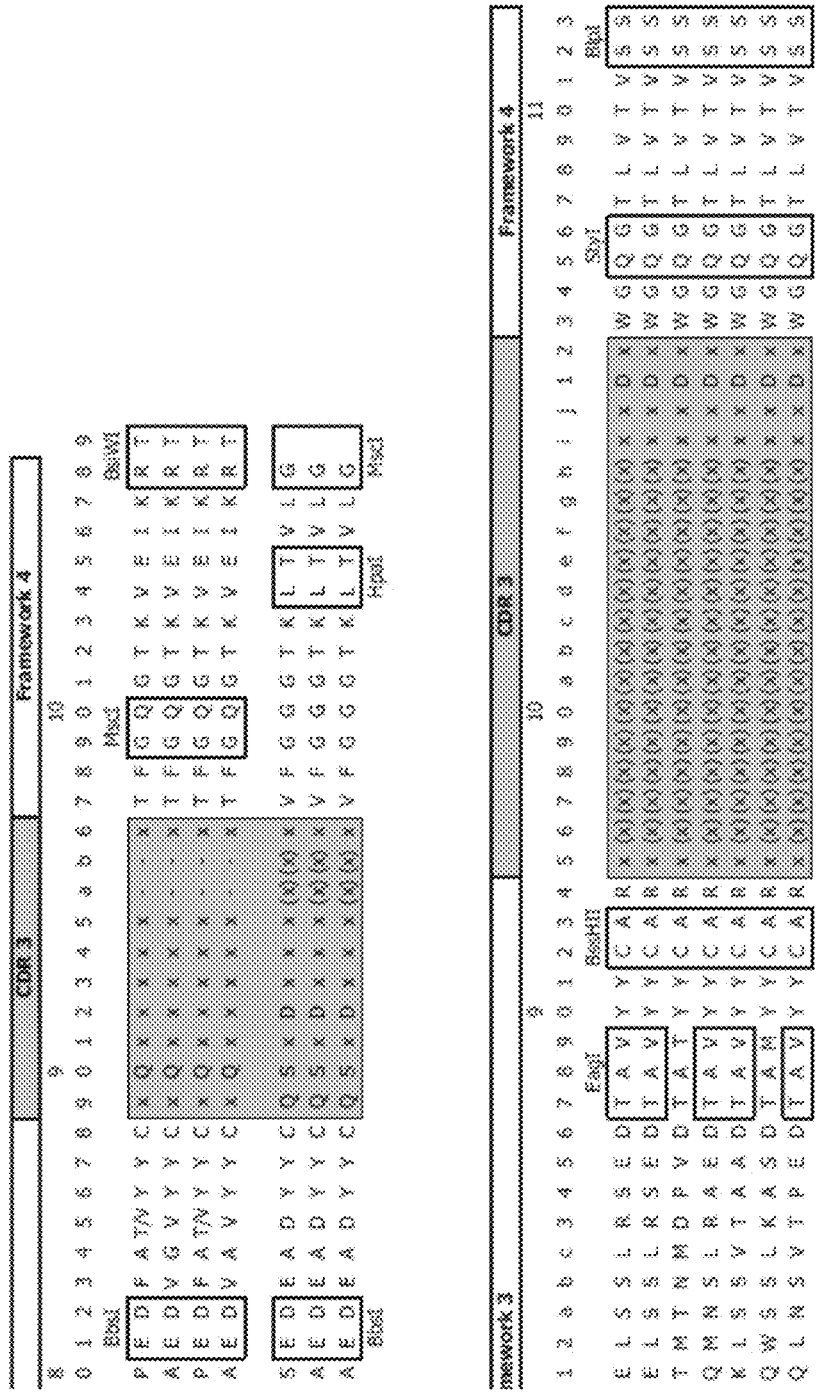
Figure 1B:
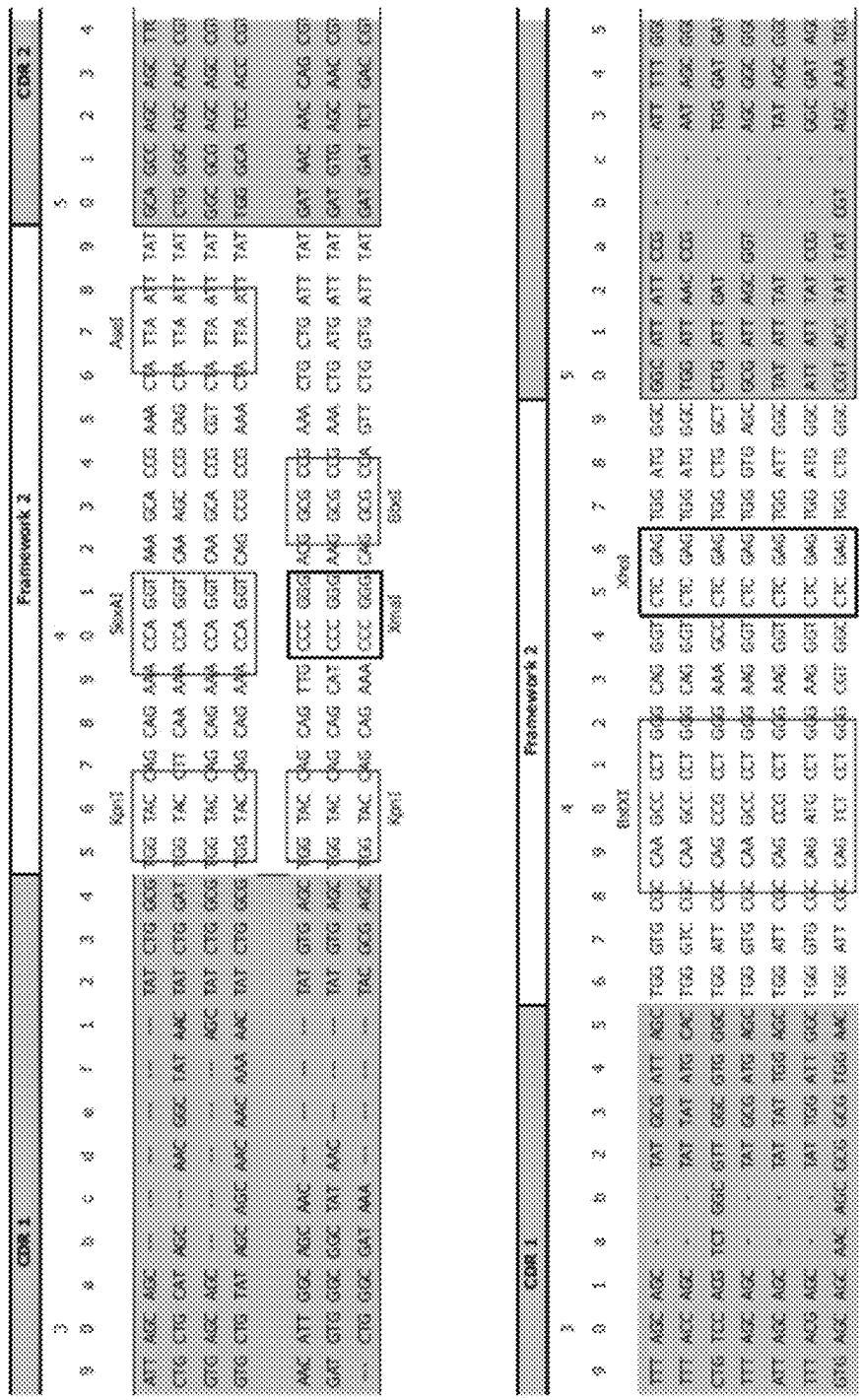
Figure 1B:
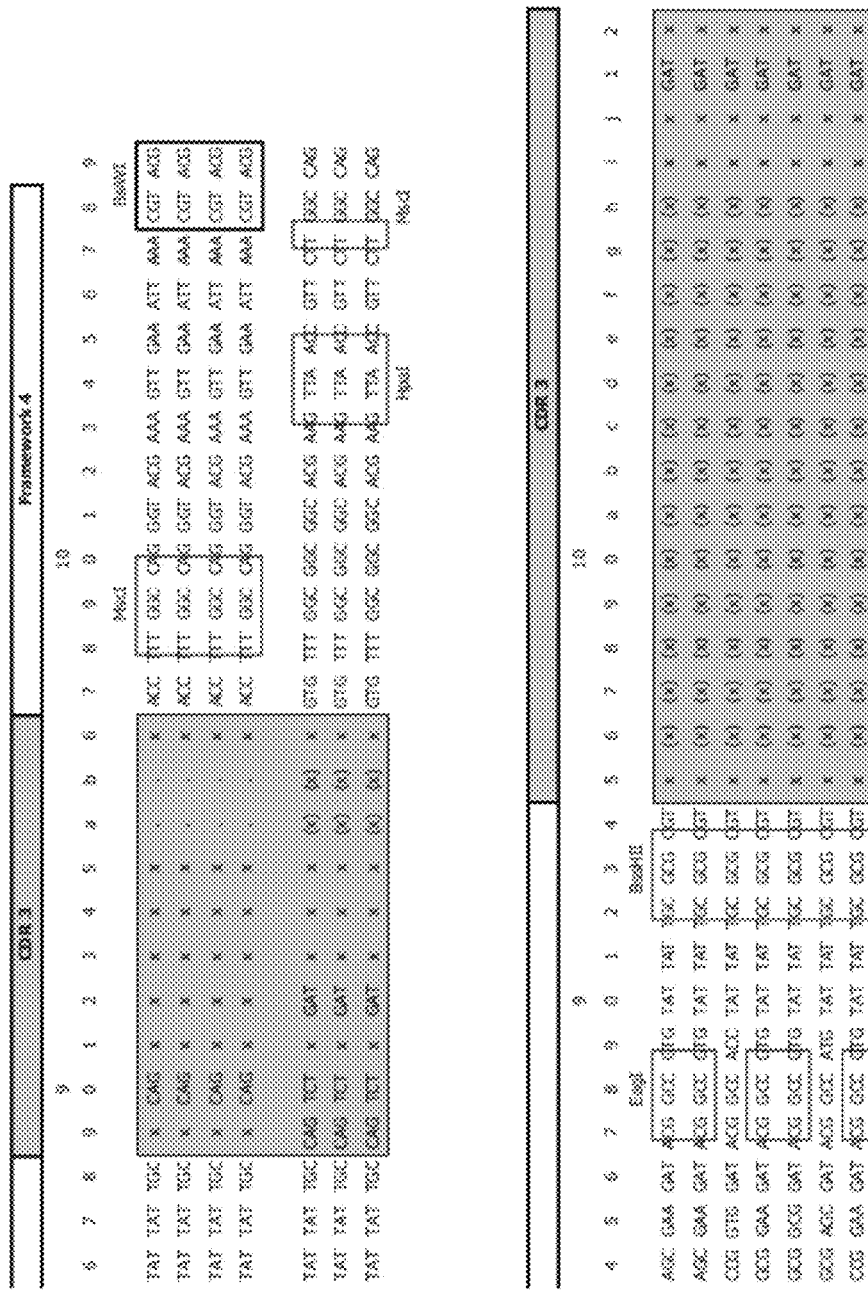

HuCAL®-Fab 1 is a fully synthetic, modular human antibody library in the Fab antibody fragment format. HuCAL®-Fab 1 was assembled starting from an antibody library in the single-chain format (HuCAL®-scFv; Knappik, (2000), *J. Mol. Biol.* 296, 57-86). Vλ positions 1 and 2. The original HuCAL® master genes were constructed with their authentic N-termini: VLλ1: QS (CAGAGC), VLλ2: QS (CAGAGC), and VLλ3: SY (AGCTAT). Sequences containing these amino acids are shown in WO 97/08320. During HuCAL® library construction, the first two amino acids were changed to DI to facilitate library cloning (EcoRI site). All HuCAL® libraries contain VLλ, genes with the EcoRV site GATATC (DI) at the 5'-end. All HuCAL® kappa genes (master genes and all genes in the library) contain DI at the 5'-end (FIGS. 1A and B).

VH position 1. The original HuCAL® master genes were constructed with their authentic N-termini: VH1A, VH1B, VH2, VH4, and VH6 with Q (=CAG) as the first amino acid and VH3 and VH5 with E (=GAA) as the first amino acid. Sequences containing these amino acids are shown in WO 97/08320. During cloning of the HuCAL®-Fab1 library, amino acid at position 1 of VH was changed to Q (CAG) in all VH genes (FIGS. 1A and B).

Design of the CDR Libraries

Vκ1/Vκ3 position 85. Because of the cassette mutagenesis procedure used to introduce the CDR3 library (Knappik, (2000), loc. cit.), position 85 of Vκ1 and Vκ3 can be either T or V. Thus, during HuCAL®-scFv1 library construction, position 85 of Vκ1 and Vκ3 was varied as follows: Vκ1 original, 85T (codon ACC); Vκ1 library, 85T or 85V (TRIM codons ACT or GTT); Vκ3 original, 85V (codon GTG); Vκ3 library, 85T or 85V (TRIM codons ACT or GTT); the same applies to HuCAL®-Fab1.

CDR3 design. All CDR3 residues, which were kept constant, are indicated in FIGS. 1A and B.

CDR3 length. The designed CDR3 length distribution is as follows. Residues, which were varied are shown in brackets (x) in FIG. 1. V kappa CDR3, 8 amino acid residues (position 89 to 96) (occasionally 7-10 residues), with Q89, S90, and D92 fixed; and VH CDR3, 5 to 28 amino acid residues (position 95 to 102) (occasionally 4-28), with D101 fixed.

Figure 2:
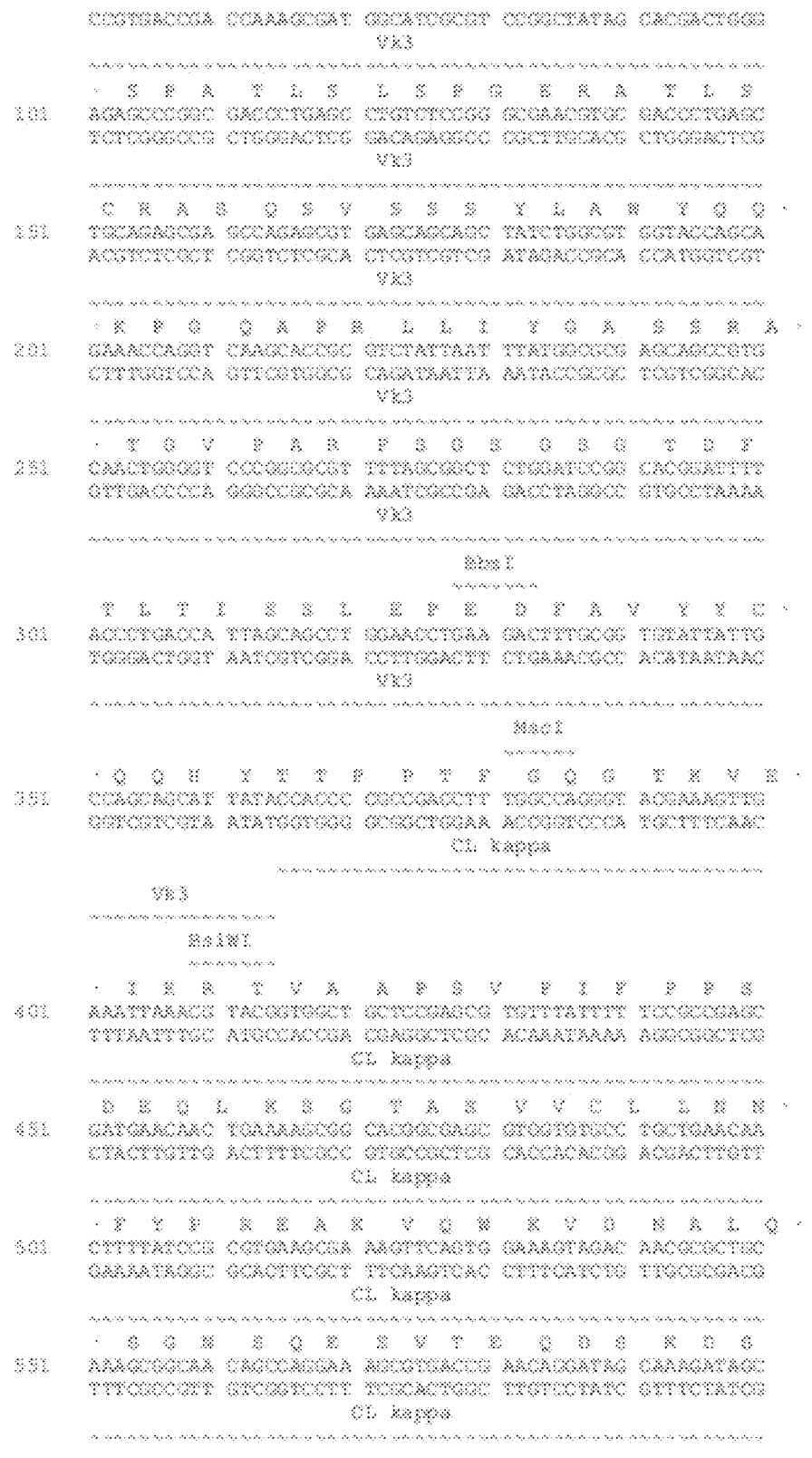
Figure 2:
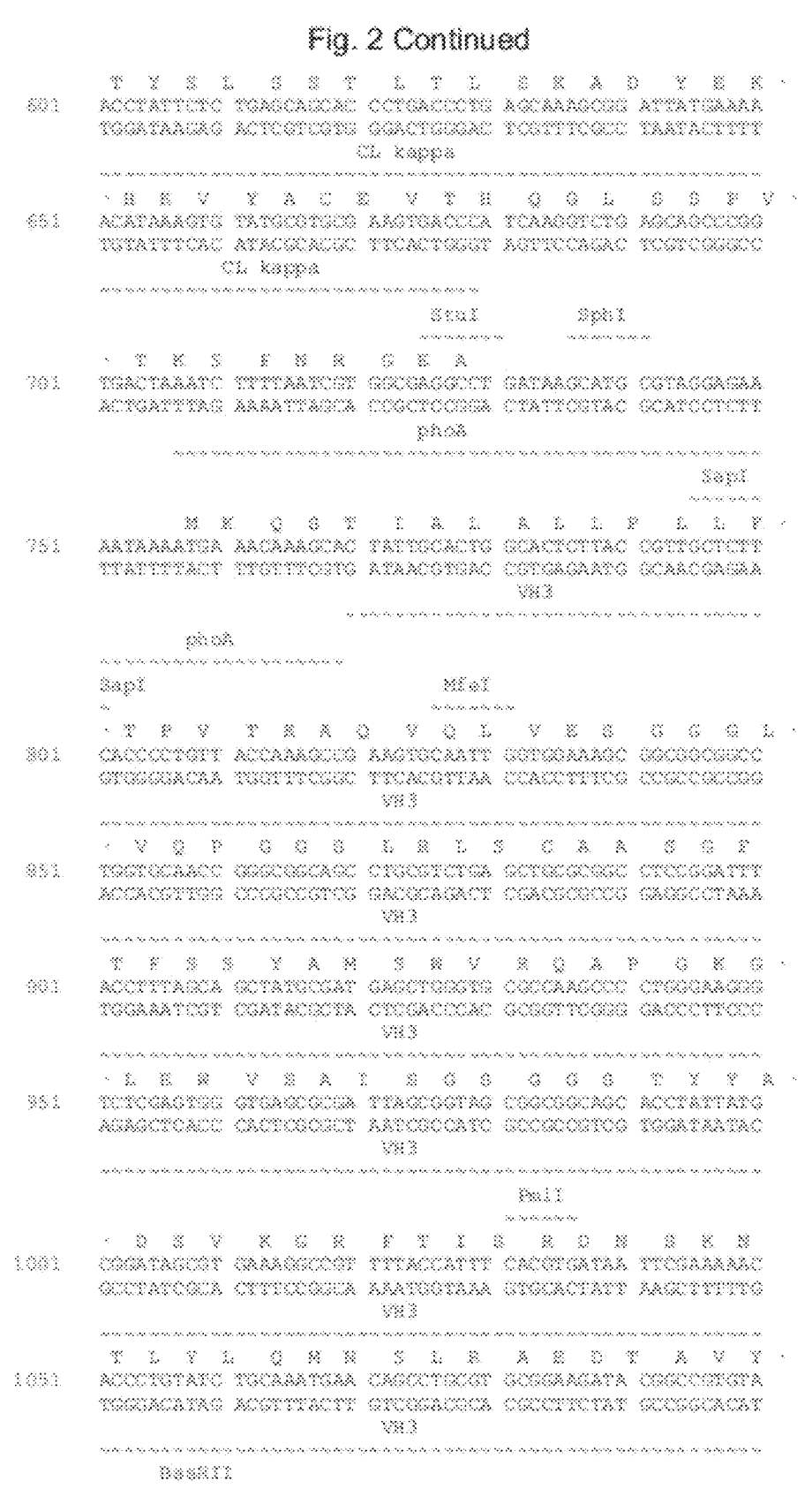

HuCAL®-Fab 1 was cloned into a phagemid expression vector pMORPH®18_Fab1 (FIG. 2). This vector comprises the Fd fragment with a phoA signal sequence fused at the C-terminus to a truncated gene III protein of filamentous phage, and further comprises the light chain VL-CL with an ompA signal sequence. Both chains are under the control of the lac operon. The constant domains Cλ Cκ and CH1 are synthetic genes fully compatible with the modular system of HuCAL® (Knappik, (2000), loc. cit.).

The whole VH-chain (MunI/StyI-fragment) was replaced by a 1205 bp dummy fragment containing the β-lactamase transcription unit (bla), thereby facilitating subsequent steps for vector fragment preparation and allowing for selection of complete VH removal.

After VH-replacement, VLλ, was removed by EcoRI/DraIII and VLκ by EcoRI/BsiWI and replaced with bacterial alkaline phosphatase (bap) gene fragment (1420 bp).

As the variability of the light chains is lower than that of the heavy chains, cloning was started with the light chain libraries. The $VL_\lambda$ and $VL_\kappa$ light chain libraries diversified in L-CDR3, which were generated for the HuCAL®-scFv library (Knappik, (2000), loc. cit.) were also used for cloning of HuCAL®-Fab1. In case of λ, they consisted of the λ1-, λ2- and λ3-HuCAL®-framework and had a total variability of $5.7 \times 10^6$. $VL_\lambda$ fragments were amplified by 15 PCR cycles (Pwo-polymerase) with primers 5'-GTGGTGGTTC-CGATATC-3' (SEQ ID NO: 28) and 5'-AGCGTCA-CACTCGGTGCGGCTTTCGGCTGGCCAA-GAACGGTTA-3' (SEQ ID NO: 29). PCR-products were digested with EcoRV/DraIII and gel-purified. In case of the $VL_\lambda$-library, the bap-dummy was removed by EcoRV/DraIII from the library vector. 2 µg of gelpurified vector were ligated with a 3-fold molar excess of $VL_\lambda$-chains for 16 h at 16° C., and the ligation mixtures were electroporated in 800 µl *E. coli* TOP10F cells (Invitrogen), yielding altogether $4.1 \times 10^8$ independent colonies. The transformants were amplified about 2000-fold in 2×YT/1% glucose/34 µg/ml chloramphenicol/100 µg/ml ampicillin, harvested and stored in 20% (w/v) glycerol at −80° C. The κ libraries comprise the κ1-, κ2-, κ3- and κ4-HuCAL® master genes with a total variability of $5.7 \times 10^6$. $VL_\kappa$-chains were obtained by restriction digest with EcoRV/BsiWI and gel-purified. In case of the $VL_\kappa$-library, the bap-dummy was removed by EcoRV/BsIWI from the library vector. 2 µg of gel-purified vector were mixed with a 5-fold molar excess of $VL_\kappa$-chains. Ligation and transformation into *E. coli* TOP10F cells (Invitrogen) was performed as described for $VL_\lambda$-chains, yielding altogether $1.6 \times 10^8$ independent colonies. DNA of the two light chain libraries was prepared and the bla-dummy was removed by MunI/StyI, thereby generating the two vectors for insertion of the VH sub-libraries.

The VH libraries of HuCAL®-scFv were used for the generation of HuCAL®-Fab1. The VH libraries of HuCAL®-scFv consist of the master genes VH1A/B-6 diversified with two VH-CDR3 trinucleotide library cassettes differing in CDR3 length separately, and each VH-library combined with the $VL_\kappa$- and with the $VL_\lambda$-library. For the generation of the HuCAL®-Fab1 DNA from these VH-libraries was prepared preserving the original variability. The DNA was digested with MunI/StyI and gel-purified. A 5-fold molar excess of the VH-chains was ligated with 3 µg of the $VL_\lambda$-library vector and with 3 µg of the $VL_\kappa$-library vector for 4 h at 22° C. The ligation mixtures were electroporated for each vector in 1200 µl *E. coli* TOP10F cells (Invitrogen), yielding altogether $2.1 \times 10^{10}$ independent colonies. The transformants were amplified about 4000-fold in 2×YT/1% glucose/34 µg/ml chloramphenicol/10 µg/ml tetracycline, harvested and stored in 20% (w/v) glycerol at −80° C. As quality control the light chain and heavy chain of single clones was sequenced with 5'-CAGGAAACAGCTATGAC-3' (SEQ ID NO: 30) and 5'-TACCGTTGCTCTTCACCCC-3' (SEQ ID NO: 31), respectively.

Phagemid Rescue, Phage Amplification and Purification

HuCAL®-Fab 1 was amplified in 2×TY medium containing 34 µg/ml chloramphenicol, 10 µg/ml tetracycline and 1% glucose (2×TY-CG). After helper phage infection (VCSM13) at 37° C. at an $OD_{600}$ of about 0.5, centrifugation and resuspension in 2×TY/34 µg/ml chloramphenicol/50 µg/ml kanamycin cells were grown overnight at 30° C. Phage were PEG-precipitated from the supernatant (Ausubel, (1998), Current protocols in molecular biology. John Wiley & Sons, Inc., New York, USA), resuspended in PBS/20% glycerol and stored at −80° C. Phage amplification between two panning rounds was conducted as follows: mid-log phase TG1-cells were infected with eluted phage and plated onto LB-agar supplemented with 1% of glucose and 34 µg/ml of chloramphenicol. After overnight incubation at 30° C. colonies were scraped off, adjusted to an $OD_{600}$ of 0.5 and helper phage added as described above.

Example 2

Solid Phase Panning

Wells of MaxiSorp™ microtiterplates F96 (Nunc) were coated with 100 µl 2.5 µM human Aβ (1-40) peptide (Bachem) dissolved in TBS containing $NaN_3$ (0.05% v/v) and the sealed plate was incubated for 3 days at 37° C. where the peptide is prone to aggregate on the plate. After blocking with 5% non-fat dried milk in TBS, $1-5 \times 10^{12}$ HuCAL®-Fab phage purified as above were added for 1 h at 20° C. After several washing steps, bound phages were eluted by pH-elution with 500 mM NaCl, 100 mM glycin pH 2.2 and subsequent neutralisation with 1M TRIS-Cl pH 7. Three rounds of panning were performed with phage amplification conducted between each round as described above, the washing stringency was increased from round to round.

Example 3

Subcloning of Selected Fab Fragments for Expression

Figure 3:
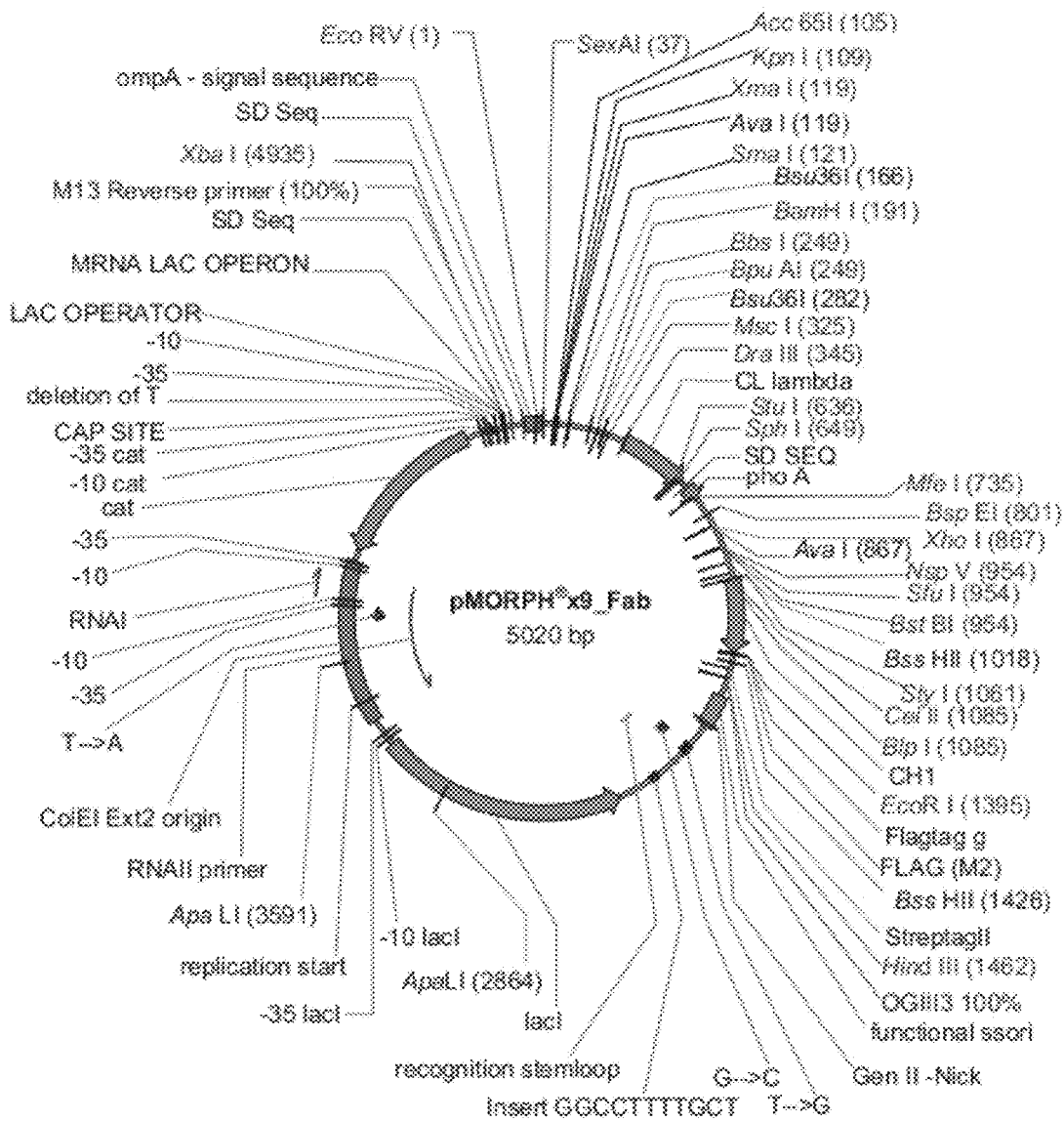
Figure 4A:
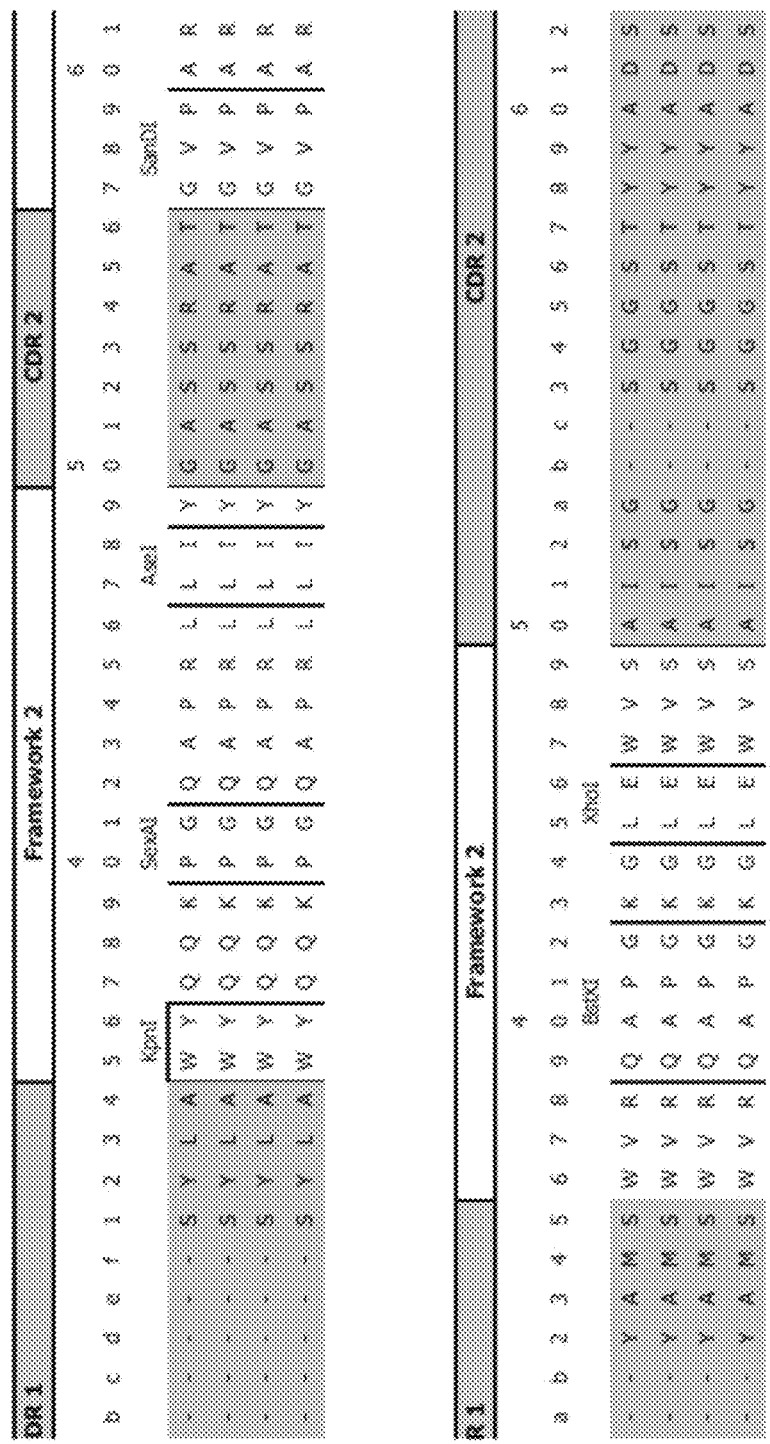
Figure 4A:
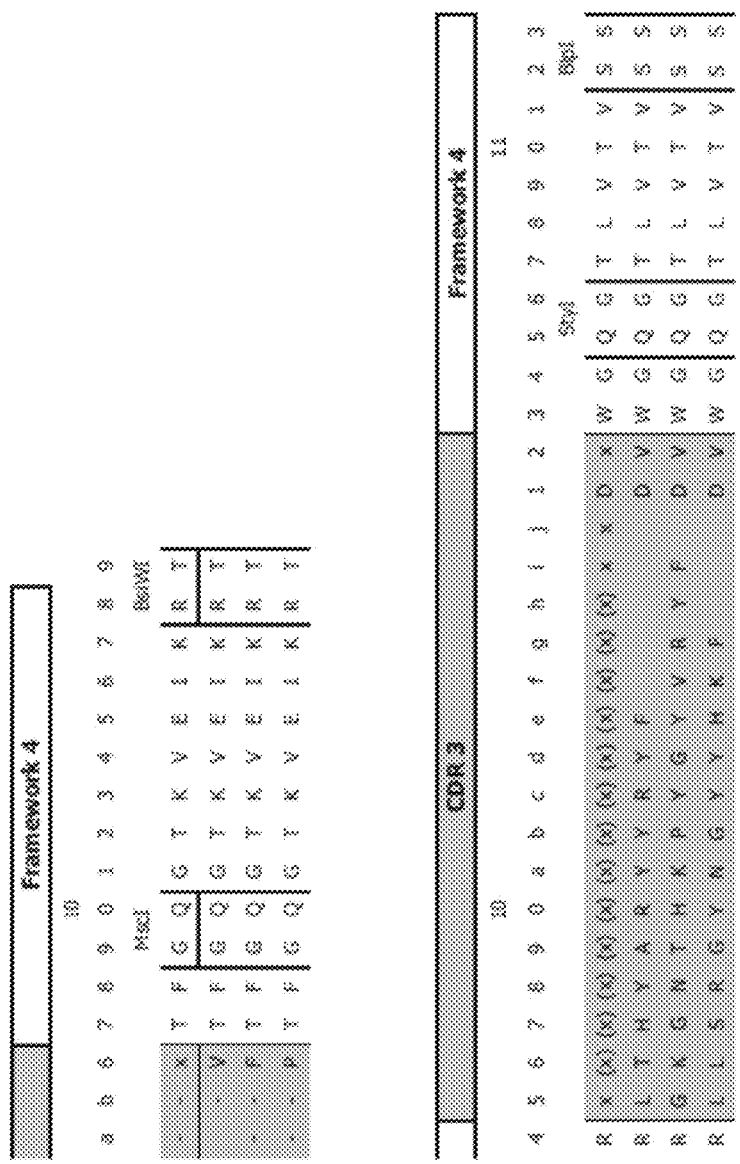
Figure 4B:
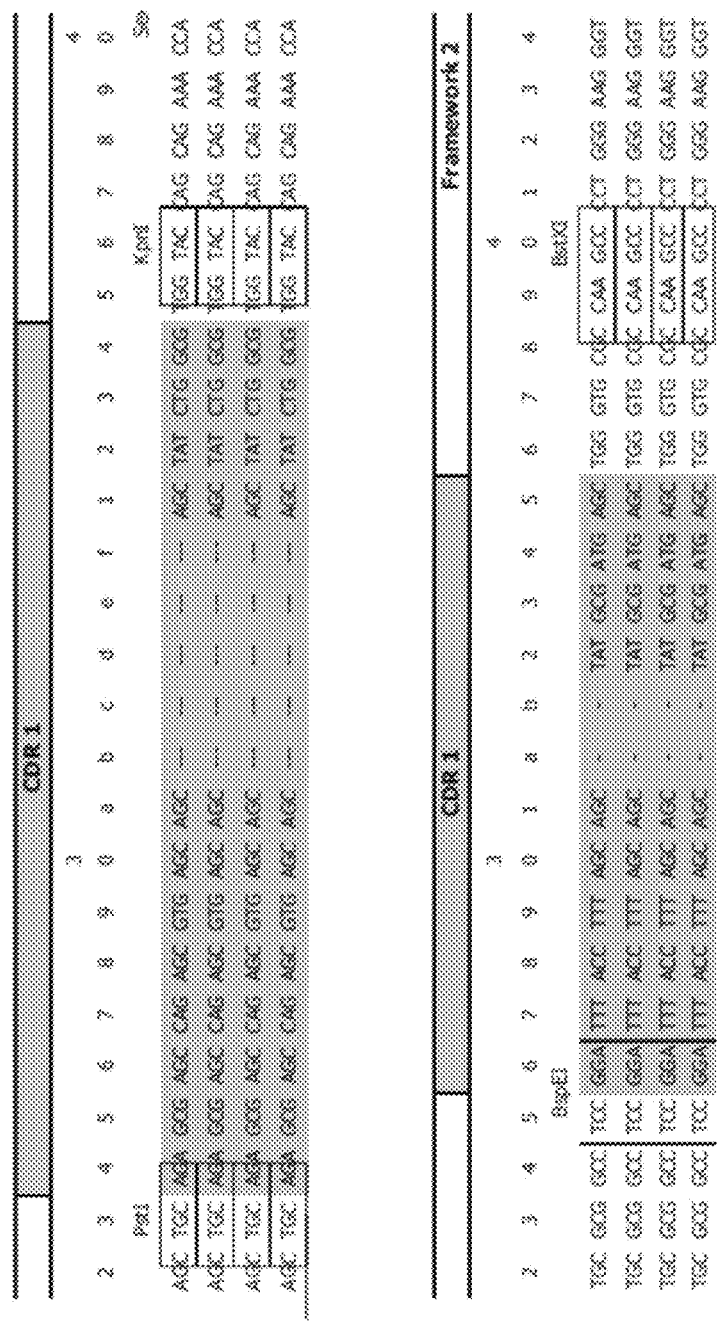
Figure 4B:
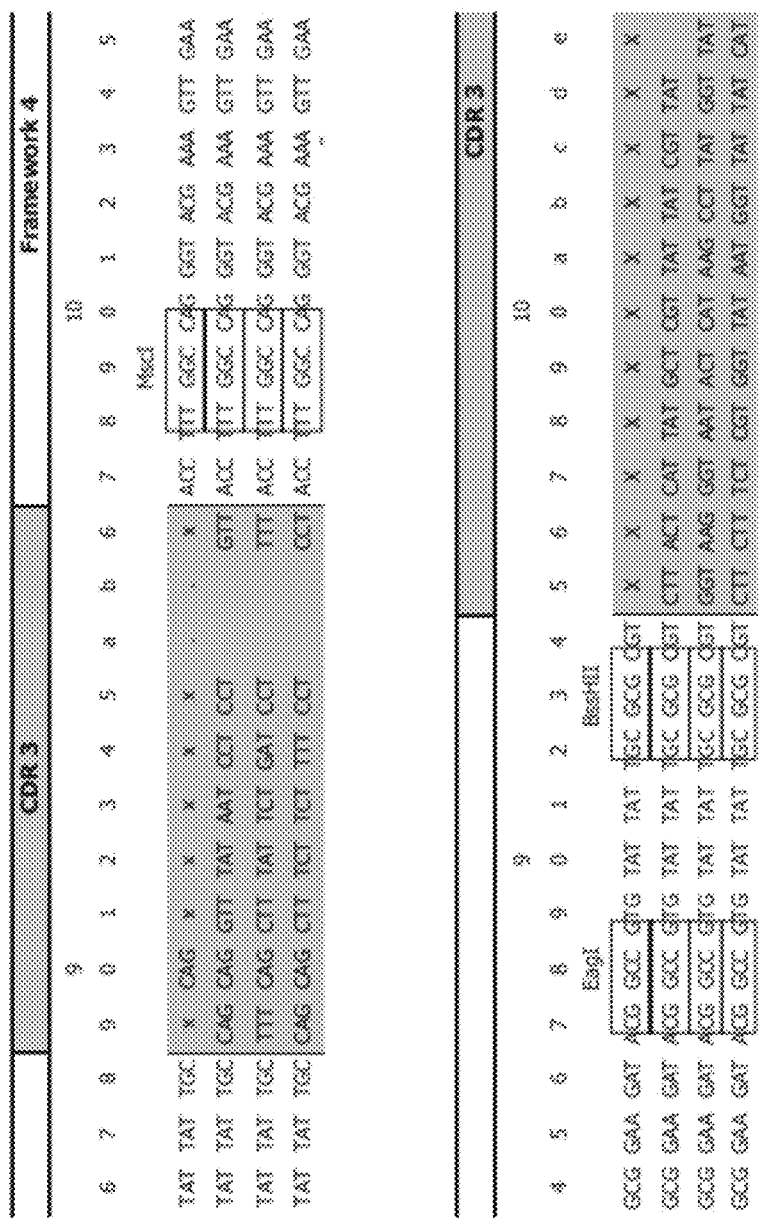
Figure 4B:
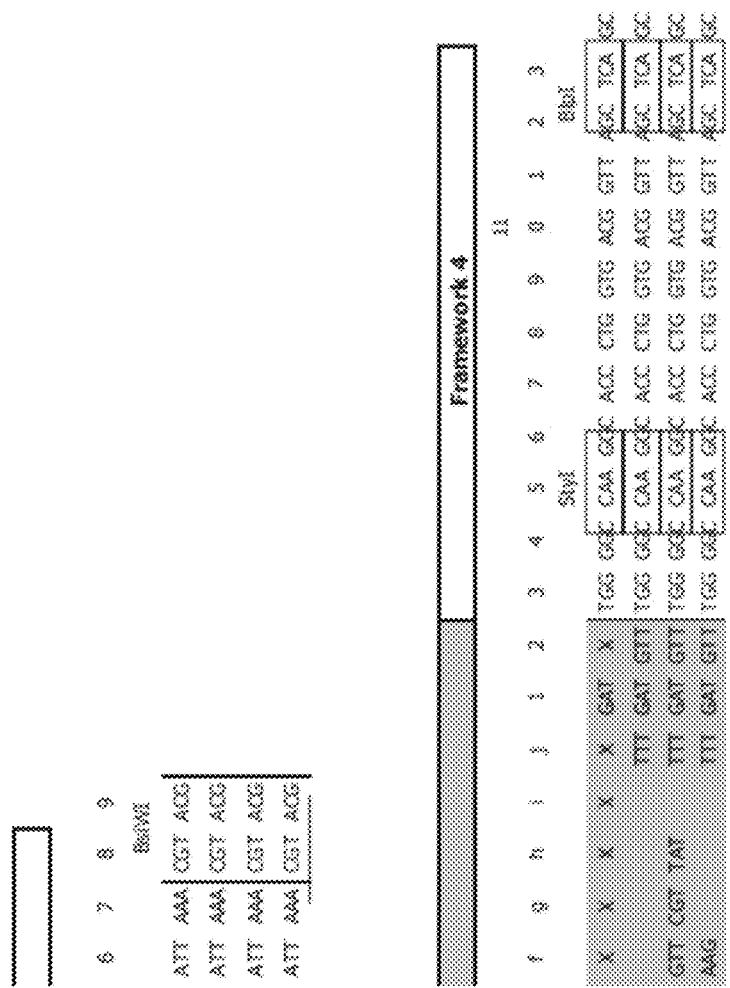

The Fab-encoding inserts of the selected HuCAL®-Fab fragments were subcloned into the expression vector pMORPH®×7_FS to facilitate rapid expression of soluble Fab. The DNA preparation of the selected HuCAL®-Fab clones was digested with XbaI/EcoRI, thus cutting out the Fab encoding insert (ompA-VL and phoA-Fd). Subcloning of the purified inserts into the XbaI/EcoRI cut vector pMORPH®×7, previously carrying a scFv insert, leads to a Fab expression vector designated pMORPH®×9_Fab1 (FIG. 3). Fabs expressed in this vector carry two C-terminal tags (FLAG and Strep) for detection and purification.

Example 4

Identification of Aβ-binding Fab Fragments by ELISA

Wells of Maxisorp™ microtiterplates F384 (Nunc) were coated with 20 µl 2.5 µM human Aβ (1-40) peptide (Bachem) dissolved in TBS containing $NaN_3$ (0.05% v/v) and the sealed plate was incubated for 3 days at 37° C., where the peptide is prone to aggregate on the plate. Expression of individual Fab was induced with 1 mM IPTG for 16 h at 22° C. Soluble Fab was extracted from *E. coli* by BEL lysis (boric acid, NaCl, EDTA and lysozyme containing buffer pH 8) and used in an ELISA. The Fab fragment was detected with an alkaline phosphatase-conjugated goat anti-Fab antibody (Dianova/Jackson Immuno Research). After excitation at 340 nm the emission at 535 nm was read out after addition of AttoPhos fluorescence substrate (Roche Diagnostics).

Example 5

Optimization of Antibody Fragments

In order to optimize the binding affinity of the selected Aβ binding antibody fragments, some of the Fab fragments, MS-Roche-3 (MSR-3), MS-Roche-7 (MSR-7) and MS-Roche-8

(MSR-8) (FIG. 4), were used to construct a library of Fab antibody fragments by replacing the parental VL κ3 chain by the pool of all kappa chains κ1-3 diversified in CDR3 from the HuCAL® library (Knappik et al., 2000).

The Fab fragments MS-Roche-3, 7 and 8 were cloned via XbaI/EcoRI from pMORPH®×9_FS into pMORPH®18, a phagemid-based vector for phage display of Fab fragments, to generate pMORPH®18_Fab1 (FIG. 2). A kappa chain pool was cloned into pMORPH®18_Fab1 via XbaI/SphI restriction sites.

The resulting Fab optimization library was screened by panning against aggregated human Aβ (1-40) peptide coated to a solid support as described in example 2.

Optimized clones were identified by koff-ranking in a Biacore assay as described in Example 8. The optimized clones MS-Roche-3.2, 3.3, 3.4, 3.6, 7.2, 7.3, 7.4, 7.9, 7.11, 7.12, 8.1, 8.2, were further characterized and showed improved affinity and biological activity compared to the starting fragment MS-Roche-3, MS-Roche-7 and MS-Roche-8 (FIG. 4). The CDRs listed refer to the HuCAL® consensus-based antibody gene VH3kappa3. The Fab fragment MS-Roche-7.12 was obtained by cloning the HCDR3 of parental clone MS-R 7 into a HuCAL®-Fab library, carrying diversity in all 6 CDR regions using a design procedure identical with that for CDR3 cassettes described in Knappik et al., 2000. The library cassettes were designed strongly biased for the known natural distribution of amino acids and following the concept of canonical CDR conformations established by Allazikani (Allazikani et al., 1997). However in contrast to the HuCAL® master genes, the clone MS-Roche 7.12 contains amino acid S at position 49 of the VL chain (see appended table 1).

Figure 5:
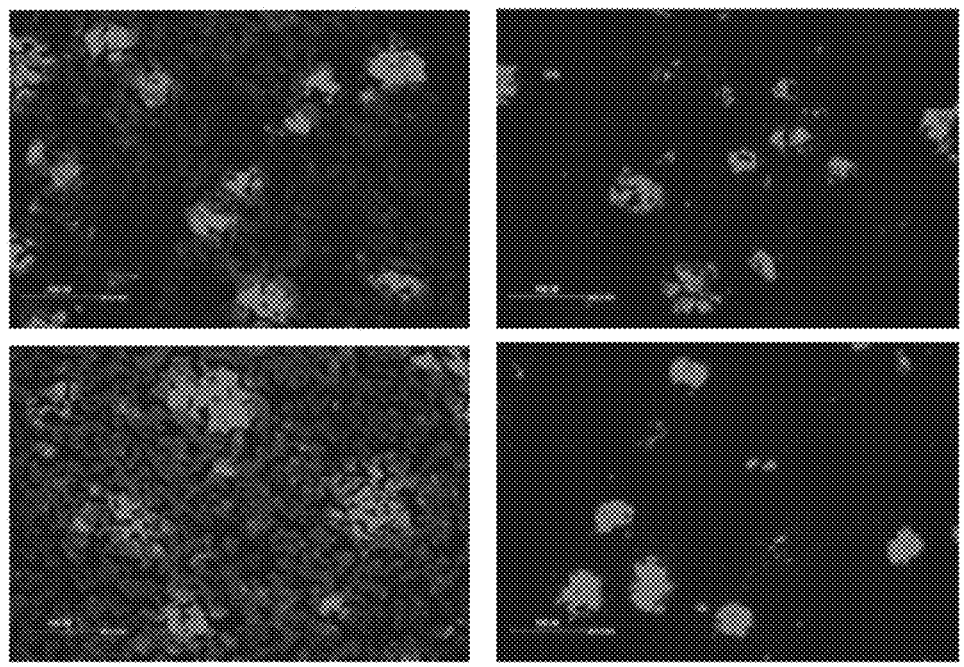
FIG. 5: Indirect immunofluorescence of amyloid-plaques from a cryostat section of human temporal cortex. The plaques were labeled with MS-R # 3.2 Fab (upper panels) and MS-R # 7.4 Fab (lower panels) at 20 µg/ml (left panels) and 5 µg/ml (right panels) under stringent blocking conditions. Bound MS-R Fab was revealed by goat anti-human-Cy3.

The optimized Fabs after the first affinity maturation round showed improved characteristics over the starting MS-Roche-3, MS-Roche-7 and MS-Roche-8 clones (FIG. 4). The binding affinities of the maturated Fabs to Aβ1-40 and Aβ1-42 were significantly increased yielding $K_D$ values in the range of 22-240 nM in comparison to 850-1714 nM of the parental clones (Table 3). Immunohistochemistry analysis of amyloid plaques in human AD brain sections also showed a significantly increased staining profile of the maturated clones, i.e. better signal to background ratios were obtained and positive plaque staining was detected at relatively low concentrations of the maturated Fabs (FIG. 5).

For further optimization, the VH CDR2 regions and the VL CDR1 regions of a set of antibody fragments derived from L-CDR3 optimized MS-Roche-3, -7 and -8 (table 1; FIG. 4) were optimized by cassette mutagenesis using trinucleotide-directed mutagenesis (Virnekäs et al., 1994). Therefore, a trinucleotide-based HCDR2 cassette and a trinucleotide-based LCDR1 cassette were constructed using a design procedure identical with that for CDR3 cassettes described in Knappik et al., 2000. The library cassettes were designed strongly biased for the known natural distribution of amino acids and following the concept of canonical CDR conformations established by Allazikani (Allazikani et al., 1997). The protocol used for the optimization of the initial selected antibody fragments would mimic the process of affinity maturation by somatic hypermutation observed during the natural immune response.

The resulting libraries were screened separately as described above leading to optimized clones either in the H-CDR2 or in the L-CDR1 region. All clones were identified as above by an improved koff towards Aβ1-40-fibers after a koff-ranking in the Biacore and showed improved affinity either to Aβ1-40 or Aβ-42 or both when compared to the corresponding parent clone (Table 3). Table 1 contains the sequence characteristics of the parental as well as sequences of the optimized clones. The CDRs listed refer to the HuCAL® consensus-based antibody gene VH3kappa3.

For example, the affinity of the MS-Roche-7 parental Fab towards Ab1-40 was improved over 35-fold from 1100 nM to 31 nM after L-CDR3 optimization (MS-Roche-7.9) and further improved to 5 nM after H-CDR2 optimization (MS-Roche-7.9H2) as illustrated in Table 3.

The H-CDR2 and L-CDR1 optimization procedure not only increased the affinity but also resulted for some of the clones in a significantly improved staining of amyloid plaques in AD brain section, as particularly seen with MS-Roche 7.9H2 and 7.9H3.

TABLE 1

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| MS-Roche #3 | RASQSVSSSYLA | Y | GASSRAT | V | QQVYNPPV | GFTFSSYAMS | W | AISGSGGSTYYADSVKG | LTHYARYYRYFDV |
| MS-Roche #3.1 | RASQSVSSSYLA | Y | GASSRAT | T | QQVYSVPP | GFTFSSYAMS | W | AISGSGGSTYYADSVKG | LTHYARYYRYFDV |
| MS-Roche #3.2 | RASQSVSSSYLA | Y | GASSRAT | V | QQIYSYPP | GFTFSSYAMS | W | AISGSGGSTYYADSVKG | LTHYARYYRYFDV |
| MS-Roche #3.3 | RASQSVSSSYLA | Y | GASSRAT | V | HQMSSYPP | GFTFSSYAMS | W | AISGSGGSTYYADSVKG | LTHYARYYRYFDV |
| MS-Roche #3.4 | RASQSVSSSYLA | Y | GASSRAT | T | QQTYDYPP | GFTFSSYAMS | W | AISGSGGSTYYADSVKG | LTHYARYYRYFDV |
| MS-Roche #3.5 | RASQSVSSSYLA | Y | GASSRAT | T | QQIYDYPP | GFTFSSYAMS | W | AISGSGGSTYYADSVKG | LTHYARYYRYFDV |
| MS-Roche #3.6 | RASQSVSSSYLA | Y | GASSRAT | V | QQTYNYPP | GFTFSSYAMS | W | AISGSGGSTYYADSVKG | LTHYARYYRYFDV |
| MS-Roche #3.2.H1 | RASQSVSSSYLA | Y | GASSRAT | V | QQIYSYPP | GFTFSSYAMS | W | AISEHGLNIYYADSVKG | LTHYARYYRYFDV |
| MS-Roche #3.2.H2 | RASQSVSSSYLA | Y | GASSRAT | V | QQIYSYPP | GFTFSSYAMS | W | AISQRGQFTYYADSVKG | LTHYARYYRYFDV |
| MS-Roche #3.3.H1 | RASQSVSSSYLA | Y | GASSRAT | V | HQMSSYPP | GFTFSSYAMS | W | VISEKSRFIYYADSVKG | LTHYARYYRYFDV |
| MS-Roche #3.3.H2 | RASQSVSSSYLA | Y | GASSRAT | V | HQMSSYPP | GFTFSSYAMS | W | VISQESQYKYYADSVKG | LTHYARYYRYFDV |
| MS-Roche #3.3.H3 | RASQSVSSSYLA | Y | GASSRAT | V | HQMSSYPP | GFTFSSYAMS | W | AISQNGFHIYYADSVKG | LTHYARYYRYFDV |
| MS-Roche #3.4.H1 | RASQSVSSSYLA | Y | GASSRAT | T | QQTYDYPP | GFTFSSYAMS | W | AISETSIRKYYADSVKG | LTHYARYYRYFDV |
| MS-Roche #3.4.H2 | RASQSVSSSYLA | Y | GASSRAT | T | QQTYDYPP | GFTFSSYAMS | W | VIDMVGHTYYADSVKG | LTHYARYYRYFDV |

TABLE 1-continued

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| MS-Roche #3.4.H3 | RASQSVSSSYLA | Y | GASSRAT | T | QQTYDYPP | GFTFSSYAMS | W | VISQTGRKIYYADSVKG | LTHYARYYRYFDV |
| MS-Roche #3.4.H4 | RASQSVSSSYLA | Y | GASSRAT | T | QQTYDYPP | GFTFSSYAMS | W | AISETGMHIYYADSVKG | LTHYARYYRYFDV |
| MS-Roche #3.4.H5 | RASQSVSSSYLA | Y | GASSRAT | T | QQTYDYPP | GFTFSSYAMS | W | VISQVGAHIYYADSVKG | LTHYARYYRYFDV |
| MS-Roche #3.4.H6 | RASQSVSSSYLA | Y | GASSRAT | T | QQTYDYPP | GFTFSSYAMS | W | AISESGWSTYYADSVKG | LTHYARYYRYFDV |
| MS-Roche #3.4.H7 | RASQSVSSSYLA | Y | GASSRAT | T | QQTYDYPP | GFTFSSYAMS | W | VISETGKNIYYADSVKG | LTHYARYYRYFDV |
| MS-Roche #3.4.H8 | RASQSVSSSYLA | Y | GASSRAT | T | QQTYDYPP | GFTFSSYAMS | W | AISEHGRFKYYADSVKG | LTHYARYYRYFDV |
| MS-Roche #3.4.H9 | RASQSVSSSYLA | Y | GASSRAT | T | QQTYDYPP | GFTFSSYAMS | W | AISESSKNKYYADSVKG | LTHYARYYRYFDV |
| MS-Roche #3.4.H10 | RASQSVSSSYLA | Y | GASSRAT | T | QQTYDYPP | GFTFSSYAMS | W | AISESGRGKYYADSVKG | LTHYARYYRYFDV |
| MS-Roche #3.4.H11 | RASQSVSSSYLA | Y | GASSRAT | T | QQTYDYPP | GFTFSSYAMS | W | AISEFGKNIYYADSVKG | LTHYARYYRYFDV |
| MS-Roche #3.4.H12 | RASQSVSSSYLA | Y | GASSRAT | T | QQTYDYPP | GFTFSSYAMS | W | VISQTGQNIYYADSVKG | LTHYARYYRYFDV |
| MS-Roche #3.4.H13 | RASQSVSSSYLA | Y | GASSRAT | T | QQTYDYPP | GFTFSSYAMS | W | AISEQGRNIYYADSVKG | LTHYARYYRYFDV |
| MS-Roche #3.4.H14 | RASQSVSSSYLA | Y | GASSRAT | T | QQTYDYPP | GFTFSSYAMS | W | AISESGQYKYYADSVKG | LTHYARYYRYFDV |
| MS-Roche #3.4.H16 | RASQSVSSSYLA | Y | GASSRAT | T | QQTYDYPP | GFTFSSYAMS | W | AISESGVNIYYADSVKG | LTHYARYYRYFDV |
| MS-Roche #3.4.H17 | RASQSVSSSYLA | Y | GASSRAT | T | QQTYDYPP | GFTFSSYAMS | W | AISEFGQFIYYADSVKG | LTHYARYYRYFDV |
| MS-Roche #3.4.H18 | RASQSVSSSYLA | Y | GASSRAT | T | QQTYDYPP | GFTFSSYAMS | W | AISQQSNFIYYADSVKG | LTHYARYYRYFDV |
| MS-Roche #3.4.L7 | RASQRLGRLYLA | Y | GASSRAT | T | QQTYDYPP | GFTFSSYAMS | W | AISGSGGSTYYADSVKG | LTHYARYYRYFDV |
| MS-Roche #3.4.L8 | RASQWITKSYLA | Y | GASSRAT | T | QQTYDYPP | GFTFSSYAMS | W | AISGSGGSTYYADSVKG | LTHYARYYRYFDV |
| MS-Roche #3.4.L9 | RASRRIHVYYLA | Y | GASSRAT | T | QQTYDYPP | GFTFSSYAMS | W | AISGSGGSTYYADSVKG | LTHYARYYRYFDV |
| MS-Roche #3.4.L11 | RASQLVGRAYLA | Y | GASSRAT | T | QQTYDYPP | GFTFSSYAMS | W | AISGSGGSTYYADSVKG | LTHYARYYRYFDV |
| MS-Roche #3.6.H1 | RASQSVSSSYLA | Y | GASSRAT | V | QQTYNYPP | GFTFSSYAMS | W | VISESGQYKYYADSVKG | LTHYARYYRYFDV |
| MS-Roche #3.6.H2 | RASQSVSSSYLA | Y | GASSRAT | V | QQTYNYPP | GFTFSSYAMS | W | VISERGINTYYADSVKG | LTHYARYYRYFDV |
| MS-Roche #3.6.H3 | RASQSVSSSYLA | Y | GASSRAT | V | QQTYNYPP | GFTFSSYAMS | W | VISETGKFIYYADSVKG | LTHYARYYRYFDV |
| MS-Roche #3.6.H4 | RASQSVSSSYLA | Y | GASSRAT | V | QQTYNYPP | GFTFSSYAMS | W | AISERGRHIYYADSVKG | LTHYARYYRYFDV |
| MS-Roche #3.6.H5 | RASQSVSSSYLA | Y | GASSRAT | V | QQTYNYPP | GFTFSSYAMS | W | AISESGKTKYYADSVKG | LTHYARYYRYFDV |
| MS-Roche #3.6.H6 | RASQSVSSSYLA | Y | GASSRAT | V | QQTYNYPP | GFTFSSYAMS | W | AISEHGTNIYYADSVKG | LTHYARYYRYFDV |
| MS-Roche #3.6.H8 | RASQSVSSSYLA | Y | GASSRAT | V | QQTYNYPP | GFTFSSYAMS | W | AISEYSKFKYYADSVKG | LTHYARYYRYFDV |
| MS-Roche #3.6.L1 | RASQFIQRFYLA | Y | GASSRAT | V | QQTYNYPP | GFTFSSYAMS | W | AISGSGGSTYYADSVKG | LTHYARYYRYFDV |
| MS-Roche #3.6.L2 | RASQFLSRYYLA | Y | GASSRAT | V | QQTYNYPP | GFTFSSYAMS | W | AISGSGGSTYYADSVKG | LTHYARYYRYFDV |
| MS-Roche #7 | RASQSVSSSYLA | Y | GASSRAT | T | FQLYSDPF | GFTFSSYAMS | W | AISGSGGSTYYADSVKG | GKGNTHKPYGYVRYFDV |
| MS-Roche #7.1 | RASQSVSSSYLA | Y | GASSRAT | V | HQLYSSPY | GFTFSSYAMS | W | AISGSGGSTYYADSVKG | GKGNTHKPYGYVRYFDV |
| MS-Roche #7.2 | RASQSVSSSYLA | Y | GASSRAT | T | QQIYSFPH | GFTFSSYAMS | W | AISGSGGSTYYADSVKG | GKGNTHKPYGYVRYFDV |
| MS-Roche #7.3 | RASQSVSSSYLA | Y | GASSRAT | V | HQVYSHPF | GFTFSSYAMS | W | AISGSGGSTYYADSVKG | GKGNTHKPYGYVRYFDV |

TABLE 1-continued

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| MS-Roche #7.4 | RASQSVSSSYLA | Y | GASSRAT | V | QQIYNFPH | GFTFSSYAMS | W | AISGSGGSTYYADSVKG | GKGNTHKPYGYVRYFDV |
| MS-Roche #7.5 | RASQSVSSSYLA | Y | GASSRAT | T | HQVYSSPF | GFTFSSYAMS | W | AISGSGGSTYYADSVKG | GKGNTHKPYGYVRYFDV |
| MS-Roche #7.6 | RASQSVSSSYLA | Y | GASSRAT | V | HQLYSPPY | GFTFSSYAMS | W | AISGSGGSTYYADSVKG | GKGNTHKPYGYVRYFDV |
| MS-Roche #7.7 | RASQSVSSSYLA | Y | GASSRAT | T | HQVYSAPF | GFTFSSYAMS | W | AISGSGGSTYYADSVKG | GKGNTHKPYGYVRYFDV |
| MS-Roche #7.8 | RASQSVSSSYLA | Y | GASSRAT | V | HQVYSFPI | GFTFSSYAMS | W | AISGSGGSTYYADSVKG | GKGNTHKPYGYVRYFDV |
| MS-Roche #7.9 | RASQSVSSSYLA | Y | GASSRAT | T | LQIYNMPI | GFTFSSYAMS | W | AISGSGGSTYYADSVKG | GKGNTHKPYGYVRYFDV |
| MS-Roche #7.10 | RASQSVSSSYLA | Y | GASSRAT | T | QQVYNPPH | GFTFSSYAMS | W | AISGSGGSTYYADSVKG | GKGNTHKPYGYVRYFDV |
| MS-Roche #7.11 | RASQSVSSSYLA | Y | GASSRAT | T | QQVYSPPH | GFTFSSYAMS | W | AISGSGGSTYYADSVKG | GKGNTHKPYGYVRYFDV |
| MS-Roche #7.12 | RASQYVSSPYLA | S | GSSNRAT | V | LQLYNIPN | GFTFSSYGMS | W | NISGSGSSTYYADSVKG | GKGNTHKPYGYVRYFDV |
| MS-Roche #7.13 | RASQSVSSSYLA | Y | GASSRAT | V | HQVYSPPF | GFTFSSYAMS | W | AISGSGGSTYYADSVKG | GKGNTHKPYGYVRYFDV |
| MS-Roche #7.2.H1 | RASQSVSSSYLA | Y | GASSRAT | T | QQIYSFPH | GFTFSSYAMS | W | AINANGLKKYYADSVKG | GKGNTHKPYGYVRYFDV |
| MS-Roche #7.2.H2 | RASQSVSSSYLA | Y | GASSRAT | T | QQIYSFPH | GFTFSSYAMS | W | AINGTGMKKYYADSVKG | GKGNTHKPYGYVRYFDV |
| MS-Roche #7.2.H3 | RASQSVSSSYLA | Y | GASSRAT | T | QQIYSFPH | GFTFSSYAMS | W | AINANGYKTYYADSVKG | GKGNTHKPYGYVRYFDV |
| MS-Roche #7.2.H4 | RASQSVSSSYLA | Y | GASSRAT | T | QQIYSFPH | GFTFSSYAMS | W | AINSKGSRIYYADSVKG | GKGNTHKPYGYVRYFDV |
| MS-Roche #7.2.H5 | RASQSVSSSYLA | Y | GASSRAT | T | QQIYSFPH | GFTFSSYAMS | W | AINATGRSKYYADSVKG | GKGNTHKPYGYVRYFDV |
| MS-Roche #7.2.H6 | RASQSVSSSYLA | Y | GASSRAT | T | QQIYSFPH | GFTFSSYAMS | W | AINARGNRTYYADSVKG | GKGNTHKPYGYVRYFDV |
| MS-Roche #7.2.H7 | RASQSVSSSYLA | Y | GASSRAT | T | QQIYSFPH | GFTFSSYAMS | W | AINSRGSDTHYADSVKG | GKGNTHKPYGYVRYFDV |
| MS-Roche #7.2.H8 | RASQSVSSSYLA | Y | GASSRAT | T | QQIYSFPH | GFTFSSYAMS | W | AINASGHKTYYADSVKG | GKGNTHKPYGYVRYFDV |
| MS-Roche #7.2.L1 | RASQYVDRTYLA | Y | GASSRAT | T | QQIYSFPH | GFTFSSYAMS | W | AISGSGGSTYYADSVKG | GKGNTHKPYGYVRYFDV |
| MS-Roche #7.2.L2 | RASQYISFRYLA | Y | GASSRAT | T | QQIYSFPH | GFTFSSYAMS | W | AISGSGGSTYYADSVKG | GKGNTHKPYGYVRYFDV |
| MS-Roche #7.2.L4 | RASQFIRRSYLA | Y | GASSRAT | T | QQIYSFPH | GFTFSSYAMS | W | AISGSGGSTYYADSVKG | GKGNTHKPYGYVRYFDV |
| MS-Roche #7.3.H1 | RASQSVSSSYLA | Y | GASSRAT | V | HQVYSHPF | GFTFSSYAMS | W | AISAISNKTYYADSVKG | GKGNTHKPYGYVRYFDV |
| MS-Roche #7.3.L1 | RASQYLHYGYLA | Y | GASSRAT | V | HQVYSHPF | GFTFSSYAMS | W | AISGSGGSTYYADSVKG | GKGNTHKPYGYVRYFDV |
| MS-Roche #7.4.H1 | RASQSVSSSYLA | Y | GASSRAT | V | QQIYNFPH | GFTFSSYAMS | W | AINATGYRTYYADSVKG | GKGNTHKPYGYVRYFDV |
| MS-Roche #7.4.H2 | RASQSVSSSYLA | Y | GASSRAT | V | QQIYNFPH | GFTFSSYAMS | W | AINYNGARIYYADSVKG | GKGNTHKPYGYVRYFDV |

TABLE 1-continued

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| MS-Roche #7.9.H1 | RASQSVSSSYLA | Y | GASSRAT | T | LQIYNMPI | GFTFSSYAMS | W | AINANGQRKFYADSVKG | GKGNTHKPYGYVRYFDV |
| MS-Roche #7.9.H2 | RASQSVSSSYLA | Y | GASSRAT | T | LQIYNMPI | GFTFSSYAMS | W | AINADGNRKYYADSVKG | GKGNTHKPYGYVRYFDV |
| MS-Roche #7.9.H3 | RASQSVSSSYLA | Y | GASSRAT | T | LQIYNMPI | GFTFSSYAMS | W | AINYQGNRKYYADSVKG | GKGNTHKPYGYVRYFDV |
| MS-Roche #7.9.H4 | RASQSVSSSYLA | Y | GASSRAT | T | LQIYNMPI | GFTFSSYAMS | W | AINAVGMKKFYADSVKG | GKGNTHKPYGYVRYFDV |
| MS-Roche #7.9.H5 | RASQSVSSSYLA | Y | GASSRAT | T | LQIYNMPI | GFTFSSYAMS | W | AINHAGNKKYYADSVKG | GKGNTHKPYGYVRYFDV |
| MS-Roche #7.9.L1 | RASQRLSPRYLA | Y | GASSRAT | T | LQIYNMPI | GFTFSSYAMS | W | AISGSGGSTYYADSVKG | GKGNTHKPYGYVRYFDV |
| MS-Roche #7.9.L2 | RASQYLHKRYLA | Y | GASSRAT | T | LQIYNMPI | GFTFSSYAMS | W | AISGSGGSTYYADSVKG | GKGNTHKPYGYVRYFDV |
| MS-Roche #7.9.H6 | RASQSVSSSYLA | Y | GASSRAT | T | QQIYSFPH | GFTFSSYAMS | W | AINARGNRTYYADSVKG | GKGNTHKPYGYVRYFDV |
| MS-Roche #7.9.H7 | RASQSVSSSYLA | Y | GASSRAT | T | LQIYNMPI | GFTFSSYAMS | W | AINASGTRTYYADSVKG | GKGNTHKPYGYVRYFDV |
| MS-Roche #7.9.H8 | RASQSVSSSYLA | Y | GASSRAT | T | LQIYNMPI | GFTFSSYAMS | W | AINASGSKIYYADSVKG | GKGNTHKPYGYVRYFDV |
| MS-Roche #7.9.H9 | RASQSVSSSYLA | Y | GASSRAT | T | LQIYNMPI | GFTFSSYAMS | W | AINGKGNKKYYADSVKG | GKGNTHKPYGYVRYFDV |
| MS-Roche #7.11.H1 | RASQSVSSSYLA | Y | GASSRAT | T | QQVYSPPH | GFTFSSYAMS | W | GINAAGFRTYYADSVKG | GKGNTHKPYGYVRYFDV |
| MS-Roche #7.11.H2 | RASQSVSSSYLA | Y | GASSRAT | T | QQVYSPPH | GFTFSSYAMS | W | AINANGYKKYYADSVKG | GKGNTHKPYGYVRYFDV |
| MS-Roche #7.11.H3 | RASQSVSSSYLA | Y | GASSRAT | T | QQVYSPPH | GFTFSSYAMS | W | GINANGNRTYYADSVKG | GKGNTHKPYGYVRYFDV |
| MS-Roche #7.11.H4 | RASQSVSSSYLA | Y | GASSRAT | T | QQVYSPPH | GFTFSSYAMS | W | AINANGYKTYYADSVKG | GKGNTHKPYGYVRYFDV |
| MS-Roche #7.11.H5 | RASQSVSSSYLA | Y | GASSRAT | T | QQVYSPPH | GFTFSSYAMS | W | AINAHGQRTYYADSVKG | GKGNTHKPYGYVRYFDV |
| MS-Roche #7.11.L1 | RASQRILRIYLA | Y | GASSRAT | T | QQVYSPPH | GFTFSSYAMS | W | AISGSGGSTYYADSVKG | GKGNTHKPYGYVRYFDV |
| MS-Roche #7.12.H1 | RASQYVFRRYLA | S | GSSNRAT | V | LQLYNIPN | GFTFSSYGMS | W | NINGNGNRKYYADSVKG | GKGNTHKPYGYVRYFDV |
| MS-Roche #7.12.L1 | RASQYVFRRYLA | S | GSSNRAT | V | LQLYNIPN | GFTFSSYGMS | W | NISGSGSSTYYADSVKG | GKGNTHKPYGYVRYFDV |
| MS-Roche #7.12.L2 | RASQRFFYKYLA | S | GSSNRAT | V | LQLYNIPN | GFTFSSYGMS | W | NISGSGSSTYYADSVKG | GKGNTHKPYGYVRYFDV |
| MS-Roche #7.12.L3 | RASQFVRRGFLA | S | GSSNRAT | V | LQLYNIPN | GFTFSSYGMS | W | NISGSGSSTYYADSVKG | GKGNTHKPYGYVRYFDV |
| MS-Roche #7.12.L4 | RASQRLKRSYLA | S | GSSNRAT | V | LQLYNIPN | GFTFSSYGMS | W | NISGSGSSTYYADSVKG | GKGNTHKPYGYVRYFDV |
| MS-Roche #7.12.L5 | RASQRLKRSYLA | S | GSSNRAT | V | LQLYNIPN | GFTFSSYGMS | W | NISGSGSSTYYADSVKG | GKGNTHKPYGYVRYFDV |
| MS-Roche #7.12.L6 | RASQYLWYRYLA | S | GSSNRAT | V | LQLYNIPN | GFTFSSYGMS | W | NISGSGSSTYYADSVKG | GKGNTHKPYGYVRYFDV |
| MS-Roche #7.12.L7 | RASQWIRKTYLA | S | GSSNRAT | V | LQLYNIPN | GFTFSSYGMS | W | NISGSGSSTYYADSVKG | GKGNTHKPYGYVRYFDV |

TABLE 1-continued

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| MS-Roche #8 | RASQSVSSSYLA | Y | GASSRAT | T | QQLSSFPP | GFTFSSYAMS | W | AISGSGGSTYYADSVKG | LLSRGYNGYYHKFDV |
| MS-Roche #8.1 | RASQSVSSSYLA | Y | GASSRAT | T | QQLSNYPP | GFTFSSYAMS | W | AISGSGGSTYYADSVKG | LLSRGYNGYYHKFDV |
| MS-Roche #8.2 | RASQSVSSSYLA | Y | GASSRAT | T | QQLSSYPP | GFTFSSYAMS | W | AISGSGGSTYYADSVKG | LLSRGYNGYYHKFDV |
| MS-Roche #8.1.H1 | RASQSVSSSYLA | Y | GASSRAT | T | QQLSNYPP | GFTFSSYAMS | W | AISRSGSNIYYADSVKG | LLSRGYNGYYHKFDV |
| MS-Roche #8.2.H1 | RASQSVSSSYLA | Y | GASSRAT | T | QQLSSYPP | GFTFSSYAMS | W | AISITGRRKYYADSVKG | LLSRGYNGYYHKFDV |
| MS-Roche #8.2.H2 | RASQSVSSSYLA | Y | GASSRAT | T | QQLSSYPP | GFTFSSYAMS | W | AISRTGSKTYYADSVKG | LLSRGYNGYYHKFDV |
| MS-Roche #8.2.H4 | RASQSVSSSYLA | Y | GASSRAT | T | QQLSSYPP | GFTFSSYAMS | W | ATSVKGKTYYADSVKG | LLSRGYNGYYHKFDV |
| MS-Roche #8.2.L1 | RASQRVSGRYLA | Y | GASSRAT | T | QQLSSYPP | GFTFSSYAMS | W | AISGSGGSTYYADSVKG | LLSRGYNGYYHKFDV |

Example 6

Construction of HuCAL® Immunoglobulin Expression Vectors

Heavy chain cloning. The multiple cloning site of pcDNA3.1+ (invitrogen) was removed (NheI/ApaI), and a stuffer compatible with the restriction sites used for HuCAL® design was inserted for the ligation of the leader sequences (NheI/EcoRI), VH-domains (MunI/), and the immunoglobulin constant regions (BlpI/ApaI). The leader sequence (EMBL 83133) was equipped with a Kozak sequence (Kozak, 1987). The constant regions of human IgG (PIR A02146), IgG4 (EMBL K01316), and serum IgA1 (EMBL J00220) were dissected into overlapping oligonucleotides with length of about 70 bases. Silent mutations were introduced to remove restriction sites non-compatible with the HuCAL® design. The oligonucleotides were spliced by overlap extension-PCR.

During sub-cloning from Fab into IgG, the VH DNA sequence of the Fab is cut out via Mfe I/Blp I and ligated into the IgG vector opened via EcoR I/Blp I. EcoR I (g/aattc) and Mfe I (c/aattg) share compatible cohesive ends (aatt) and the DNA sequence of the original Mfe I site in the Fab changes from: c/aattg to: g/aattg after ligation into the IgG expression vector, thereby destroying both Mfe I and EcoR I site, and thus also leading to an amino acid change from Q (codon: caa) to E (codon: gaa). The $V_H$ DNA sequence of the IgG of antibody molecule 7.9H7 after subcloning is shown in SEQ ID No.: 424, and the corresponding amino acid sequence is shown in SEQ ID No: 425.

Light chain cloning. The multiple cloning site of pcDNA3.1/Zeo+ (Invitrogen) was replaced by two different stuffers. The κ-stuffer provided restriction sites for insertion of a κ-leader (NheI/EcoRV), HuCAL®-scFv VK-domains (EcoRV/BsiWI), and the κ-chain constant region (BsiWI/ApaI). The corresponding restriction sites in the λ-stuffer were NheI/EcoRV (λ-leader), EcoRV/HpaI (Vλ-domains), and HpaI/ApaI (λ-chain constant region). The κ-leader (EMBL Z00022) as well as the λ-leader (EMBL J00241) were both equipped with Kozak sequences. The constant regions of the human κ- (EMBL L00241) and λ-chain (EMBL M18645) were assembled by overlap extension-PCR as described above.

Generation of IgG-expressing CHO-cells. CHO-K1 cells were co-transfected with an equimolar mixture of IgG heavy and light chain expression vectors. Double-resistant transfectants were selected with 600 μg/ml G418 and 300 μg/ml Zeocin (Invitrogen) followed by limiting dilution. The supernatant of single clones was assessed for IgG expression by capture-ELISA. Positive clones were expanded in RPMI-1640 medium supplemented with 10% ultra-low IgG-FCS (Life Technologies). After adjusting the pH of the supernatant to 8.0 and sterile filtration, the solution was subjected to standard protein A column chromatography (Poros 20 A, PE Biosystems).

Example 7

Pepspot Analysis with Decapeptides

The following aminoacid sequence encompassing Aβ (1-42) was divided into 43 overlapping decapeptides with a frameshift of 1 aminoacid.

ISEVKM$^1$DAEF RHDSGYEVHH QKLVFFAEDV GSNKGAIIGL MVGGVVI$^{42}$ATV IV (SEQ ID NO: 414). Accordingly, DAEF RHDSGYEVHH QKLVFFAEDV GSNKGAIIGL MVGGVVIA (SEQ ID NO: 27) as enclosed represents amino acids 1 to 42 of Aβ4/8-A4 peptide.

The 43 decapeptides were synthesized with N-terminal acetylation and C-terminal covalent attachment to a cellulose sheet ("pepspot") by a commercial supplier (Jerini BioTools, Berlin). The cellulose sheet is incubated for 2 hours on a rocking platform with monoclonal antibody (2 μg/ml) in blocking buffer (50 mM Tris HCl, 140 mM NaCl, 5 mM NaEDTA, 0.05% NP40 (Fluka), 0.25% gelatine (Sigma), 1% bovine serum albumine fraction V (Sigma), pH 7.4). The sheet is washed 3 times 3 minutes on a rocking platform with TBS (10 mM Tris.HCl, 150 mM NaCl, pH 7.5). It is then wetted with cathode buffer (25 mM Tris base, 40 mM 6-Aminohexane acid, 0.01% SDS, 20% methanol) and transferred to a semi-dry blotting stack with the peptide side facing a PVDF membrane (Biorad) of equal size.

The semi-dry blotting stack consists out of freshly wetted filter papers (Whatman No. 3) slightly larger than the peptide sheet:
3 papers wetted with Cathode buffer
the peptide sheet
a sheet of PVDF membrane wetted with methanol
3 papers wetted with Anode buffer 1 (30 mM Tris base, 20% methanol)
3 papers wetted with Anode buffer 2 (0.3 mM Tris base, 20% methanol)

The transfer is conducted at a current density between Cathode and Anode of 0.8 mA/cm$^2$ for 40 minutes which is sufficient to elute most of the antibody from the cellulose sheet and deposit it on the PVDF membrane. The PVDF membrane is then exchanged for a $2^{nd}$ PVDF membrane and transferred for another 40 minutes to ensure complete elution from the cellulose sheet.

The PVDF membrane is immersed in blocking buffer for 10 minutes. Then HRP-labeled anti-human Ig H+ L (Pierce) is added at 1:1000 dilution and the membrane is incubated on a rocking platform for 1 hour. It is washed 3×10 minutes with TBST (TBS with 0.005% Tween20). Color is developed by immersing the membrane into a solution made of 3 mg 4-chloronaphthol dissolved in 9 ml methanol with 41 ml PBS (20 mM Na-phosphate, 150 mM NaCl, pH 7.2) an 10 µl 30% hydrogen peroxide (Merck). After the development of blue-black spots the membrane is washed extensively with water and dried.

The assignment of antibody-reactive pepspots is made by visual inspection through a transparent spot matrix. The epitopes of the antibody in question is defined as the minimal aminoacid sequence in reactive peptides. For comparison mouse monoclonal antibodies (BAP-2, BAP-1, BAP-17 BAP-21, BAP-24, and 4G8) are analyzed in the same way, except using HRP-labeled anti-mouse Ig instead of anti-human Ig.

It is of note that affinity maturation and conversion of the monovalent Fab fragments into full-length IgG1 antibodies results usually in some broadening of the epitope recognition sequence as indicated by pepspot and ELISA analyses. This may be related to the recruitment of more contact points in the antibody-antigen interaction area as a consequence of the affinity maturation or to a stronger binding to the minimal epitope such that also weak interactions with adjacent amino acid can be detected. The latter may be the case when Aβ-derived peptides are probed with full-length IgG antibodies. As illustrated in Table 2 for the pepspot analysis, the recognition sequences of the N-terminal and middle epitopes are extended by up to three amino acids when parent Fabs and corresponding fully maturated IgG antibodies are compared. However, it has to be kept in mind that the decapeptides are modified for covalent attachment at the C-terminal amino acid and this amino acid may therefore not easily be accessible to the full-length antibody due to steric hindrance. If this is the case the last C-terminal amino acid does not significantly contribute to the epitope recognition sequence and a potential reduction of the minimal recognition sequence by one amino acid at the C-terminal end has to be considered in the pepspot analysis as used in the present invention.

TABLE 2

Pepspot analysis of binding Fabs and full-length IgG antibodies to decapeptides on a cellulose sheet.

| antibody | position | position |
| --- | --- | --- |
| MSR-3 Fab | 3-4 | 18-23 |
| MSR-7 Fab | 3-5 | 19-24 |
| MSR-8 Fab | 4-5 | 18-21 |
| MSR-9 Fab | (1)3-9 | 18-24 |
| MSR-10 Fab | (4-10) | 19-20 |
| MSR-11 Fab | 3-7 | (18-20) |
| MSR-26 Fab | 3-5 | (16)-19-23 |
| MSR-27 Fab | (3)6-9 | 13-18(20) |
| MSR-29 Fab | | 14-16(20) |
| MSR-37 Fab | (4-6) | (19-24) |
| MSR-41 Fab | 3-7 | (17-21) |
| MSR-42 Fab | (4-9) | (18-24) |
| MSR 3.4.H7 IgG1 | 1-3 | 19-26 |
| MSR 7.9.H2 IgG1 | 1-4 | 19-24 |
| MSR 7.9.H7 IgG1 | 4-6 | 19-26 |

TABLE 2-continued

Pepspot analysis of binding Fabs and full-length IgG antibodies to decapeptides on a cellulose sheet.

| antibody | position | position |
| --- | --- | --- |
| MSR 7.2.H2x7.2.L1 IgG1 | (1-4) 5-9 | 18-26 |
| MSR 7.11.H1x7.2.L1 IgG1 | 4-6 | 19-26 |
| BAP-2 | 4-6 | |
| 4G8 | | 19-20(23) |
| BAP-21 | | 32-34 |
| BAP-24 | | 38-40 |
| BAP-1 | 4-6 | |
| BAP-17 | | 38-40 |

The numbers refer to the essential amino acids from the Aβ1-40 sequence which have to be present in the decapeptide for optimal binding of antibody.
A weak peptide reactivity, and hence a weak contribution to the epitope, is indicated by brackets.

Example 8

Determination of $K_D$ Values for MS-R Fab and MS-R IgG1 Antibody Binding to Aβ1-40 and Aβ1-42 Fibers in vitro by Surface Plasmon Resonance (SPR)

Binding of anti-Aβ antibodies (Fabs and IgG1) to fibrillar Aβ was measured online by surface plasmon resonance (SPR), and the affinities of the molecular interactions were determined as described by Johnson, *Anal. Biochem.* 1991, 198, 268-277, and Richalet-Sécordel, *Anal. Biochem.* 1997, 249, 165-173. Biacore2000 and Biacore3000 instruments were used for these measurements. Aβ1-40 and Aβ1-42 fibers were generated in vitro by incubation of synthetic peptides at a concentration of 200 µg/ml in 10 mM Na-acetat buffer (pH 4.0) for three days at 37° C. Electron microscopic analysis confirmed a fibrillar structure for both peptides, Aβ1-40 showing predominantly shorter (<1 micron) and Aβ1-42 predominantly longer (>1 micron) fibers. These fibers are assumed to represent aggregated Aβ peptides in human AD brain more closely than ill-defined mixtures of amorphous aggregates and unstructured precipitates. The fibers were diluted 1:10 and directly coupled to a "Pioneer Sensor Chip F1" as described in the Instruction Manual of the manufacturer (BIAapplication Handbook, version AB, Biacore AB, Uppsala, 1998). In initial experiments it was found that selected MS-Roche Fabs differed substantially in their reaction kinetics and therefore the mode of data analysis had to be chosen accordingly. For binders with slow kinetics $K_D$ values were calculated by curve fitting of the time-dependent sensor responses, i.e. from the ratio of $k_{off}/k_{on}$. Binders with fast kinetics were analyzed by fitting the concentration-dependent sensor responses at equilibrium (adsorption-isotherms). $K_D$ values were calculated from the Biacore sensograms based on the total Fab concentration as determined by a protein assay. For the clones derived from the $1^{st}$ and $2^{nd}$ affinity maturation cycle the content of active Fab in each preparation was determined in the Biacore according to a method described by Christensen, Analytical Biochemistry (1997) 249, 153-164. Briefly, time-dependent protein binding to Aβ1-40 fibers immobilized on the Biacore chip was measured during the association phase under mass-limited conditions at different flow rates of the analyte solution. The conditions of mass limitation were realized by immobilizing high amounts of Aβ fibers (2300 response units) on the chip surface of a measuring channel and by working at relatively low analyte concentrations, i.e. 160 nM (based on the total Fab protein concentration).

A summary of the $K_D$ values of selected MS-Roche clones identified in the primary screen of the HuCAL library and their corresponding maturated derivatives after the $1^{st}$ and $2^{nd}$ affinity maturation cycle is shown in Table 3. In the $1^{st}$ affinity maturation cycle the heavy chain CDR3 (VH-CDR3) was kept constant and optimization was focussed on diversification of the light chain CDR3 (VL-CDR3). In the $2^{nd}$ affinity cycle diversification of VL-CDR1 and VH-CDR2 was performed. Some of the binders from the $1^{st}$ maturation cycle were converted to full-length human IgG1 antibodies according to the technology developed by MorphoSys as described in Example 6 and $K_D$ values determined in the Biacore as described above. The $K_D$ values for full-length IgG1 binding to Aβ1-40 and Aβ1-42 fibers are shown in Table 4.

Matured derivatives from both the L-CDR1 as well as H-CDR2 library after the $2^{nd}$ maturation cycle were identified and allowed combination of light and heavy chains. The cross-cloning strategy is described in Example 13. Either whole light chains, LCDR1 or L-CDR1+2 were exchanged. $K_D$ values of selected cross-cloned Fabs are shown in Table 8. Some of the Fabs from the $1^{st}$ and $2^{nd}$ maturation cycles and from the cross-cloned binders were converted to full-length human IgG1 antibodies according to the technology developed by MorphoSys as described in Example 6. $K_D$ values of IgG binding to Aβ1-40 and Aβ1-42 fibers were determined in the Biacore. Briefly, a kinetic model for the stepwise formation of a bivalent complex was used, and $K_D$ values were calculated by Scatchard type analysis of equilibrium binding. Due to the very slow association process at low antibody concentration (several hours to reach equilibrium) equilibrium binding data were obtained by extrapolation of the association curves to long time intervals. The on- and off rates for the formation of the monovalent and bivalent complex were determined via the curve fit procedure and used for the extrapolation. Based on these $R_{eq}$ values a Scatchard analysis was performed and $K_D$ values for the formation of the monovalent and the bivalent complex were determined. The data are summarized in Table 5. From the curvilinear Scatchard plot a higher (bivalent) and lower (monovalent) affinity interaction was derived for the MS-R IgGs derived from the $2^{nd}$ affinity maturation cycle and cross-clones. These two affinities represent the lower and upper $K_D$ values of the range indicated in Table 5.

TABLE 3

| Secreted clones from | MS-R # | $K_D$ Aβ$_{1-40}$ nM | $K_D$ Aβ$_{1-42}$ nM | MS-R # | $K_D$ Aβ$_{1-40}$ nM | $K_D$ Aβ$_{1-42}$ nM | MS-R # | $K_D$ Aβ$_{1-40}$ nM | $K_D$ Aβ$_{1-42}$ nM |
|---|---|---|---|---|---|---|---|---|---|
| primary screen | 3 | 930 | 1300 | 7 | 1100 | 1714 | 8 | 850 | 1000 |
| $1^{st}$ affinity maturation | 3.2 | 52 | 240 | 7.2 | 22 | 58 | 8.1 | 24 | 42 |
| | 3.3 | 38 | 104 | 7.3 | 23 | 88 | 8.2 | 24 | 64 |
| | 3.4 | 32 | 103 | 7.4 | 28 | 103 | | | |
| | 3.6 | 40 | 68 | 7.9 | 31 | 93 | | | |
| | | | | 7.11 | 22 | 74 | | | |
| | | | | 7.12 | 28 | 60 | | | |
| $2^{nd}$ affinity maturation | 3.2H1 | 4.4 | 3.3 | 7.2H1 | 9.3 | 10.2 | 8.1H1 | 13.6 | 9.2 |
| | 3.2H2 | 5.2 | 1.1 | 7.2H2 | 8.2 | 8.2 | 8.2H1 | 1.6$^a$ | 2.1$^a$ |
| | 3.3H1 | 17.1 | 19.4 | 7.2H3 | 45.4 | 5.3 | 8.2H3 | n.d. | 3.1 |
| | 3.3H2 | 10.6 | 22.8 | 7.2H4 | 5.9 | 5.0 | 8.2H4 | 12.1 | 11.9 |
| | 3.3H3 | 1.4 | 3.3 | 7.2H5 | 8.0 | 10.1 | 8.2L1 | 4.8 | 3.7 |
| | 3.4H1 | 13.5 | 14.0 | 7.2H6 | 1.0 | n.d. | | | |
| | 3.4H3 | 6.7 | 8.4 | 7.2H7 | 15.5 | 8.1 | | | |
| | 3.4H4 | 33.0 | 43.0 | 7.2H8 | 1.5 | 2.1 | | | |
| | 3.4H5 | 26.5 | 36.0 | 7.2L1 | 13.3 | 12.7 | | | |
| | 3.4H6 | 49.0 | 60.0 | 7.2L2 | 5.6 | 4.0 | | | |
| | 3.4H7 | 19.2 | 31.7 | 7.2L4 | 1.1 | 1.1 | | | |
| | 3.4H8 | 10.7 | 26.5 | 7.3H1 | 8.0 | 11.2 | | | |
| | 3.4H9 | 21.7 | 18.6 | 7.3L1 | 4.5 | 6.0 | | | |
| | 3.4H10 | 8.1 | 10.1 | 7.4H1 | 8.0 | 6.6 | | | |
| | 3.4H11 | 19.5 | 8.3 | 7.4H2 | 9.9 | 6.2 | | | |
| | 3.4H12 | 25.5 | 27.0 | 7.9H1 | 4.9 | 5.4 | | | |
| | 3.4H13 | 32.3 | 18.8 | 7.9H2 | 5.0 | 5.7 | | | |
| | 3.4H14 | 13.3 | 16.8 | 7.9H3 | 4.2 | 2.8 | | | |
| | 3.4H16 | 25.5 | 15.6 | 7.9H4 | 4.8 | 4.2 | | | |
| | 3.4H17 | 2.0 | 4.3 | 7.9H5 | 1.7 | 1.8 | | | |
| | 3.4H18 | 17.1 | 10.0 | 7.9H6 | 1.2 | 1.2 | | | |
| | 3.4L7 | 9.3 | 9.3 | 7.9H7 | 1.0 | 0.9 | | | |
| | 3.4L8 | 6.2 | 13.0 | 7.9H8 | 0.8 | 0.7 | | | |
| | 3.4L9 | 16.3 | 9.1 | 7.9H9 | 0.9 | 0.9 | | | |
| | 3.4L11 | 5.3 | 2.6 | 7.9L1 | 1.0 | 1.1 | | | |
| | 3.6H1 | 18.9 | 23.1 | 7.9L2 | 1.0 | 0.5 | | | |
| | 3.6H2 | 19.8 | 54.0 | 7.11H1 | 12.7 | 6.7 | | | |
| | 3.6H3 | 5.4 | 7.5 | 7.11H2 | 0.3 | 0.3 | | | |
| | 3.6H4 | 13.0 | 7.8 | 7.11H3 | 6.6 | 4.4 | | | |
| | 3.6H5 | 8.2 | 6.0 | 7.11H4 | 1.0 | 1.7 | | | |
| | 3.6H6 | 36.0 | 11.8 | 7.11H5 | 3.4 | 1.7 | | | |
| | 3.6H8 | 2.5 | 2.5 | 7.11L1 | 1.1 | 1.2 | | | |
| | 3.6L1 | 15.6 | 11.1 | 7.12H1 | 0.6 | 0.8 | | | |
| | 3.6L2 | 13.7 | 13.1 | 7.12L1 | n.d. | 3.8 | | | |
| | | | | 7.12L2 | 4.0 | 5.4 | | | |
| | | | | 7.12L3 | 0.8 | 0.9 | | | |
| | | | | 7.12L4 | 2.0 | 0.6 | | | |
| | | | | 7.12L5 | 0.8 | 0.6 | | | |

TABLE 3-continued

| Secreted clones from | MS-R # | $K_D$ A$\beta_{1-40}$ nM | $K_D$ A$\beta_{1-42}$ nM | MS-R # | $K_D$ A$\beta_{1-40}$ nM | $K_D$ A$\beta_{1-42}$ nM | MS-R # | $K_D$ A$\beta_{1-40}$ nM | $K_D$ A$\beta_{1-42}$ nM |
|---|---|---|---|---|---|---|---|---|---|
| | | | | 7.12L6 | n.d. | n.d. | | | |
| | | | | 7.12L7 | n.d. | n.d. | | | |

Table 3: $K_D$ values for MS-R Fab binding to A$\beta$1-40 and A$\beta$1-42 fibers as determined in the Biacore. For the clones derived from the 1$^{st}$ and 2$^{nd}$ affinity maturation cycle the values are corrected for the content of active Fab present in each sample as described in the text.
$^a$values were calculated from the concentration-dependent sensor responses at equilibrium;
n.d., not determined

TABLE 4

| MS-R # | $K_D$ A$\beta_{1-40}$ nM | $K_D$ A$\beta_{1-42}$ nM |
|---|---|---|
| 3.3 IgG1 | 3.7 | 6.6 |
| 7.11 IgG1 | 2.3 | 5.7 |
| 7.12 IgG1 | 3.1 | 13.7 |
| 8.1 IgG1 | 6.6 | 12.3 |

Table 4: $K_D$ values for MS-R IgG1 binding to A$\beta$1-40 and A$\beta$1-42 fibers as determined in the Biacore. The IgGs were derived from MS-R Fabs selected after the 1$^{st}$ affinity maturation cycle. The values are corrected for the content of active MS-R IgGs present in each sample as described in the text.

TABLE 5

| Selected clones from | MS-R IgG1 | $K_D$ A$\beta_{1-40}$ nM | $K_D$ A$\beta_{1-42}$ nM |
|---|---|---|---|
| 1$^{st}$ affinity maturation | 3.3 | 3.7 | 6.6 |
| | 7.11 | 2.3 | 5.7 |
| | 7.12 | 3.1 | 13.7 |
| | 8.1 | 6.6 | 12.3 |
| 2$^{nd}$ affinity maturation | 3.4.H7 | 0.10-0.30 | 0.10-0.30 |
| | 7.2.H4 | 0.09-0.30 | 0.10-0.66 |
| | 7.9.H2 | 0.12-0.42 | 0.11-0.38 |
| | 7.9.H3 | 0.10-0.50 | 0.10-0.40 |
| | 7.9.H7 | 0.25-0.69 | 0.24-0.70 |
| | 7.12.L1 | 1.20-3.50 | 0.74-2.90 |
| | 8.2.H2 | 0.16-1.00 | 0.12-0.92 |
| cross-cloned Fabs | 3.6.H5x3.6.L2 | 0.20-1.03 | 0.20-0.95 |
| | 3.6.H8x3.6.L2 | 0.22-0.95 | 0.22-0.82 |
| | 7.4.H2x7.2.L1 | 0.12-0.63 | 0.12-0.56 |
| | 7.11.H1x7.2.L1 | 0.14-0.66 | 0.15-0.67 |
| | 7.11.H1x7.11.L1 | 0.11-0.70 | 0.13-0.70 |

$K_D$ values for MS-R IgG1 binding to A$\beta$1-40 and A$\beta$1-42 fibers as determined in the Biacore. The IgGs were derived from MS-R Fabs selected after the 1$^{st}$ and 2$^{nd}$ affinity maturation cycle and from crosscloned Fabs. The values are corrected for the content of active MS-R IgGs present in each sample as described in the text. The two $K_D$ values given for MS-R IgGs derived from the 2$^{nd}$ affinity maturation step and cross-cloned binders represent higher and lower affinity interaction as calculated from the curvilinear Scatchard plots. With a number of additional MS-R IgGs (for example MS-R IgG 7.9.H2x7.12.L2 and MS-R IgG 7.9.H4x7.12.L2), complex curvilinear Scatchard blots were obtained and determination of $K_D$-values was therefore not possible.

Example 9

Figure 6:
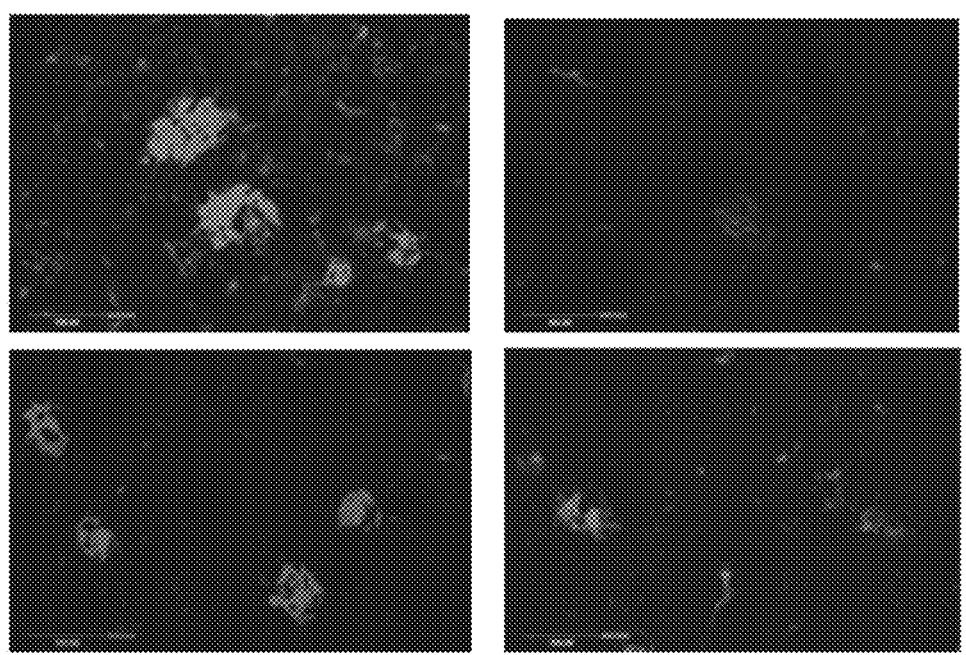
FIG. 6: Indirect immunofluorescence of amyloid-plaques from a cryostat section of human temporal cortex. The plaques were labeled with MS-R # 3.3 IgG1 (upper panels) and MS-R # 7.12 IgG1 (lower panels) at 0.05 µg/ml (left panels) and 0.01 µg/ml (right panels) under stringent blocking conditions. Bound MS-R IgG1 antibody was revealed by goat anti-human (H+L)-Cy3.
Figure 7:
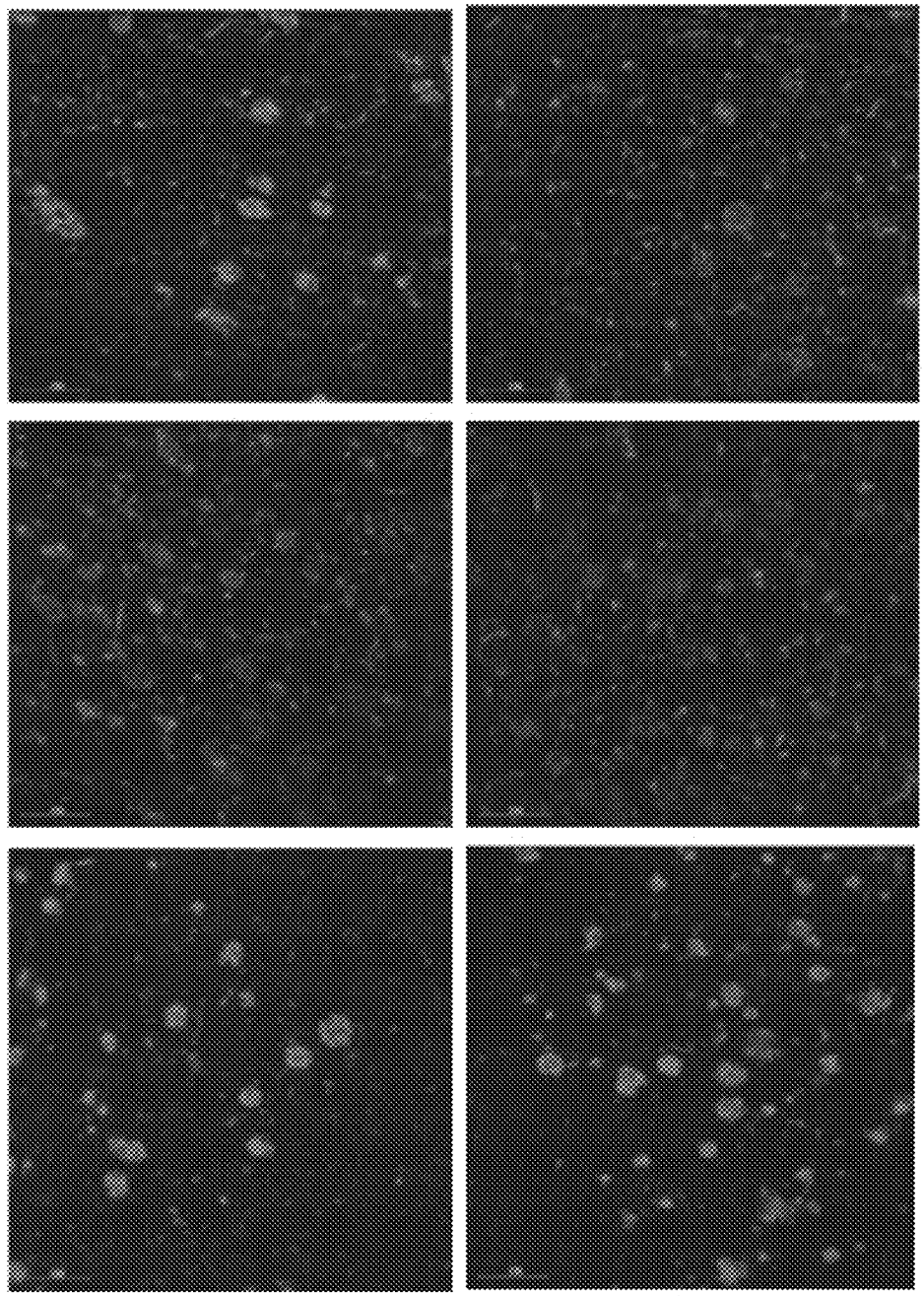
FIG. 7: Indirect immunofluorescence of amyloid-plaques from a cryostat section of human temporal cortex using antibodies after final affinity maturation. The plaques were labeled with MS-R # 7.9.H7 IgG1 (MAB 31, top panel), MS-R #7.11.H1×7.2.L1 IgG1 (MAB 11, middle panel) and MS-R # 3.4.H7, bottom panel). Antibodies were used at 0.05 µg/ml (left panels) and 0.01 µg/ml (right panels) under stringent blocking conditions. Bound MS-R IgG1 antibody was revealed by goat anti-human (H+L)-Cy3.

Staining of Genuine Human Amyloid Plaques in Brain Sections of an Alzheimer's Disease Patient by Indirect Immunofluorescence Selected MS-Roche Fabs and full-length IgG1 were tested for binding to β-amyloid plaques by immunohistochemistry analysis. Cryostat sections of unfixed tissue from human temporal cortex (obtained postmortem from a patient that was positively diagnosed for Alzheimer's disease) were labeled by indirect immunofluorescence using MS-Roche Fabs or full-length human IgG1 antibodies at various concentrations. Fabs and IgG1 antibodies were revealed by goat anti-human affinity-purified F(ab')$_2$ fragment conjugated to Cy3 and goat anti-human (H+L) conjugated to Cy3, respectively. Both secondary reagents were obtained from Jackson Immuno Research. Controls included an unrelated Fab and the secondary antibodies alone, which all gave negative results. Typical examples of plaque stainings with selected MS-Roche Fabs and MS-Roche IgG1 antibodies are shown in FIGS. 5 to 7.

Example 10

Polymerization Assay: Prevention of Aβ Aggregation

Synthetic Aβ when incubated in aqueous buffer over several days spontaneously aggregates and forms fibrillar structures which are similar to those seen in amyloid deposits in the brains of Alzheimer's Disease patients. We have developed an in vitro assay to measure incorporation of biotinylated Aβ into preformed Aβ aggregates in order to analyze the Aβ-neutralizing potential of anti-Aβ antibodies and other Aβ-binding proteins such as albumin (Bohrmann et al., 1999, J. Biol. Chem. 274, 15990-15995). The effect of small molecules on Aβ aggregation can also be analyzed in this assay.
Experimental Procedure:

NUNC Maxisorb microtiter plates (MTP) are coated with a 1:1 mixture of Aβ1-40 and Aβ1-42 (2 μM each, 100 μl per well) at 37° C. for three days. Under these conditions highly aggregated, fibrillar Aβ is adsorbed and immobilized on the surface of the well. The coating solution is then removed and the plates are dried at room temperature for 2-4 hours. (The dried plates can be stored at −20° C.). Residual binding sites are blocked by adding 300 μl/well phosphate-buffered saline containing 0.05% Tween 20 (T-PBS) and 1% bovine serum albumin (BSA). After 1-2 hours incubation at room temperature the plates are washed 1× with 300 μl T-PBS. A solution of 20 nM biotinylated Aβ1-40 in 20 mM Tris-HCl, 150 mM NaCl pH 7.2 (TBS) containing 0.05% NaN$_3$ and serially diluted antibody is added (100 μl/well) and the plate incubated at 37° C. overnight. After washing 3× with 300 μl T-PBS a streptavidin-POD conjugate (Roche Molecular Biochemicals), diluted 1:1000 in T-PBS containing 1% BSA, is added (100 μl/well) and incubated at room temperature for 2 hours. The wells are washed 3× with T-PBS and 100 μl/well of a freshly prepared tetramethyl-benzidine (TMB) solution are added. [Preparation of the TMB solution: 10 ml 30 mM citric acid pH 4.1 (adjusted with KOH)+0.5 ml TMB (12 mg TMB in 1 ml acetone+9 ml methanol)+0.01 ml 35% H$_2$O$_2$]. The reaction is stopped by adding 100 μl/well 1 N H$_2$SO$_4$ and absorbance is read at 450 nm in a microtiter plate reader.
Result:

FIG. 8 shows that MS-Roche IgG1 antibodies prevented incorporation of biotinylated Aβ1-40 into preformed Aβ1-40/Aβ1-42 aggregates. The Aβ-neutralizing capacity of these full-length human IgGs was similar to that of the mouse monoclonal antibody BAP-1 which had been generated by a standard immunization procedure and specifically recognizes amino acid residues 4-6 of the Aβ peptide when analyzed by the Pepspot technique as described in example 7. Mouse monoclonal antibody BAP-2 which also reacts exclusively with amino acids 4-6 (Brockhaus, unpublished) was significantly less active in this assay. An even lower activity was found with the Aβ1-40 C-terminal specific antibody BAP-17

(Brockhaus, Neuroreport 9 (1998), 1481-1486) and the monoclonal antibody 4G8 which recognizes an epitope between position 17 and 24 in the Aβ sequence (Kim, 1988, Neuroscience Research Communication Vol. 2, 121-130). BSA at a concentration of up to 10 μg/ml did not affect incorporation of biotinylated Aβ and served as a negative control. However, at higher concentrations, i.e. >100 μg/ml, BSA has been reported to inhibit binding of biotinylated Aβ into preformed Aβ fibers (Bohrmann, (1999) *J Biol Chem* 274 (23), 15990-5) indicating that the interaction of BSA with Aβ is not of high affinity.

Example 11

De-polymerization Assay: Release of Biotinylated Aβ from Aggregated Aβ

In a similar experimental setup we have tested the potential of MS-Roche IgG antibodies to induce depolymerization of aggregated Aβ. Biotinylated Aβ1-40 was first incorporated into preformed Aβ1-40/Aβ1-42 fibers before treatment with various anti-Aβ antibodies. Liberation of biotinylated Aβ was measured using the same assay as described in the polymerization assay.

Experimental Procedure:

NUNC Maxisorb microtiter plates (MTP) are coated with a 1:1 mixture of Aβ1-40 and Aβ1-42 as described in the polymerization assay. For incorporation of biotinylated Aβ the coated plates are incubated with 200 μl/well 20 nM biotinylated Aβ1-40 in TBS containing 0.05 $NaN_3$ at 37° C. overnight. After washing the plate with 3×300 μl/well T-PBS, antibodies serially diluted in TBS containing 0.05% $NaN_3$ were added and incubated at 37° C. for 3 hours. The plate was washed and analyzed for the presence of biotinylated Aβ1-40 as described above.

Result:

FIGS. 9A to D shows that the inventive antibodies induced de-polymerization of aggregated Aβ as measured by the release of incorporated biotinylated Aβ1-40. The MS-R antibodies and the mouse monoclonal antibody BAP-1 were similarly active whereas the BAP-2, BAP-17 and 4G8 antibodies were clearly less efficient in liberating biotinylated Aβ from the bulk of immobilized Aβ aggregates. BAP-1 can clearly be differentiated from the MS-R antibodies by its reactivity with cell surface full-length APP (see FIG. 15), and antibodies like BAP-1 with such properties are not useful for therapeutic applications as potential autoimmunological reactions may be induced. It is interesting to note that BAP-2, despite its specificity for amino acid residue 4-6 which is exposed in aggregated Aβ has a clearly lower activity in this assay indicating that not all N-terminus specific antibodies a priori are equally efficient in releasing Aβ from preformed aggregates. The MS-Roche IgGs are clearly superior to BAP-2 with respect to the depolymerizing activity. The relatively low efficiency of BAP-17 (C-terminus-specific) and 4G8 (amino acid residues 16-24-specific) in this assay is due to the cryptic nature of these two epitopes in aggregated Aβ. As already noted in the polymerization assay, BSA at the concentrations used here had no effect on aggregated Aβ.

The MS-R antibodies derived from the $2^{nd}$ affinity maturation cycle and from the cross-cloned binders show in general a higher efficacy in the de-polymerization assay (comparison of FIG. 9A with FIGS. 9B and C), which is consistent with the increased binding affinity of these antibodies (see tables 3-5). The monoclonal antibodies AMY-33 and 6F/3D have been reported to prevent Aβ aggregation in vitro under certain experimental conditions (Solomon, (1996) Proc. Natl. Acad. Sci. USA 93, 452-455; AMY-33 and 6F/3D antibodies were obtained from Zymed Laboratories Inc., San Francisco (Order No. 13-0100) and Dako Diagnostics AG, Zug, Switzerland (Order No. M087201), respectively). As demonstrated in FIG. 9D both of these antibodies were completely inactive in the de-polymerization assay.

Example 12

Epitope Analysis by ELISA on Peptide Conjugates

The following heptapeptides (single letter code) were obtained by solid-phase synthesis and purified by liquid chromatography using the techniques known in the art.

```
AEFRHDC

EFRHDSC

FRHDSGC

RHDSGYC

HDSGYEC

DSGYEVC

SGYEVHC

YEVHHQC

EVHHQKC

VHHQKLC

HHQKLVC

HQKLVFC

QKLVFFC

KLVFFAC

LVFFAEC

VFFAEDC

FFAEDVC

FAEDVGC

AEDVGSC

EDVGSNC

DVGSNKC

VGSNKGC

GSNKGAC

CSNKGAI

CNKGAII

CKGAIIG

CGLMVGG

CMVGGVV

CGGVVIA
```

The peptides were dissolved in DMSO to arrive at 10 mM concentration.

Bovine Albumin (essentially fatty acid free BSA, Sigma Lot 112F-9390) was dissolved to 10 mg/ml in 0.1M sodium bicarbonate and activated by addition per ml of 50 μl of a 26 mg/ml solution of N-succinmidyl-maleinimido propionate (NSMP, Pierce) in DMSO. After 15 minutes reaction at room temperature the activated BSA was purified by gel filtration (NAP-10, Pharmacia) in PBS with 0.1% sodium azide as solvent. 50 µl of NSMP activated BSA (6.7 mg/ml) was diluted with 50 µl of PBS, 0.1% sodium azide and 10 µl of peptide solution (1 mM in DMSO) was added. As negative control activated BSA was mock-treated without peptide addition. After 4 hrs at room temperature the reaction was stopped by addition of 10 µl of 10 mM Cystein. An aliquot of the conjugate reaction mixture was diluted 1:100 with 0.1M sodium bicarbonate buffer and immediately filled into the wells (100 µl) of ELISA plates (Nunc Immuno-Plate). After standing 16 hrs at 4° C. 100 µl blocking buffer (as above) was added to each well and incubated for another 30 minutes. The plates were washed with 2×300 µl/well TBST (as above) and filled with 100 µl antibody at 10 µg/ml or 2 µg/ml in blocking buffer. The plates were kept 16 hours at 4° C. and washed with 2×300 µl TBST. 100 µl/well HRP-conjugated anti-human Ig H+ L (Pierce, dilution 1:1000 with blocking buffer) was added and incubated for 1 hour at ambient temperature. The plates were washed with 3×300 ul/well TBST. Colour development was started by addition of 100 µl tetra-methyl benzidine/hydrogen peroxide reagent. The reaction was stopped after 5 minutes by addition of 100 µl/well 1M sulfuric acid and the optical density is measured by an opticalreader (Microplate Reader 3550, BioRad) at 450 nm. For comparison mouse monoclonal antibodies were analysed in the same way, except using as revealing agent HRP-labelled anti-mouse Ig instead of anti-human Ig.

Employing specific of the above described heptapeptides derived from Aβ, specific ELISA-tests as described herein above were carried out. Preferably, inventive antibodies comprise antibodies which show, as measured by of optical densities, a signal to background ratio above "10" when their reactivity with an A-beta derived peptide (AEFRHD, SEQ ID NO: 415; amino acid 2 to 7 of A-beta) is compared to an non-related protein/peptide like BSA. Most preferably, the ratio of optical densities is above "5" for a corresponding reaction with at least one of the following three Aβ derived peptides: (VFFAED, SEQ ID NO: 421; amino acid 18 to 23 of Aβ) or (FFAEDV, SEQ ID NO: 423; amino acid 19 to 24 of Aβ) or (LVFFAE, SEQ ID NO: 420; amino acid 17 to 22 of Aβ).

Corresponding results for the inventive parental and/or maturated antibodies are shown in the following two tables:

TABLE 6

Reactivity of MS-R Fabs with BSA-conjugated Abeta heptapeptides 2-7 (AEFRHD, SEQ ID NO: 415), 17-22 (LVFFAE, SEQ ID NO: 420), 18-23 (VFFAED, SEQ ID NO: 421) and 19-24 (FFAEDV, SEQ ID NO: 423).

| MS-R # | Peptide2-7 2-7/BSA | Peptide 17-22 17-22/BSA | Peptide 18-23 18-23/BSA | Peptide 19-24 19-24/BSA | Peptide-ratio 17-22/2-7 | Peptide-ratio 18-23/2-7 | Peptide-ration 19-24/2-7 |
|---|---|---|---|---|---|---|---|
| 7 | 24 | 4 | 7 | 4 | 0.17 | 0.29 | 0.17 |
| 8 | 28 | 10 | 29 | 25 | 0.36 | 1.04 | 0.89 |
| 7.2 | 34 | 12 | 16 | 9 | 0.35 | 0.47 | 0.26 |
| 7.3 | 34 | 11 | 15 | 9 | 0.32 | 0.44 | 0.26 |
| 7.4 | 36 | 10 | 13 | 6 | 0.28 | 0.36 | 0.17 |
| 7.9 | 28 | 9 | 13 | 8 | 0.32 | 0.46 | 0.29 |
| 7.11 | 37 | 11 | 15 | 9 | 0.30 | 0.41 | 0.24 |
| 7.12 | 38 | 6 | 8 | 7 | 0.16 | 0.21 | 0.18 |
| 8.1 | 30 | 1 | 11 | 8 | 0.03 | 0.37 | 0.27 |
| 8.2 | 32 | 4 | 28 | 23 | 0.13 | 0.88 | 0.72 |
| 3.2H2 | 26 | 12 | 23 | 20 | 0.46 | 0.88 | 0.77 |
| 3.3H1 | 23 | 4 | 12 | 8 | 0.17 | 0.52 | 0.35 |
| 3.3H3 | 31 | 2 | 5 | 2 | 0.06 | 0.16 | 0.06 |
| 3.4H1 | 27 | 2 | 8 | 2 | 0.07 | 0.30 | 0.07 |
| 3.4H2 | 16 | 11 | 1 | 1 | 0.69 | 0.06 | 0.06 |
| 3.4H3 | 22 | 9 | 17 | 11 | 0.41 | 0.77 | 0.50 |
| 3.4H5 | 28 | 5 | 13 | 4 | 0.18 | 0.46 | 0.14 |
| 3.4H7 | 24 | 2 | 6 | 5 | 0.08 | 0.25 | 0.21 |
| 3.4H17 | 28 | 5 | 12 | 11 | 0.18 | 0.43 | 0.39 |
| 3.4L11 | 31 | 6 | 20 | 5 | 0.19 | 0.65 | 0.16 |
| 3.6H6 | 25 | 1 | 4 | 7 | 0.04 | 0.16 | 0.28 |
| 3.6H1 | 23 | 3 | 13 | 5 | 0.13 | 0.57 | 0.22 |
| 3.6H2 | 19 | 2 | 8 | 3 | 0.11 | 0.42 | 0.16 |
| 7.2H1 | 38 | 8 | 11 | 9 | 0.21 | 0.29 | 0.24 |
| 7.2H2 | 16 | 10 | 10 | 10 | 0.63 | 0.63 | 0.63 |
| 7.2H3 | 33 | 17 | 20 | 18 | 0.52 | 0.61 | 0.55 |
| 7.2H4 | 23 | 12 | 13 | 12 | 0.52 | 0.57 | 0.52 |
| 7.2H5 | 30 | 13 | 18 | 15 | 0.43 | 0.60 | 0.50 |
| 7.2L1 | 24 | 14 | 16 | 11 | 0.57 | 0.68 | 0.45 |
| 7.4H1 | 31 | 16 | 20 | 16 | 0.52 | 0.65 | 0.51 |
| 7.4H2 | 36 | 17 | 20 | 16 | 0.47 | 0.56 | 0.46 |
| 7.9H1 | 32 | 7 | 12 | 6 | 0.23 | 0.36 | 0.19 |
| 7.9H2 | 35 | 3 | 6 | 8 | 0.08 | 0.16 | 0.23 |
| 7.9H3 | 35 | 11 | 20 | 9 | 0.31 | 0.57 | 0.27 |
| 7.9H4 | 30 | 10 | 15 | 7 | 0.32 | 0.49 | 0.22 |
| 7.11H1 | 31 | 8 | 9 | 8 | 0.25 | 0.29 | 0.25 |
| 7.11H2 | 34 | 10 | 12 | 14 | 0.29 | 0.36 | 0.41 |
| 7.12L1 | 16 | 10 | 12 | 10 | 0.60 | 0.70 | 0.59 |
| 8.1H1 | 29 | 22 | 25 | 25 | 0.77 | 0.88 | 0.86 |
| 8.2H1 | 22 | 7 | 23 | 20 | 0.34 | 1.05 | 0.94 |
| 8.2L1 | 26 | 15 | 32 | 31 | 0.60 | 1.26 | 1.22 |

The ratios of the ELISA read-out (optical density) obtained with peptide-conjugated and non-conjugated BSA are given. The signal intensities obtained with the 17-22, 18-23 and 19-24 peptides in relation to the 2-7 peptide are also indicated.

TABLE 7

Reactivity of MS-R IgGs and mouse monoclonal antibodies BAP-1, BAP-2, 4G8, 6E10 Amy-33 and 6F/3D with BSA-conjugated Aβ heptapeptides 2-7 (AEFRHD, SEQ ID NO: 415), 17-22 (LVFFAE, SEQ ID NO: 420), 18-23 (VFFAED, SEQ ID NO: 421) and 19-24 (FFAEDV, SEQ ID NO: 423).

| MS-R IgG # | AEFRHD (SEQ ID No. 415) 2-7/BSA | LVFFAE (SEQ ID No. 420) 17-22/BSA | VFFAED (SEQ ID No. 421) 18-23/BSA | FFAEDV (SEQ ID No. 423) 19-24/BSA | Peptide-ratio 17-22/2-7 | Peptide-ratio 18-23/2-7 | Peptide-ratio 19-24/2-7 |
|---|---|---|---|---|---|---|---|
| 3.3 | 17 | 11 | 16 | 11 | 0.65 | 0.94 | 0.65 |
| 7.12 | 19 | 11 | 13 | 11 | 0.58 | 0.68 | 0.58 |
| 8.1 | 16 | 7 | 16 | 14 | 0.44 | 1.00 | 0.88 |
| 3.4H7 | 22 | 3 | 16 | 15 | 0.14 | 0.73 | 0.68 |
| 7.9H2 | 13 | 5 | 8 | 6 | 0.38 | 0.62 | 0.46 |
| 7.9H3 | 13 | 6 | 8 | 6 | 0.46 | 0.62 | 0.46 |
| 7.9.H7 | 30 | 5 | 16 | 10 | 0.17 | 0.53 | 0.33 |
| 7.11H2 | 10 | 6 | 7 | 6 | 0.60 | 0.70 | 0.60 |
| 8.2.H2 | 18 | 10 | 15 | 14 | 0.56 | 0.83 | 0.78 |
| 3.6.H5x3.6.L2 | 11 | 7 | 9 | 8 | 0.64 | 0.82 | 0.73 |
| 7.11.H2x7.9.L1 (L1) | 14 | 8 | 10 | 9 | 0.57 | 0.71 | 0.64 |
| 8.2.H2x8.2.L1 | 13 | 20 | 25 | 25 | 1.54 | 1.92 | 1.92 |
| Mouse mab | | | | | | | |
| BAP-1 | 21 | 1 | 1 | 1 | 0.05 | 0.05 | 0.05 |
| BAP-2 | 21 | 1 | 1 | 1 | 0.05 | 0.05 | 0.05 |
| 4G8 | 1 | 23 | 20 | 1 | 23 | 20 | 1 |
| 6E10 | 18 | 1 | 1 | 1 | 0.06 | 0.06 | 0.06 |
| 6F/3D* | 1 | 1 | 1 | 1 | 1 | 1 | 1 |
| Amy 33 | 16 | 2 | 1 | 3 | 0.13 | 0.06 | 0.19 |

The ratios of the ELISA read-out (optical density) obtained with peptide-conjugated and non-conjugated BSA are given. The signal intensities obtained with the 17-22, 18-23 and 19-24 peptides in relation to the 2-7 peptide are also indicated.
*this antibody is specific for sequence 8-17 and does not recognize N-terminal or middle epitope sequences.

Example 13

Combination of Optimized H-CDR2 and L-CDR1 by Cross-cloning

The modular design of the HuCAL library allows exchange of complementarity determining regions (CDRs) of two different Fab encoding genes in a simple cloning step. For a further improvement of affinity the independently optimized H-CDR2 and L-CDR1 from matured clones with the same H-CDR3 were combined, because there was a high probability that this combination would lead to a further gain of affinity (Yang et al., 1995, J. Mol. Biol. 254, 392-403; Schier et al., 1996b, J. Mol. Biol. 263, 551-567; Chen et al., 1999, J. Mol. Biol. 293, 865-881). Whole light chains, or fragments thereof, were transferred from an L-CDR1 optimized donor clone to a H-CDR2 optimized recipient clone. Donor and recipient clones were only combined, if both carried identical H-CDR3 sequences. All donor and recipient clones carried the VH3-Vκ3 framework.

This was accomplished by transferring whole light chains from the L-CDR1-optimized donor clone to the H-CDR2-optimized recipient clone. Epitope specificity was conserved by only combining clones with the same H-CDR3. By light chain exchange a H-CDR2-optimized clone obtained only an optimized L-CDR1, if the exchange occurred between clones with the same L-CDR3. If the L-CDR3 of the clones to be combined was different, the H-CDR2-optimized clone acquired in addition to the optimized L-CDR1 another L-CDR3 (L-CDR2 remained the HuCAL consensus sequence (Knappik et al., 2000)) and when derivatives of MS-Roche #7.12 were used as donors of the light chain L-CDR1, 2 and 3 were exchanged in the H-CDR2-optimized acceptor clone. Three different cloning strategies were employed:

1) Using restriction endonucleases XbaI and SphI the whole antibody light chain fragment was excised from plasmid 1 (e.g. pMx9_Fab_MS-Roche#7.11.H1_FS) and the thereby obtained vector backbone was then ligated to the light chain fragment of plasmid 2 (e.g. pMx9_Fab_MS-Roche#7.2.L1_FS) generated by XbaI and SphI digest. Thereby a new plasmid (nomenclature: pMx9_Fab_MS-Roche#7.11.H1×7.2.L1_FS) was created encoding L-CDR1,2,3 of parental clone #7.2.L1 and H-CDR1,2,3 of parental clone #7.11.H1.

2) Using restriction endonucleases XbaI and Acc65I an L-CDR1 coding fragment was excised from plasmid 1 (e.g. pMx9_Fab_MS-Roche#7.11.H2_FS) and the thereby obtained vector backbone was then ligated to the L-CDR1 fragment of plasmid 2 (e.g. pMx9_Fab_MS-Roche#7.12.L1_FS) generated by XbaI and Acc65I. Thereby a new plasmid (nomenclature: pMx9_Fab_MS-Roche#7.11.H2×7.12.L1 (L-CDR1)_FS) was created encoding L-CDR1 of parental clone #7.12.L1 while L-CDR2,3 and H-CDR1,2,3 are derived from parental clone #7.11.H2.

3) Using restriction endonucleases XbaI and BamHI an L-CDR1 and L-CDR2 coding fragment was excised from plasmid 1 (e.g. pMx9_Fab_MS-Roche#7.11.H2_FS) and the thereby obtained vector backbone was then ligated to the L-CDR1 and L-CDR2 fragment of plasmid 2 (e.g. pMx9_Fab_MS-Roche#7.12.L1_FS) generated by XbaI and BamHI digest. Thereby a new plasmid (nomenclature: pMx9_Fab_MS-Roche#7.11.H2×7.12.L1(L-CDR1+2)_FS) was created encoding L-CDR1 and L-CDR2 of parental clone #7.12.L1 while L-CDR3 and H-CDR1,2,3 are derived from parental clone #7.11.H2.

Illustrative examples for the different cloning strategies as well as for sequences donor and recipient clones are given in table 8.

After large scale expression and purification their affinities were determined on Aβ (1-40) fibers. Furthermore, $K_D$ values for selected cross-cloned MS-R Fab/antibodies are given in appended Table 9.

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| cloning strategy 1) | → | | | | → | | | | |
| MS-Roche #7.11.H1 | RASQSVSSSYLA | Y | GASSRAT | T | QQVYSPPH | GFTFSSYAMS | W | GINAAGFRTYYADSVKG | GKGNTHKPYGYVRYFDV |
| MS-Roche #7.2.L1 | RASQVDRTYLA | Y | GASSRAT | T | QQIYSFPH | GFTFSSYGMS | W | AISGSGGSTYYADSVKG | GKGNTHKPYGYVRYFDV |
| MS-Roche #7.11.H1x7.2.L1 cloning strategy 2) | RASQVDRTYLA | Y | GASSRAT | T | QQIYSFPH | GFTFSSYAMS | W | GINAAGFRTYYADSVKG | GKGNTHKPYGYVRYFDV |
| | | → | | | | | | | |
| MS-Roche #7.11.H2 | RASQSVSSSYLA | Y | GASSRAT | T | QQVYSPPH | GFTFSSYAMS | W | AINANGYKKYYADSVKG | GKGNTHKPYGYVRYFDV |
| MS-Roche #7.12.L1 | RASQVFRRYLA | S | GSSNRAT | V | LQLYNIPN | GFTFSSYGMS | W | NISGSGSTYYADSVKG | GKGNTHKPYGYVRYFDV |
| MS Roche #7.11.H2x7.12.L1(LCDR1) cloning strategy 3) | RASQVFRRYLA | Y | GASSRAT | T | QQVYSPPH | GFTFSSYAMS | W | AINANGYKKYYADSVKG | GKGNTHKPYGYVRYFDV |
| | → | | → | | | | | | |
| MS-Roche #7.11.H2 | RASQSVSSSYLA | Y | GASSRAT | T | QQTYNYPP | GFTFSSYAMS | W | AINANGYKKYYADSVKG | GKGNTHKPYGYVRYFDV |
| MS-Roche #7.12.L1 | RASQVFRRYLA | S | GSSNRAT | V | LQLYNIPN | GFTFSSYGMS | W | NISGSGSTYYADSVKG | GKGNTHKPYGYVRYFDV |
| MS Roche #7.11.H2x7.12.L1(LCDR1 + 2) | RASQVFRRYLA | S | GSSNRAT | T | QQVYSPPH | GFTFSSYAMS | W | AINANGYKKYYADSVKG | GKGNTHKPYGYVRYFDV |
| MS-Roche #3.6H5 | RASQFLSRYLA | Y | GASSRAT | V | QQTYNYPP | GFTFSSYAMS | W | AISESGKTKYYADSVKG | LTHYARYRYFDV |
| MS-Roche #3.6L2 | RASQFLSRYLA | Y | GASSRAT | V | QQTYNYPP | GFTFSSYAMS | W | AISGSGGSTYYADSVKG | LTHYARYRYFDV |
| MS-Roche #3.6H5x3.6L2 | RASQSVSSSYLA | Y | GASSRAT | V | QQTYNYPP | GFTFSSYAMS | W | AISESGKTKYYADSVKG | LTHYARYRYFDV |
| MS-Roche #3.6H8 | RASQFLSRYLA | Y | GASSRAT | V | QQTYNYPP | GFTFSSYAMS | W | AISEYSKFKYYADSVKG | LTHYARYRYFDV |
| MS-Roche #3.6L2 | RASQSVSSSYLA | Y | GASSRAT | V | QQTYNYPP | GFTFSSYAMS | W | AISGSGGSTYYADSVKG | LTHYARYRYFDV |
| MS-Roche #3.6H8x3.6L2 | RASQFLSRYLA | Y | GASSRAT | V | QQTYNYPP | GFTFSSYAMS | W | AISEYSKFKYYADSVKG | LTHYARYRYFDV |
| MS-Roche #7.4.H2 | RASQSVSSSYLA | Y | GASSRAT | V | QQIYNFPH | GFTFSSYAMS | W | AINYNGARIYYADSVKG | GKGNTHKPYGYVRYFDV |

-continued

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| MS-Roche #7.2.L1 | RASQVVDRTYLA | Y | GASSRAT | T | QQIYSFPH | GFTFSSYAMS | W | AISGSGGSTYYADSVKG | GKGNTHKPYGYVRYFDV |
| MS-Roche #7.4.H2x7.2.L1 | RASQVVDRTYLA | Y | GASSRAT | T | QQIYSFPH | GFTFSSYAMS | W | AINYNGARIYYADSVKG | GKGNTHKPYGYVRYFDV |
| MS-Roche #7.9H2 | RASQSVSSSYLA | Y | GASSRAT | T | LQIYNMPI | GFTFSSYAMS | W | AINADGNRKYYADSVKG | GKGNTHKPYGYVRYFDV |
| MS-Roche #7.12L2 | RASQRFFYKYLA | S | GSSNRAT | V | LQLYNIPN | GFTFSSYGMS | W | NISGSGGSTYYADSVKG | GKGNTHKPYGYVRYFDV |
| MS-Roche #7.9H2x7.12L2 | RASQRFFYKYLA | Y | GSSNRAT | V | LQIYNMPI | GFTFSSYAMS | W | AINADGNRKYYADSVKG | GKGNTHKPYGYVRYFDV |
| MS-Roche #7.9H4 | RASQRFFYKYLA | S | GSSNRAT | V | LQLYNIPN | GFTFSSYGMS | W | AINAVGMKKFYADSVKG | GKGNTHKPYGYVRYFDV |
| MS-Roche #7.12.L2 | RASQSVSSSYLA | S | GSSNRAT | V | LQLYNIPN | GFTFSSYAMS | W | AINAVGMKKFYADSVKG | GKGNTHKPYGYVRYFDV |
| MS-Roche #7.9H4x7.12L2 | RASQSVSSSYLA | Y | GASSRAT | T | QQVYSPPH | GFTFSSYAMS | W | GINAAGFRTYYADSVKG | GKGNTHKPYGYVRYFDV |
| MS-Roche #7.11H1 | RASQRILRIYLA | Y | GASSRAT | T | QQVYSPPH | GFTFSSYAMS | W | AISGSGGSTYYADSVKG | GKGNTHKPYGYVRYFDV |
| MS-Roche #7.11L1 | RASQRILRIYLA | Y | GASSRAT | T | QQIYSFPH | GFTFSSYAMS | W | GINAAGFRTYYADSVKG | GKGNTHKPYGYVRYFDV |
| MS-Roche #7.11H1x7.11L1 | RASQVVDRTYLA | Y | GASSRAT | T | QQIYSFPH | GFTFSSYAMS | W | AISGSGGSTYYADSVKG | GKGNTHKPYGYVRYFDV |
| MS-Roche #7.2L1 | RASQVVDRTYLA | Y | GASSRAT | T | QQIYSFPH | GFTFSSYAMS | W | GINAAGFRTYYADSVKG | GKGNTHKPYGYVRYFDV |
| MS-Roche #7.11H1x7.2L1 | RASQSVSSSYLA | Y | GASSRAT | V | HQMSSYPP | GFTFSSYAMS | W | VISEKSRFIYYADSVKG | LTHYARYYRYFDV |
| MS-Roche #3.3H1 | RASRRIHVYYLA | Y | GASSRAT | T | QQTYDYPP | GFTFSSYAMS | W | AISGSGGSTYYADSVKG | LTHYARYYRYFDV |
| MS-Roche #3.4L9 | RASRRIHVYYLA | Y | GASSRAT | T | QQTYDYPP | GFTFSSYAMS | W | VISEKSRFIYYADSVKG | LTHYARYYRYFDV |
| MS-Roche #3.3H1x3.4L9 | RASQSVSSSYLA | Y | GASSRAT | T | QQTYDYPP | GFTFSSYAMS | W | AISETSIRKYYADSVKG | LTHYARYYRYFDV |
| MS-Roche #3.4H1 | RASRRIHVYYLA | Y | GASSRAT | T | QQTYDYPP | GFTFSSYAMS | W | AISETSIRKYYADSVKG | LTHYARYYRYFDV |
| MS-Roche #3.4L9 | RASRRIHVYYLA | Y | GASSRAT | T | QQTYDYPP | GFTFSSYAMS | W | VISQTGRKIYYADSVKG | LTHYARYYRYFDV |
| MS-Roche #3.4H3 | RASQRLGRLYLA | Y | GASSRAT | T | QQTYDYPP | GFTFSSYAMS | W | AISGSGGSTYYADSVKG | LTHYARYYRYFDV |
| MS-Roche #3.4L7 | RASQSVSSSYLA | Y | GASSRAT | T | QQTYDYPP | GFTFSSYAMS | W | VISQTGRKIYYADSVKG | LTHYARYYRYFDV |
| MS-Roche #3.4H3x3.4L7 | RASRRIHVYYLA | Y | GASSRAT | T | QQTYDYPP | GFTFSSYAMS | W | VISQTGRKIYYADSVKG | LTHYARYYRYFDV |
| MS-Roche #3.4L9 | RASRRIHVYYLA | Y | GASSRAT | T | QQTYDYPP | GFTFSSYAMS | W | AISGSGGSTYYADSVKG | LTHYARYYRYFDV |
| MS-Roche #3.4H3x3.4L9 | RASRRIHVYYLA | Y | GASSRAT | T | QQTYDYPP | GFTFSSYAMS | W | VISQTGRKIYYADSVKG | LTHYARYYRYFDV |

-continued

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| MS-Roche #3.4H7 | RASQVSSSYLA | Y | GASSRAT | T | QQTYDYPP | GFTFSSYAMS | W | VISETGKNIYYADSVKG | LTHYARYRYFDV |
| MS-Roche #3.4L9 | RASRRIHVYYLA | Y | GASSRAT | T | QQTYDYPP | GFTFSSYAMS | W | AISGSGGSTYYADSVKG | LTHYARYRYFDV |
| MS-Roche #3.4H7x3.4L9 | RASRRIHVYYLA | Y | GASSRAT | T | QQTYDYPP | GFTFSSYAMS | W | VISETGKNIYYADSVKG | LTHYARYRYFDV |
| MS-Roche #3.4H7 | RASQVSSSYLA | Y | GASSRAT | T | QQTYDYPP | GFTFSSYAMS | W | AISGSGGSTYYADSVKG | LTHYARYRYFDV |
| MS-Roche #3.4L7 | RASQRLGRLYLA | Y | GASSRAT | T | QQTYDYPP | GFTFSSYAMS | W | VISETGKNIYYADSVKG | LTHYARYRYFDV |
| MS-Roche #3.4H7x3.4L7 | RASQRLGRLYLA | Y | GASSRAT | T | QQTYDYPP | GFTFSSYAMS | W | AISESGKTKYYADSVKG | LTHYARYRYFDV |
| MS-Roche #3.6H5 | RASQVSSSYLA | Y | GASSRAT | V | QQTYNYPP | GFTFSSYAMS | W | AISGSGGSTYYADSVKG | LTHYARYRYFDV |
| MS-Roche #3.6L11 | RASQFIQRPFLA | Y | GASSRAT | V | QQTYNYPP | GFTFSSYAMS | W | AISESGKTKYYADSVKG | LTHYARYRYFDV |
| MS-Roche #3.6H5x3.6L11 | RASQFIQRPFLA | Y | GASSRAT | V | QQTYNYPP | GFTFSSYAMS | W | AISGSGGSTYYADSVKG | LTHYARYRYFDV |
| MS-Roche #7.2H2 | RASQVSSSYLA | Y | GASSRAT | T | QQIYSFPH | GFTFSSYAMS | W | AINGTGMKKYYADSVKG | GKGNTHKPYGYVRYFDV |
| MS-Roche #7.2L1 | RASQVDRTYLA | Y | GASSRAT | T | QQIYSFPH | GFTFSSYAMS | W | AISGSGGSTYYADSVKG | GKGNTHKPYGYVRYFDV |
| MS-Roche #7.2H2x7.2L1 | RASQVDRTYLA | Y | GASSRAT | T | QQIYSFPH | GFTFSSYAMS | W | AINGTGMKKYYADSVKG | GKGNTHKPYGYVRYFDV |
| MS-Roche #7.4H2 | RASQVSSSYLA | Y | GASSRAT | V | QQIYNFPH | GFTFSSYAMS | W | AINVNGARIYYADSVKG | GKGNTHKPYGYVRYFDV |
| MS-Roche #7.12L2 | RASQRFFYKYLA | S | GSSNRAT | V | LQLYNIPN | GFTFSSYGMS | W | NISGSGGSTYYADSVKG | GKGNTHKPYGYVRYFDV |
| MS-Roche #7.4H2x7.12L2 | RASQRFFYKYLA | S | GSSNRAT | V | LQLYNIPN | GFTFSSYAMS | W | AINVNGARIYYADSVKG | GKGNTHKPYGYVRYFDV |
| MS-Roche #7.9H2 | RASQVSSSYLA | Y | GASSRAT | T | LQIYNMPI | GFTFSSYAMS | W | AINADGNRKYYADSVKG | GKGNTHKPYGYVRYFDV |
| MS-Roche #7.2L1 | RASQVDRTYLA | Y | GASSRAT | T | QQIYSFPH | GFTFSSYAMS | W | AISGSGGSTYYADSVKG | GKGNTHKPYGYVRYFDV |
| MS-Roche #7.9H2x7.2L1 | RASQVDRTYLA | Y | GASSRAT | T | QQVYSFPH | GFTFSSYAMS | W | AINADGNRKYYADSVKG | GKGNTHKPYGYVRYFDV |
| MS-Roche #7.11H2 | RASQVSSSYLA | Y | GASSRAT | T | QQIYSFPH | GFTFSSYAMS | W | AINANGYKKYYADSVKG | GKGNTHKPYGYVRYFDV |
| MS-Roche #7.2L1 | RASQVDRTYLA | Y | GASSRAT | T | QQIYSFPH | GFTFSSYAMS | W | AISGSGGSTYYADSVKG | GKGNTHKPYGYVRYFDV |
| MS-Roche #7.11H2x7.2L1 | RASQVDRTYLA | Y | GASSRAT | T | QQIYSFPH | GFTFSSYAMS | W | AINANGYKKYYADSVKG | GKGNTHKPYGYVRYFDV |
| MS-Roche #7.9H2 | RASQVSSSYLA | Y | GASSRAT | T | LQIYNMPI | GFTFSSYAMS | W | AINADGNRKYYADSVKG | GKGNTHKPYGYVRYFDV |
| MS-Roche #7.12L1 | RASQVFRRYLA | S | GSSNRAT | V | LQLYNIPN | GFTFSSYGMS | W | NISGSGGSTYYADSVKG | GKGNTHKPYGYVRYFDV |
| MS-Roche #7.9H2x7.12L1 | RASQVFRRYLA | S | GSSNRAT | V | LQLYNIPN | GFTFSSYAMS | W | AINADGNRKYYADSVKG | GKGNTHKPYGYVRYFDV |
| MS-Roche #7.11H2 | RASQVSSSYLA | Y | GASSRAT | T | QQVYSPPH | GFTFSSYAMS | W | AINANGYKKYYADSVKG | GKGNTHKPYGYVRYFDV |

-continued

| Binder name | L-CDR1 | pos. 49 | L-CDR2 | pos. 85 | L-CDR3 | H-CDR1 | pos. 47 | H-CDR2 | H-CDR3 |
|---|---|---|---|---|---|---|---|---|---|
| MS-Roche #7.9L1 | RASQRLSPRYLA | Y | GASSRAT | T | LQIYNMPI | GFTFSSYAMS | W | AISGSGGSTYYADSVKG | GKGNTHKPYGYVRYFDV |
| MS-Roche #7.11H2x7.9L1 | RASQRLSPRYLA | Y | GASSRAT | T | LQIYNMPI | GFTFSSYAMS | W | AINANGYKKYYADSVKG | GKGNTHKPYGYVRYFDV |
| MS-Roche #8.1H1 | RASQSVSSSYLA | Y | GASSRAT | T | QQLSNYPP | GFTFSSYAMS | W | AISRSGSNIYYADSVKG | LLSRGYNGYYHKFDV |
| MS-Roche #8.2L1 | RASQRVSGRYLA | Y | GASSRAT | T | QQLSSYPP | GFTFSSYAMS | W | AISGSGGSTYYADSVKG | LLSRGYNGYYHKFDV |
| MS-Roche #8.1H1x8.2L1 | RASQRVSGRYLA | Y | GASSRAT | T | QQLSSYPP | GFTFSSYAMS | W | AISRSGSNIYYADSVKG | LLSRGYNGYYHKFDV |
| MS-Roche #7.11H2 | RASQSVSSSYLA | Y | GASSRAT | T | QQVYSPPH | GFTFSSYAMS | W | AINANGYKKYYADSVKG | GKGNTHKPYGYVRYFDV |
| MS-Roche #7.12L1 | RASQYVFRRYLA | S | GSSNRAT | V | LQLYNIPN | GFTFSSYGMS | W | NISGSGSSTYYADSVKG | GKGNTHKPYGYVRYFDV |
| MS-Roche #7.11H2x7.12L1 | RASQYVFRRYLA | S | GSSNRAT | V | LQLYNIPN | GFTFSSYAMS | W | AINANGYKKYYADSVKG | GKGNTHKPYGYVRYFDV |

Table 8 Arrows indicate the location of restriction enzyme sites used to digest corresponding plasmids

TABLE 9

| MS-R # | $K_D$ A$\beta_{1-40}$ nM | $K_D$ A$\beta_{1-42}$ nM |
|---|---|---|
| 3.3H1x3.4L9 | 2.16 | 2.97 |
| 3.4H1x3.4L9 | 0.25 | 0.5 |
| 3.4H3x3.4L7 | 0.92 | 0.92 |
| 3.4H3x3.4L9 | 1.05 | 0.93 |
| 3.4H7x3.4L9 | 2.66 | 3.51 |
| 3.4H7x3.4L7 | 1.19 | 1.23 |
| 3.6H5x3.6L1 | 1.25 | 1.04 |
| 3.6H5x3.6L2 | 1.26 | 0.84 |
| 7.2H2x7.2L1 | 1.29 | 1.43 |
| 7.4H2x7.2L1 | 1.4 | 1.4 |
| 7.4H2x7.12L2 | 1.4 | 1.8 |
| 7.9H2x7.2L1(L1) | 1.4 | 1.4 |
| 7.9H2x7.12L1 | 1.2 | 1.1 |
| 7.9H2x7.12L2(L1 + 2) | 0.4 | 0.4 |
| 7.11H1x7.2L1 | 1.75 | 1.39 |
| 7.11H1x7.11L1 | 0.41 | 0.47 |
| 7.11H2x7.2L1(L1) | 1 | 0.6 |
| 7.11H2x7.9L1(L1) | 0.1 | 1 |
| 8.1H1x8.2L1 | 1.3 | 1.6 |

$K_D$ values for crosscloned MS-R Fab binding to A$\beta$1-40 and A$\beta$1-42 fibers as determined in the Biacore. The preparation of crosscloned Fabs is described in example 13. The $K_D$ values were determined by kinetic curve fittings and corrected for the content of active Fab present in each sample as described in the text. Some of the Fabs were additionally purified by size exclusion chromatography or preparative ultracentrifugation to remove aggregated material. (L1), the H-CDR2-matured acceptor clone received only L-CDR1 from the L-CDR1 improved donor clone; (L1 + 2), the H-CDR2-matured acceptor clone received L-CDR1 + 2 from the L-CDR1 improved donor clone.

Example 14

In vivo Amyloid Plaque Decoration in a Mouse Model of Alzheimer's Disease as Revealed by Confocal Laser Scanning Microscopy and Colocalization Analysis Selected MS-R IgG1 antibodies were tested in APP/PS2 double transgenic mice (Reference: Richards et al., Soc. Neurosci. Abstr., Vol. 27, Program No. 5467, 2001) for amyloid plaque decoration in vivo. The antibodies (1 mg/mouse) were administered i.v. and after 3 days the brains were perfused with saline and prepared for cryosection. In another study the mice were exposed to higher concentrations of the antibodies, i.e. 2 mg injected i.v. at day 0, 3, and 6, and sacrificed at day nine. The presence of the antibodies bound to amyloid plaques was assessed on unfixed cryostat sections by double-labeled indirect immunofluorescence using goat anti-human IgG (H+ L) conjugated to either Cy3 (#109-165-003, Jackson Immuno Research) followed by BAP-2-Alexa488 immunoconjugate. Imaging was done by confocal laser microscopy and image processing for quantitative detection of colocalizations by IMARIS and COLOCALIZATION software (Bitplane, Switzerland). Typical examples are shown in FIGS. 10-14. All of the MS-R antibodies tested were found positive in immunodecoration of amyloid plaques in vivo, although some variability was noted.

Example 15

Investigation of Binding of Different Monoclonal Antibodies to Amyloid Precursor Protein (APP) on the Surface of HEK293 Cells APP is widely expressed in the central nervous system. Binding of antibody to cell surface APP may lead to complement activation and cell destruction in healthy brain areas. Therefore, it is mandatory for therapeutic A-beta antibodies to be devoid of reactivity towards APP. High affinity antibodies against the N-terminal domain of A-beta (e.g. BAP-1, BAP-2) recognize the respective epitope also in the framework of APP. In contrast, the antibodies against the middle epitope (e.g. 4G8), and the antibodies of the invention are surprisingly unable to recognize to cell surface APP. Thus, antibodies of the invention which decorate A-beta, but not APP in vivo, are superior to non-selective antibodies.

The method of flow cytometry is well known in the art. Relative units of fluorescence (FL1-H) measured by flow cytometry indicate cell surface binding of the respective antibody. A fluorescence shift on APP transfected HEK293 compared to untransfected HEK293 cells indicates the unwanted reaction with cell surface APP. As an example, antibodies BAP-1 and BAP-2 against the N-terminal domain show a significant shift of FL-1 signal in HEK293/APP (thick line) compared to untransfected HEK293 cells (dotted line). The 4G8 antibody (specific for the middle A-beta epitope) and all antibodies of the invention (specific for N-terminal and middle A-beta epitopes) show no significant shift in fluorescence. Differences in basal fluorescence between HE293/APP ad HEK293 cells are due to different cell size. A FACScan instrument was used in combination with the Cellquest Pro Software package (both Becton Dickinson).

Example 16

List of Identified SEQ ID NOs Relating to Inventive Antibody Molecules

The appended table 10 relates to sequences as defined herein for some specific inventive antibody molecules.

TABLE 10

Identification of SEQ ID NOs for parental antibodies as well as optimized, matured and/or cross-cloned antibody molecules

| Molecule # | VH prot | VL prot | VH DNA | VL DNA | HCDR3 prot | HCDR3 DNA | LCDR3 prot | LCDR3 DNA |
|---|---|---|---|---|---|---|---|---|
| 3 | 4 | 10 | 3 | 9 | 22 | 21 | 16 | 15 |
| 7 | 6 | 12 | 5 | 11 | 24 | 23 | 18 | 17 |
| 8 | 8 | 14 | 7 | 13 | 26 | 25 | 20 | 19 |
| 3.6H5 x 3.6L2 | 33 | 47 | 32 | 46 | 61 | 60 | 75 | 74 |
| 3.6H8 x 3.6L2 | 35 | 49 | 34 | 48 | 63 | 62 | 77 | 76 |
| 7.4H2 x 7.2L1 | 37 | 51 | 36 | 50 | 65 | 64 | 79 | 78 |
| 7.9H2 x 7.12L2 | 39 | 53 | 38 | 52 | 67 | 66 | 81 | 80 |
| 7.9H4 x 7.12L2 | 41 | 55 | 40 | 54 | 69 | 68 | 83 | 82 |
| 7.11H1x7.11L1 | 43 | 57 | 42 | 56 | 71 | 70 | 85 | 84 |
| 7.11H1x7.2L1 | 45 | 59 | 44 | 58 | 73 | 72 | 87 | 86 |
| 7.9H7 | 89 | 91 | 88 | 90 | 93 | 92 | 95 | 94 |
| 3.3H1x3.4L9 | 295 | 325 | 294 | 324 | 355 | 354 | 385 | 384 |

TABLE 10-continued

Identification of SEQ ID NOs for parental antibodies as well as optimized, matured and/or cross-cloned antibody molecules

| Molecule # | VH prot | VL prot | VH DNA | VL DNA | HCDR3 prot | HCDR3 DNA | LCDR3 prot | LCDR3 DNA |
|---|---|---|---|---|---|---|---|---|
| 3.4H1x3.4L9 | 297 | 327 | 296 | 326 | 357 | 356 | 387 | 386 |
| 3.4H3x3.4L7 | 299 | 329 | 298 | 328 | 359 | 358 | 389 | 388 |
| 3.4H3x3.4L9 | 301 | 331 | 300 | 330 | 361 | 360 | 391 | 390 |
| 3.4H7x3.4L9 | 303 | 333 | 302 | 332 | 363 | 362 | 393 | 392 |
| 3.4H7x3.4L7 | 305 | 335 | 304 | 334 | 365 | 364 | 395 | 394 |
| 3.6H5x3.6L1 | 307 | 337 | 306 | 336 | 367 | 366 | 397 | 396 |
| 7.2H2x7.2L1 | 309 | 339 | 308 | 338 | 369 | 368 | 399 | 398 |
| 7.4H2x7.12L2 | 311 | 341 | 310 | 340 | 371 | 370 | 401 | 400 |
| 7.9H2x7.2L1 | 313 | 343 | 312 | 342 | 373 | 372 | 403 | 402 |
| 7.9H2x7.12L1 | 315 | 345 | 314 | 344 | 375 | 374 | 405 | 404 |
| 7.11H2x7.2L1 | 317 | 347 | 316 | 346 | 377 | 376 | 407 | 406 |
| 7.11H2x7.9L1 | 319 | 349 | 318 | 348 | 379 | 378 | 409 | 408 |
| 7.11H2x7.12L1 | 321 | 351 | 320 | 350 | 381 | 380 | 411 | 410 |
| 8.1H1x8.2L1 | 323 | 353 | 322 | 352 | 383 | 382 | 413 | 412 |

The invention claimed is:

1. A nucleic acid molecule comprising a sequence encoding the variable $V_L$-Region the variable $V_H$-Region or both the variable $V_L$-Region and the variable $V_H$-Region of an antibody which antibody comprises:
   (a) a variable $V_L$-Region comprising complementary determining regions, L-CDR1, L-CDR2, L-CDR3, wherein:
   (1) L-CDR1 comprises SEQ ID NO: 143;
   (2) L-CDR2 comprises SEQ ID NO: 144; and
   (3) L-CDR3 comprises SEQ ID NO: 95; and
   (b) a variable $V_H$-Region comprising complementary determining regions, H-CDR1, H-CDR2, H-CDR3, wherein:
   (1) H-CDR1 comprises SEQ ID NO: 146;
   (2) H-CDR2 comprises SEQ ID NOs: 192; and
   (3) H-CDR3 comprises SEQ ID NOs: 93.

2. The nucleic acid molecule according to claim 1, wherein the nucleic acid molecule comprises a sequence that encodes an antibody of the IgG1 subtype.

3. The nucleic acid molecule according to claim 1, wherein the nucleic acid molecule comprises a sequence that encodes the variable $V_L$-Region.

4. The nucleic acid molecule according to claim 1, wherein the nucleic acid molecule comprises a sequence that encodes the variable $V_H$-Region.

5. The nucleic acid molecule according to claim 1, wherein the nucleic acid molecule comprises a sequence that encodes both the variable $V_L$-Region and the variable $V_H$-Region.

6. The nucleic acid molecule according to claim 1, wherein:
   (a) the variable $V_L$-region comprises an amino acid sequence shown in SEQ ID NO: 91, and
   (b) the variable $V_H$-region comprises an amino acid sequence shown in SEQ ID NO: 89.

7. The nucleic acid molecule according to claim 6, wherein the nucleic acid molecule comprises a sequence that encodes the variable $V_L$-region.

8. The nucleic acid molecule according to claim 6, wherein the nucleic acid molecule comprises a sequence that encodes the variable $V_H$-region.

9. The nucleic acid molecule according to claim 6, wherein the nucleic acid molecule comprises a sequence that encodes both the variable $V_L$-region and the variable $V_H$-region.

10. The nucleic acid molecule according to claim 6, wherein the nucleic acid molecule comprises a sequence that encodes an antibody of the IgG1 subtype.

11. The nucleic acid molecule according to claim 1, wherein:
    (a) the variable $V_L$-region comprises an amino acid sequence shown in SEQ ID NO: 91, and
    (b) the variable $V_H$-region comprises an amino acid sequence shown in SEQ ID NO: 425.

12. The nucleic acid molecule according to claim 11, wherein the nucleic acid molecule comprises a sequence that encodes a variable $V_L$-region.

13. The nucleic acid molecule according to claim 11, wherein the nucleic acid molecule comprises a sequence that encodes a variable $V_H$-region.

14. The nucleic acid molecule according to claim 11, wherein the nucleic acid molecule comprises a sequence that encodes both a variable $V_L$-region and a variable $V_H$-region.

15. The nucleic acid molecule according to claim 11, wherein the nucleic acid molecule comprises a sequence that encodes an antibody of the IgG1 subtype.

16. The nucleic acid molecule according to claim 1, comprising a sequence shown in SEQ ID NO: 90.

17. The nucleic acid molecule according to claim 1, comprising a sequence shown in SEQ ID NO: 88.

18. The nucleic acid molecule according to claim 1, comprising a sequence shown in SEQ ID NO: 424.

19. A vector comprising the nucleic acid molecule of claim 1.

20. The vector according to claim 19, wherein the vector comprises a sequence shown in SEQ ID NO: 90.

21. The vector according to claim 19, wherein the vector comprises a sequence shown in SEQ ID NO: 88.

22. The vector according to claim 19, wherein the vector comprises a sequence shown in SEQ ID NO: 424.

23. The vector according to claim 19, wherein the vector comprises a sequence shown in SEQ ID NO: 90 and a sequence shown in SEQ ID NO: 88.

24. The vector according to claim 19, wherein the vector comprises a sequence shown in SEQ ID NO: 90 and a sequence shown in SEQ ID NO: 424.

25. An isolated host cell comprising the vector of claim 19.

26. The host cell according to claim 25, wherein the host cell is a CHO-K1 cell.

27. The host cell according to claim 25, wherein the host cell comprises a sequence shown in SEQ ID NO: 90.

28. The host cell according to claim 25, wherein the host cell comprises a sequence shown in SEQ ID NO: 88.

29. The host cell according to claim 25, wherein the host cell comprises a sequence shown in SEQ ID NO: 424.

30. The host cell according to claim 25, wherein the host cell comprises a sequence shown in SEQ ID NO: 90 and a sequence shown in SEQ ID NO: 88.

31. The host cell according to claim 25, wherein the host cell comprises a sequence shown in SEQ ID NO: 90 and a sequence shown in SEQ ID NO: 424.

32. A method for making a vector of claim 19 comprising inserting the nucleic acid molecule into a plasmid, cosmid, virus, or a bacteriophage vector.

33. The method according to claim 32, wherein the vector further comprises an expression control element, and wherein the nucleic acid molecule is operably linked to the expression control element.

* * * * *

SEQUENCE LISTING

```
<160> NUMBER OF SEQ ID NOS: 425

<210> SEQ ID NO 1
<211> LENGTH: 9
<212> TYPE: PRT
<213> ORGANISM: artificial sequence
<220> FEATURE:
<223> OTHER INFORMATION: synthetic construct; first region of beta-A4
      peptide

<400> SEQUENCE: 1

Ala Glu Phe Arg His Asp Ser Gly Tyr
1               5

<210> SEQ ID NO 2
<211> LENGTH: 14
<212> TYPE: PRT
<213> ORGANISM: artificial sequence
<220> FEATURE:
<223> OTHER INFORMATION: synthetic construct; second region of beta-A4
      peptide

<400> SEQUENCE: 2

Val His His Gln Lys Leu Val Phe Phe Ala Glu Asp Val Gly
1               5                  10

<210> SEQ ID NO 3
<211> LENGTH: 368
<212> TYPE: DNA
<213> ORGANISM: artificial sequence
<220> FEATURE:
<223> OTHER INFORMATION: synthetic construct; VH-region of MS-Roche#3

<400> SEQUENCE: 3
caggtgcaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcgcg attagcggta gcggcggcag cacctattat     180
gcggatagcg tgaaaggccg ttttaccatt tcacgtgata attcgaaaaa cacgctgtat     240
ctgcaaatga acagcctgcg tgcggaagat acggccgtgt attattgcgc gcgtcttact     300
cattatgctc gttattatcg ttattttgat gtttggggcc aaggcaccct ggtgacggtt     360
```

```
agctcagc                                                             368
```

<210> SEQ ID NO 4
<211> LENGTH: 122
<212> TYPE: PRT
<213> ORGANISM: artificial sequence
<220> FEATURE:
<223> OTHER INFORMATION: synthetic construct; VH-region of MS-Roche#3

<400> SEQUENCE: 4

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Thr His Tyr Ala Arg Tyr Tyr Arg Tyr Phe Asp Val Trp
            100                 105                 110

Gly Gln Gly Thr Leu Val Thr Val Ser Ser
        115                 120
```

<210> SEQ ID NO 5
<211> LENGTH: 379
<212> TYPE: DNA
<213> ORGANISM: artificial sequence
<220> FEATURE:
<223> OTHER INFORMATION: synthetic construct; VH-region of MS-Roche#7

<400> SEQUENCE: 5

```
caggtgcaat tggtggaaag cggcggcggc ctggtgcaac cgggcggcag cctgcgtctg    60
agctgcgcgg cctccggatt tacctttagc agctatgcga tgagctgggt gcgccaagcc   120
cctgggaagg gtctcgagtg ggtgagcgcg attagcggta gcggcggcag cacctattat   180
gcggatagcg tgaaaggccg tttaccattt cacgtgataa ttcgaaaaac accctgtatc   240
tgcaaatgaa cagcctgcgt gcggaagata cggccgtgta ttattgcgcg cgtggtaagg   300
gtaatactca taagccttat ggttatgttc gttattttga tgtttgggc caaggcaccc    360 tggtgacggt tagctcagc                                                379
```

<210> SEQ ID NO 6
<211> LENGTH: 126
<212> TYPE: PRT
<213> ORGANISM: artificial sequence
<220> FEATURE:
<223> OTHER INFORMATION: synthetic construct; VH-region of MS-Roche#7

<400> SEQUENCE: 6

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Lys Gly Asn Thr His Lys Pro Tyr Gly Tyr Val Arg Tyr
                100                 105                 110

Phe Asp Val Trp Gly Gln Gly Thr Leu Val Thr Val Ser Ser
                115                 120                 125

<210> SEQ ID NO 7
<211> LENGTH: 374
<212> TYPE: DNA
<213> ORGANISM: artificial sequence
<220> FEATURE:
<223> OTHER INFORMATION: synthetic construct; VH-region of MS-Roche#8

<400> SEQUENCE: 7
caggtgcaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcgcg attagcggta gcggcggcag cacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtcttctt     300
tctcgtggtt ataatggtta ttatcataag tttgatgttt ggggccaagg caccctggtg     360
acggttagct cagc                                                        374

<210> SEQ ID NO 8
<211> LENGTH: 124
<212> TYPE: PRT
<213> ORGANISM: artificial sequence
<220> FEATURE:
<223> OTHER INFORMATION: synthetic construct; VH-region of MS-Roche#8

<400> SEQUENCE: 8

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Leu Ser Arg Gly Tyr Asn Gly Tyr Tyr His Lys Phe Asp
                100                 105                 110

Val Trp Gly Gln Gly Thr Leu Val Thr Val Ser Ser
                115                 120

<210> SEQ ID NO 9
<211> LENGTH: 330
<212> TYPE: DNA
<213> ORGANISM: artificial sequence
<220> FEATURE:
<223> OTHER INFORMATION: synthetic construct; VL-region of MS-Roche#3
```

-continued

<400> SEQUENCE: 9

```
gatatcgtgc tgacccagag cccggcgacc ctgagcctgt ctccgggcga acgtgcgacc    60
ctgagctgca gagcgagcca gagcgtgagc agcagctatc tggcgtggta ccagcagaaa   120
ccaggtcaag caccgcgtct attaatttat ggcgcgagca gccgtgcaac tggggtcccg   180
gcgcgtttta gcggctctgg atccggcacg gattttaccc tgaccattag cagcctggaa   240
cctgaagact ttgcggttta ttattgccag caggtttata atcctcctgt tacctttggc   300
cagggtacga agttgaaat taaacgtacg                                      330
```

<210> SEQ ID NO 10
<211> LENGTH: 110
<212> TYPE: PRT
<213> ORGANISM: artificial sequence
<220> FEATURE:
<223> OTHER INFORMATION: synthetic construct; VL-region of MS-Roche#3

<400> SEQUENCE: 10

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Val Tyr Asn Pro Pro
                 85                  90                  95

Val Thr Phe Gly Gln Gly Thr Lys Val Glu Ile Lys Arg Thr
             100                 105                 110
```

<210> SEQ ID NO 11
<211> LENGTH: 330
<212> TYPE: DNA
<213> ORGANISM: artificial sequence
<220> FEATURE:
<223> OTHER INFORMATION: synthetic construct; VL-region of MS-Roche#7

<400> SEQUENCE: 11

```
gatatcgtgc tgacccagag cccggcgacc ctgagcctgt ctccgggcga acgtgcgacc    60
ctgagctgca gagcgagcca gagcgtgagc agcagctatc tggcgtggta ccagcagaaa   120
ccaggtcaag caccgcgtct attaatttat ggcgcgagca gccgtgcaac tggggtcccg   180
gcgcgtttta gcggctctgg atccggcacg gattttaccc tgaccattag cagcctggaa   240
cctgaagact ttgcgactta ttattgcttt cagctttatt ctgatccttt tacctttggc   300
cagggtacga agttgaaat taaacgtacg                                      330
```

<210> SEQ ID NO 12
<211> LENGTH: 110
<212> TYPE: PRT
<213> ORGANISM: artificial sequence
<220> FEATURE:
<223> OTHER INFORMATION: synthetic construct; VL-region of MS-Roche#7

<400> SEQUENCE: 12

```
Asp Ile Val Leu Thr Gln Ser Pro Ala Thr Leu Ser Leu Ser Pro Gly
 1               5                  10                  15
```

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Leu Tyr Ser Asp Pro
                85                  90                  95

Phe Thr Phe Gly Gln Gly Thr Lys Val Glu Ile Lys Arg Thr
                100                 105                 110
```

<210> SEQ ID NO 13
<211> LENGTH: 330
<212> TYPE: DNA
<213> ORGANISM: artificial sequence
<220> FEATURE:
<223> OTHER INFORMATION: synthetic construct; VL-region of MS-Roche#8

<400> SEQUENCE: 13

```
gatatcgtgc tgacccagag cccggcgacc ctgagcctgt ctccgggcga acgtgcgacc      60
ctgagctgca gcgcagcca gagcgtgagc agcagctatc tggcgtggta ccagcagaaa     120
ccaggtcaag caccgcgtct attaatttat ggcgcgagca gccgtgcaac tggggtcccg     180
gcgcgtttta gcggctctgg atccggcacg gatttttaccc tgaccattag cagcctggaa    240
cctgaagact ttgcgactta ttattgccag cagctttctt cttttcctcc tacctttggc     300
cagggtacga agttgaaat taaacgtacg                                       330
```

<210> SEQ ID NO 14
<211> LENGTH: 110
<212> TYPE: PRT
<213> ORGANISM: artificial sequence
<220> FEATURE:
<223> OTHER INFORMATION: synthetic construct; VL-region of MS-Roche#8

<400> SEQUENCE: 14

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Leu Ser Ser Phe Pro
                85                  90                  95

Pro Thr Phe Gly Gln Gly Thr Lys Val Glu Ile Lys Arg Thr
                100                 105                 110
```

<210> SEQ ID NO 15
<211> LENGTH: 24
<212> TYPE: DNA
<213> ORGANISM: artificial sequence
<220> FEATURE:
<223> OTHER INFORMATION: synthetic construct; CDR3 of VL-region of MS-
      Roche#3

```
<400> SEQUENCE: 15
cagcaggttt ataatcctcc tgtt                                              24

<210> SEQ ID NO 16
<211> LENGTH: 8
<212> TYPE: PRT
<213> ORGANISM: artificial sequence
<220> FEATURE:
<223> OTHER INFORMATION: synthetic construct; CDR3 of VL-region of MS-
      Roche#3

<400> SEQUENCE: 16

Gln Gln Val Tyr Asn Pro Pro Val
1               5

<210> SEQ ID NO 17
<211> LENGTH: 24
<212> TYPE: DNA
<213> ORGANISM: artificial sequence
<220> FEATURE:
<223> OTHER INFORMATION: synthetic construct; CDR3 of VL-region of MS-
      Roche#7

<400> SEQUENCE: 17
tttcagcttt attctgatcc tttt                                              24

<210> SEQ ID NO 18
<211> LENGTH: 8
<212> TYPE: PRT
<213> ORGANISM: artificial sequence
<220> FEATURE:
<223> OTHER INFORMATION: synthetic construct; CDR3 of VL-region of MS-
      Roche#7

<400> SEQUENCE: 18

Phe Gln Leu Tyr Ser Asp Pro Phe
1               5

<210> SEQ ID NO 19
<211> LENGTH: 24
<212> TYPE: DNA
<213> ORGANISM: artificial sequence
<220> FEATURE:
<223> OTHER INFORMATION: synthetic construct; CDR3 of VL-region of MS-
      Roche#8

<400> SEQUENCE: 19
cagcagcttt cttctttcc tcct                                               24

<210> SEQ ID NO 20
<211> LENGTH: 8
<212> TYPE: PRT
<213> ORGANISM: artificial sequence
<220> FEATURE:
<223> OTHER INFORMATION: synthetic construct; CDR3 of VL-region of MS-
      Roche#8

<400> SEQUENCE: 20

Gln Gln Leu Ser Ser Phe Pro Pro
1               5

<210> SEQ ID NO 21
<211> LENGTH: 39
<212> TYPE: DNA
<213> ORGANISM: artificial sequence
<220> FEATURE:
<223> OTHER INFORMATION: synthetic construct; CDR3 of VH-region of MS-
      Roche#3
```

-continued

```
<400> SEQUENCE: 21
cttactcatt atgctcgtta ttatcgttat tttgatgtt                                  39

<210> SEQ ID NO 22
<211> LENGTH: 13
<212> TYPE: PRT
<213> ORGANISM: artificial sequence
<220> FEATURE:
<223> OTHER INFORMATION: synthetic construct; CDR3 of VH-region of MS-
      Roche#3

<400> SEQUENCE: 22

Leu Thr His Tyr Ala Arg Tyr Tyr Arg Tyr Phe Asp Val
1               5                   10

<210> SEQ ID NO 23
<211> LENGTH: 51
<212> TYPE: DNA
<213> ORGANISM: artificial sequence
<220> FEATURE:
<223> OTHER INFORMATION: synthetic construct; CDR3 of VH-region of MS-
      Roche#7

<400> SEQUENCE: 23
ggtaagggta atactcataa gccttatggt tatgttcgtt attttgatgt t                    51

<210> SEQ ID NO 24
<211> LENGTH: 17
<212> TYPE: PRT
<213> ORGANISM: artificial sequence
<220> FEATURE:
<223> OTHER INFORMATION: synthetic construct; CDR3 of VH-region of MS-
      Roche#7

<400> SEQUENCE: 24

Gly Lys Gly Asn Thr His Lys Pro Tyr Gly Tyr Val Arg Tyr Phe Asp
1               5                   10                  15

Val

<210> SEQ ID NO 25
<211> LENGTH: 45
<212> TYPE: DNA
<213> ORGANISM: artificial sequence
<220> FEATURE:
<223> OTHER INFORMATION: synthetic construct; CDR3 of VH-region of MS-
      Roche#8

<400> SEQUENCE: 25
cttctttctc gtggttataa tggttattat cataagtttg atgtt                           45

<210> SEQ ID NO 26
<211> LENGTH: 15
<212> TYPE: PRT
<213> ORGANISM: artificial sequence
<220> FEATURE:
<223> OTHER INFORMATION: synthetic construct; CDR3 of VH-region of MS-
      Roche#8

<400> SEQUENCE: 26

Leu Leu Ser Arg Gly Tyr Asn Gly Tyr Tyr His Lys Phe Asp Val
1               5                   10                  15

<210> SEQ ID NO 27
<211> LENGTH: 42
<212> TYPE: PRT
<213> ORGANISM: artificial sequence
```

-continued

```
<220> FEATURE:
<223> OTHER INFORMATION: synthetic construct; beta-A4 peptide

<400> SEQUENCE: 27

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 28
<211> LENGTH: 17
<212> TYPE: DNA
<213> ORGANISM: artificial sequence
<220> FEATURE:
<223> OTHER INFORMATION: synthetic construct; VL-primer for

<400> SEQUENCE: 28
gtggtggttc cgatatc                                                   17

<210> SEQ ID NO 29
<211> LENGTH: 43
<212> TYPE: DNA
<213> ORGANISM: artificial sequence
<220> FEATURE:
<223> OTHER INFORMATION: synthetic construct; VL-primer back

<400> SEQUENCE: 29
agcgtcacac tcggtgcggc tttcggctgg ccaagaacgg tta                      43

<210> SEQ ID NO 30
<211> LENGTH: 17
<212> TYPE: DNA
<213> ORGANISM: artificial sequence
<220> FEATURE:
<223> OTHER INFORMATION: synthetic construct; control primer for

<400> SEQUENCE: 30
caggaaacag ctatgac                                                   17

<210> SEQ ID NO 31
<211> LENGTH: 19
<212> TYPE: DNA
<213> ORGANISM: artificial sequence
<220> FEATURE:
<223> OTHER INFORMATION: synthetic construct; control primer back

<400> SEQUENCE: 31
taccgttgct cttcacccc                                                 19

<210> SEQ ID NO 32
<211> LENGTH: 360
<212> TYPE: DNA
<213> ORGANISM: artificial sequence
<220> FEATURE:
<223> OTHER INFORMATION: synthetic construct; VH MS-Roche#3.6H5 x 3.6L2

<400> SEQUENCE: 32
caattggtgg aaagcggcgg cggcctggtg caaccgggcg gcagcctgcg tctgagctgc    60
gcggcctccg gatttacctt tagcagctat gcgatgagct gggtgcgcca agcccctggg   120
aagggtctcg agtgggtgag cgctattttct gagtctggta agactaagta ttatgctgat   180
tctgttaagg gtcgttttac catttcacgt gataattcga aaaacaccct gtatctgcaa   240
```

```
atgaacagcc tgcgtgcgga agatacggcc gtgtattatt gcgcgcgtct tactcattat    300
gctcgttatt atcgttattt tgatgtttgg ggccaaggca ccctggtgac ggttagctca    360
```

<210> SEQ ID NO 33
<211> LENGTH: 120
<212> TYPE: PRT
<213> ORGANISM: artificial sequence
<220> FEATURE:
<223> OTHER INFORMATION: synthetic construct; VH MS-Roche#3.6H5 x 3.6L2

<400> SEQUENCE: 33

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Glu Ser Gly Lys Thr Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Thr His Tyr Ala Arg Tyr Tyr Arg Tyr Phe Asp Val Trp Gly Gln
            100                 105                 110

Gly Thr Leu Val Thr Val Ser Ser
        115                 120

<210> SEQ ID NO 34
<211> LENGTH: 360
<212> TYPE: DNA
<213> ORGANISM: artificial sequence
<220> FEATURE:
<223> OTHER INFORMATION: synthetic construct; VH MS-Roche#3.6H8 x 3.6L2

<400> SEQUENCE: 34

```
caattggtgg aaagcggcgg cggcctggtg caaccgggcg cagcctgcg tctgagctgc    60 gcggcctccg gatttacctt tagcagctat gcgatgagct gggtgcgcca gcccctggg   120 aagggtctcg agtgggtgag cgctatttct gagtattcta gtttaagta ttatgctgat   180 tctgttaagg gtcgtttac catttcacgt gataattcga aaacaccct gtatctgcaa    240 atgaacagcc tgcgtgcgga agatacggcc gtgtattatt gcgcgcgtct tactcattat    300
gctcgttatt atcgttattt tgatgtttgg ggccaaggca ccctggtgac ggttagctca    360
```

<210> SEQ ID NO 35
<211> LENGTH: 120
<212> TYPE: PRT
<213> ORGANISM: artificial sequence
<220> FEATURE:
<223> OTHER INFORMATION: synthetic construct; VH MS-Roche#3.6H8 x 3.6L2

<400> SEQUENCE: 35

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Glu Tyr Ser Lys Phe Lys Tyr Tyr Ala Asp Ser Val Lys Gly

```
                 50                  55                  60
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Leu Thr His Tyr Ala Arg Tyr Tyr Arg Tyr Phe Asp Val Trp Gly Gln
                100                 105                 110

Gly Thr Leu Val Thr Val Ser Ser
            115                 120

<210> SEQ ID NO 36
<211> LENGTH: 372
<212> TYPE: DNA
<213> ORGANISM: artificial sequence
<220> FEATURE:
<223> OTHER INFORMATION: synthetic construct; VH MS-Roche#7.4H2 x 7.2L1

<400> SEQUENCE: 36
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgctattaat tataatggtg ctcgtattta ttatgctgat     180
tctgttaagg gtcgttttac catttcacgt gataattcga aaaacaccct gtatctgcaa     240
atgaacagcc tgcgtgcgga agatacggcc gtgtattatt gcgcgcgtgg taagggtaat     300
actcataagc cttatggtta tgttcgttat tttgatgttt ggggccaagg caccctggtg     360
acggttagct ca                                                         372

<210> SEQ ID NO 37
<211> LENGTH: 124
<212> TYPE: PRT
<213> ORGANISM: artificial sequence
<220> FEATURE:
<223> OTHER INFORMATION: synthetic construct; VH MS-Roche#7.4H2 x 7.2L1

<400> SEQUENCE: 37

Gln Leu Val Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
                20                  25                  30

Ser Trp Val Arg Gln Ala Pro Gly Lys Gly Leu Glu Trp Val Ser Ala
            35                  40                  45

Ile Asn Tyr Asn Gly Ala Arg Ile Tyr Tyr Ala Asp Ser Val Lys Gly
         50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
                100                 105                 110

Val Trp Gly Gln Gly Thr Leu Val Thr Val Ser Ser
            115                 120

<210> SEQ ID NO 38
<211> LENGTH: 372
<212> TYPE: DNA
<213> ORGANISM: artificial sequence
<220> FEATURE:
<223> OTHER INFORMATION: synthetic construct; VH MS-Roche#7.9H2 x 7.12L2
```

-continued

<400> SEQUENCE: 38

```
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgctattaat gctgatggta atcgtaagta ttatgctgat     180
tctgttaagg gtcgttttac catttcacgt gataattcga aaacaccct gtatctgcaa      240
atgaacagcc tgcgtgcgga agatacggcc gtgtattatt gcgcgcgtgg taagggtaat     300
actcataagc cttatggtta tgttcgttat tttgatgttt ggggccaagg caccctggtg     360
acggttagct ca                                                         372
```

<210> SEQ ID NO 39
<211> LENGTH: 124
<212> TYPE: PRT
<213> ORGANISM: artificial sequence
<220> FEATURE:
<223> OTHER INFORMATION: synthetic construct; VH MS-Roche#7.9H2 x 7.12L2

<400> SEQUENCE: 39

```
Gln Leu Val Glu Ser Gly Gly Gly Leu Val Gln Pro Gly Gly Ser Leu
1               5                   10                  15
Arg Leu Ser Cys Ala Ala Ser Gly Phe Thr Phe Ser Ser Tyr Ala Met
            20                  25                  30
Ser Trp Val Arg Gln Ala Pro Gly Lys Gly Leu Glu Trp Val Ser Ala
        35                  40                  45
Ile Asn Ala Asp Gly Asn Arg Lys Tyr Tyr Ala Asp Ser Val Lys Gly
    50                  55                  60
Arg Phe Thr Ile Ser Arg Asp Asn Ser Lys Asn Thr Leu Tyr Leu Gln
65                  70                  75                  80
Met Asn Ser Leu Arg Ala Glu Asp Thr Ala Val Tyr Tyr Cys Ala Arg
                85                  90                  95
Gly Lys Gly Asn Thr His Lys Pro Tyr Gly Tyr Val Arg Tyr Phe Asp
            100                 105                 110
Val Trp Gly Gln Gly Thr Leu Val Thr Val Ser Ser
        115                 120
```

<210> SEQ ID NO 40
<211> LENGTH: 372
<212> TYPE: DNA
<213> ORGANISM: artificial sequence
<220> FEATURE:
<223> OTHER INFORMATION: synthetic construct; VH MS-Roche#7.9H4 x 7.12L2

<400> SEQUENCE: 40

```
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgctattaat gctgttggta tgaagaagtt ttatgctgat     180
tctgttaagg gtcgttttac catttcacgt gataattcga aaacaccct gtatctgcaa      240
atgaacagcc tgcgtgcgga agatacggcc gtgtattatt gcgcgcgtgg taagggtaat     300
actcataagc cttatggtta tgttcgttat tttgatgttt ggggccaagg caccctggtg     360
acggttagct ca                                                         372
```

<210> SEQ ID NO 41
<211> LENGTH: 124
<212> TYPE: PRT
<213> ORGANISM: artificial sequence
<220> FEATURE:

<223> OTHER INFORMATION: synthetic construct; VH MS-Roche#7.9H4 x 7.12L2

<400> SEQUENCE: 41

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Asn Ala Val Gly Met Lys Lys Phe Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
            115                 120
```

<210> SEQ ID NO 42
<211> LENGTH: 372
<212> TYPE: DNA
<213> ORGANISM: artificial sequence
<220> FEATURE:
<223> OTHER INFORMATION: synthetic construct; VH MS-Roche#7.11H1 x 7.11L1

<400> SEQUENCE: 42

```
caattggtgg aaagcggcgg cggcctggtg caaccgggcg gcagcctgcg tctgagctgc      60
gcggcctccg gatttacctt tagcagctat gcgatgagct gggtgcgcca gcccctgggg    120
aagggtctcg agtgggtgag cggtattaat gctgctggtt ttcgtactta ttatgctgat    180
tctgttaagg gtcgttttac catttcacgt gataattcga aaacacccct gtatctgcaa    240
atgaacagcc tgcgtgcgga agatacggcc gtgtattatt gcgcgcgtgg taagggtaat    300
actcataagc cttatggtta tgttcgttat tttgatgttt ggggccaagg caccctggtg    360
acggttagct ca                                                         372
```

<210> SEQ ID NO 43
<211> LENGTH: 124
<212> TYPE: PRT
<213> ORGANISM: artificial sequence
<220> FEATURE:
<223> OTHER INFORMATION: synthetic construct; VH MS-Roche#7.11H1 x 7.11L1

<400> SEQUENCE: 43

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Gly
        35                  40                  45

Ile Asn Ala Ala Gly Phe Arg Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
```

```
                       85                  90                  95
Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
        115                 120

<210> SEQ ID NO 44
<211> LENGTH: 372
<212> TYPE: DNA
<213> ORGANISM: artificial sequence
<220> FEATURE:
<223> OTHER INFORMATION: synthetic construct; VH MS-Roche#7.11H1 x 7.2L1

<400> SEQUENCE: 44
caattggtgg aaagcggcgg cggcctggtg caaccgggcg gcagcctgcg tctgagctgc      60
gcggcctccg gatttacctt tagcagctat gcgatgagct gggtgcgcca gcccctggg     120 aagggtctcg agtgggtgag cggtattaat gctgctggtt ttcgtactta ttatgctgat    180
tctgttaagg gtcgttttac catttcacgt gataattcga aaacaccct gtatctgcaa     240 atgaacagcc tgcgtgcgga agatacggcc gtgtattatt gcgcgcgtgg taagggtaat    300
actcataagc cttatggtta tgttcgttat tttgatgttt ggggccaagg caccctggtg    360
acggttagct ca                                                        372

<210> SEQ ID NO 45
<211> LENGTH: 124
<212> TYPE: PRT
<213> ORGANISM: artificial sequence
<220> FEATURE:
<223> OTHER INFORMATION: synthetic construct; VH MS-Roche#7.11H1 x 7.2L1

<400> SEQUENCE: 45

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Gly
        35                  40                  45

Ile Asn Ala Ala Gly Phe Arg Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
        115                 120

<210> SEQ ID NO 46
<211> LENGTH: 330
<212> TYPE: DNA
<213> ORGANISM: artificial sequence
<220> FEATURE:
<223> OTHER INFORMATION: synthetic construct; VL MS-Roche#3.6H5 x 3.6L2

<400> SEQUENCE: 46
gatatcgtgc tgacccagag cccggcgacc ctgagcctgt ctccgggcga acgtgcgacc     60
ctgagctgca gagcgagcca gtttctttct cgttattatc tggcgtggta ccagcagaaa   120
```

```
ccaggtcaag caccgcgtct attaatttat ggcgcgagca gccgtgcaac tggggtcccg      180
gcgcgtttta gcggctctgg atccggcacg gatttaccc tgaccattag cagcctggaa       240
cctgaagact ttgcggttta ttattgccag cagacttata attatcctcc tacctttggc      300
cagggtacga agttgaaat taaacgtacg                                         330
```

<210> SEQ ID NO 47
<211> LENGTH: 110
<212> TYPE: PRT
<213> ORGANISM: artificial sequence
<220> FEATURE:
<223> OTHER INFORMATION: synthetic construct; VL MS-Roche#3.6H5 x 3.6L2

<400> SEQUENCE: 47

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Leu Ser Arg Tyr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Thr Tyr Asn Tyr Pro
                85                  90                  95

Pro Thr Phe Gly Gln Gly Thr Lys Val Glu Ile Lys Arg Thr
            100                 105                 110
```

<210> SEQ ID NO 48
<211> LENGTH: 330
<212> TYPE: DNA
<213> ORGANISM: artificial sequence
<220> FEATURE:
<223> OTHER INFORMATION: synthetic construct; VL MS-Roche#3.6H8 x 3.6L2

<400> SEQUENCE: 48

```
gatatcgtgc tgacccagag cccggcgacc ctgagcctgt ctccgggcga acgtgcgacc      60
ctgagctgca gagcgagcca gtttctttct cgttattatc tggcgtggta ccagcagaaa     120
ccaggtcaag caccgcgtct attaatttat ggcgcgagca gccgtgcaac tggggtcccg     180
gcgcgtttta gcggctctgg atccggcacg gatttaccc tgaccattag cagcctggaa      240
cctgaagact ttgcggttta ttattgccag cagacttata attatcctcc tacctttggc     300
cagggtacga agttgaaat taaacgtacg                                        330
```

<210> SEQ ID NO 49
<211> LENGTH: 110
<212> TYPE: PRT
<213> ORGANISM: artificial sequence
<220> FEATURE:
<223> OTHER INFORMATION: synthetic construct; VL MS-Roche#3.6H8 x 3.6L2

<400> SEQUENCE: 49

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Leu Ser Arg Tyr
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Thr Tyr Asn Tyr Pro
                 85                  90                  95

Pro Thr Phe Gly Gln Gly Thr Lys Val Glu Ile Lys Arg Thr
            100                 105                 110
```

<210> SEQ ID NO 50
<211> LENGTH: 330
<212> TYPE: DNA
<213> ORGANISM: artificial sequence
<220> FEATURE:
<223> OTHER INFORMATION: synthetic construct; VL MS-Roche#7.4H2 x 7.2L1

<400> SEQUENCE: 50

```
gatatcgtgc tgacccagag cccggcgacc ctgagcctgt ctccgggcga acgtgcgacc      60
ctgagctgca gagcgagcca gtatgttgat cgtacttatc tggcgtggta ccagcagaaa     120
ccaggtcaag caccgcgtct attaatttat ggcgcgagca gccgtgcaac tggggtcccg     180
gcgcgtttta gcggctctgg atccggcacg gattttaccc tgaccattag cagcctggaa     240
cctgaagact ttgcgactta ttattgccag cagatttatt cttttcctca tacctttggc     300
cagggtacga agttgaaat taaacgtacg                                        330
```

<210> SEQ ID NO 51
<211> LENGTH: 110
<212> TYPE: PRT
<213> ORGANISM: artificial sequence
<220> FEATURE:
<223> OTHER INFORMATION: synthetic construct; VL MS-Roche#7.4H2 x 7.2L1

<400> SEQUENCE: 51

```
Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Tyr Val Asp Arg Thr
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Gln Gln Ile Tyr Ser Phe Pro
                 85                  90                  95

His Thr Phe Gly Gln Gly Thr Lys Val Glu Ile Lys Arg Thr
            100                 105                 110
```

<210> SEQ ID NO 52
<211> LENGTH: 330
<212> TYPE: DNA
<213> ORGANISM: artificial sequence
<220> FEATURE:
<223> OTHER INFORMATION: synthetic construct; VL MS-Roche#7.9H2 x 7.12L2

<400> SEQUENCE: 52

```
gatatcgtgc tgacccagag cccggcgacc ctgagcctgt ctccgggcga acgtgcgacc      60
ctgagctgca gagcgagcca gcgttttttt tataagtatc tggcgtggta ccagcagaaa     120
ccaggtcaag caccgcgtct attaatttct ggttcttcta accgtgcaac tggggtcccg     180
```

```
gcgcgtttta gcggctctgg atccggcacg gattttaccc tgaccattag cagcctggaa      240
cctgaagact ttgcggttta ttattgcctt cagctttata atattcctaa tacctttggc      300
cagggtacga agttgaaat taaacgtacg                                         330
```

<210> SEQ ID NO 53
<211> LENGTH: 110
<212> TYPE: PRT
<213> ORGANISM: artificial sequence
<220> FEATURE:
<223> OTHER INFORMATION: synthetic construct; VL MS-Roche#7.9H2 x 7.12L2

<400> SEQUENCE: 53

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Phe Phe Tyr Lys
            20                  25                  30

Tyr Leu Ala Trp Tyr Gln Gln Lys Pro Gly Gln Ala Pro Arg Leu Leu
        35                  40                  45

Ile Ser Gly Ser Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Leu Gln Leu Tyr Asn Ile Pro
                85                  90                  95

Asn Thr Phe Gly Gln Gly Thr Lys Val Glu Ile Lys Arg Thr
            100                 105                 110
```

<210> SEQ ID NO 54
<211> LENGTH: 330
<212> TYPE: DNA
<213> ORGANISM: artificial sequence
<220> FEATURE:
<223> OTHER INFORMATION: synthetic construct; VL MS-Roche#7.9H4 x 7.12L2

<400> SEQUENCE: 54

```
gatatcgtgc tgacccagag cccggcgacc ctgagcctgt ctccgggcga acgtgcgacc      60
ctgagctgca gcgagcca gcgttttttt tataagtatc tggcgtggta ccagcagaaa       120
ccaggtcaag caccgcgtct attaatttct ggttcttcta accgtgcaac tggggtcccg      180
gcgcgtttta gcggctctgg atccggcacg gattttaccc tgaccattag cagcctggaa      240
cctgaagact ttgcggttta ttattgcctt cagctttata atattcctaa tacctttggc      300
cagggtacga agttgaaat taaacgtacg                                         330
```

<210> SEQ ID NO 55
<211> LENGTH: 110
<212> TYPE: PRT
<213> ORGANISM: artificial sequence
<220> FEATURE:
<223> OTHER INFORMATION: synthetic construct; VL MS-Roche#7.9H4 x 7.12L2

<400> SEQUENCE: 55

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Phe Phe Tyr Lys
            20                  25                  30

Tyr Leu Ala Trp Tyr Gln Gln Lys Pro Gly Gln Ala Pro Arg Leu Leu
        35                  40                  45

Ile Ser Gly Ser Ser Asn Arg Ala Thr Gly Val Pro Ala Arg Phe Ser
```

```
                  50                  55                  60
Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Leu Gln Leu Tyr Asn Ile Pro
                 85                  90                  95

Asn Thr Phe Gly Gln Gly Thr Lys Val Glu Ile Lys Arg Thr
            100                 105                 110
```

<210> SEQ ID NO 56
<211> LENGTH: 330
<212> TYPE: DNA
<213> ORGANISM: artificial sequence
<220> FEATURE:
<223> OTHER INFORMATION: synthetic construct; VL MS-Roche#7.11H1 x
      7.11L1

<400> SEQUENCE: 56
gatatcgtgc tgacccagag cccggcgacc ctgagcctgt ctccgggcga acgtgcgacc      60
ctgagctgca gagcgagcca gcgtattctt cgtatttatc tggcgtggta ccagcagaaa     120
ccaggtcaag caccgcgtct attaatttat ggcgcgagca gccgtgcaac tgggtcccg      180 gcgcgttta gcggctctgg atccggcacg gattttaccc tgaccattag cagcctggaa      240
cctgaagact ttgcgactta ttattgccag caggtttatt ctcctcctca tacctttggc     300
cagggtacga agttgaaat taaacgtacg                                       330

<210> SEQ ID NO 57
<211> LENGTH: 110
<212> TYPE: PRT
<213> ORGANISM: artificial sequence
<220> FEATURE:
<223> OTHER INFORMATION: synthetic construct; VL MS-Roche#7.11H1 x
      7.11L1

<400> SEQUENCE: 57

```
Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Arg Ile Leu Arg Ile
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Gln Gln Val Tyr Ser Pro Pro
                 85                  90                  95

His Thr Phe Gly Gln Gly Thr Lys Val Glu Ile Lys Arg Thr
            100                 105                 110
```

<210> SEQ ID NO 58
<211> LENGTH: 330
<212> TYPE: DNA
<213> ORGANISM: artificial sequence
<220> FEATURE:
<223> OTHER INFORMATION: synthetic construct; VL MS-Roche#7.11H1 x 7.2L1

<400> SEQUENCE: 58
gatatcgtgc tgacccagag cccggcgacc ctgagcctgt ctccgggcga acgtgcgacc      60
ctgagctgca gagcgagcca gtatgttgat cgtacttatc tggcgtggta ccagcagaaa     120

```
ccaggtcaag caccgcgtct attaatttat ggcgcgagca gccgtgcaac tggggtcccg      180
gcgcgtttta gcggctctgg atccggcacg gattttaccc tgaccattag cagcctggaa      240
cctgaagact ttgcgactta ttattgccag cagatttatt cttttcctca tacctttggc      300
cagggtacga agttgaaat  taaacgtacg                                       330
```

<210> SEQ ID NO 59
<211> LENGTH: 110
<212> TYPE: PRT
<213> ORGANISM: artificial sequence
<220> FEATURE:
<223> OTHER INFORMATION: synthetic construct; VL MS-Roche#7.11H1 x 7.2L1

<400> SEQUENCE: 59

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Tyr Val Asp Arg Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Ile Tyr Ser Phe Pro
                85                  90                  95

His Thr Phe Gly Gln Gly Thr Lys Val Glu Ile Lys Arg Thr
            100                 105                 110

<210> SEQ ID NO 60
<211> LENGTH: 39
<212> TYPE: DNA
<213> ORGANISM: artificial sequence
<220> FEATURE:
<223> OTHER INFORMATION: HCDR3 MS-Roche#3.6H5 x 3.6L2

<400> SEQUENCE: 60

```
cttactcatt atgctcgtta ttatcgttat tttgatgtt                              39
```

<210> SEQ ID NO 61
<211> LENGTH: 13
<212> TYPE: PRT
<213> ORGANISM: artificial sequence
<220> FEATURE:
<223> OTHER INFORMATION: HCDR3 MS-Roche#3.6H5 x 3.6L2

<400> SEQUENCE: 61

Leu Thr His Tyr Ala Arg Tyr Tyr Arg Tyr Phe Asp Val
1               5                   10

<210> SEQ ID NO 62
<211> LENGTH: 39
<212> TYPE: DNA
<213> ORGANISM: artificial sequence
<220> FEATURE:
<223> OTHER INFORMATION: HCDR3 MS-Roche#3.6H8 x 3.6L2

<400> SEQUENCE: 62

```
cttactcatt atgctcgtta ttatcgttat tttgatgtt                              39
```

<210> SEQ ID NO 63
<211> LENGTH: 13
<212> TYPE: PRT

-continued

<213> ORGANISM: artificial sequence
<220> FEATURE:
<223> OTHER INFORMATION: HCDR3 MS-Roche#3.6H8 x 3.6L2

<400> SEQUENCE: 63

Leu Thr His Tyr Ala Arg Tyr Tyr Arg Tyr Phe Asp Val
1               5                   10

<210> SEQ ID NO 64
<211> LENGTH: 51
<212> TYPE: DNA
<213> ORGANISM: artificial sequence
<220> FEATURE:
<223> OTHER INFORMATION: HCDR3 MS-Roche#7.4H2x7.2L1

<400> SEQUENCE: 64 ggtaaggta atactcataa gccttatggt tatgttcgtt attttgatgt t         51

<210> SEQ ID NO 65
<211> LENGTH: 17
<212> TYPE: PRT
<213> ORGANISM: artificial sequence
<220> FEATURE:
<223> OTHER INFORMATION: HCDR3 MS-Roche#7.4H2x7.2L1

<400> SEQUENCE: 65

Gly Lys Gly Asn Thr His Lys Pro Tyr Gly Tyr Val Arg Tyr Phe Asp
1               5                   10                  15
Val

<210> SEQ ID NO 66
<211> LENGTH: 51
<212> TYPE: DNA
<213> ORGANISM: artificial sequence
<220> FEATURE:
<223> OTHER INFORMATION: HCDR3 MS-Roche#7.9H2x7.12L2

<400> SEQUENCE: 66 ggtaaggta atactcataa gccttatggt tatgttcgtt attttgatgt t         51

<210> SEQ ID NO 67
<211> LENGTH: 17
<212> TYPE: PRT
<213> ORGANISM: artificial sequence
<220> FEATURE:
<223> OTHER INFORMATION: HCDR3 MS-Roche#7.9H2x7.12L2

<400> SEQUENCE: 67

Gly Lys Gly Asn Thr His Lys Pro Tyr Gly Tyr Val Arg Tyr Phe Asp
1               5                   10                  15
Val

<210> SEQ ID NO 68
<211> LENGTH: 51
<212> TYPE: DNA
<213> ORGANISM: artificial sequence
<220> FEATURE:
<223> OTHER INFORMATION: HCDR3 MS-Roche#7.9H4x7.12L2

<400> SEQUENCE: 68 ggtaaggta atactcataa gccttatggt tatgttcgtt attttgatgt t         51

<210> SEQ ID NO 69
<211> LENGTH: 17
<212> TYPE: PRT
<213> ORGANISM: artificial sequence

```
<220> FEATURE:
<223> OTHER INFORMATION: HCDR3 MS-Roche#7.9H4x7.12L2

<400> SEQUENCE: 69

Gly Lys Gly Asn Thr His Lys Pro Tyr Gly Tyr Val Arg Tyr Phe Asp
1               5                   10                  15
Val

<210> SEQ ID NO 70
<211> LENGTH: 51
<212> TYPE: DNA
<213> ORGANISM: artificial sequence
<220> FEATURE:
<223> OTHER INFORMATION: HCDR3 MS-Roche#7.11H1x7.11L1

<400> SEQUENCE: 70
ggtaagggta atactcataa gccttatggt tatgttcgtt attttgatgt t          51

<210> SEQ ID NO 71
<211> LENGTH: 17
<212> TYPE: PRT
<213> ORGANISM: artificial sequence
<220> FEATURE:
<223> OTHER INFORMATION: HCDR3 MS-Roche#7.11H1x7.11L1

<400> SEQUENCE: 71

Gly Lys Gly Asn Thr His Lys Pro Tyr Gly Tyr Val Arg Tyr Phe Asp
1               5                   10                  15
Val

<210> SEQ ID NO 72
<211> LENGTH: 51
<212> TYPE: DNA
<213> ORGANISM: artificial sequence
<220> FEATURE:
<223> OTHER INFORMATION: HCDR3 MS-Roche#7.11H1x7.2L1

<400> SEQUENCE: 72
ggtaagggta atactcataa gccttatggt tatgttcgtt attttgatgt t          51

<210> SEQ ID NO 73
<211> LENGTH: 17
<212> TYPE: PRT
<213> ORGANISM: artificial sequence
<220> FEATURE:
<223> OTHER INFORMATION: HCDR3 MS-Roche#7.11H1x7.2L1

<400> SEQUENCE: 73

Gly Lys Gly Asn Thr His Lys Pro Tyr Gly Tyr Val Arg Tyr Phe Asp
1               5                   10                  15
Val

<210> SEQ ID NO 74
<211> LENGTH: 24
<212> TYPE: DNA
<213> ORGANISM: artificial sequence
<220> FEATURE:
<223> OTHER INFORMATION: LCDR3 MS-Roche#3.6H5 x 3.6L2

<400> SEQUENCE: 74
cagcagactt ataattatcc tcct                                        24

<210> SEQ ID NO 75
<211> LENGTH: 8
<212> TYPE: PRT
```

```
<213> ORGANISM: artificial sequence
<220> FEATURE:
<223> OTHER INFORMATION: LCDR3 MS-Roche#3.6H5 x 3.6L2

<400> SEQUENCE: 75

Gln Gln Thr Tyr Asn Tyr Pro Pro
1               5

<210> SEQ ID NO 76
<211> LENGTH: 24
<212> TYPE: DNA
<213> ORGANISM: artificial sequence
<220> FEATURE:
<223> OTHER INFORMATION: LCDR3 MS-Roche#3.6H8 x 3.6L2

<400> SEQUENCE: 76
cagcagactt ataattatcc tcct                                          24

<210> SEQ ID NO 77
<211> LENGTH: 8
<212> TYPE: PRT
<213> ORGANISM: artificial sequence
<220> FEATURE:
<223> OTHER INFORMATION: LCDR3 MS-Roche#3.6H8 x 3.6L2

<400> SEQUENCE: 77

Gln Gln Thr Tyr Asn Tyr Pro Pro
1               5

<210> SEQ ID NO 78
<211> LENGTH: 24
<212> TYPE: DNA
<213> ORGANISM: artificial sequence
<220> FEATURE:
<223> OTHER INFORMATION: LCDR3 MS-Roche#7.4H2x7.2L1

<400> SEQUENCE: 78
cagcagattt attcttttcc tcat                                          24

<210> SEQ ID NO 79
<211> LENGTH: 8
<212> TYPE: PRT
<213> ORGANISM: artificial sequence
<220> FEATURE:
<223> OTHER INFORMATION: LCDR3 MS-Roche#7.4H2x7.2L1

<400> SEQUENCE: 79

Gln Gln Ile Tyr Ser Phe Pro His
1               5

<210> SEQ ID NO 80
<211> LENGTH: 24
<212> TYPE: DNA
<213> ORGANISM: artificial sequence
<220> FEATURE:
<223> OTHER INFORMATION: LCDR3 MS-Roche#7.9H2x7.12L2

<400> SEQUENCE: 80
cttcagcttt ataatattcc taat                                          24

<210> SEQ ID NO 81
<211> LENGTH: 8
<212> TYPE: PRT
<213> ORGANISM: artificial sequence
<220> FEATURE:
<223> OTHER INFORMATION: LCDR3 MS-Roche#7.9H2x7.12L2

<400> SEQUENCE: 81
```

-continued

Leu Gln Leu Tyr Asn Ile Pro Asn
1               5

<210> SEQ ID NO 82
<211> LENGTH: 24
<212> TYPE: DNA
<213> ORGANISM: artificial sequence
<220> FEATURE:
<223> OTHER INFORMATION: LCDR3 MS-Roche#7.9H4x7.12L2

<400> SEQUENCE: 82
cttcagcttt ataatattcc taat                                          24

<210> SEQ ID NO 83
<211> LENGTH: 8
<212> TYPE: PRT
<213> ORGANISM: artificial sequence
<220> FEATURE:
<223> OTHER INFORMATION: LCDR3 MS-Roche#7.9H4x7.12L2

<400> SEQUENCE: 83

Leu Gln Leu Tyr Asn Ile Pro Asn
1               5

<210> SEQ ID NO 84
<211> LENGTH: 24
<212> TYPE: DNA
<213> ORGANISM: artificial sequence
<220> FEATURE:
<223> OTHER INFORMATION: LCDR3 MS-Roche#7.11H1x7.11L1

<400> SEQUENCE: 84
cagcaggttt attctcctcc tcat                                          24

<210> SEQ ID NO 85
<211> LENGTH: 8
<212> TYPE: PRT
<213> ORGANISM: artificial sequence
<220> FEATURE:
<223> OTHER INFORMATION: LCDR3 MS-Roche#7.11H1x7.11L1

<400> SEQUENCE: 85

Gln Gln Val Tyr Ser Pro Pro His
1               5

<210> SEQ ID NO 86
<211> LENGTH: 24
<212> TYPE: DNA
<213> ORGANISM: artificial sequence
<220> FEATURE:
<223> OTHER INFORMATION: LCDR3 MS-Roche#7.11H1x7.2L1

<400> SEQUENCE: 86
cagcagattt attcttttcc tcat                                          24

<210> SEQ ID NO 87
<211> LENGTH: 8
<212> TYPE: PRT
<213> ORGANISM: artificial sequence
<220> FEATURE:
<223> OTHER INFORMATION: LCDR3 MS-Roche#7.11H1x7.2L1

<400> SEQUENCE: 87

Gln Gln Ile Tyr Ser Phe Pro His
1               5

```
<210> SEQ ID NO 88
<211> LENGTH: 378
<212> TYPE: DNA
<213> ORGANISM: artificial sequence
<220> FEATURE:
<223> OTHER INFORMATION: synthetic construct; VH MS-Roche#7.9H7

<400> SEQUENCE: 88
caggtgcaat tggtggaaag cggcggcggc ctggtgcaac cgggcggcag cctgcgtctg        60
agctgcgcgg cctccggatt tacctttagc agctatgcga tgagctgggt gcgccaagcc       120
cctgggaagg gtctcgagtg ggtgagcgct attaatgctt ctggtactcg tacttattat       180
gctgattctg ttaagggtcg ttttaccatt tcacgtgata attcgaaaaa caccctgtat       240
ctgcaaatga acagcctgcg tgcggaagat acggccgtgt attattgcgc gcgtggtaag       300
ggtaatactc ataagcctta tggttatgtt cgttattttg atgtttgggg ccaaggcacc       360
ctggtgacgg ttagctca                                                    378

<210> SEQ ID NO 89
<211> LENGTH: 126
<212> TYPE: PRT
<213> ORGANISM: artificial sequence
<220> FEATURE:
<223> OTHER INFORMATION: synthetic construct; VH MS-Roche#7.9H7

<400> SEQUENCE: 89

Gln Val Gln Leu Val Glu Ser Gly Gly Gly Leu Val Gln Pro Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Asn Ala Ser Gly Thr Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser
        115                 120                 125

<210> SEQ ID NO 90
<211> LENGTH: 330
<212> TYPE: DNA
<213> ORGANISM: artificial sequence
<220> FEATURE:
<223> OTHER INFORMATION: synthetic construct; VL MS-Roche#7.9H7

<400> SEQUENCE: 90
gatatcgtgc tgacccagag cccggcgacc ctgagcctgt ctccgggcga acgtgcgacc        60
ctgagctgca gcgcagcca gagcgtgagc agcagctatc tggcgtggta ccagcagaaa       120
ccaggtcaag caccgcgtct attaatttat ggcgcgagca gccgtgcaac tggggtcccg       180
gcgcgtttta gcggctctgg atccggcacg gattttaccc tgaccattag cagcctggaa       240
cctgaagact ttgcgactta ttattgcctt cagatttata atatgcctat tacctttggc       300
cagggtacga aagttgaaat taaacgtacg                                       330
```

```
<210> SEQ ID NO 91
<211> LENGTH: 110
<212> TYPE: PRT
<213> ORGANISM: artificial sequence
<220> FEATURE:
<223> OTHER INFORMATION: synthetic construct; VL MS-Roche#7.9H7

<400> SEQUENCE: 91

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr
            100                 105                 110

<210> SEQ ID NO 92
<211> LENGTH: 51
<212> TYPE: DNA
<213> ORGANISM: artificial sequence
<220> FEATURE:
<223> OTHER INFORMATION: synthetic construct; HCDR3 MS-Roche#7.9H7

<400> SEQUENCE: 92
ggtaagggta atactcataa gccttatggt tatgttcgtt attttgatgt t          51

<210> SEQ ID NO 93
<211> LENGTH: 17
<212> TYPE: PRT
<213> ORGANISM: artificial sequence
<220> FEATURE:
<223> OTHER INFORMATION: synthetic construct; HCDR3 MS-Roche#7.9H7

<400> SEQUENCE: 93

Gly Lys Gly Asn Thr His Lys Pro Tyr Gly Tyr Val Arg Tyr Phe Asp
1               5                   10                  15

Val

<210> SEQ ID NO 94
<211> LENGTH: 24
<212> TYPE: DNA
<213> ORGANISM: artificial sequence
<220> FEATURE:
<223> OTHER INFORMATION: synthetic construct; LCDR3 MS-Roche#7.9H7

<400> SEQUENCE: 94
cttcagattt ataatatgcc tatt                                        24

<210> SEQ ID NO 95
<211> LENGTH: 8
<212> TYPE: PRT
<213> ORGANISM: artificial sequence
<220> FEATURE:
<223> OTHER INFORMATION: synthetic construct; LCDR3 MS-Roche#7.9H7

<400> SEQUENCE: 95

Leu Gln Ile Tyr Asn Met Pro Ile
```

<210> SEQ ID NO 96
<211> LENGTH: 12
<212> TYPE: PRT
<213> ORGANISM: artificial sequence
<220> FEATURE:
<223> OTHER INFORMATION: synthetic construct; LCDR1 of MS-Roche#3

<400> SEQUENCE: 96

Arg Ala Ser Gln Ser Val Ser Ser Ser Tyr Leu Ala
1               5                   10

<210> SEQ ID NO 97
<211> LENGTH: 7
<212> TYPE: PRT
<213> ORGANISM: artificial sequence
<220> FEATURE:
<223> OTHER INFORMATION: synthetic construct; LCDR2 of MS-Roche#3

<400> SEQUENCE: 97

Gly Ala Ser Ser Arg Ala Thr
1               5

<210> SEQ ID NO 98
<211> LENGTH: 8
<212> TYPE: PRT
<213> ORGANISM: artificial sequence
<220> FEATURE:
<223> OTHER INFORMATION: synthetic construct; LCDR3 of MS-Roche#3

<400> SEQUENCE: 98

Gln Gln Val Tyr Asn Pro Pro Val
1               5

<210> SEQ ID NO 99
<211> LENGTH: 10
<212> TYPE: PRT
<213> ORGANISM: artificial sequence
<220> FEATURE:
<223> OTHER INFORMATION: synthetic construct; HCDR1 of MS-Roche#3

<400> SEQUENCE: 99

Gly Phe Thr Phe Ser Ser Tyr Ala Met Ser
1               5                   10

<210> SEQ ID NO 100
<211> LENGTH: 17
<212> TYPE: PRT
<213> ORGANISM: artificial sequence
<220> FEATURE:
<223> OTHER INFORMATION: synthetic construct; HCDR2 of MS-Roche#3

<400> SEQUENCE: 100

Ala Ile Ser Gly Ser Gly Gly Ser Thr Tyr Tyr Ala Asp Ser Val Lys
1               5                   10                  15
Gly

<210> SEQ ID NO 101
<211> LENGTH: 13
<212> TYPE: PRT
<213> ORGANISM: artificial sequence
<220> FEATURE:
<223> OTHER INFORMATION: synthetic construct; HCDR3 of MS-Roche#3

<400> SEQUENCE: 101

Leu Thr His Tyr Ala Arg Tyr Tyr Arg Tyr Phe Asp Val

<210> SEQ ID NO 102
<211> LENGTH: 8
<212> TYPE: PRT
<213> ORGANISM: artificial sequence
<220> FEATURE:
<223> OTHER INFORMATION: synthetic construct; LCDR3 of MS-Roche#3.1

<400> SEQUENCE: 102

Gln Gln Val Tyr Ser Val Pro Pro
1               5

<210> SEQ ID NO 103
<211> LENGTH: 8
<212> TYPE: PRT
<213> ORGANISM: artificial sequence
<220> FEATURE:
<223> OTHER INFORMATION: synthetic construct; LCDR3 of MS-Roche#3.2

<400> SEQUENCE: 103

Gln Gln Ile Tyr Ser Tyr Pro Pro
1               5

<210> SEQ ID NO 104
<211> LENGTH: 8
<212> TYPE: PRT
<213> ORGANISM: artificial sequence
<220> FEATURE:
<223> OTHER INFORMATION: synthetic construct; LCDR3 of MS-Roche#3.3

<400> SEQUENCE: 104

His Gln Met Ser Ser Tyr Pro Pro
1               5

<210> SEQ ID NO 105
<211> LENGTH: 8
<212> TYPE: PRT
<213> ORGANISM: artificial sequence
<220> FEATURE:
<223> OTHER INFORMATION: synthetic construct; LCDR3 of MS-Roche#3.4

<400> SEQUENCE: 105

Gln Gln Thr Tyr Asp Tyr Pro Pro
1               5

<210> SEQ ID NO 106
<211> LENGTH: 8
<212> TYPE: PRT
<213> ORGANISM: artificial sequence
<220> FEATURE:
<223> OTHER INFORMATION: synthetic construct; LCDR3 of MS-Roche#3.5

<400> SEQUENCE: 106

Gln Gln Ile Tyr Asp Tyr Pro Pro
1               5

<210> SEQ ID NO 107
<211> LENGTH: 8
<212> TYPE: PRT
<213> ORGANISM: artificial sequence
<220> FEATURE:
<223> OTHER INFORMATION: synthetic construct; LCDR3 of MS-Roche#3.6

<400> SEQUENCE: 107

Gln Gln Thr Tyr Asn Tyr Pro Pro
1               5

```
<210> SEQ ID NO 108
<211> LENGTH: 17
<212> TYPE: PRT
<213> ORGANISM: artificial sequence
<220> FEATURE:
<223> OTHER INFORMATION: synthetic construct; HCDR2 of MS-Roche#3.2H1

<400> SEQUENCE: 108

Ala Ile Ser Glu His Gly Leu Asn Ile Tyr Tyr Ala Asp Ser Val Lys
1               5                   10                  15

Gly

<210> SEQ ID NO 109
<211> LENGTH: 17
<212> TYPE: PRT
<213> ORGANISM: artificial sequence
<220> FEATURE:
<223> OTHER INFORMATION: synthetic construct; HCDR2 of MS-Roche#3.2H2

<400> SEQUENCE: 109

Ala Ile Ser Gln Arg Gly Gln Phe Thr Tyr Tyr Ala Asp Ser Val Lys
1               5                   10                  15

Gly

<210> SEQ ID NO 110
<211> LENGTH: 17
<212> TYPE: PRT
<213> ORGANISM: artificial sequence
<220> FEATURE:
<223> OTHER INFORMATION: synthetic construct; HCDR2 of MS-Roche#3.3H1

<400> SEQUENCE: 110

Val Ile Ser Glu Lys Ser Arg Phe Ile Tyr Tyr Ala Asp Ser Val Lys
1               5                   10                  15

Gly

<210> SEQ ID NO 111
<211> LENGTH: 17
<212> TYPE: PRT
<213> ORGANISM: artificial sequence
<220> FEATURE:
<223> OTHER INFORMATION: synthetic construct; HCDR2 of MS-Roche#3.3H2

<400> SEQUENCE: 111

Val Ile Ser Gln Glu Ser Gln Tyr Lys Tyr Tyr Ala Asp Ser Val Lys
1               5                   10                  15

Gly

<210> SEQ ID NO 112
<211> LENGTH: 17
<212> TYPE: PRT
<213> ORGANISM: artificial sequence
<220> FEATURE:
<223> OTHER INFORMATION: synthetic construct; HCDR2 of MS-Roche#3.3H3

<400> SEQUENCE: 112

Ala Ile Ser Gln Asn Gly Phe His Ile Tyr Tyr Ala Asp Ser Val Lys
1               5                   10                  15

Gly

<210> SEQ ID NO 113
<211> LENGTH: 17
<212> TYPE: PRT
<213> ORGANISM: artificial sequence
```

```
<220> FEATURE:
<223> OTHER INFORMATION: synthetic construct; HCDR2 of MS-Roche#3.4H1

<400> SEQUENCE: 113

Ala Ile Ser Glu Thr Ser Ile Arg Lys Tyr Tyr Ala Asp Ser Val Lys
1               5                   10                  15
Gly

<210> SEQ ID NO 114
<211> LENGTH: 16
<212> TYPE: PRT
<213> ORGANISM: artificial sequence
<220> FEATURE:
<223> OTHER INFORMATION: synthetic construct; HCDR2 of MS-Roche#3.4H2

<400> SEQUENCE: 114

Val Ile Asp Met Val Gly His Thr Tyr Tyr Ala Asp Ser Val Lys Gly
1               5                   10                  15

<210> SEQ ID NO 115
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H3

<400> SEQUENCE: 115

Val Ile Ser Gln Thr Gly Arg Lys Ile Tyr Tyr Ala Asp Ser Val Lys
1               5                   10                  15
Gly

<210> SEQ ID NO 116
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H4

<400> SEQUENCE: 116

Ala Ile Ser Glu Thr Gly Met His Ile Tyr Tyr Ala Asp Ser Val Lys
1               5                   10                  15
Gly

<210> SEQ ID NO 117
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H5

<400> SEQUENCE: 117

Val Ile Ser Gln Val Gly Ala His Ile Tyr Tyr Ala Asp Ser Val Lys
1               5                   10                  15
Gly

<210> SEQ ID NO 118
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H6

<400> SEQUENCE: 118

Ala Ile Ser Glu Ser Gly Trp Ser Thr Tyr Tyr Ala Asp Ser Val Lys
1               5                   10                  15
```

<210> SEQ ID NO 119
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H7

<400> SEQUENCE: 119

Val Ile Ser Glu Thr Gly Lys Asn Ile Tyr Tyr Ala Asp Ser Val Lys
1               5                   10                  15
Gly

<210> SEQ ID NO 120
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H8

<400> SEQUENCE: 120

Ala Ile Ser Glu His Gly Arg Phe Lys Tyr Tyr Ala Asp Ser Val Lys
1               5                   10                  15
Gly

<210> SEQ ID NO 121
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H9

<400> SEQUENCE: 121

Ala Ile Ser Glu Ser Ser Lys Asn Lys Tyr Tyr Ala Asp Ser Val Lys
1               5                   10                  15
Gly

<210> SEQ ID NO 122
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H10

<400> SEQUENCE: 122

Ala Ile Ser Glu Ser Gly Arg Gly Lys Tyr Tyr Ala Asp Ser Val Lys
1               5                   10                  15
Gly

<210> SEQ ID NO 123
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H11

<400> SEQUENCE: 123

Ala Ile Ser Glu Phe Gly Lys Asn Ile Tyr Tyr Ala Asp Ser Val Lys
1               5                   10                  15
Gly

<210> SEQ ID NO 124

```
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H12

<400> SEQUENCE: 124

Val Ile Ser Gln Thr Gly Gln Asn Ile Tyr Tyr Ala Asp Ser Val Lys
1               5                   10                  15
Gly

<210> SEQ ID NO 125
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H13

<400> SEQUENCE: 125

Ala Ile Ser Glu Gln Gly Arg Asn Ile Tyr Tyr Ala Asp Ser Val Lys
1               5                   10                  15
Gly

<210> SEQ ID NO 126
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H14

<400> SEQUENCE: 126

Ala Ile Ser Glu Ser Gly Gln Tyr Lys Tyr Tyr Ala Asp Ser Val Lys
1               5                   10                  15
Gly

<210> SEQ ID NO 127
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H16

<400> SEQUENCE: 127

Ala Ile Ser Glu Ser Gly Val Asn Ile Tyr Tyr Ala Asp Ser Val Lys
1               5                   10                  15
Gly

<210> SEQ ID NO 128
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H17

<400> SEQUENCE: 128

Ala Ile Ser Glu Phe Gly Gln Phe Ile Tyr Tyr Ala Asp Ser Val Lys
1               5                   10                  15
Gly

<210> SEQ ID NO 129
<211> LENGTH: 17
<212> TYPE: PRT
<213> ORGANISM: artificial sequence
<220> FEATURE:
<223> OTHER INFORMATION: synthetic construct; HCDR2 of MS-Roche#3.4H18
```

```
<400> SEQUENCE: 129

Ala Ile Ser Gln Gln Ser Asn Phe Ile Tyr Tyr Ala Asp Ser Val Lys
1               5                   10                  15

Gly

<210> SEQ ID NO 130
<211> LENGTH: 12
<212> TYPE: PRT
<213> ORGANISM: artificial sequence
<220> FEATURE:
<223> OTHER INFORMATION: synthetic construct; LCDR1 of MS-Roche#3.4L7

<400> SEQUENCE: 130

Arg Ala Ser Gln Arg Leu Gly Arg Leu Tyr Leu Ala
1               5                   10

<210> SEQ ID NO 131
<211> LENGTH: 12
<212> TYPE: PRT
<213> ORGANISM: artificial sequence
<220> FEATURE:
<223> OTHER INFORMATION: synthetic construct; LCDR1 of MS-Roche#3.4L8

<400> SEQUENCE: 131

Arg Ala Ser Gln Trp Ile Thr Lys Ser Tyr Leu Ala
1               5                   10

<210> SEQ ID NO 132
<211> LENGTH: 12
<212> TYPE: PRT
<213> ORGANISM: artificial sequence
<220> FEATURE:
<223> OTHER INFORMATION: synthetic construct; LCDR1 of MS-Roche#3.4L9

<400> SEQUENCE: 132

Arg Ala Ser Arg Arg Ile His Val Tyr Tyr Leu Ala
1               5                   10

<210> SEQ ID NO 133
<211> LENGTH: 12
<212> TYPE: PRT
<213> ORGANISM: artificial sequence
<220> FEATURE:
<223> OTHER INFORMATION: synthetic construct; LCDR1 of MS-Roche#3.4L11

<400> SEQUENCE: 133

Arg Ala Ser Gln Leu Val Gly Arg Ala Tyr Leu Ala
1               5                   10

<210> SEQ ID NO 134
<211> LENGTH: 17
<212> TYPE: PRT
<213> ORGANISM: artificial sequence
<220> FEATURE:
<223> OTHER INFORMATION: synthetic construct; HCDR2 of MS-Roche#3.6H1

<400> SEQUENCE: 134

Val Ile Ser Glu Ser Gly Gln Tyr Lys Tyr Tyr Ala Asp Ser Val Lys
1               5                   10                  15

Gly

<210> SEQ ID NO 135
<211> LENGTH: 17
<212> TYPE: PRT
<213> ORGANISM: artificial sequence
```

```
<220> FEATURE:
<223> OTHER INFORMATION: synthetic construct; HCDR2 of MS-Roche#3.6H2

<400> SEQUENCE: 135

Val Ile Ser Glu Arg Gly Ile Asn Thr Tyr Tyr Ala Asp Ser Val Lys
1               5                   10                  15
Gly

<210> SEQ ID NO 136
<211> LENGTH: 17
<212> TYPE: PRT
<213> ORGANISM: artificial sequence
<220> FEATURE:
<223> OTHER INFORMATION: synthetic construct; HCDR2 of MS-Roche#3.6H3

<400> SEQUENCE: 136

Val Ile Ser Glu Thr Gly Lys Phe Ile Tyr Tyr Ala Asp Ser Val Lys
1               5                   10                  15
Gly

<210> SEQ ID NO 137
<211> LENGTH: 17
<212> TYPE: PRT
<213> ORGANISM: artificial sequence
<220> FEATURE:
<223> OTHER INFORMATION: synthetic construct; HCDR2 of MS-Roche#3.6H4

<400> SEQUENCE: 137

Ala Ile Ser Glu Arg Gly Arg His Ile Tyr Tyr Ala Asp Ser Val Lys
1               5                   10                  15
Gly

<210> SEQ ID NO 138
<211> LENGTH: 17
<212> TYPE: PRT
<213> ORGANISM: artificial sequence
<220> FEATURE:
<223> OTHER INFORMATION: synthetic construct; HCDR2 of MS-Roche#3.6H5

<400> SEQUENCE: 138

Ala Ile Ser Glu Ser Gly Lys Thr Lys Tyr Tyr Ala Asp Ser Val Lys
1               5                   10                  15
Gly

<210> SEQ ID NO 139
<211> LENGTH: 17
<212> TYPE: PRT
<213> ORGANISM: artificial sequence
<220> FEATURE:
<223> OTHER INFORMATION: synthetic construct; HCDR2 of MS-Roche#3.6H6

<400> SEQUENCE: 139

Ala Ile Ser Glu His Gly Thr Asn Ile Tyr Tyr Ala Asp Ser Val Lys
1               5                   10                  15
Gly

<210> SEQ ID NO 140
<211> LENGTH: 17
<212> TYPE: PRT
<213> ORGANISM: artificial sequence
<220> FEATURE:
<223> OTHER INFORMATION: synthetic construct; HCDR2 of MS-Roche#3.6H8

<400> SEQUENCE: 140
```

```
Ala Ile Ser Glu Tyr Ser Lys Phe Lys Tyr Tyr Ala Asp Ser Val Lys
1               5                   10                  15
Gly

<210> SEQ ID NO 141
<211> LENGTH: 12
<212> TYPE: PRT
<213> ORGANISM: artificial sequence
<220> FEATURE:
<223> OTHER INFORMATION: synthetic construct; LCDR1 of MS-Roche#3.6L1

<400> SEQUENCE: 141

Arg Ala Ser Gln Phe Ile Gln Arg Phe Tyr Leu Ala
1               5                   10

<210> SEQ ID NO 142
<211> LENGTH: 12
<212> TYPE: PRT
<213> ORGANISM: artificial sequence
<220> FEATURE:
<223> OTHER INFORMATION: synthetic construct; LCDR1 of MS-Roche#3.6L2

<400> SEQUENCE: 142

Arg Ala Ser Gln Phe Leu Ser Arg Tyr Tyr Leu Ala
1               5                   10

<210> SEQ ID NO 143
<211> LENGTH: 12
<212> TYPE: PRT
<213> ORGANISM: artificial sequence
<220> FEATURE:
<223> OTHER INFORMATION: synthetic construct; LCDR1 of MS-Roche#7

<400> SEQUENCE: 143

Arg Ala Ser Gln Ser Val Ser Ser Ser Tyr Leu Ala
1               5                   10

<210> SEQ ID NO 144
<211> LENGTH: 7
<212> TYPE: PRT
<213> ORGANISM: artificial sequence
<220> FEATURE:
<223> OTHER INFORMATION: synthetic construct; LCDR2 of MS-Roche#7

<400> SEQUENCE: 144

Gly Ala Ser Ser Arg Ala Thr
1               5

<210> SEQ ID NO 145
<211> LENGTH: 8
<212> TYPE: PRT
<213> ORGANISM: artificial sequence
<220> FEATURE:
<223> OTHER INFORMATION: synthetic construct; LCDR3 of MS-Roche#7

<400> SEQUENCE: 145

Phe Gln Leu Tyr Ser Asp Pro Phe
1               5

<210> SEQ ID NO 146
<211> LENGTH: 10
<212> TYPE: PRT
<213> ORGANISM: artificial sequence
<220> FEATURE:
<223> OTHER INFORMATION: synthetic construct; HCDR1 of MS-Roche#7

<400> SEQUENCE: 146
```

```
Gly Phe Thr Phe Ser Ser Tyr Ala Met Ser
1               5                   10
```

<210> SEQ ID NO 147
<211> LENGTH: 17
<212> TYPE: PRT
<213> ORGANISM: artificial sequence
<220> FEATURE:
<223> OTHER INFORMATION: synthetic construct; HCDR2 of MS-Roche#7

<400> SEQUENCE: 147

```
Ala Ile Ser Gly Ser Gly Gly Ser Thr Tyr Tyr Ala Asp Ser Val Lys
1               5                   10                  15
Gly
```

<210> SEQ ID NO 148
<211> LENGTH: 17
<212> TYPE: PRT
<213> ORGANISM: artificial sequence
<220> FEATURE:
<223> OTHER INFORMATION: synthetic construct; HCDR3 of MS-Roche#7

<400> SEQUENCE: 148

```
Gly Lys Gly Asn Thr His Lys Pro Tyr Gly Tyr Val Arg Tyr Phe Asp
1               5                   10                  15
Val
```

<210> SEQ ID NO 149
<211> LENGTH: 8
<212> TYPE: PRT
<213> ORGANISM: artificial sequence
<220> FEATURE:
<223> OTHER INFORMATION: synthetic construct; LCDR3 of MS-Roche#7.1

<400> SEQUENCE: 149

```
His Gln Leu Tyr Ser Ser Pro Tyr
1               5
```

<210> SEQ ID NO 150
<211> LENGTH: 8
<212> TYPE: PRT
<213> ORGANISM: artificial sequence
<220> FEATURE:
<223> OTHER INFORMATION: synthetic construct; LCDR3of MS-Roche#7.2

<400> SEQUENCE: 150

```
Gln Gln Ile Tyr Ser Phe Pro His
1               5
```

<210> SEQ ID NO 151
<211> LENGTH: 8
<212> TYPE: PRT
<213> ORGANISM: artificial sequence
<220> FEATURE:
<223> OTHER INFORMATION: synthetic construct; LCDR3 of MS-Roche#7.3

<400> SEQUENCE: 151

```
His Gln Val Tyr Ser His Pro Phe
1               5
```

<210> SEQ ID NO 152
<211> LENGTH: 8
<212> TYPE: PRT
<213> ORGANISM: artificial sequence
<220> FEATURE:
<223> OTHER INFORMATION: synthetic construct; LCDR3 of MS-Roche#7.4

```
<400> SEQUENCE: 152

Gln Gln Ile Tyr Asn Phe Pro His
1               5

<210> SEQ ID NO 153
<211> LENGTH: 8
<212> TYPE: PRT
<213> ORGANISM: artificial sequence
<220> FEATURE:
<223> OTHER INFORMATION: synthetic construct; LCDR3 of MS-Roche#7.5

<400> SEQUENCE: 153

His Gln Val Tyr Ser Ser Pro Phe
1               5

<210> SEQ ID NO 154
<211> LENGTH: 8
<212> TYPE: PRT
<213> ORGANISM: artificial sequence
<220> FEATURE:
<223> OTHER INFORMATION: synthetic construct; LCDR3 of MS-Roche#7.6

<400> SEQUENCE: 154

His Gln Leu Tyr Ser Pro Pro Tyr
1               5

<210> SEQ ID NO 155
<211> LENGTH: 8
<212> TYPE: PRT
<213> ORGANISM: artificial sequence
<220> FEATURE:
<223> OTHER INFORMATION: synthetic construct; LCDR3 of MS-Roche#7.7

<400> SEQUENCE: 155

His Gln Val Tyr Ser Ala Pro Phe
1               5

<210> SEQ ID NO 156
<211> LENGTH: 8
<212> TYPE: PRT
<213> ORGANISM: artificial sequence
<220> FEATURE:
<223> OTHER INFORMATION: synthetic construct; LCDR3 of MS-Roche#7.8

<400> SEQUENCE: 156

His Gln Val Tyr Ser Phe Pro Ile
1               5

<210> SEQ ID NO 157
<211> LENGTH: 8
<212> TYPE: PRT
<213> ORGANISM: artificial sequence
<220> FEATURE:
<223> OTHER INFORMATION: synthetic construct; LCDR3 of MS-Roche#7.9

<400> SEQUENCE: 157

Leu Gln Ile Tyr Asn Met Pro Ile
1               5

<210> SEQ ID NO 158
<211> LENGTH: 8
<212> TYPE: PRT
<213> ORGANISM: artificial sequence
<220> FEATURE:
<223> OTHER INFORMATION: synthetic construct; LCDR3 of MS-Roche#7.10

<400> SEQUENCE: 158
```

```
Gln Gln Val Tyr Asn Pro Pro His
1               5

<210> SEQ ID NO 159
<211> LENGTH: 8
<212> TYPE: PRT
<213> ORGANISM: artificial sequence
<220> FEATURE:
<223> OTHER INFORMATION: synthetic construct; LCDR3 of MS-Roche#7.11

<400> SEQUENCE: 159

Gln Gln Val Tyr Ser Pro Pro His
1               5

<210> SEQ ID NO 160
<211> LENGTH: 12
<212> TYPE: PRT
<213> ORGANISM: artificial sequence
<220> FEATURE:
<223> OTHER INFORMATION: synthetic construct; LCDR1 of MS-Roche#7.12

<400> SEQUENCE: 160

Arg Ala Ser Gln Tyr Val Ser Ser Pro Tyr Leu Ala
1               5                   10

<210> SEQ ID NO 161
<211> LENGTH: 7
<212> TYPE: PRT
<213> ORGANISM: artificial sequence
<220> FEATURE:
<223> OTHER INFORMATION: synthetic construct; LCDR2 of MS-Roche#7.12

<400> SEQUENCE: 161

Gly Ser Ser Asn Arg Ala Thr
1               5

<210> SEQ ID NO 162
<211> LENGTH: 8
<212> TYPE: PRT
<213> ORGANISM: artificial sequence
<220> FEATURE:
<223> OTHER INFORMATION: synthetic construct; LCDR3 of MS-Roche#7.12

<400> SEQUENCE: 162

Leu Gln Leu Tyr Asn Ile Pro Asn
1               5

<210> SEQ ID NO 163
<211> LENGTH: 10
<212> TYPE: PRT
<213> ORGANISM: artificial sequence
<220> FEATURE:
<223> OTHER INFORMATION: synthetic construct; HCDR1 of MS-Roche#7.12

<400> SEQUENCE: 163

Gly Phe Thr Phe Ser Ser Tyr Gly Met Ser
1               5                   10

<210> SEQ ID NO 164
<211> LENGTH: 17
<212> TYPE: PRT
<213> ORGANISM: artificial sequence
<220> FEATURE:
<223> OTHER INFORMATION: synthetic construct; HCDR2 of MS-Roche#7.12

<400> SEQUENCE: 164

Asn Ile Ser Gly Ser Gly Ser Ser Thr Tyr Tyr Ala Asp Ser Val Lys
1               5                   10                  15
```

Gly

<210> SEQ ID NO 165
<211> LENGTH: 17
<212> TYPE: PRT
<213> ORGANISM: artificial sequence
<220> FEATURE:
<223> OTHER INFORMATION: synthetic construct; HCDR3 of MS-Roche#7.12

<400> SEQUENCE: 165

Gly Lys Gly Asn Thr His Lys Pro Tyr Gly Tyr Val Arg Tyr Phe Asp
1               5                   10                  15
Val

<210> SEQ ID NO 166
<211> LENGTH: 8
<212> TYPE: PRT
<213> ORGANISM: artificial sequence
<220> FEATURE:
<223> OTHER INFORMATION: synthetic construct; LCDR3 of MS-Roche#7.13

<400> SEQUENCE: 166

His Gln Val Tyr Ser Pro Pro Phe
1               5

<210> SEQ ID NO 167
<211> LENGTH: 17
<212> TYPE: PRT
<213> ORGANISM: artificial sequence
<220> FEATURE:
<223> OTHER INFORMATION: synthetic construct; HCDR2 of MS-Roche#7.2H1

<400> SEQUENCE: 167

Ala Ile Asn Ala Asn Gly Leu Lys Lys Tyr Tyr Ala Asp Ser Val Lys
1               5                   10                  15
Gly

<210> SEQ ID NO 168
<211> LENGTH: 17
<212> TYPE: PRT
<213> ORGANISM: artificial sequence
<220> FEATURE:
<223> OTHER INFORMATION: synthetic construct; HCDR2 of MS-Roche#7.2H2

<400> SEQUENCE: 168

Ala Ile Asn Gly Thr Gly Met Lys Lys Tyr Tyr Ala Asp Ser Val Lys
1               5                   10                  15
Gly

<210> SEQ ID NO 169
<211> LENGTH: 17
<212> TYPE: PRT
<213> ORGANISM: artificial sequence
<220> FEATURE:
<223> OTHER INFORMATION: synthetic construct; HCDR2 of MS-Roche#7.2H3

<400> SEQUENCE: 169

Ala Ile Asn Ala Asn Gly Tyr Lys Thr Tyr Tyr Ala Asp Ser Val Lys
1               5                   10                  15
Gly

<210> SEQ ID NO 170
<211> LENGTH: 17
<212> TYPE: PRT

<213> ORGANISM: artificial sequence
<220> FEATURE:
<223> OTHER INFORMATION: synthetic construct; HCDR2 of MS-Roche#7.2H4

<400> SEQUENCE: 170

Ala Ile Asn Ser Lys Gly Ser Arg Ile Tyr Tyr Ala Asp Ser Val Lys
1               5                   10                  15
Gly

<210> SEQ ID NO 171
<211> LENGTH: 17
<212> TYPE: PRT
<213> ORGANISM: artificial sequence
<220> FEATURE:
<223> OTHER INFORMATION: synthetic construct; HCDR2 of MS-Roche#7.2H5

<400> SEQUENCE: 171

Ala Ile Asn Ala Thr Gly Arg Ser Lys Tyr Tyr Ala Asp Ser Val Lys
1               5                   10                  15
Gly

<210> SEQ ID NO 172
<211> LENGTH: 17
<212> TYPE: PRT
<213> ORGANISM: artificial sequence
<220> FEATURE:
<223> OTHER INFORMATION: synthetic construct; HCDR2 of MS-Roche#7.2H6

<400> SEQUENCE: 172

Ala Ile Asn Ala Arg Gly Asn Arg Thr Tyr Tyr Ala Asp Ser Val Lys
1               5                   10                  15
Gly

<210> SEQ ID NO 173
<211> LENGTH: 17
<212> TYPE: PRT
<213> ORGANISM: artificial sequence
<220> FEATURE:
<223> OTHER INFORMATION: synthetic construct; HCDR2 of MS-Roche#7.2H7

<400> SEQUENCE: 173

Ala Ile Asn Ser Arg Gly Ser Asp Thr His Tyr Ala Asp Ser Val Lys
1               5                   10                  15
Gly

<210> SEQ ID NO 174
<211> LENGTH: 17
<212> TYPE: PRT
<213> ORGANISM: artificial sequence
<220> FEATURE:
<223> OTHER INFORMATION: synthetic construct; HCDR2 of MS-Roche#7.2H8

<400> SEQUENCE: 174

Ala Ile Asn Ala Ser Gly His Lys Thr Tyr Tyr Ala Asp Ser Val Lys
1               5                   10                  15
Gly

<210> SEQ ID NO 175
<211> LENGTH: 12
<212> TYPE: PRT
<213> ORGANISM: artificial sequence
<220> FEATURE:
<223> OTHER INFORMATION: synthetic construct; LCDR1 of MS-Roche#7.2L1

<400> SEQUENCE: 175

Arg Ala Ser Gln Tyr Val Asp Arg Thr Tyr Leu Ala
1               5                   10

<210> SEQ ID NO 176
<211> LENGTH: 12
<212> TYPE: PRT
<213> ORGANISM: artificial sequence
<220> FEATURE:
<223> OTHER INFORMATION: synthetic construct; LCDR1 of MS-Roche#7.2L2

<400> SEQUENCE: 176

Arg Ala Ser Gln Tyr Ile Ser Phe Arg Tyr Leu Ala
1               5                   10

<210> SEQ ID NO 177
<211> LENGTH: 12
<212> TYPE: PRT
<213> ORGANISM: artificial sequence
<220> FEATURE:
<223> OTHER INFORMATION: synthetic construct; LCDR1 of MS-Roche#7.2L4

<400> SEQUENCE: 177

Arg Ala Ser Gln Phe Ile Arg Arg Ser Tyr Leu Ala
1               5                   10

<210> SEQ ID NO 178
<211> LENGTH: 8
<212> TYPE: PRT
<213> ORGANISM: artificial sequence
<220> FEATURE:
<223> OTHER INFORMATION: synthetic construct; LCDR3 of MS-Roche#7.3H1

<400> SEQUENCE: 178

His Gln Val Tyr Ser His Pro Phe
1               5

<210> SEQ ID NO 179
<211> LENGTH: 17
<212> TYPE: PRT
<213> ORGANISM: artificial sequence
<220> FEATURE:
<223> OTHER INFORMATION: synthetic construct; HCDR2 of MS-Roche#7.3H1

<400> SEQUENCE: 179

Ala Ile Ser Ala Ile Ser Asn Lys Thr Tyr Tyr Ala Asp Ser Val Lys
1               5                   10                  15

Gly

<210> SEQ ID NO 180
<211> LENGTH: 12
<212> TYPE: PRT
<213> ORGANISM: artificial sequence
<220> FEATURE:
<223> OTHER INFORMATION: synthetic construct; LCDR1 of MS-Roche#7.3L1

<400> SEQUENCE: 180

Arg Ala Ser Gln Tyr Leu His Tyr Gly Tyr Leu Ala
1               5                   10

<210> SEQ ID NO 181
<211> LENGTH: 17
<212> TYPE: PRT
<213> ORGANISM: artificial sequence
<220> FEATURE:
<223> OTHER INFORMATION: synthetic construct; HCDR2 of MS-Roche#7.4H1

<400> SEQUENCE: 181

```
Ala Ile Asn Ala Thr Gly Tyr Arg Thr Tyr Tyr Ala Asp Ser Val Lys
1               5                   10                  15
Gly

<210> SEQ ID NO 182
<211> LENGTH: 17
<212> TYPE: PRT
<213> ORGANISM: artificial sequence
<220> FEATURE:
<223> OTHER INFORMATION: synthetic construct; HCDR2 of MS-Roche#7.4H2

<400> SEQUENCE: 182

Ala Ile Asn Tyr Asn Gly Ala Arg Ile Tyr Tyr Ala Asp Ser Val Lys
1               5                   10                  15
Gly

<210> SEQ ID NO 183
<211> LENGTH: 8
<212> TYPE: PRT
<213> ORGANISM: artificial sequence
<220> FEATURE:
<223> OTHER INFORMATION: synthetic construct; LCDR3 of MS-Roche#7.9H1

<400> SEQUENCE: 183

Leu Gln Ile Tyr Asn Met Pro Ile
1               5

<210> SEQ ID NO 184
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H1

<400> SEQUENCE: 184

Ala Ile Asn Ala Asn Gly Gln Arg Lys Phe Tyr Ala Asp Ser Val Lys
1               5                   10                  15
Gly

<210> SEQ ID NO 185
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H2

<400> SEQUENCE: 185

Ala Ile Asn Ala Asp Gly Asn Arg Lys Tyr Tyr Ala Asp Ser Val Lys
1               5                   10                  15
Gly

<210> SEQ ID NO 186
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H3

<400> SEQUENCE: 186

Ala Ile Asn Tyr Gln Gly Asn Arg Lys Tyr Tyr Ala Asp Ser Val Lys
1               5                   10                  15
Gly
```

```
<210> SEQ ID NO 187
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H4

<400> SEQUENCE: 187

Ala Ile Asn Ala Val Gly Met Lys Lys Phe Tyr Ala Asp Ser Val Lys
1               5                   10                  15

Gly

<210> SEQ ID NO 188
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H5

<400> SEQUENCE: 188

Ala Ile Asn His Ala Gly Asn Lys Lys Tyr Tyr Ala Asp Ser Val Lys
1               5                   10                  15

Gly

<210> SEQ ID NO 189
<211> LENGTH: 12
<212> TYPE: PRT
<213> ORGANISM: artificial sequence
<220> FEATURE:
<223> OTHER INFORMATION: synthetic construct; LCDR1 of MS-Roche#7.9L1

<400> SEQUENCE: 189

Arg Ala Ser Gln Arg Leu Ser Pro Arg Tyr Leu Ala
1               5                   10

<210> SEQ ID NO 190
<211> LENGTH: 12
<212> TYPE: PRT
<213> ORGANISM: artificial sequence
<220> FEATURE:
<223> OTHER INFORMATION: synthetic construct; LCDR1 of MS-Roche#7.9L2

<400> SEQUENCE: 190

Arg Ala Ser Gln Tyr Leu His Lys Arg Tyr Leu Ala
1               5                   10

<210> SEQ ID NO 191
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H6

<400> SEQUENCE: 191

Ala Ile Asn Ala Ser Gly Arg Leu Thr Tyr Tyr Ala Asp Ser Val Lys
1               5                   10                  15

Gly

<210> SEQ ID NO 192
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H7

<400> SEQUENCE: 192
```

Ala Ile Asn Ala Ser Gly Thr Arg Thr Tyr Tyr Ala Asp Ser Val Lys
1               5                   10                  15

Gly

<210> SEQ ID NO 193
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H8

<400> SEQUENCE: 193

Ala Ile Asn Ala Ser Gly Ser Lys Ile Tyr Tyr Ala Asp Ser Val Lys
1               5                   10                  15

Gly

<210> SEQ ID NO 194
<211> LENGTH: 17
<212> TYPE: PRT
<213> ORGANISM: artificial sequence
<220> FEATURE:
<223> OTHER INFORMATION: synthetic construct; HCDR2 of MS-Roche#7.9H9

<400> SEQUENCE: 194

Ala Ile Asn Gly Lys Gly Asn Lys Lys Tyr Tyr Ala Asp Ser Val Lys
1               5                   10                  15

Gly

<210> SEQ ID NO 195
<211> LENGTH: 17
<212> TYPE: PRT
<213> ORGANISM: artificial sequence
<220> FEATURE:
<223> OTHER INFORMATION: synthetic construct; HCDR2 of MS-Roche#7.11H1

<400> SEQUENCE: 195

Gly Ile Asn Ala Ala Gly Phe Arg Thr Tyr Tyr Ala Asp Ser Val Lys
1               5                   10                  15

Gly

<210> SEQ ID NO 196
<211> LENGTH: 17
<212> TYPE: PRT
<213> ORGANISM: artificial sequence
<220> FEATURE:
<223> OTHER INFORMATION: synthetic construct; HCDR2 of MS-Roche#7.11H2

<400> SEQUENCE: 196

Ala Ile Asn Ala Asn Gly Tyr Lys Lys Tyr Tyr Ala Asp Ser Val Lys
1               5                   10                  15

Gly

<210> SEQ ID NO 197
<211> LENGTH: 17
<212> TYPE: PRT
<213> ORGANISM: artificial sequence
<220> FEATURE:
<223> OTHER INFORMATION: synthetic construct; HCDR2 of MS-Roche#7.11H3

<400> SEQUENCE: 197

Gly Ile Asn Ala Asn Gly Asn Arg Thr Tyr Tyr Ala Asp Ser Val Lys
1               5                   10                  15

Gly

```
<210> SEQ ID NO 198
<211> LENGTH: 17
<212> TYPE: PRT
<213> ORGANISM: artificial sequence
<220> FEATURE:
<223> OTHER INFORMATION: synthetic construct; HCDR2 of MS-Roche#7.11H4

<400> SEQUENCE: 198

Ala Ile Asn Ala Asn Gly Tyr Lys Thr Tyr Tyr Ala Asp Ser Val Lys
1               5                   10                  15

Gly

<210> SEQ ID NO 199
<211> LENGTH: 17
<212> TYPE: PRT
<213> ORGANISM: artificial sequence
<220> FEATURE:
<223> OTHER INFORMATION: synthetic construct; HCDR2 of MS-Roche#7.11H5

<400> SEQUENCE: 199

Ala Ile Asn Ala His Gly Gln Arg Thr Tyr Tyr Ala Asp Ser Val Lys
1               5                   10                  15

Gly

<210> SEQ ID NO 200
<211> LENGTH: 12
<212> TYPE: PRT
<213> ORGANISM: artificial sequence
<220> FEATURE:
<223> OTHER INFORMATION: synthetic construct; LCDR1 of MS-Roche#7.11L1

<400> SEQUENCE: 200

Arg Ala Ser Gln Arg Ile Leu Arg Ile Tyr Leu Ala
1               5                   10

<210> SEQ ID NO 201
<211> LENGTH: 12
<212> TYPE: PRT
<213> ORGANISM: artificial sequence
<220> FEATURE:
<223> OTHER INFORMATION: synthetic construct; LCDR1 of MS-Roche#7.12H1

<400> SEQUENCE: 201

Arg Ala Ser Gln Tyr Val Phe Arg Arg Tyr Leu Ala
1               5                   10

<210> SEQ ID NO 202
<211> LENGTH: 8
<212> TYPE: PRT
<213> ORGANISM: artificial sequence
<220> FEATURE:
<223> OTHER INFORMATION: synthetic construct; LCDR3 of MS-Roche#7.12H1

<400> SEQUENCE: 202

Leu Gln Leu Tyr Asn Ile Pro Asn
1               5

<210> SEQ ID NO 203
<211> LENGTH: 10
<212> TYPE: PRT
<213> ORGANISM: artificial sequence
<220> FEATURE:
<223> OTHER INFORMATION: synthetic construct; HCDR1 of MS-Roche#7.12H1

<400> SEQUENCE: 203

Gly Phe Thr Phe Ser Ser Tyr Gly Met Ser
```

```
<210> SEQ ID NO 204
<211> LENGTH: 17
<212> TYPE: PRT
<213> ORGANISM: artificial sequence
<220> FEATURE:
<223> OTHER INFORMATION: synthetic construct; HCDR2 of MS-Roche#7.12H1

<400> SEQUENCE: 204

Asn Ile Asn Gly Asn Gly Asn Arg Lys Tyr Tyr Ala Asp Ser Val Lys
1               5                   10                  15
Gly

<210> SEQ ID NO 205
<211> LENGTH: 17
<212> TYPE: PRT
<213> ORGANISM: artificial sequence
<220> FEATURE:
<223> OTHER INFORMATION: synthetic construct; HCDR2 of MS-Roche#7.12L1

<400> SEQUENCE: 205

Asn Ile Ser Gly Ser Gly Ser Ser Thr Tyr Tyr Ala Asp Ser Val Lys
1               5                   10                  15
Gly

<210> SEQ ID NO 206
<211> LENGTH: 12
<212> TYPE: PRT
<213> ORGANISM: artificial sequence
<220> FEATURE:
<223> OTHER INFORMATION: synthetic construct; LCDR1 of MS-Roche#7.12L2

<400> SEQUENCE: 206

Arg Ala Ser Gln Arg Phe Phe Tyr Lys Tyr Leu Ala
1               5                   10

<210> SEQ ID NO 207
<211> LENGTH: 12
<212> TYPE: PRT
<213> ORGANISM: artificial sequence
<220> FEATURE:
<223> OTHER INFORMATION: synthetic construct; LCDR1 of MS-Roche#7.12L3

<400> SEQUENCE: 207

Arg Ala Ser Gln Phe Val Arg Arg Gly Phe Leu Ala
1               5                   10

<210> SEQ ID NO 208
<211> LENGTH: 12
<212> TYPE: PRT
<213> ORGANISM: artificial sequence
<220> FEATURE:
<223> OTHER INFORMATION: synthetic construct; LCDR1 of MS-Roche#7.12L4

<400> SEQUENCE: 208

Arg Ala Ser Gln Arg Leu Lys Arg Ser Tyr Leu Ala
1               5                   10

<210> SEQ ID NO 209
<211> LENGTH: 12
<212> TYPE: PRT
<213> ORGANISM: artificial sequence
<220> FEATURE:
<223> OTHER INFORMATION: synthetic construct; LCDR1 of MS-Roche#7.12L6

<400> SEQUENCE: 209
```

Arg Ala Ser Gln Tyr Leu Trp Tyr Arg Tyr Leu Ala
1               5                   10

<210> SEQ ID NO 210
<211> LENGTH: 12
<212> TYPE: PRT
<213> ORGANISM: artificial sequence
<220> FEATURE:
<223> OTHER INFORMATION: synthetic construct; LCDR1 of MS-Roche#7.12L7

<400> SEQUENCE: 210

Arg Ala Ser Gln Trp Ile Arg Lys Thr Tyr Leu Ala
1               5                   10

<210> SEQ ID NO 211
<211> LENGTH: 12
<212> TYPE: PRT
<213> ORGANISM: artificial sequence
<220> FEATURE:
<223> OTHER INFORMATION: synthetic construct; LCDR1 of MS-Roche#8

<400> SEQUENCE: 211

Arg Ala Ser Gln Ser Val Ser Ser Ser Tyr Leu Ala
1               5                   10

<210> SEQ ID NO 212
<211> LENGTH: 7
<212> TYPE: PRT
<213> ORGANISM: artificial sequence
<220> FEATURE:
<223> OTHER INFORMATION: synthetic construct; LCDR2 of MS-Roche#8

<400> SEQUENCE: 212

Gly Ala Ser Ser Arg Ala Thr
1               5

<210> SEQ ID NO 213
<211> LENGTH: 8
<212> TYPE: PRT
<213> ORGANISM: artificial sequence
<220> FEATURE:
<223> OTHER INFORMATION: synthetic construct; LCDR3 of MS-Roche#8

<400> SEQUENCE: 213

Gln Gln Leu Ser Ser Phe Pro Pro
1               5

<210> SEQ ID NO 214
<211> LENGTH: 10
<212> TYPE: PRT
<213> ORGANISM: artificial sequence
<220> FEATURE:
<223> OTHER INFORMATION: synthetic construct; HCDR1 of MS-Roche#8

<400> SEQUENCE: 214

Gly Phe Thr Phe Ser Ser Tyr Ala Met Ser
1               5                   10

<210> SEQ ID NO 215
<211> LENGTH: 17
<212> TYPE: PRT
<213> ORGANISM: artificial sequence
<220> FEATURE:
<223> OTHER INFORMATION: synthetic construct; HCDR2 of MS-Roche#8

<400> SEQUENCE: 215

Ala Ile Ser Gly Ser Gly Gly Ser Thr Tyr Tyr Ala Asp Ser Val Lys

Gly

<210> SEQ ID NO 216
<211> LENGTH: 15
<212> TYPE: PRT
<213> ORGANISM: artificial sequence
<220> FEATURE:
<223> OTHER INFORMATION: synthetic construct; HCDR3 of MS-Roche#8

<400> SEQUENCE: 216

Leu Leu Ser Arg Gly Tyr Asn Gly Tyr Tyr His Lys Phe Asp Val
1               5                   10                  15

<210> SEQ ID NO 217
<211> LENGTH: 8
<212> TYPE: PRT
<213> ORGANISM: artificial sequence
<220> FEATURE:
<223> OTHER INFORMATION: synthetic construct; LCDR3 of MS-Roche#8.1

<400> SEQUENCE: 217

Gln Gln Leu Ser Asn Tyr Pro Pro
1               5

<210> SEQ ID NO 218
<211> LENGTH: 8
<212> TYPE: PRT
<213> ORGANISM: artificial sequence
<220> FEATURE:
<223> OTHER INFORMATION: synthetic construct; LCDR3 of MS-Roche#8.2

<400> SEQUENCE: 218

Gln Gln Leu Ser Ser Tyr Pro Pro
1               5

<210> SEQ ID NO 219
<211> LENGTH: 17
<212> TYPE: PRT
<213> ORGANISM: artificial sequence
<220> FEATURE:
<223> OTHER INFORMATION: synthetic construct; HCDR2 of MS-Roche#8.1H1

<400> SEQUENCE: 219

Ala Ile Ser Arg Ser Gly Ser Asn Ile Tyr Tyr Ala Asp Ser Val Lys
1               5                   10                  15
Gly

<210> SEQ ID NO 220
<211> LENGTH: 8
<212> TYPE: PRT
<213> ORGANISM: artificial sequence
<220> FEATURE:
<223> OTHER INFORMATION: synthetic construct; LCDR3 of MS-Roche#8.2H1

<400> SEQUENCE: 220

Gln Gln Leu Ser Ser Tyr Pro Pro
1               5

<210> SEQ ID NO 221
<211> LENGTH: 17
<212> TYPE: PRT
<213> ORGANISM: artificial sequence
<220> FEATURE:
<223> OTHER INFORMATION: synthetic construct; HCDR2 of MS-Roche#8.2H1

<400> SEQUENCE: 221

```
Ala Ile Ser Ile Thr Gly Arg Arg Lys Tyr Tyr Ala Asp Ser Val Lys
1               5                   10                  15
Gly

<210> SEQ ID NO 222
<211> LENGTH: 17
<212> TYPE: PRT
<213> ORGANISM: artificial sequence
<220> FEATURE:
<223> OTHER INFORMATION: synthetic construct; HCDR2 of MS-Roche#8.2H2

<400> SEQUENCE: 222

Ala Ile Ser Arg Thr Gly Ser Lys Thr Tyr Tyr Ala Asp Ser Val Lys
1               5                   10                  15
Gly

<210> SEQ ID NO 223
<211> LENGTH: 16
<212> TYPE: PRT
<213> ORGANISM: artificial sequence
<220> FEATURE:
<223> OTHER INFORMATION: synthetic construct; HCDR2 of MS-Roche#8.2H4

<400> SEQUENCE: 223

Ala Thr Ser Val Lys Gly Lys Thr Tyr Tyr Ala Asp Ser Val Lys Gly
1               5                   10                  15

<210> SEQ ID NO 224
<211> LENGTH: 12
<212> TYPE: PRT
<213> ORGANISM: artificial sequence
<220> FEATURE:
<223> OTHER INFORMATION: synthetic construct; LCDR1 of MS-Roche#8.2L1

<400> SEQUENCE: 224

Arg Ala Ser Gln Arg Val Ser Gly Arg Tyr Leu Ala
1               5                   10

<210> SEQ ID NO 225
<211> LENGTH: 109
<212> TYPE: PRT
<213> ORGANISM: artificial sequence
<220> FEATURE:
<223> OTHER INFORMATION: synthetic construct; VL kappa1
<220> FEATURE:
<221> NAME/KEY: MISC_FEATURE
<222> LOCATION: (96)..(96)
<223> OTHER INFORMATION: Xaa = any amino acid of a mixture of Ala, Asp,
      Glu, Phe, Gly, His, Ile, Lys, Leu, Met, Asn, Pro, Gln, Arg, Ser,
      Thr, Val, Trp, or Tyr
<220> FEATURE:
<221> NAME/KEY: MISC_FEATURE
<222> LOCATION: (93)..(93)
<223> OTHER INFORMATION: Xaa = any amino acid of a mixture of Ala, Asp,
      Gly, His, Leu, Asn or Ser
<220> FEATURE:
<221> NAME/KEY: MISC_FEATURE
<222> LOCATION: (92)..(92)
<223> OTHER INFORMATION: Xaa = any amino acid of a mixture of Asp, Gly,
      Asn, Ser or Tyr
<220> FEATURE:
<221> NAME/KEY: MISC_FEATURE
<222> LOCATION: (91)..(91)
<223> OTHER INFORMATION: Xaa = any amino acid of a mixture of Ala, Asp,
      Glu, Phe, Gly, His, Ile, Lys, Leu, Met,  Asn, Gln, Arg, Ser, Thr,
      Val, Trp or Tyr
<220> FEATURE:
<221> NAME/KEY: MISC_FEATURE
<222> LOCATION: (89)..(89)
<223> OTHER INFORMATION: Xaa = any amino acid of a mixture of Phe, His,
```

```
        Ile, Leu, Met or Gln,
<220> FEATURE:
<221> NAME/KEY: MISC_FEATURE
<222> LOCATION: (85)..(85)
<223> OTHER INFORMATION: Xaa = can be Thr or Val
<220> FEATURE:
<221> NAME/KEY: MISC_FEATURE
<222> LOCATION: (94)..(94)
<223> OTHER INFORMATION: Xaa = any amino acid of a mixture of Ala, Asp,
      Glu, Phe, Gly, His, Ile, Lys, Leu, Met, Asn, Pro, Gln, Arg, Ser,
      Thr, Val, Trp, or Tyr
<220> FEATURE:
<221> NAME/KEY: MISC_FEATURE
<222> LOCATION: (95)..(95)
<223> OTHER INFORMATION: Xaa = any amino acid of a mixture of Leu, Pro
      or Ser

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Xaa Tyr Tyr Cys Xaa Gln Xaa Xaa Xaa Xaa Xaa Xaa
                85                  90                  95

Thr Phe Gly Gln Gly Thr Lys Val Glu Ile Lys Arg Thr
            100                 105

<210> SEQ ID NO 226
<211> LENGTH: 114
<212> TYPE: PRT
<213> ORGANISM: artificial sequence
<220> FEATURE:
<223> OTHER INFORMATION: synthetic construct; VL kappa2
<220> FEATURE:
<221> NAME/KEY: misc_feature
<222> LOCATION: (101)..(101)
<223> OTHER INFORMATION: Xaa = any amino acid of a mixture of Ala, Asp,
      Glu, Phe, Gly, His, Ile, Lys, Leu, Met, Asn, Pro, Gln, Arg, Ser,
      Thr, Val, Trp, or Tyr
<220> FEATURE:
<221> NAME/KEY: misc_feature
<222> LOCATION: (94)..(94)
<223> OTHER INFORMATION: Xaa = any amino acid of a mixture of Phe, His,
      Ile, Leu, Met or Gln,
<220> FEATURE:
<221> NAME/KEY: misc_feature
<222> LOCATION: (96)..(96)
<223> OTHER INFORMATION: Xaa = any amino acid of a mixture of Ala, Asp,
      Glu, Phe, Gly, His, Ile, Lys, Leu, Met, Asn, Gln, Arg, Ser, Thr,
      Val, Trp or Tyr
<220> FEATURE:
<221> NAME/KEY: misc_feature
<222> LOCATION: (97)..(97)
<223> OTHER INFORMATION: Xaa = any amino acid of a mixture of Asp, Gly,
      Asn, Ser or Tyr
<220> FEATURE:
<221> NAME/KEY: misc_feature
<222> LOCATION: (98)..(98)
<223> OTHER INFORMATION: Xaa = any amino acid of a mixture of Ala, Asp,
      Gly, His, Leu, Asn or Ser
<220> FEATURE:
<221> NAME/KEY: misc_feature
<222> LOCATION: (99)..(99)
<223> OTHER INFORMATION: Xaa = any amino acid of a mixture of Ala, Asp,
      Glu, Phe, Gly, His, Ile, Lys, Leu, Met, Asn, Pro, Gln, Arg, Ser,
      Thr, Val, Trp, or Tyr
```

-continued

```
<220> FEATURE:
<221> NAME/KEY: misc_feature
<222> LOCATION: (100)..(100)
<223> OTHER INFORMATION: Xaa = any amino acid of a mixture of Leu, Pro
      or Ser

<400> SEQUENCE: 226

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Xaa Gln Xaa
                85                  90                  95

Xaa Xaa Xaa Xaa Xaa Thr Phe Gly Gln Gly Thr Lys Val Glu Ile Lys
            100                 105                 110

Arg Thr

<210> SEQ ID NO 227
<211> LENGTH: 110
<212> TYPE: PRT
<213> ORGANISM: artificial sequence
<220> FEATURE:
<223> OTHER INFORMATION: synthetic construct; VL kappa3
<220> FEATURE:
<221> NAME/KEY: misc_feature
<222> LOCATION: (97)..(97)
<223> OTHER INFORMATION: Xaa = any amino acid of a mixture of Ala, Asp,
      Glu, Phe, Gly, His, Ile, Lys, Leu, Met, Asn, Pro, Gln, Arg, Ser,
      Thr, Val, Trp, or Tyr
<220> FEATURE:
<221> NAME/KEY: misc_feature
<222> LOCATION: (90)..(90)
<223> OTHER INFORMATION: Xaa = any amino acid of a mixture of Phe, His,
      Ile, Leu, Met or Gln,
<220> FEATURE:
<221> NAME/KEY: misc_feature
<222> LOCATION: (86)..(86)
<223> OTHER INFORMATION: Xaa = Thr or Val
<220> FEATURE:
<221> NAME/KEY: misc_feature
<222> LOCATION: (92)..(92)
<223> OTHER INFORMATION: Xaa = any amino acid of a mixture of Ala, Asp,
      Glu, Phe, Gly, His, Ile, Lys, Leu, Met,  Asn, Gln, Arg, Ser, Thr,
      Val, Trp or Tyr
<220> FEATURE:
<221> NAME/KEY: misc_feature
<222> LOCATION: (93)..(93)
<223> OTHER INFORMATION: Xaa = any amino acid of a mixture of Asp, Gly,
      Asn, Ser or Tyr
<220> FEATURE:
<221> NAME/KEY: misc_feature
<222> LOCATION: (94)..(94)
<223> OTHER INFORMATION: Xaa = any amino acid of a mixture of Ala, Asp,
      Gly, His, Leu, Asn or Ser
<220> FEATURE:
<221> NAME/KEY: misc_feature
<222> LOCATION: (95)..(95)
<223> OTHER INFORMATION: Xaa = any amino acid of a mixture of Ala, Asp,
      Glu, Phe, Gly, His, Ile, Lys, Leu, Met, Asn, Pro, Gln, Arg, Ser,
      Thr, Val, Trp, or Tyr
<220> FEATURE:
<221> NAME/KEY: misc_feature
<222> LOCATION: (96)..(96)
<223> OTHER INFORMATION: Xaa = any amino acid of a mixture of Leu, Pro
      or Ser
```

<400> SEQUENCE: 227

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Xaa Tyr Tyr Cys Xaa Gln Xaa Xaa Xaa Xaa Xaa
                85                  90                  95

Xaa Thr Phe Gly Gln Gly Thr Lys Val Glu Ile Lys Arg Thr
            100                 105                 110

<210> SEQ ID NO 228
<211> LENGTH: 115
<212> TYPE: PRT
<213> ORGANISM: artificial sequence
<220> FEATURE:
<223> OTHER INFORMATION: synthetic construct; VL kappa4
<220> FEATURE:
<221> NAME/KEY: MISC_FEATURE
<222> LOCATION: (102)..(102)
<223> OTHER INFORMATION: Xaa = any amino acid of a mixture of Ala, Asp,
      Glu, Phe, Gly, His, Ile, Lys, Leu, Met, Asn, Pro, Gln, Arg, Ser,
      Thr, Val, Trp, or Tyr
<220> FEATURE:
<221> NAME/KEY: MISC_FEATURE
<222> LOCATION: (95)..(95)
<223> OTHER INFORMATION: Xaa = any amino acid of a mixture of Phe, His,
      Ile, Leu, Met or Gln,
<220> FEATURE:
<221> NAME/KEY: MISC_FEATURE
<222> LOCATION: (97)..(97)
<223> OTHER INFORMATION: Xaa = any amino acid of a mixture of Ala, Asp,
      Glu, Phe, Gly, His, Ile, Lys, Leu, Met, Asn, Gln, Arg, Ser, Thr,
      Val, Trp or Tyr
<220> FEATURE:
<221> NAME/KEY: MISC_FEATURE
<222> LOCATION: (98)..(98)
<223> OTHER INFORMATION: Xaa = any amino acid of a mixture of Asp, Gly,
      Asn, Ser or Tyr
<220> FEATURE:
<221> NAME/KEY: MISC_FEATURE
<222> LOCATION: (99)..(99)
<223> OTHER INFORMATION: Xaa = any amino acid of a mixture of Ala, Asp,
      Gly, His, Leu, Asn or Ser
<220> FEATURE:
<221> NAME/KEY: MISC_FEATURE
<222> LOCATION: (100)..(100)
<223> OTHER INFORMATION: Xaa = any amino acid of a mixture of Ala, Asp,
      Glu, Phe, Gly, His, Ile, Lys, Leu, Met, Asn, Pro, Gln, Arg, Ser,
      Thr, Val, Trp, or Tyr
<220> FEATURE:
<221> NAME/KEY: MISC_FEATURE
<222> LOCATION: (101)..(101)
<223> OTHER INFORMATION: Xaa = any amino acid of a mixture of Leu, Pro
      or Ser

<400> SEQUENCE: 228

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

```
Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Xaa Gln
                 85                  90                  95

Xaa Xaa Xaa Xaa Xaa Xaa Thr Phe Gly Gln Gly Thr Lys Val Glu Ile
            100                 105                 110

Lys Arg Thr
        115

<210> SEQ ID NO 229
<211> LENGTH: 111
<212> TYPE: PRT
<213> ORGANISM: artificial sequence
<220> FEATURE:
<223> OTHER INFORMATION: synthetic construct; VL lambda1
<220> FEATURE:
<221> NAME/KEY: MISC_FEATURE
<222> LOCATION: (99)..(99)
<223> OTHER INFORMATION: Xaa = any amino acid
<220> FEATURE:
<221> NAME/KEY: MISC_FEATURE
<222> LOCATION: (97)..(98)
<223> OTHER INFORMATION: Xaa = any amino acid except a Cys or a deletion
<220> FEATURE:
<221> NAME/KEY: MISC_FEATURE
<222> LOCATION: (94)..(96)
<223> OTHER INFORMATION: Xaa = any amino acid except a Cys
<220> FEATURE:
<221> NAME/KEY: MISC_FEATURE
<222> LOCATION: (92)..(92)
<223> OTHER INFORMATION: Xaa = any amino acid of Cys, Phe, His, Arg, Trp
      or Tyr

<400> SEQUENCE: 229

Asp Ile Val Leu Thr Gln Pro Pro Ser Val Ser Gly Ala Pro Gly Gln
 1               5                  10                  15

Arg Val Thr Ile Ser Cys Ser Gly Ser Ser Asn Ile Gly Ser Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Gln Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Ser Xaa Asp Xaa Xaa Xaa
                 85                  90                  95

Xaa Xaa Xaa Val Phe Gly Gly Gly Thr Lys Leu Thr Val Leu Gly
            100                 105                 110

<210> SEQ ID NO 230
<211> LENGTH: 112
<212> TYPE: PRT
<213> ORGANISM: artificial sequence
<220> FEATURE:
<223> OTHER INFORMATION: synthetic construct; VL lambda2
<220> FEATURE:
<221> NAME/KEY: MISC_FEATURE
<222> LOCATION: (100)..(100)
<223> OTHER INFORMATION: Xaa = any amino acid
<220> FEATURE:
<221> NAME/KEY: MISC_FEATURE
<222> LOCATION: (93)..(93)
<223> OTHER INFORMATION: Xaa = any amino acid of Cys, Phe, His, Arg, Trp
      or Tyr
```

```
<220> FEATURE:
<221> NAME/KEY: MISC_FEATURE
<222> LOCATION: (95)..(97)
<223> OTHER INFORMATION: Xaa = any amino acid except a Cys
<220> FEATURE:
<221> NAME/KEY: MISC_FEATURE
<222> LOCATION: (98)..(99)
<223> OTHER INFORMATION: Xaa = any amino acid except a Cys or a deletion

<400> SEQUENCE: 230

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Xaa Asp Xaa Xaa
                85                  90                  95

Xaa Xaa Xaa Xaa Val Phe Gly Gly Gly Thr Lys Leu Thr Val Leu Gly
            100                 105                 110

<210> SEQ ID NO 231
<211> LENGTH: 109
<212> TYPE: PRT
<213> ORGANISM: artificial sequence
<220> FEATURE:
<223> OTHER INFORMATION: synthetic construct; VL lambda3
<220> FEATURE:
<221> NAME/KEY: MISC_FEATURE
<222> LOCATION: (97)..(97)
<223> OTHER INFORMATION: Xaa = any amino acid
<220> FEATURE:
<221> NAME/KEY: MISC_FEATURE
<222> LOCATION: (90)..(90)
<223> OTHER INFORMATION: Xaa = any amino acid of Cys, Phe, His, Arg, Trp
      or Tyr
<220> FEATURE:
<221> NAME/KEY: MISC_FEATURE
<222> LOCATION: (92)..(94)
<223> OTHER INFORMATION: Xaa = any amino acid except a Cys
<220> FEATURE:
<221> NAME/KEY: MISC_FEATURE
<222> LOCATION: (95)..(96)
<223> OTHER INFORMATION: Xaa = any amino acid except a Cys or a deletion

<400> SEQUENCE: 231

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Xaa Asp Xaa Xaa Xaa Xaa Xaa
                85                  90                  95

Xaa Val Phe Gly Gly Gly Thr Lys Leu Thr Val Leu Gly
            100                 105
```

-continued

<210> SEQ ID NO 232
<211> LENGTH: 127
<212> TYPE: PRT
<213> ORGANISM: artificial sequence
<220> FEATURE:
<223> OTHER INFORMATION: synthetic construct; VH1A
<220> FEATURE:
<221> NAME/KEY: MISC_FEATURE
<222> LOCATION: (99)..(112)
<223> OTHER INFORMATION: Xaa = any amino acid or a deletion
<220> FEATURE:
<221> NAME/KEY: MISC_FEATURE
<222> LOCATION: (116)..(116)
<223> OTHER INFORMATION: Xaa = any amino acid out of a mixture of Phe,
      His, Ile, Leu, Asn, Pro, Ser, Val, Trp or Tyr
<220> FEATURE:
<221> NAME/KEY: MISC_FEATURE
<222> LOCATION: (114)..(114)
<223> OTHER INFORMATION: Xaa = any amino acid out of a mixture of Ala,
      Asp, Glu, Phe, Gly, Ile, Leu, Met, Pro, Gln, Ser, Thr, Val or Tyr
<220> FEATURE:
<221> NAME/KEY: MISC_FEATURE
<222> LOCATION: (113)..(113)
<223> OTHER INFORMATION: Xaa = any amino acid

<400> SEQUENCE: 232

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Xaa Asp Xaa Trp Gly Gln Gly Thr Leu Val Thr Val Ser Ser
        115                 120                 125

<210> SEQ ID NO 233
<211> LENGTH: 127
<212> TYPE: PRT
<213> ORGANISM: artificial sequence
<220> FEATURE:
<223> OTHER INFORMATION: synthetic construct; VH1B
<220> FEATURE:
<221> NAME/KEY: MISC_FEATURE
<222> LOCATION: (99)..(112)
<223> OTHER INFORMATION: Xaa = any amino acid or a deletion
<220> FEATURE:
<221> NAME/KEY: MISC_FEATURE
<222> LOCATION: (113)..(113)
<223> OTHER INFORMATION: Xaa = any amino acid
<220> FEATURE:
<221> NAME/KEY: MISC_FEATURE
<222> LOCATION: (114)..(114)
<223> OTHER INFORMATION: Xaa = any amino acid out of a mixture of Ala,
      Asp, Glu, Phe, Gly, Ile, Leu, Met, Pro, Gln, Ser, Thr, Val or Tyr
<220> FEATURE:
<221> NAME/KEY: MISC_FEATURE
<222> LOCATION: (116)..(116)
<223> OTHER INFORMATION: Xaa = any amino acid out of a mixture of Phe,
      His, Ile, Leu, Asn, Pro, Ser, Val, Trp or Tyr

<400> SEQUENCE: 233

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65              70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Xaa Asp Xaa Trp Gly Gln Gly Thr Leu Val Thr Val Ser Ser
        115                 120                 125

<210> SEQ ID NO 234
<211> LENGTH: 128
<212> TYPE: PRT
<213> ORGANISM: artificial sequence
<220> FEATURE:
<223> OTHER INFORMATION: synthetic construct; VH2
<220> FEATURE:
<221> NAME/KEY: MISC_FEATURE
<222> LOCATION: (100)..(113)
<223> OTHER INFORMATION: Xaa = any amino acid or a deletion
<220> FEATURE:
<221> NAME/KEY: MISC_FEATURE
<222> LOCATION: (114)..(114)
<223> OTHER INFORMATION: Xaa = any amino acid
<220> FEATURE:
<221> NAME/KEY: MISC_FEATURE
<222> LOCATION: (117)..(117)
<223> OTHER INFORMATION: Xaa = any amino acid out of a mixture of Phe,
      His, Ile, Leu, Asn, Pro, Ser, Val, Trp or Tyr
<220> FEATURE:
<221> NAME/KEY: MISC_FEATURE
<222> LOCATION: (115)..(115)
<223> OTHER INFORMATION: Xaa = any amino acid out of a mixture of Ala,
      Asp, Glu, Phe, Gly, Ile, Leu, Met, Pro, Gln, Ser, Thr, Val or Tyr

<400> SEQUENCE: 234

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Asp Trp Asp Asp Lys Tyr Tyr Ser Thr Ser
        50                  55                  60

Leu Lys Thr Arg Leu Thr Ile Ser Lys Asp Thr Ser Lys Asn Gln Val
65              70                  75                  80

Val Leu Thr Met Thr Asn Met Asp Pro Val Asp Thr Ala Thr Tyr Tyr
                85                  90                  95

Cys Ala Arg Xaa Xaa Xaa Xaa Xaa Xaa Xaa Xaa Xaa Xaa Xaa Xaa Xaa
            100                 105                 110

Xaa Xaa Xaa Asp Xaa Trp Gly Gln Gly Thr Leu Val Thr Val Ser Ser
        115                 120                 125

<210> SEQ ID NO 235
<211> LENGTH: 127
<212> TYPE: PRT

```
<213> ORGANISM: artificial sequence
<220> FEATURE:
<223> OTHER INFORMATION: synthetic construct; VH3
<220> FEATURE:
<221> NAME/KEY: MISC_FEATURE
<222> LOCATION: (99)..(112)
<223> OTHER INFORMATION: Xaa = any amino acid or a deletion
<220> FEATURE:
<221> NAME/KEY: MISC_FEATURE
<222> LOCATION: (113)..(113)
<223> OTHER INFORMATION: Xaa = any amino acid
<220> FEATURE:
<221> NAME/KEY: MISC_FEATURE
<222> LOCATION: (116)..(116)
<223> OTHER INFORMATION: Xaa = any amino acid out of a mixture of Phe,
      His, Ile, Leu, Asn, Pro, Ser, Val, Trp or Tyr
<220> FEATURE:
<221> NAME/KEY: MISC_FEATURE
<222> LOCATION: (114)..(114)
<223> OTHER INFORMATION: Xaa = any amino acid out of a mixture of Ala,
      Asp, Glu, Phe, Gly, Ile, Leu, Met, Pro, Gln, Ser, Thr, Val or Tyr

<400> SEQUENCE: 235

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Xaa Asp Xaa Trp Gly Gln Gly Thr Leu Val Thr Val Ser Ser
        115                 120                 125

<210> SEQ ID NO 236
<211> LENGTH: 126
<212> TYPE: PRT
<213> ORGANISM: artificial sequence
<220> FEATURE:
<223> OTHER INFORMATION: synthetic construct; VH4
<220> FEATURE:
<221> NAME/KEY: MISC_FEATURE
<222> LOCATION: (98)..(111)
<223> OTHER INFORMATION: Xaa = any amino acid or a deletion
<220> FEATURE:
<221> NAME/KEY: MISC_FEATURE
<222> LOCATION: (112)..(112)
<223> OTHER INFORMATION: Xaa = any amino acid
<220> FEATURE:
<221> NAME/KEY: MISC_FEATURE
<222> LOCATION: (113)..(113)
<223> OTHER INFORMATION: Xaa = any amino acid out of a mixture of Ala,
      Asp, Glu, Phe, Gly, Ile, Leu, Met, Pro, Gln, Ser, Thr, Val or Tyr
<220> FEATURE:
<221> NAME/KEY: MISC_FEATURE
<222> LOCATION: (115)..(115)
<223> OTHER INFORMATION: Xaa = any amino acid out of a mixture of Phe,
      His, Ile, Leu, Asn, Pro, Ser, Val, Trp or Tyr

<400> SEQUENCE: 236

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
```

```
                    20                  25                  30
Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Xaa Xaa Xaa Xaa Xaa Xaa Xaa Xaa Xaa Xaa Xaa Xaa Xaa
            100                 105                 110

Xaa Asp Xaa Trp Gly Gln Gly Thr Leu Val Thr Val Ser Ser
        115                 120                 125

<210> SEQ ID NO 237
<211> LENGTH: 127
<212> TYPE: PRT
<213> ORGANISM: artificial sequence
<220> FEATURE:
<223> OTHER INFORMATION: synthetic construct; VH5
<220> FEATURE:
<221> NAME/KEY: MISC_FEATURE
<222> LOCATION: (99)..(112)
<223> OTHER INFORMATION: Xaa = any amino acid or a deletion
<220> FEATURE:
<221> NAME/KEY: MISC_FEATURE
<222> LOCATION: (113)..(113)
<223> OTHER INFORMATION: Xaa = any amino acid
<220> FEATURE:
<221> NAME/KEY: MISC_FEATURE
<222> LOCATION: (116)..(116)
<223> OTHER INFORMATION: Xaa = any amino acid out of a mixture of Phe,
      His, Ile, Leu, Asn, Pro, Ser, Val, Trp or Tyr
<220> FEATURE:
<221> NAME/KEY: MISC_FEATURE
<222> LOCATION: (114)..(114)
<223> OTHER INFORMATION: Xaa = any amino acid out of a mixture of Ala,
      Asp, Glu, Phe, Gly, Ile, Leu, Met, Pro, Gln, Ser, Thr, Val or Tyr

<400> SEQUENCE: 237

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Xaa Xaa Xaa Xaa Xaa Xaa Xaa Xaa Xaa Xaa Xaa Xaa Xaa
            100                 105                 110

Xaa Xaa Asp Xaa Trp Gly Gln Gly Thr Leu Val Thr Val Ser Ser
        115                 120                 125

<210> SEQ ID NO 238
<211> LENGTH: 130
<212> TYPE: PRT
<213> ORGANISM: artificial sequence
<220> FEATURE:
<223> OTHER INFORMATION: synthetic construct; VH6
<220> FEATURE:
```

```
<221> NAME/KEY: MISC_FEATURE
<222> LOCATION: (102)..(115)
<223> OTHER INFORMATION: Xaa = any amino acid or a deletion
<220> FEATURE:
<221> NAME/KEY: MISC_FEATURE
<222> LOCATION: (116)..(116)
<223> OTHER INFORMATION: Xaa = any amino acid
<220> FEATURE:
<221> NAME/KEY: MISC_FEATURE
<222> LOCATION: (119)..(119)
<223> OTHER INFORMATION: Xaa = any amino acid out of a mixture of Phe,
      His, Ile, Leu, Asn, Pro, Ser, Val, Trp or Tyr
<220> FEATURE:
<221> NAME/KEY: MISC_FEATURE
<222> LOCATION: (117)..(117)
<223> OTHER INFORMATION: Xaa = any amino acid out of a mixture of Ala,
      Asp, Glu, Phe, Gly, Ile, Leu, Met, Pro, Gln, Ser, Thr, Val or Tyr

<400> SEQUENCE: 238

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Xaa Xaa Xaa Xaa Xaa Xaa Xaa Xaa Xaa Xaa
            100                 105                 110

Xaa Xaa Xaa Xaa Xaa Asp Xaa Trp Gly Gln Gly Thr Leu Val Thr Val
        115                 120                 125

Ser Ser
    130

<210> SEQ ID NO 239
<211> LENGTH: 327
<212> TYPE: DNA
<213> ORGANISM: artificial sequence
<220> FEATURE:
<223> OTHER INFORMATION: synthetic construct; VL kappa1
<220> FEATURE:
<221> NAME/KEY: misc_feature
<222> LOCATION: (286)..(288)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT
<220> FEATURE:
<221> NAME/KEY: misc_feature
<222> LOCATION: (271)..(273)
<223> OTHER INFORMATION: nnn = GCT, GAT, GAG, TTT, GGT, CAT, ATT, AAG,
      CTT, ATG, AAT, CAG, CGT, TCT, ACT, GTT, TGG or TAT
<220> FEATURE:
<221> NAME/KEY: misc_feature
<222> LOCATION: (265)..(267)
<223> OTHER INFORMATION: nnn = TTT, CAT, CTT, ATG or CAG
<220> FEATURE:
<221> NAME/KEY: misc_feature
<222> LOCATION: (253)..(256)
<223> OTHER INFORMATION: nnn = can be ACT or GTT
<220> FEATURE:
<221> NAME/KEY: misc_feature
<222> LOCATION: (283)..(285)
<223> OTHER INFORMATION: nnn = CTT, CCT or TCT
<220> FEATURE:
<221> NAME/KEY: misc_feature
<222> LOCATION: (280)..(282)
<223> OTHER INFORMATION: nnn = GCT, GAT, GAG, TTT, GGT, CAT, ATT, AAG,
```

```
        CTT, ATG, AAT, CCT, CAG, CGT, TCT, ACT, GTT, TGG or TAT
<220> FEATURE:
<221> NAME/KEY: misc_feature
<222> LOCATION: (277)..(279)
<223> OTHER INFORMATION: nnn = GCT, GAT, GGT, CAT, CTT, AAT or TCT
<220> FEATURE:
<221> NAME/KEY: misc_feature
<222> LOCATION: (274)..(276)
<223> OTHER INFORMATION: nnn = GAT, GGT, AAT, TCT or TAT

<400> SEQUENCE: 239
gatatccaga tgacccagag cccgtctagc ctgagcgcga gcgtgggtga tcgtgtgacc      60
attacctgca gagcgagcca gggcattagc agctatctgg cgtggtacca gcagaaacca    120
ggtaaagcac cgaaactatt aatttatgca gccagcagct tgcaaagcgg ggtcccgtcc    180
cgttttagcg gctctggatc cggcactgat tttaccctga ccattagcag cctgcaacct    240
gaagactttg cgnnntatta ttgcnnncag nnnnnnnnnn nnnnnnnnac ctttggccag    300
ggtacgaaag ttgaaattaa acgtacg                                        327

<210> SEQ ID NO 240
<211> LENGTH: 328
<212> TYPE: DNA
<213> ORGANISM: artificial sequence
<220> FEATURE:
<223> OTHER INFORMATION: synthetic construct; VL kappa2
<220> FEATURE:
<221> NAME/KEY: misc_feature
<222> LOCATION: (289)..(289)
<223> OTHER INFORMATION: n = GCT, GAT, GAG, TTT, GGT, CAT, ATT, AAG,
      CTT, ATG, AAT, CCT, CAG, CGT, TCT, ACT, GTT, TGG or TAT
<220> FEATURE:
<221> NAME/KEY: misc_feature
<222> LOCATION: (280)..(280)
<223> OTHER INFORMATION: n = TTT, CAT, CTT, ATG or CAG
<220> FEATURE:
<221> NAME/KEY: misc_feature
<222> LOCATION: (284)..(284)
<223> OTHER INFORMATION: n = GCT, GAT, GAG, TTT, GGT, CAT, ATT, AAG,
      CTT, ATG, AAT, CAG, CGT, TCT, ACT, GTT, TGG or TAT
<220> FEATURE:
<221> NAME/KEY: misc_feature
<222> LOCATION: (285)..(285)
<223> OTHER INFORMATION: n = GAT, GGT, AAT, TCT or TAT
<220> FEATURE:
<221> NAME/KEY: misc_feature
<222> LOCATION: (286)..(289)
<223> OTHER INFORMATION: n = GCT, GAT, GGT, CAT, CTT, AAT or TCT
<220> FEATURE:
<221> NAME/KEY: misc_feature
<222> LOCATION: (287)..(287)
<223> OTHER INFORMATION: n = GCT, GAT, GAG, TTT, GGT, CAT, ATT, AAG,
      CTT, ATG, AAT, CCT, CAG, CGT, TCT, ACT, GTT, TGG or TAT
<220> FEATURE:
<221> NAME/KEY: misc_feature
<222> LOCATION: (288)..(288)
<223> OTHER INFORMATION: n = CTT, CCT or TCT

<400> SEQUENCE: 240
gatatcgtga tgacccagag cccactgagc ctgccagtga ctccgggcga gcctgcgagc      60
attagctgca gaagcagcca aagcctgctg catagcaacg gctataacta tctggattgg    120
taccttcaaa aaccaggtca aagcccgcag ctattaattt atctgggcag caaccgtgcc    180
agtggggtcc cggatcgttt tagcggctct ggatccggca ccgattttac cctgaaaatt    240
agccgtgtgg aagctgaaga cgtgggcgtg tattattgcn cagnnnnnna cctttggcca    300
gggtacgaaa gttgaaatta aacgtacg                                      328

<210> SEQ ID NO 241
<211> LENGTH: 330
```

```
<212> TYPE: DNA
<213> ORGANISM: artificial sequence
<220> FEATURE:
<223> OTHER INFORMATION: synthetic construct; VL kappa3
<220> FEATURE:
<221> NAME/KEY: misc_feature
<222> LOCATION: (289)..(291)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT
<220> FEATURE:
<221> NAME/KEY: misc_feature
<222> LOCATION: (256)..(258)
<223> OTHER INFORMATION: nnn = can be ACT or GTT
<220> FEATURE:
<221> NAME/KEY: misc_feature
<222> LOCATION: (265)..(276)
<223> OTHER INFORMATION: nnn = TTT, CAT, CTT, ATG or CAG
<220> FEATURE:
<221> NAME/KEY: misc_feature
<222> LOCATION: (274)..(276)
<223> OTHER INFORMATION: nnn = GCT, GAT, GAG, TTT, GGT, CAT, ATT, AAG,
      CTT, ATG, AAT, CAG, CGT, TCT, ACT, GTT, TGG or TAT
<220> FEATURE:
<221> NAME/KEY: misc_feature
<222> LOCATION: (277)..(279)
<223> OTHER INFORMATION: nnn = GAT, GGT, AAT, TCT or TAT
<220> FEATURE:
<221> NAME/KEY: misc_feature
<222> LOCATION: (280)..(282)
<223> OTHER INFORMATION: nnn = GCT, GAT, GGT, CAT, CTT, AAT or TCT
<220> FEATURE:
<221> NAME/KEY: misc_feature
<222> LOCATION: (283)..(285)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT
<220> FEATURE:
<221> NAME/KEY: misc_feature
<222> LOCATION: (286)..(288)
<223> OTHER INFORMATION: nnn = CTT, CCT or TCT

<400> SEQUENCE: 241
gatatcgtgc tgacccagag cccggcgacc ctgagcctgt ctccgggcga acgtgcgacc      60
ctgagctgca gagcgagcca gagcgtgagc agcagctatc tggcgtggta ccagcagaaa     120
ccaggtcaag caccgcgtct attaatttat ggcgcgagca gccgtgcaac tggggtcccg     180
gcgcgtttta gcggctctgg atccggcacg gattttaccc tgaccattag cagcctggaa     240
cctgaagact ttgcgnnnta ttattgcnnn cagnnnnnnn nnnnnnnnnn nacctttggc     300
cagggtacga agttgaaat taaacgtacg                                       330

<210> SEQ ID NO 242
<211> LENGTH: 345
<212> TYPE: DNA
<213> ORGANISM: artificial sequence
<220> FEATURE:
<223> OTHER INFORMATION: synthetic construct; VL kappa4
<220> FEATURE:
<221> NAME/KEY: misc_feature
<222> LOCATION: (304)..(306)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT
<220> FEATURE:
<221> NAME/KEY: misc_feature
<222> LOCATION: (283)..(285)
<223> OTHER INFORMATION: nnn = TTT, CAT, CTT, ATG or CAG
<220> FEATURE:
<221> NAME/KEY: misc_feature
<222> LOCATION: (289)..(291)
<223> OTHER INFORMATION: nnn = GCT, GAT, GAG, TTT, GGT, CAT, ATT, AAG,
      CTT, ATG, AAT, CAG, CGT, TCT, ACT, GTT, TGG or TAT
<220> FEATURE:
<221> NAME/KEY: misc_feature
<222> LOCATION: (292)..(294)
<223> OTHER INFORMATION: nnn = GAT, GGT, AAT, TCT or TAT
<220> FEATURE:
```

-continued

```
<221> NAME/KEY: misc_feature
<222> LOCATION: (295)..(297)
<223> OTHER INFORMATION: nnn = GCT, GAT, GGT, CAT, CTT, AAT or TCT
<220> FEATURE:
<221> NAME/KEY: misc_feature
<222> LOCATION: (298)..(300)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT
<220> FEATURE:
<221> NAME/KEY: misc_feature
<222> LOCATION: (301)..(303)
<223> OTHER INFORMATION: nnn = CTT, CCT or TCT

<400> SEQUENCE: 242
gatatcgtga tgacccagag cccggatagc ctggcggtga gcctgggcga acgtgcgacc      60
attaactgca gaagcagcca gagcgtgctg tatagcagca acaacaaaaa ctatctggcg     120
tggtaccagc agaaaccagg tcagccgccg aaactattaa tttattgggc atccacccgt    180
gaaagcgggg tcccggatcg ttttagcggc tctggatccg gcactgattt taccctgacc    240
atttcgtccc tgcaagctga agacgtgcg gtgtattatt gcnnncagnn nnnnnnnnn      300 nnnnnnacct ttggccaggg tacgaaagtt gaaattaaac gtacg                    345

<210> SEQ ID NO 243
<211> LENGTH: 322
<212> TYPE: DNA
<213> ORGANISM: artificial sequence
<220> FEATURE:
<223> OTHER INFORMATION: synthetic construct; VL lambda1
<220> FEATURE:
<221> NAME/KEY: misc_feature
<222> LOCATION: (274)..(274)
<223> OTHER INFORMATION: n = TGT, TTT, CAT, CGT, TGG or TAT
<220> FEATURE:
<221> NAME/KEY: misc_feature
<222> LOCATION: (278)..(280)
<223> OTHER INFORMATION: n = GCT, GAT, GAG, TTT, GGT, CAT, ATT, AAG,
      CTT, ATG, AAT, CCT, CAG, CGT, TCT, ACT, GTT, TGG or TAT
<220> FEATURE:
<221> NAME/KEY: misc_feature
<222> LOCATION: (281)..(282)
<223> OTHER INFORMATION: n = GCT, GAT, GAG, TTT, GGT, CAT, ATT, AAG,
      CTT, ATG, AAT, CCT, CAG, CGT, TCT, ACT, GTT, TGG or TAT or a
      deletion
<220> FEATURE:
<221> NAME/KEY: misc_feature
<222> LOCATION: (283)..(283)
<223> OTHER INFORMATION: n = GCT, TGT, GAT, GAG, TTT, GGT, CAT, ATT,
      AAG, CTT, ATG, AAT, CCT, CAG, CGT, TCT, ACT, GTT, TGG or TAT

<400> SEQUENCE: 243
gatatcgtgc tgacccagcc gccttcagtg agtggcgcac caggtcagcg tgtgaccatc      60
tcgtgtagcg gcagcagcag caacattggc agcaactatg tgagctggta ccagcagttg    120
cccgggacgg cgccgaaact gctgatttat gataacaacc agcgtccctc aggcgtgccg    180
gatcgtttta gcggatccaa aagcggcacc agcgcgagcc ttgcgattac gggcctgcaa    240
agcgaagacg aagcggatta ttattgccag tctngatnnn nnngtgtttg gcggcggcac    300
gaagttaacc gttcttggcc ag                                              322

<210> SEQ ID NO 244
<211> LENGTH: 336
<212> TYPE: DNA
<213> ORGANISM: artificial sequence
<220> FEATURE:
<223> OTHER INFORMATION: synthetic construct; VL lambda2
<220> FEATURE:
<221> NAME/KEY: misc_feature
<222> LOCATION: (274)..(276)
<223> OTHER INFORMATION: nnn = TGT, TTT, CAT, CGT, TGG or TAT
```

```
<220> FEATURE:
<221> NAME/KEY: misc_feature
<222> LOCATION: (290)..(295)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT or a
      deletion
<220> FEATURE:
<221> NAME/KEY: misc_feature
<222> LOCATION: (296)..(298)
<223> OTHER INFORMATION: nnn = GCT, TGT, GAT, GAG, TTT, GGT, CAT, ATT,
      AAG, CTT, ATG, AAT, CCT, CAG, CGT, TCT, ACT, GTT, TGG or TAT
<220> FEATURE:
<221> NAME/KEY: misc_feature
<222> LOCATION: (280)..(289)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT

<400> SEQUENCE: 244
gatatcgcac tgacccagcc agcttcagtg agcggctcac caggtcagag cattaccatc    60
tcgtgtacgg gtactagcag cgatgtgggc ggctataact atgtgagctg gtaccagcag   120
catcccggga aggcgccgaa actgatgatt tatgatgtga gcaaccgtcc ctcaggcgtg   180
agcaaccgtt ttagcggatc caaaagcggc aacaccgcga gcctgaccat tagcggcctg   240
caagcggaag acgaagcgga ttattattgc cagnnngatn nnnnnnnnnn nnnnnnngtg   300
tttggcggcg gcacgaagtt aaccgttctt ggccag                             336

<210> SEQ ID NO 245
<211> LENGTH: 327
<212> TYPE: DNA
<213> ORGANISM: artificial sequence
<220> FEATURE:
<223> OTHER INFORMATION: synthetic construct; VL lambda3
<220> FEATURE:
<221> NAME/KEY: misc_feature
<222> LOCATION: (265)..(267)
<223> OTHER INFORMATION: nnn = TGT, TTT, CAT, CGT, TGG or TAT
<220> FEATURE:
<221> NAME/KEY: misc_feature
<222> LOCATION: (286)..(288)
<223> OTHER INFORMATION: nnn = GCT, TGT, GAT, GAG, TTT, GGT, CAT, ATT,
      AAG, CTT, ATG, AAT, CCT, CAG, CGT, TCT, ACT, GTT, TGG or TAT
<220> FEATURE:
<221> NAME/KEY: misc_feature
<222> LOCATION: (280)..(285)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT or a
      deletion
<220> FEATURE:
<221> NAME/KEY: misc_feature
<222> LOCATION: (271)..(279)
<223> OTHER INFORMATION: nnn = GCT, GAT, GAG, TTT, GGT, CAT, ATT, AAG,
      CTT, ATG, AAT, CCT, CAG, CGT, TCT, ACT, GTT, TGG or TAT

<400> SEQUENCE: 245
gatatcgaac tgacccagcc gccttcagtg agcgttgcac aggtcagac cgcgcgtatc    60 tcgtgtagcg gcgatgcgct gggcgataaa tacgcgagct ggtaccagca gaaacccggg   120
caggcgccag ttctggtgat ttatgatgat tctgaccgtc cctcaggcat cccggaacgc   180
tttagcggat ccaacagcgg caacaccgcg accctgacca ttagcggcac tcaggcggaa   240
gacgaagcgg attattattg ccagnnngat nnnnnnnnnn nnnnnnnngt gtttggcggc   300
ggcacgaagt taaccgttct tggccag                                       327

<210> SEQ ID NO 246
<211> LENGTH: 382
<212> TYPE: DNA
<213> ORGANISM: artificial sequence
<220> FEATURE:
<223> OTHER INFORMATION: synthetic construct; VH1A
```

-continued

```
<220> FEATURE:
<221> NAME/KEY: misc_feature
<222> LOCATION: (345)..(347)
<223> OTHER INFORMATION: nnn = TTT, CAT, ATT, CTT, AAT, CCT, TCT, GTT,
      TGG or TAT
<220> FEATURE:
<221> NAME/KEY: misc_feature
<222> LOCATION: (339)..(341)
<223> OTHER INFORMATION: nnn = GCT, GAT, GAG, TTT, GGT, ATT, CTT, ATG,
      CCT, CAG, TCT, ACT, GTT or TAT
<220> FEATURE:
<221> NAME/KEY: misc_feature
<222> LOCATION: (336)..(338)
<223> OTHER INFORMATION: nnn = GCT, TGT, GAT, GAG, TTT, GGT, CAT, ATT,
      AAG, CTT, ATG, AAT, CCT, CAG, CGT, TCT, ACT, GTT, TGG or TAT
<220> FEATURE:
<221> NAME/KEY: misc_feature
<222> LOCATION: (295)..(335)
<223> OTHER INFORMATION: nnn = GCT, TGT, GAT, GAG, TTT, GGT, CAT, ATT,
      AAG, CTT, ATG, AAT, CCT, CAG, CGT, TCT, ACT, GTT, TGG or TAT or a
      deletion

<400> SEQUENCE: 246
caggtgcaat tggttcagtc tggcgcggaa gtgaaaaaac cgggcagcag cgtgaaagtg      60
agctgcaaag cctccggagg cacttttagc agctatgcga ttagctgggt gcgccaagcc    120
cctgggcagg gtctcgagtg gatgggcggc attattccga tttttggcac ggcgaactac    180
gcgcagaagt ttcagggccg ggtgaccatt accgcggatg aaagcaccag caccgcgtat    240
atggaactga gcagcctgcg tagcgaagat acggccgtgt attattgcgc gcgtnnnnnn    300
nnnnnnnnnn nnnnnnnnnn nnnnnnnnnn nnnnnnnnnn ngatnnntgg ggccaaggca    360
ccctggtgac ggttagctca gc                                             382

<210> SEQ ID NO 247
<211> LENGTH: 383
<212> TYPE: DNA
<213> ORGANISM: artificial sequence
<220> FEATURE:
<223> OTHER INFORMATION: synthetic construct; VH1B
<220> FEATURE:
<221> NAME/KEY: misc_feature
<222> LOCATION: (346)..(348)
<223> OTHER INFORMATION: nnn = TTT, CAT, ATT, CTT, AAT, CCT, TCT, GTT,
      TGG or TAT
<220> FEATURE:
<221> NAME/KEY: misc_feature
<222> LOCATION: (295)..(336)
<223> OTHER INFORMATION: nnn = GCT, TGT, GAT, GAG, TTT, GGT, CAT, ATT,
      AAG, CTT, ATG, AAT, CCT, CAG, CGT, TCT, ACT, GTT, TGG or TAT or a
      deletion
<220> FEATURE:
<221> NAME/KEY: misc_feature
<222> LOCATION: (337)..(339)
<223> OTHER INFORMATION: nnn = GCT, TGT, GAT, GAG, TTT, GGT, CAT, ATT,
      AAG, CTT, ATG, AAT, CCT, CAG, CGT, TCT, ACT, GTT, TGG or TAT
<220> FEATURE:
<221> NAME/KEY: misc_feature
<222> LOCATION: (340)..(342)
<223> OTHER INFORMATION: nnn = GCT, GAT, GAG, TTT, GGT, ATT, CTT, ATG,
      CCT, CAG, TCT, ACT, GTT or TAT

<400> SEQUENCE: 247
caggtgcaat tggttcagag cggcgcggaa gtgaaaaaac cgggcgcgag cgtgaaagtg      60
agctgcaaag cctccggata ccctttacc agctattata tgcactgggt ccgccaagcc    120
cctgggcagg gtctcgagtg gatgggctgg attaacccga atagcggcgg cacgaactac    180
gcgcagaagt ttcagggccg ggtgaccatg acccgtgata ccagcattag caccgcgtat    240
atggaactga gcagcctgcg tagcgaagat acggccgtgt attattgcgc gcgtnnnnnn    300
nnnnnnnnnn nnnnnnnnnn nnnnnnnnnn nnnnnnnnnn nngatnnntg gggccaaggc    360
```
accctggtga cggttagctc agc    383

<210> SEQ ID NO 248
<211> LENGTH: 386
<212> TYPE: DNA
<213> ORGANISM: artificial sequence
<220> FEATURE:
<223> OTHER INFORMATION: synthetic construct; VH2
<220> FEATURE:
<221> NAME/KEY: misc_feature
<222> LOCATION: (349)..(351)
<223> OTHER INFORMATION: nnn = TTT, CAT, ATT, CTT, AAT, CCT, TCT, GTT, TGG or TAT
<220> FEATURE:
<221> NAME/KEY: misc_feature
<222> LOCATION: (298)..(339)
<223> OTHER INFORMATION: nnn = GCT, TGT, GAT, GAG, TTT, GGT, CAT, ATT, AAG, CTT, ATG, AAT, CCT, CAG, CGT, TCT, ACT, GTT, TGG or TAT or a deletion
<220> FEATURE:
<221> NAME/KEY: misc_feature
<222> LOCATION: (340)..(342)
<223> OTHER INFORMATION: nnn = GCT, TGT, GAT, GAG, TTT, GGT, CAT, ATT, AAG, CTT, ATG, AAT, CCT, CAG, CGT, TCT, ACT, GTT, TGG or TAT
<220> FEATURE:
<221> NAME/KEY: misc_feature
<222> LOCATION: (343)..(345)
<223> OTHER INFORMATION: nnn = GCT, GAT, GAG, TTT, GGT, ATT, CTT, ATG, CCT, CAG, TCT, ACT, GTT or TAT

<400> SEQUENCE: 248
caggtgcaat tgaaagaaag cggcccggcc ctggtgaaac cgacccaaac cctgaccctg    60
acctgtacct tttccggatt tagcctgtcc acgtctggcg ttggcgtggg ctggattcgc    120
cagccgcctg ggaaagccct cgagtggctg gctctgattg attgggatga tgataagtat    180
tatagcacca gcctgaaaac gcgtctgacc attagcaaag atacttcgaa aaatcaggtg    240
gtgctgacta tgaccaacat ggacccggtg gatacggcca cctattattg cgcgcgtnnn    300 nnnnnnnnn nnnnnnnnn nnnnnnnnn nnnnnnnnn nnnngatnn ntggggccaa    360 ggcaccctgg tgacggttag ctcagc    386

<210> SEQ ID NO 249
<211> LENGTH: 349
<212> TYPE: DNA
<213> ORGANISM: artificial sequence
<220> FEATURE:
<223> OTHER INFORMATION: synthetic construct; VH3
<220> FEATURE:
<221> NAME/KEY: misc_feature
<222> LOCATION: (314)..(314)
<223> OTHER INFORMATION: n = TTT, CAT, ATT, CTT, AAT, CCT, TCT, GTT, TGG or TAT
<220> FEATURE:
<221> NAME/KEY: misc_feature
<222> LOCATION: (295)..(308)
<223> OTHER INFORMATION: n = GCT, TGT, GAT, GAG, TTT, GGT, CAT, ATT, AAG, CTT, ATG, AAT, CCT, CAG, CGT, TCT, ACT, GTT, TGG or TAT or a deletion
<220> FEATURE:
<221> NAME/KEY: misc_feature
<222> LOCATION: (309)..(309)
<223> OTHER INFORMATION: n = GCT, TGT, GAT, GAG, TTT, GGT, CAT, ATT, AAG, CTT, ATG, AAT, CCT, CAG, CGT, TCT, ACT, GTT, TGG or TAT
<220> FEATURE:
<221> NAME/KEY: misc_feature
<222> LOCATION: (310)..(310)
<223> OTHER INFORMATION: n = GCT, GAT, GAG, TTT, GGT, ATT, CTT, ATG, CCT, CAG, TCT, ACT, GTT or TAT

<400> SEQUENCE: 249
caggtgcaat tggtggaaag cggcggcggc ctggtgcaac cggcggcag cctgcgtctg    60

```
agctgcgcgg cctccggatt tacctttagc agctatgcga tgagctgggt gcgccaagcc      120
cctgggaagg gtctcgagtg ggtgagcgcg attagcggta gcggcggcag cacctattat      180
gcggatagcg tgaaaggccg ttttaccatt tcacgtgata attcgaaaaa cacsctgtat      240
```
gcggatagcg tgaaaggccg ttttaccatt tcacgtgata attcgaaaaa cacccctgtat      240 ctgcaaatga acagcctgcg tgcggaagat acggccgtgt attattgcgc gcgtnnnnnn      300
nnnnnnnnnn gatntggggc caaggcaccc tggtgacggt tagctcagc                  349

<210> SEQ ID NO 250
<211> LENGTH: 346
<212> TYPE: DNA
<213> ORGANISM: artificial sequence
<220> FEATURE:
<223> OTHER INFORMATION: synthetic construct; VH4
<220> FEATURE:
<221> NAME/KEY: misc_feature
<222> LOCATION: (311)..(311)
<223> OTHER INFORMATION: n = TTT, CAT, ATT, CTT, AAT, CCT, TCT, GTT,
      TGG or TAT
<220> FEATURE:
<221> NAME/KEY: misc_feature
<222> LOCATION: (292)..(305)
<223> OTHER INFORMATION: n = GCT, TGT, GAT, GAG, TTT, GGT, CAT, ATT,
      AAG, CTT, ATG, AAT, CCT, CAG, CGT, TCT, ACT, GTT, TGG or TAT or
      a deletion
<220> FEATURE:
<221> NAME/KEY: misc_feature
<222> LOCATION: (306)..(306)
<223> OTHER INFORMATION: n = GCT, TGT, GAT, GAG, TTT, GGT, CAT, ATT,
      AAG, CTT, ATG, AAT, CCT, CAG, CGT, TCT, ACT, GTT, TGG or TAT
<220> FEATURE:
<221> NAME/KEY: misc_feature
<222> LOCATION: (307)..(307)
<223> OTHER INFORMATION: n = GCT, GAT, GAG, TTT, GGT, ATT, CTT, ATG,
      CCT, CAG, TCT, ACT, GTT or TAT

<400> SEQUENCE: 250
caggtgcaat tgcaagaaag tggtccgggc ctggtgaaaac cgagcgaaac cctgagcctg      60
acctgcaccg tttccggagg cagcattagc agctattatt ggagctggat tcgccagccg      120
cctgggaagg gtctcgagtg gattggctat atttattata gcggcagcac caactataat      180
ccgagcctga aaagccgggt gaccattagc gttgatactt cgaaaaacca gtttagcctg      240
aaactgagca gcgtgaccgg cggcggatacg gccgtgtatt attgcgcgcg tnnnnnnnnn      300
nnnnnnngat ntggggccaa ggcaccctgg tgacggttag ctcagc                      346

<210> SEQ ID NO 251
<211> LENGTH: 349
<212> TYPE: DNA
<213> ORGANISM: artificial sequence
<220> FEATURE:
<223> OTHER INFORMATION: synthetic construct; VH5
<220> FEATURE:
<221> NAME/KEY: misc_feature
<222> LOCATION: (314)..(314)
<223> OTHER INFORMATION: n = TTT, CAT, ATT, CTT, AAT, CCT, TCT, GTT,
      TGG or TAT
<220> FEATURE:
<221> NAME/KEY: misc_feature
<222> LOCATION: (295)..(304)
<223> OTHER INFORMATION: n = GCT, TGT, GAT, GAG, TTT, GGT, CAT, ATT,
      AAG, CTT, ATG, AAT, CCT, CAG, CGT, TCT, ACT, GTT, TGG or TAT or
      a deletion
<220> FEATURE:
<221> NAME/KEY: misc_feature
<222> LOCATION: (305)..(307)
<223> OTHER INFORMATION: n = GCT, TGT, GAT, GAG, TTT, GGT, CAT, ATT,
      AAG, CTT, ATG, AAT, CCT, CAG, CGT, TCT, ACT, GTT, TGG or TAT
<220> FEATURE:
<221> NAME/KEY: misc_feature
<222> LOCATION: (308)..(310)

```
<223> OTHER INFORMATION: n = GCT, GAT, GAG, TTT, GGT, ATT, CTT, ATG,
      CCT, CAG, TCT, ACT, GTT or TAT

<400> SEQUENCE: 251
caggtgcaat tggttcagag cggcgcggaa gtgaaaaaac cgggcgaaag cctgaaaatt    60
agctgcaaag gttccggata ttcctttacg agctattgga ttggctgggt gcgccagatg   120
cctgggaagg gtctcgagtg gatgggcatt atttatccgg gcgatagcga tacccgttat   180
tctccgagct ttcagggcca ggtgaccatt agcgcggata aaagcattag caccgcgtat   240
cttcaatgga gcagcctgaa agcgagcgat acgccatgt attattgcgc gcgtnnnnnn    300
nnnnnnnnnn gatntggggc caaggcaccc tggtgacggt tagctcagc              349

<210> SEQ ID NO 252
<211> LENGTH: 392
<212> TYPE: DNA
<213> ORGANISM: artificial sequence
<220> FEATURE:
<223> OTHER INFORMATION: synthetic construct; VH6
<220> FEATURE:
<221> NAME/KEY: misc_feature
<222> LOCATION: (355)..(357)
<223> OTHER INFORMATION: nnn = TTT, CAT, ATT, CTT, AAT, CCT, TCT, GTT,
      TGG or TAT
<220> FEATURE:
<221> NAME/KEY: misc_feature
<222> LOCATION: (304)..(345)
<223> OTHER INFORMATION: nnn = GCT, TGT, GAT, GAG, TTT, GGT, CAT, ATT,
      AAG, CTT, ATG, AAT, CCT, CAG, CGT, TCT, ACT, GTT, TGG or TAT or a
      deletion
<220> FEATURE:
<221> NAME/KEY: misc_feature
<222> LOCATION: (346)..(348)
<223> OTHER INFORMATION: nnn = GCT, TGT, GAT, GAG, TTT, GGT, CAT, ATT,
      AAG, CTT, ATG, AAT, CCT, CAG, CGT, TCT, ACT, GTT, TGG or TAT
<220> FEATURE:
<221> NAME/KEY: misc_feature
<222> LOCATION: (349)..(351)
<223> OTHER INFORMATION: nnn = GCT, GAT, GAG, TTT, GGT, ATT, CTT, ATG,
      CCT, CAG, TCT, ACT, GTT or TAT

<400> SEQUENCE: 252
caggtgcaat tgcaacagtc tggtccgggc ctggtgaaac cgagccaaac cctgagcctg    60
acctgtgcga tttccggaga tagcgtgagc agcaacagcg cggcgtggaa ctggattcgc   120
cagtctcctg gcgtggcct cgagtggctg ggccgtacct attatcgtag caatggtat    180 aacgattatg cggtgagcgt gaaaagccgg attaccatca acccggatac ttcgaaaaac   240
cagtttagcc tgcaactgaa cagcgtgacc ccggaagata cggccgtgta ttattgcgcg   300
cgtnnnnnnn nnnnnnnnnn nnnnnnnnnn nnnnnnnnnn nnnnnnnnnn ngatnnntgg   360
ggccaaggca ccctggtgac ggttagctca gc                                392

<210> SEQ ID NO 253
<211> LENGTH: 4151
<212> TYPE: DNA
<213> ORGANISM: artificial sequence
<220> FEATURE:
<223> OTHER INFORMATION: synthetic construct; pMORPH 18 Fab_5'

<400> SEQUENCE: 253
tctagataac gagggcaaaa aatgaaaaag acagctatcg cgattgcagt ggcactggct    60
ggtttcgcta ccgtagcgca ggccgatatc gtgctgaccc agagcccggc gaccctgagc   120
ctgtctccgg gcgaacgtgc gaccctgagc tgcagagcga ccagagcgt gagcagcagc   180 tatctggcgt ggtaccagca gaaaccaggt caagcaccgc gtctattaat ttatggcgcg   240
```

-continued

```
agcagccgtg caactggggt cccggcgcgt tttagcggct ctggatccgg cacggatttt     300
accctgacca ttagcagcct ggaacctgaa gactttgcgg tgtattattg ccagcagcat     360
tataccaccc cgccgacctt tggccagggt acgaaagttg aaattaaacg tacggtggct     420
gctccgagcg tgtttatttt tccgccgagc gatgaacaac tgaaaagcgg cacggcgagc     480
gtggtgtgcc tgctgaacaa cttttatccg cgtgaagcga agttcagtg gaaagtagac      540 aacgcgctgc aaagcggcaa cagccaggaa agcgtgaccg aacaggatag caaagatagc     600
acctattctc tgagcagcac cctgaccctg agcaaagcgg attatgaaaa acataaagtg     660
tatgcgtgcg aagtgaccca tcaaggtctg agcagcccgg tgactaaatc ttttaatcgt     720
ggcgaggcct gataagcatg cgtaggagaa aataaaatga acaaagcac tattgcactg       780 gcactcttac cgttgctctt cacccctgtt accaaagccg aagtgcaatt ggtgaaaagc     840
ggcggcggcc tggtgcaacc gggcggcagc ctgcgtctga gctgcgcggc ctccggatttt    900 acctttagca gctatgcgat gagctgggtg cgccaagccc ctgggaaggg tctcgagtgg     960
gtgagcgcga ttagcggtag cggcggcagc acctattatg cggatagcgt gaaaggccgt     1020
tttaccattt cacgtgataa ttcgaaaaac accctgtatc tgcaaatgaa cagcctgcgt     1080
gcggaagata cggccgtgta ttattgcgcg cgttggggcg gcgatggctt ttatgcgatg     1140
gattattggg gccaaggcac cctggtgacg gttagctcag cgtcgaccaa aggtccaagc     1200
gtgtttccgc tggctccgag cagcaaaagc accagcggcg gcacggctgc cctgggctgc     1260
ctggttaaag attatttccc ggaaccagtc accgtgagct ggaacagcgg ggcgctgacc     1320
agcggcgtgc atacctttcc ggcggtgctg caaagcagcg gcctgtatag cctgagcagc     1380
gttgtgaccg tgccgagcag cagcttaggc actcagacct atatttgcaa cgtgaaccat     1440
aaaccgagca acaccaaagt ggataaaaaa gtggaaccga aaagcgaatt cggggagggg      1500
agcgggagcg gtgattttga ttatgaaaag atggcaaacg ctaataaggg ggctatgacc      1560
gaaaatgccg atgaaaacgc gctacagtct gacgctaaag gcaaacttga ttctgtcgct     1620
actgattacg gtgctgctat cgatggtttc attggtgacg tttccggcct tgctaatggt     1680
aatggtgcta ctggtgattt tgctggctct aattcccaaa tggctcaagt cggtgacggt     1740
gataattcac ctttaatgaa taatttccgt caatatttac cttccctccc tcaatcggtt     1800
gaatgtcgcc cttttgtctt tggcgctggt aaaccatatg aatttctat tgattgtgac       1860 aaaataaact tattccgtgg tgtctttgcg tttcttttat atgttgccac ctttatgtat     1920
gtattttcta cgtttgctaa catactgcgt aataaggagt cttgataagc ttgacctgtg     1980
aagtgaaaaa tggcgcagat tgtgcgacat ttttttttgtc tgccgtttaa tgaaattgta     2040
aacgttaata ttttgttaaa attgcgtta aattttgtt aaatcagctc atttttttaac       2100 caataggccg aaatcggcaa aatcccttat aaatcaaaag aatagaccga gatagggttg     2160
agtgttgttc cagtttggaa caagagtcca ctattaaaga acgtggactc caacgtcaaa     2220
gggcgaaaaa ccgtctatca gggcgatggc ccactacgag aaccatcacc ctaatcaagt     2280 tttttgggt cgaggtgccg taaagcacta atcggaacc ctaaagggag ccccgattt         2340 agagcttgac ggggaaagcc ggcgaacgtg gcgagaaagg aagggaagaa agcgaaagga     2400
gcgggcgcta gggcgctggc aagtgtagcg gtcacgctgc gcgtaaccac cacacccgcc     2460
gcgcttaatg cgccgctaca gggcgcgtgc tagccatgtg agcaaaaggc cagcaaaagg     2520
ccaggaaccg taaaaaggcc gcgttgctgg cgttttttcca taggctccgc cccccctgacg    2580 agcatcacaa aaatcgacgc tcaagtcaga ggtggcgaaa cccgacagga ctataaagat     2640
```

```
accaggcgtt tccccctgga agctccctcg tgcgctctcc tgttccgacc ctgccgctta    2700
ccggatacct gtccgccttt ctcccttcgg gaagcgtggc gctttctcat agctcacgct    2760
gtaggtatct cagttcggtg taggtcgttc gctccaagct gggctgtgtg cacgaacccc    2820
ccgttcagtc cgaccgctgc gccttatccg gtaactatcg tcttgagtcc aacccggtaa    2880
gacacgactt atcgccactg gcagcagcca ctggtaacag gattagcaga gcgaggtatg    2940
taggcggtgc tacagagttc ttgaagtggt ggcctaacta cggctacact agaagaacag    3000
tatttggtat ctgcgctctg ctgtagccag ttaccttcgg aaaaagagtt ggtagctctt    3060
gatccggcaa acaaaccacc gctggtagcg gtggtttttt tgtttgcaag cagcagatta    3120
cgcgcagaaa aaaaggatct caagaagatc ctttgatctt ttctacgggg tctgacgctc    3180
agtggaacga aaactcacgt taagggattt tggtcagatc tagcaccagg cgtttaaggg    3240
caccaataac tgccttaaaa aaattacgcc ccgccctgcc actcatcgca gtactgttgt    3300
aattcattaa gcattctgcc gacatggaag ccatcacaaa cggcatgatg aacctgaatc    3360
gccagcggca tcagcacctt gtcgccttgc gtataatatt tgcccatagt gaaaacgggg    3420
gcgaagaagt tgtccatatt ggctacgttt aaatcaaaac tggtgaaact cacccaggga    3480
ttggctgaga cgaaaaacat attctcaata aacccttag ggaaataggc caggttttca    3540
ccgtaacacg ccacatcttg cgaatatatg tgtagaaact gccggaaatc gtcgtggtat    3600
tcactccaga gcgatgaaaa cgtttcagtt tgctcatgga aaacggtgta acaagggtga    3660
acactatccc atatcaccag ctcaccgtct tcattgcca tacggaactc cgggtgagca    3720
ttcatcaggc gggcaagaat gtgaataaag gccggataaa acttgtgctt attttttcttt    3780
acggtcttta aaaaggccgt aatatccagc tgaacggtct ggttataggt acattgagca    3840
actgactgaa atgcctcaaa atgttcttta cgatgccatt gggatatatc aacggtggta    3900
tatccagtga tttttttctc cattttagct tccttagctc ctgaaaatct cgataactca    3960
aaaaatacgc ccggtagtga tcttatttca ttatggtgaa agttggaacc tcacccgacg    4020
tctaatgtga gttagctcac tcattaggca ccccaggctt tacactttat gcttccggct    4080
cgtatgttgt gtggaattgt gagcggataa caatttcaca caggaaacag ctatgaccat    4140
gattacgaat t                                                         4151
```

<210> SEQ ID NO 254
<211> LENGTH: 638
<212> TYPE: PRT
<213> ORGANISM: artificial sequence
<220> FEATURE:
<223> OTHER INFORMATION: synthetic construct; pMORPH18_Fab protein

<400> SEQUENCE: 254

Met Lys Lys Thr Ala Ile Ala Ile Ala Val Ala Leu Ala Gly Phe Ala
1               5                   10                  15

Thr Val Ala Gln Ala Asp Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Ser Ser Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Val
65                  70                  75                  80

Pro Ala Arg Phe Ser Gly Ser Gly Ser Gly Thr Asp Phe Thr Leu Thr
                85                  90                  95

```
Ile Ser Ser Leu Glu Pro Glu Asp Phe Ala Val Tyr Tyr Cys Gln Gln
                100                 105                 110

His Tyr Thr Thr Pro Pro Thr Phe Gly Gln Gly Thr Lys Val Glu Ile
                115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Ala Met Lys Gln Ser
225                 230                 235                 240

Thr Ile Ala Leu Ala Leu Leu Pro Leu Leu Phe Thr Pro Val Thr Lys
                245                 250                 255

Ala Gln Val Gln Leu Val Glu Ser Gly Gly Gly Leu Val Gln Pro Gly
            260                 265                 270

Gly Ser Leu Arg Leu Ser Cys Ala Ala Ser Gly Phe Thr Phe Ser Ser
            275                 280                 285

Tyr Ala Met Ser Trp Val Arg Gln Ala Pro Gly Lys Gly Leu Glu Trp
            290                 295                 300

Val Ser Ala Ile Ser Gly Ser Gly Gly Ser Thr Tyr Tyr Ala Asp Ser
305                 310                 315                 320

Val Lys Gly Arg Phe Thr Ile Ser Arg Asp Asn Ser Lys Asn Thr Leu
                325                 330                 335

Tyr Leu Gln Met Asn Ser Leu Arg Ala Glu Asp Thr Ala Val Tyr Tyr
            340                 345                 350

Cys Ala Arg Trp Gly Gly Asp Gly Phe Tyr Ala Met Asp Tyr Trp Gly
            355                 360                 365

Gln Gly Thr Leu Val Thr Val Ser Ser Ala Ser Thr Lys Gly Pro Ser
            370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
            420                 425                 430

Val Leu Gln Ser Ser Gly Leu Tyr Ser Leu Ser Ser Val Val Thr Val
            435                 440                 445

Pro Ser Ser Ser Leu Gly Thr Gln Thr Tyr Ile Cys Asn Val Asn His
            450                 455                 460

Lys Pro Ser Asn Thr Lys Val Asp Lys Val Glu Pro Lys Ser Glu
465                 470                 475                 480

Phe Gly Gly Gly Ser Gly Ser Gly Asp Phe Asp Tyr Glu Lys Met Ala
                485                 490                 495

Asn Ala Asn Lys Gly Ala Met Thr Glu Asn Ala Asp Glu Asn Ala Leu
            500                 505                 510

Gln Ser Asp Ala Lys Gly Lys Leu Asp Ser Val Ala Thr Asp Tyr Gly
            515                 520                 525
```

Ala Ala Ile Asp Gly Phe Ile Gly Asp Val Ser Gly Leu Ala Asn Gly
    530                 535                 540

Asn Gly Ala Thr Gly Asp Phe Ala Gly Ser Asn Ser Gln Met Ala Gln
545                 550                 555                 560

Val Gly Asp Gly Asp Asn Ser Pro Leu Met Asn Asn Phe Arg Gln Tyr
                565                 570                 575

Leu Pro Ser Leu Pro Gln Ser Val Glu Cys Arg Pro Phe Val Phe Gly
            580                 585                 590

Ala Gly Lys Pro Tyr Glu Phe Ser Ile Asp Cys Asp Lys Ile Asn Leu
        595                 600                 605

Phe Arg Gly Val Phe Ala Phe Leu Leu Tyr Val Ala Thr Phe Met Tyr
    610                 615                 620

Val Phe Ser Thr Phe Ala Asn Ile Leu Arg Asn Lys Glu Ser
625                 630                 635

<210> SEQ ID NO 255
<211> LENGTH: 5020
<212> TYPE: DNA
<213> ORGANISM: artificial sequence
<220> FEATURE:
<223> OTHER INFORMATION: synthetic construct; pMORPH x9

<400> SEQUENCE: 255

```
atcgtgctga cccagccgcc ttcagtgagt ggcgcaccag gtcagcgtgt gaccatctcg      60
tgtagcggca gcagcagcaa cattggcagc aactatgtga gctggtacca gcagttgccc     120
gggacggcgc cgaaactgct gatttatgat aacaaccagc gtccctcagg cgtgccggat     180
cgttttagcg gatccaaaag cggcaccagc gcgagccttg cgattacggg cctgcaaagc     240
gaagacgaag cggattatta ttgccagagc tatgacatgc tcaggctgt gtttggcggc      300
ggcacgaagt taaccgttc ttggccagcc gaaagccgca ccgagtgtga cgctgtttcc      360
gccgagcagc gaagaattgc aggcgaacaa agcgaccctg gtgtgcctga ttagcgactt     420
ttatccggga gccgtgacag tggcctggaa ggcagatagc agcccgtca aggcgggagt      480
ggagaccacc acaccctcca aacaaagcaa caacaagtac gcggccagca gctatctgag     540
cctgacgcct gagcagtgga gtcccacag aagctacagc tgccaggtca cgcatgaggg      600
gagcaccgtg gaaaaaaccg ttgcgccgac tgaggcctga taagcatgcg taggagaaaa     660
taaaatgaaa caaagcacta ttgcactggc actcttaccg ttgctcttca ccctgttac      720
caaagcccag gtcaattga agaaagcgg cccggccctg gtgaaaccga cccaaaccct      780
gaccctgacc tgtaccttt ccggatttag cctgtccacg tctggcgttg gcgtgggctg      840
gattcgccag ccgcctggga aagccctcga gtggctggct ctgattgatt gggatgatga     900
taagtattat agcaccagcc tgaaaacgcg tctgaccatt agcaaagata cttcgaaaaa     960
tcaggtggtg ctgactatga ccaacatgga cccggtggat acggccacct attattgcgc    1020
gcgttctcct cgttatcgtg gtgcttttga ttattgggc caaggcaccc tggtgacggt    1080
tagctcagcg tcgaccaaag gtccaagcgt gtttccgctg ctccagca gcaaaagcac     1140
cagcggcggc acggctgccc tgggctgcct ggttaaagat tatttcccgg aaccagtcac    1200
cgtgagctgg aacagcgggg cgctgaccag cggcgtgcat accttccgg cggtgctgca    1260
aagcagcggc ctgtatagcc tgagcagcgt tgtgaccgtg ccgagcagca gcttaggcac    1320
tcagacctat atttgcaacg tgaaccataa accgagcaac accaaagtgg ataaaaaagt    1380
ggaaccgaaa agcgaattcg actataaaga tgacgatgac aaaggcgcgc cgtggagcca    1440
```

-continued

```
cccgcagttt gaaaaatgat aagcttgacc tgtgaagtga aaaatggcgc agattgtgcg    1500
acattttttt tgtctgccgt ttaattaaag gggggggggg gccggcctgg ggggggtgt    1560 acatgaaatt gtaaacgtta atattttgtt aaaattcgcg ttaaattttt gttaaatcag    1620 ctcattttt aaccaatagg ccgaaatcgg caaaatccct tataaatcaa agaatagac    1680 cgagataggg ttgagtgttg ttccagtttg gaacaagagt ccactattaa agaacgtgga    1740
ctccaacgtc aaagggcgaa aaaccgtcta tcagggcgat ggcccactac gagaaccatc    1800
accctaatca gtttttttgg ggtcgaggtg ccgtaaagca ctaaatcgga accctaaagg    1860
gagcccccga tttagagctt gacggggaaa gccggcgaac gtggcgagaa aggaagggaa    1920
gaaagcgaaa ggagcgggcg ctagggcgct ggcaagtgta gcggtcacgc tgcgcgtaac    1980
caccacaccc gccgcgctta atgcgccgct acagggcgcg tgctagacta gtgtttaaac    2040
cggaccgggg gggggcttaa gtgggctgca aaacaaaacg gcctcctgtc aggaagccgc    2100
ttttatcggg tagcctcact gcccgctttc cagtcgggaa acctgtcgtg ccagctgcat    2160
cagtgaatcg gccaacgcgc ggggagaggc ggtttgcgta ttgggagcca gggtggtttt    2220
tcttttcacc agtgagacgg gcaacagctg attgcccttc accgcctggc cctgagagag    2280
ttgcagcaag cggtccacgc tggtttgccc cagcaggcga aaatcctgtt tgatggtggt    2340
cagcggcggg atataacatg agctgtcctc ggtatcgtcg tatcccacta ccagatgtc    2400 cgcaccaacg cgcagcccgg actcggtaat ggcacgcatt gcgcccagcg ccatctgatc    2460
gttggcaacc agcatcgcag tgggaacgat gccctcattc agcatttgca tggtttgttg    2520
aaaaccggac atggcactcc agtcgccttc ccgttccgct atcggctgaa tttgattgcg    2580
agtgagatat ttatgccagc cagccagacg cagacgcgcc gagacagaac ttaatgggcc    2640
agctaacagc gcgatttgct ggtggcccaa tgcgaccaga tgctccacgc ccagtcgcgt    2700
accgtcctca tgggagaaaa taatactgtt gatgggtgtc tggtcagaga catcaagaaa    2760
taacgccgga acattagtgc aggcagcttc cacagcaata gcatcctggt catccagcgg    2820
atagttaata atcagcccac tgacacgttg cgcgagaaga ttgtgcaccg ccgctttaca    2880
ggcttcgacg ccgcttcgtt ctaccatcga cacgaccacg ctggcaccca gttgatcggc    2940
gcgagattta atcgccgcga caatttgcga cggcgcgtgc agggccagac tggaggtggc    3000
aacgccaatc agcaacgact gtttgcccgc cagttgttgt gccacgcggt taggaatgta    3060
attcagctcc gccatcgccg cttccacttt ttcccgcgtt ttcgcagaaa cgtggctggc    3120
ctggttcacc acgcgggaaa cggtctgata agagacaccg gcatactctg cgacatcgta    3180
taacgttact ggtttcacat tcaccaccct gaattgactc tcttccgggc gctatcatgc    3240
cataccgcga aaggttttgc gccattcgat gctagccatg tgagcaaaag gcagcaaaa    3300 ggccaggaac cgtaaaaagg ccgcgttgct ggcgtttttc cataggctcc gcccccctga    3360
cgagcatcac aaaaatcgac gctcaagtca gaggtggcga acccgacag gactataaag    3420 ataccaggcg tttccccctg gaagctccct cgtgcgctct cctgttccga ccctgccgct    3480
taccggatac ctgtccgcct ttctcccttc gggaagcgtg gcgctttctc atagctcacg    3540
ctgtaggtat ctcagttcgg tgtaggtcgt tcgctccaag ctgggctgtg tgcacgaacc    3600
ccccgttcag cccgaccgct gcgccttatc cggtaactat cgtcttgagt ccaacccggt    3660
aagacacgac ttatcgccac tggcagcagc cactggtaac aggattagca gagcgaggta    3720
tgtaggcggt gctacagagt tcttgaagtg gtggcctaac tacggctaca ctagaagaac    3780
agtatttggt atctgcgctc tgctgtagcc agttaccttc ggaaaaagag ttggtagctc    3840
```

```
ttgatccggc aaacaaacca ccgctggtag cggtggtttt tttgtttgca agcagcagat    3900
tacgcgcaga aaaaaggat  ctcaagaaga tcctttgatc ttttctacgg ggtctgacgc    3960
tcagtggaac gaaaactcac gttaagggat tttggtcaga tctagcacca ggcgtttaag    4020
ggcaccaata actgccttaa aaaaattacg ccccgccctg ccactcatcg cagtactgtt    4080
gtaattcatt aagcattctg ccgacatgga agccatcaca aacggcatga tgaacctgaa    4140
tcgccagcgg catcagcacc ttgtcgcctt gcgtataata tttgcccata gtgaaaacgg    4200
gggcgaagaa gttgtccata ttggctacgt ttaaatcaaa actggtgaaa ctcacccagg    4260
gattggctga gacgaaaaac atattctcaa taaacccttt agggaaatag gccaggtttt    4320
caccgtaaca cgccacatct tgcgaatata tgtgtagaaa ctgccggaaa tcgtcgtggt    4380
attcactcca gagcgatgaa aacgtttcag tttgctcatg gaaaacggtg taacaagggt    4440
gaacactatc ccatatcacc agctcaccgt ctttcattgc catacggaac tccgggtgag    4500
cattcatcag gcgggcaaga atgtgaataa aggccggata aaacttgtgc ttattttct     4560
ttacggtctt taaaaaggcc gtaatatcca gctgaacggt ctggttatag gtacattgag    4620
caactgactg aaatgcctca aaatgttctt tacgatgcca ttgggatata tcaacggtgg    4680
tatatccagt gatttttttc tccattttag cttccttagc tcctgaaaat ctcgataact    4740
caaaaaatac gcccggtagt gatcttattt cattatggtg aaagttggaa cctcacccga    4800
cgtctaatgt gagttagctc actcattagg cacccccagg ctttacacttt atgcttccgg    4860
ctcgtatgtt gtgtggaatt gtgagcggat aacaatttca cacaggaaac agctatgacc    4920
atgattacga atttctagat aacgagggca aaaatgaaa aagacagcta tcgcgattgc     4980
agtggcactg gctggtttcg ctaccgtagc gcaggccgat                           5020

<210> SEQ ID NO 256
<211> LENGTH: 7
<212> TYPE: PRT
<213> ORGANISM: artificial sequence
<220> FEATURE:
<223> OTHER INFORMATION: synthetic construct

<400> SEQUENCE: 256

Ala Glu Phe Arg His Asp Cys
1               5

<210> SEQ ID NO 257
<211> LENGTH: 7
<212> TYPE: PRT
<213> ORGANISM: artificial sequence
<220> FEATURE:
<223> OTHER INFORMATION: synthetic construct

<400> SEQUENCE: 257

Glu Phe Arg His Asp Ser Cys
1               5

<210> SEQ ID NO 258
<211> LENGTH: 7
<212> TYPE: PRT
<213> ORGANISM: artificial sequence
<220> FEATURE:
<223> OTHER INFORMATION: synthetic construct

<400> SEQUENCE: 258

Phe Arg His Asp Ser Gly Cys
1               5
```

```
<210> SEQ ID NO 259
<211> LENGTH: 7
<212> TYPE: PRT
<213> ORGANISM: artificial sequence
<220> FEATURE:
<223> OTHER INFORMATION: synthetic construct

<400> SEQUENCE: 259

Arg His Asp Ser Gly Tyr Cys
1               5

<210> SEQ ID NO 260
<211> LENGTH: 7
<212> TYPE: PRT
<213> ORGANISM: artificial sequence
<220> FEATURE:
<223> OTHER INFORMATION: synthetic construct

<400> SEQUENCE: 260

His Asp Ser Gly Tyr Glu Cys
1               5

<210> SEQ ID NO 261
<211> LENGTH: 7
<212> TYPE: PRT
<213> ORGANISM: artificial sequence
<220> FEATURE:
<223> OTHER INFORMATION: synthetic construct

<400> SEQUENCE: 261

Asp Ser Gly Tyr Glu Val Cys
1               5

<210> SEQ ID NO 262
<211> LENGTH: 7
<212> TYPE: PRT
<213> ORGANISM: artificial sequence
<220> FEATURE:
<223> OTHER INFORMATION: synthetic construct

<400> SEQUENCE: 262

Ser Gly Tyr Glu Val His Cys
1               5

<210> SEQ ID NO 263
<211> LENGTH: 7
<212> TYPE: PRT
<213> ORGANISM: artificial sequence
<220> FEATURE:
<223> OTHER INFORMATION: synthetic construct

<400> SEQUENCE: 263

Tyr Glu Val His His Gln Cys
1               5

<210> SEQ ID NO 264
<211> LENGTH: 7
<212> TYPE: PRT
<213> ORGANISM: artificial sequence
<220> FEATURE:
<223> OTHER INFORMATION: synthetic construct

<400> SEQUENCE: 264

Glu Val His His Gln Lys Cys
1               5

<210> SEQ ID NO 265
<211> LENGTH: 7
```

```
<212> TYPE: PRT
<213> ORGANISM: artificial sequence
<220> FEATURE:
<223> OTHER INFORMATION: synthetic construct

<400> SEQUENCE: 265

Val His His Gln Lys Leu Cys
1               5

<210> SEQ ID NO 266
<211> LENGTH: 7
<212> TYPE: PRT
<213> ORGANISM: artificial sequence
<220> FEATURE:
<223> OTHER INFORMATION: synthetic construct

<400> SEQUENCE: 266

His His Gln Lys Leu Val Cys
1               5

<210> SEQ ID NO 267
<211> LENGTH: 7
<212> TYPE: PRT
<213> ORGANISM: artificial sequence
<220> FEATURE:
<223> OTHER INFORMATION: synthetic construct

<400> SEQUENCE: 267

His Gln Lys Leu Val Phe Cys
1               5

<210> SEQ ID NO 268
<211> LENGTH: 7
<212> TYPE: PRT
<213> ORGANISM: artificial sequence
<220> FEATURE:
<223> OTHER INFORMATION: synthetic construct

<400> SEQUENCE: 268

Gln Lys Leu Val Phe Phe Cys
1               5

<210> SEQ ID NO 269
<211> LENGTH: 7
<212> TYPE: PRT
<213> ORGANISM: artificial sequence
<220> FEATURE:
<223> OTHER INFORMATION: synthetic construct

<400> SEQUENCE: 269

Lys Leu Val Phe Phe Ala Cys
1               5

<210> SEQ ID NO 270
<211> LENGTH: 7
<212> TYPE: PRT
<213> ORGANISM: artificial sequence
<220> FEATURE:
<223> OTHER INFORMATION: synthetic construct

<400> SEQUENCE: 270

Leu Val Phe Phe Ala Glu Cys
1               5

<210> SEQ ID NO 271
<211> LENGTH: 7
<212> TYPE: PRT
<213> ORGANISM: artificial sequence
```

<220> FEATURE:
<223> OTHER INFORMATION: synthetic construct

<400> SEQUENCE: 271

Val Phe Phe Ala Glu Asp Cys
1               5

<210> SEQ ID NO 272
<211> LENGTH: 7
<212> TYPE: PRT
<213> ORGANISM: artificial sequence
<220> FEATURE:
<223> OTHER INFORMATION: synthetic construct

<400> SEQUENCE: 272

Phe Phe Ala Glu Asp Val Cys
1               5

<210> SEQ ID NO 273
<211> LENGTH: 7
<212> TYPE: PRT
<213> ORGANISM: artificial sequence
<220> FEATURE:
<223> OTHER INFORMATION: synthetic construct

<400> SEQUENCE: 273

Phe Ala Glu Asp Val Gly Cys
1               5

<210> SEQ ID NO 274
<211> LENGTH: 7
<212> TYPE: PRT
<213> ORGANISM: artificial sequence
<220> FEATURE:
<223> OTHER INFORMATION: synthetic construct

<400> SEQUENCE: 274

Ala Glu Asp Val Gly Ser Cys
1               5

<210> SEQ ID NO 275
<211> LENGTH: 7
<212> TYPE: PRT
<213> ORGANISM: artificial sequence
<220> FEATURE:
<223> OTHER INFORMATION: synthetic construct

<400> SEQUENCE: 275

Glu Asp Val Gly Ser Asn Cys
1               5

<210> SEQ ID NO 276
<211> LENGTH: 7
<212> TYPE: PRT
<213> ORGANISM: artificial sequence
<220> FEATURE:
<223> OTHER INFORMATION: synthetic construct

<400> SEQUENCE: 276

Asp Val Gly Ser Asn Lys Cys
1               5

<210> SEQ ID NO 277
<211> LENGTH: 7
<212> TYPE: PRT
<213> ORGANISM: artificial sequence
<220> FEATURE:
<223> OTHER INFORMATION: synthetic construct

```
<400> SEQUENCE: 277

Val Gly Ser Asn Lys Gly Cys
1               5

<210> SEQ ID NO 278
<211> LENGTH: 7
<212> TYPE: PRT
<213> ORGANISM: artificial sequence
<220> FEATURE:
<223> OTHER INFORMATION: synthetic construct

<400> SEQUENCE: 278

Gly Ser Asn Lys Gly Ala Cys
1               5

<210> SEQ ID NO 279
<211> LENGTH: 7
<212> TYPE: PRT
<213> ORGANISM: artificial sequence
<220> FEATURE:
<223> OTHER INFORMATION: synthetic construct

<400> SEQUENCE: 279

Cys Ser Asn Lys Gly Ala Ile
1               5

<210> SEQ ID NO 280
<211> LENGTH: 7
<212> TYPE: PRT
<213> ORGANISM: artificial sequence
<220> FEATURE:
<223> OTHER INFORMATION: synthetic construct

<400> SEQUENCE: 280

Cys Asn Lys Gly Ala Ile Ile
1               5

<210> SEQ ID NO 281
<211> LENGTH: 7
<212> TYPE: PRT
<213> ORGANISM: artificial sequence
<220> FEATURE:
<223> OTHER INFORMATION: synthetic construct

<400> SEQUENCE: 281

Cys Lys Gly Ala Ile Ile Gly
1               5

<210> SEQ ID NO 282
<211> LENGTH: 7
<212> TYPE: PRT
<213> ORGANISM: artificial sequence
<220> FEATURE:
<223> OTHER INFORMATION: synthetic construct

<400> SEQUENCE: 282

Cys Gly Leu Met Val Gly Gly
1               5

<210> SEQ ID NO 283
<211> LENGTH: 7
<212> TYPE: PRT
<213> ORGANISM: artificial sequence
<220> FEATURE:
<223> OTHER INFORMATION: synthetic construct

<400> SEQUENCE: 283
```

```
Cys Met Val Gly Gly Val Val
1               5

<210> SEQ ID NO 284
<211> LENGTH: 7
<212> TYPE: PRT
<213> ORGANISM: artificial sequence
<220> FEATURE:
<223> OTHER INFORMATION: synthetic construct

<400> SEQUENCE: 284

Cys Gly Gly Val Val Ile Ala
1               5

<210> SEQ ID NO 285
<211> LENGTH: 6
<212> TYPE: PRT
<213> ORGANISM: artificial sequence
<220> FEATURE:
<223> OTHER INFORMATION: synthetic construct; peptide 1 A beta

<400> SEQUENCE: 285

Ala Glu Phe Arg His Asp
1               5

<210> SEQ ID NO 286
<211> LENGTH: 7
<212> TYPE: PRT
<213> ORGANISM: artificial sequence
<220> FEATURE:
<223> OTHER INFORMATION: synthetic construct; peptide 2 A beta

<400> SEQUENCE: 286

Glu Phe Arg His Asp Ser Gly
1               5

<210> SEQ ID NO 287
<211> LENGTH: 5
<212> TYPE: PRT
<213> ORGANISM: artificial sequence
<220> FEATURE:
<223> OTHER INFORMATION: synthetic construct; peptide 3 A beta

<400> SEQUENCE: 287

Glu Phe Arg His Asp
1               5

<210> SEQ ID NO 288
<211> LENGTH: 4
<212> TYPE: PRT
<213> ORGANISM: artificial sequence
<220> FEATURE:
<223> OTHER INFORMATION: synthetic construct; peptide 4 A beta

<400> SEQUENCE: 288

His Asp Ser Gly
1

<210> SEQ ID NO 289
<211> LENGTH: 5
<212> TYPE: PRT
<213> ORGANISM: artificial sequence
<220> FEATURE:
<223> OTHER INFORMATION: synthetic construct; peptide 5 A beta

<400> SEQUENCE: 289

His His Gln Lys Leu
```

<210> SEQ ID NO 290
<211> LENGTH: 6
<212> TYPE: PRT
<213> ORGANISM: artificial sequence
<220> FEATURE:
<223> OTHER INFORMATION: synthetic construct; peptide 6 A beta

<400> SEQUENCE: 290

Leu Val Phe Phe Ala Glu
1               5

<210> SEQ ID NO 291
<211> LENGTH: 6
<212> TYPE: PRT
<213> ORGANISM: artificial sequence
<220> FEATURE:
<223> OTHER INFORMATION: synthetic construct; peptide 7 A beta

<400> SEQUENCE: 291

Val Phe Phe Ala Glu Asp
1               5

<210> SEQ ID NO 292
<211> LENGTH: 4
<212> TYPE: PRT
<213> ORGANISM: artificial sequence
<220> FEATURE:
<223> OTHER INFORMATION: synthetic construct; peptide 8 A beta

<400> SEQUENCE: 292

Val Phe Phe Ala
1

<210> SEQ ID NO 293
<211> LENGTH: 6
<212> TYPE: PRT
<213> ORGANISM: artificial sequence
<220> FEATURE:
<223> OTHER INFORMATION: synthetic construct; peptide 9 A beta

<400> SEQUENCE: 293

Phe Phe Ala Glu Asp Val
1               5

<210> SEQ ID NO 294
<211> LENGTH: 360
<212> TYPE: DNA
<213> ORGANISM: artificial sequence
<220> FEATURE:
<223> OTHER INFORMATION: synthetic construct

<400> SEQUENCE: 294
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgttatttct gagaagtctc gttttatttta ttatgctgat    180 tctgttaagg gtcgttttac catttcacgt gataattcga aaaacaccct gtatctgcaa     240
atgaacagcc tgcgtgcgga agatacggcc gtgtattatt gcgcgcgtct tactcattat    300
gctcgttatt atcgttattt tgatgtttgg ggccaaggca ccctggtgac ggttagctca    360

<210> SEQ ID NO 295
<211> LENGTH: 120
<212> TYPE: PRT

<213> ORGANISM: artificial sequence
<220> FEATURE:
<223> OTHER INFORMATION: synthetic construct

<400> SEQUENCE: 295

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Val
        35                  40                  45

Ile Ser Glu Lys Ser Arg Phe Ile Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Thr His Tyr Ala Arg Tyr Tyr Arg Tyr Phe Asp Val Trp Gly Gln
            100                 105                 110

Gly Thr Leu Val Thr Val Ser Ser
        115                 120

<210> SEQ ID NO 296
<211> LENGTH: 360
<212> TYPE: DNA
<213> ORGANISM: artificial sequence
<220> FEATURE:
<223> OTHER INFORMATION: synthetic construct

<400> SEQUENCE: 296
caattggtgg aaagcggcgg cggcctggtg caaccgggcg gcagcctgcg tctgagctgc     60
gcggcctccg gatttacctt tagcagctat gcgatgagct gggtgcgcca agccctgggg   120
aagggtctcg agtgggtgag cgctatttct gagacttcta ttcgtaagta ttatgctgat   180
tctgttaagg gtcgttttac catttcacgt gataattcga aaacacccct gtatctgcaa   240
atgaacagcc tgcgtgcgga agatacggcc gtgtattatt gcgcgcgtct tactcattat   300
gctcgttatt atcgttattt tgatgtttgg ggccaaggca ccctggtgac ggttagctca   360

<210> SEQ ID NO 297
<211> LENGTH: 120
<212> TYPE: PRT
<213> ORGANISM: artificial sequence
<220> FEATURE:
<223> OTHER INFORMATION: synthetic construct

<400> SEQUENCE: 297

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Glu Thr Ser Ile Arg Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Thr His Tyr Ala Arg Tyr Tyr Arg Tyr Phe Asp Val Trp Gly Gln
            100                 105                 110

Gly Thr Leu Val Thr Val Ser Ser
        115                 120

<210> SEQ ID NO 298
<211> LENGTH: 360
<212> TYPE: DNA
<213> ORGANISM: artificial sequence
<220> FEATURE:
<223> OTHER INFORMATION: synthetic construct

<400> SEQUENCE: 298
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgttatttct cagactggtc gtaagattta ttatgctgat     180
tctgttaagg gtcgttttac catttcacgt gataattcga aaacaccct gtatctgcaa      240 atgaacagcc tgcgtgcgga agatacggcc gtgtattatt gcgcgcgtct tactcattat     300
gctcgttatt atcgttattt tgatgtttgg ggccaaggca ccctggtgac ggttagctca     360

<210> SEQ ID NO 299
<211> LENGTH: 120
<212> TYPE: PRT
<213> ORGANISM: artificial sequence
<220> FEATURE:
<223> OTHER INFORMATION: synthetic construct

<400> SEQUENCE: 299

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Val
        35                  40                  45

Ile Ser Gln Thr Gly Arg Lys Ile Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Thr His Tyr Ala Arg Tyr Tyr Arg Tyr Phe Asp Val Trp Gly Gln
            100                 105                 110

Gly Thr Leu Val Thr Val Ser Ser
        115                 120

<210> SEQ ID NO 300
<211> LENGTH: 360
<212> TYPE: DNA
<213> ORGANISM: artificial sequence
<220> FEATURE:
<223> OTHER INFORMATION: synthetic construct

<400> SEQUENCE: 300
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgttatttct cagactggtc gtaagattta ttatgctgat     180
tctgttaagg gtcgttttac catttcacgt gataattcga aaacaccct gtatctgcaa      240

```
atgaacagcc tgcgtgcgga agatacggcc gtgtattatt gcgcgcgtct tactcattat    300
gctcgttatt atcgttattt tgatgtttgg ggccaaggca ccctggtgac ggttagctca    360
```

<210> SEQ ID NO 301
<211> LENGTH: 120
<212> TYPE: PRT
<213> ORGANISM: artificial sequence
<220> FEATURE:
<223> OTHER INFORMATION: synthetic construct

<400> SEQUENCE: 301

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Val
        35                  40                  45

Ile Ser Gln Thr Gly Arg Lys Ile Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Thr His Tyr Ala Arg Tyr Tyr Arg Tyr Phe Asp Val Trp Gly Gln
            100                 105                 110

Gly Thr Leu Val Thr Val Ser Ser
        115                 120
```

<210> SEQ ID NO 302
<211> LENGTH: 360
<212> TYPE: DNA
<213> ORGANISM: artificial sequence
<220> FEATURE:
<223> OTHER INFORMATION: synthetic construct

<400> SEQUENCE: 302

```
caattggtgg aaagcggcgg cggcctggtg caaccgggcg gcagcctgcg tctgagctgc    60
gcggcctccg gatttacctt tagcagctat gcgatgagct gggtgcgcca gcccctgggg    120
aagggtctcg agtgggtgag cgttatttct gagactggta agaatattta ttatgctgat    180
tctgttaagg gtcgttttac catttcacgt gataattcga aaacacccct gtatctgcaa    240
atgaacagcc tgcgtgcgga agatacggcc gtgtattatt gcgcgcgtct tactcattat    300
gctcgttatt atcgttattt tgatgtttgg ggccaaggca ccctggtgac ggttagctca    360
```

<210> SEQ ID NO 303
<211> LENGTH: 120
<212> TYPE: PRT
<213> ORGANISM: artificial sequence
<220> FEATURE:
<223> OTHER INFORMATION: synthetic construct

<400> SEQUENCE: 303

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Val
        35                  40                  45

Ile Ser Glu Thr Gly Lys Asn Ile Tyr Tyr Ala Asp Ser Val Lys Gly
```

```
                50                  55                  60
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Leu Thr His Tyr Ala Arg Tyr Tyr Arg Tyr Phe Asp Val Trp Gly Gln
                100                 105                 110

Gly Thr Leu Val Thr Val Ser Ser
            115                 120

<210> SEQ ID NO 304
<211> LENGTH: 360
<212> TYPE: DNA
<213> ORGANISM: artificial sequence
<220> FEATURE:
<223> OTHER INFORMATION: synthetic construct

<400> SEQUENCE: 304
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgttatttct gagactggta agaatattta ttatgctgat     180
tctgttaagg gtcgttttac catttcacgt gataattcga aaacacccct gtatctgcaa     240
atgaacagcc tgcgtgcgga agatacggcc gtgtattatt gcgcgcgtct tactcattat     300
gctcgttatt atcgttattt tgatgtttgg ggccaaggca ccctggtgac ggttagctca     360

<210> SEQ ID NO 305
<211> LENGTH: 120
<212> TYPE: PRT
<213> ORGANISM: artificial sequence
<220> FEATURE:
<223> OTHER INFORMATION: synthetic construct

<400> SEQUENCE: 305

Gln Leu Val Glu Ser Gly Gly Gly Leu Val Gln Pro Gly Gly Ser Leu
  1               5                  10                  15

Arg Leu Ser Cys Ala Ala Ser Gly Phe Thr Phe Ser Ser Tyr Ala Met
             20                  25                  30

Ser Trp Val Arg Gln Ala Pro Gly Lys Gly Leu Glu Trp Val Ser Val
         35                  40                  45

Ile Ser Glu Thr Gly Lys Asn Ile Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Leu Thr His Tyr Ala Arg Tyr Tyr Arg Tyr Phe Asp Val Trp Gly Gln
                100                 105                 110

Gly Thr Leu Val Thr Val Ser Ser
            115                 120

<210> SEQ ID NO 306
<211> LENGTH: 360
<212> TYPE: DNA
<213> ORGANISM: artificial sequence
<220> FEATURE:
<223> OTHER INFORMATION: synthetic construct

<400> SEQUENCE: 306
```

```
caattggtgg aaagcggcgg cggcctggtg caaccgggcg gcagcctgcg tctgagctgc      60
gcggcctccg gatttacctt tagcagctat gcgatgagct gggtgcgcca agccctggg       120 aagggtctcg agtgggtgag cgctatttct gagtctggta agactaagta ttatgctgat      180
tctgttaagg gtcgttttac catttcacgt gataattcga aaacaccct gtatctgcaa       240 atgaacagcc tgcgtgcgga agatacggcc gtgtattatt gcgcgcgtct tactcattat      300
gctcgttatt atcgttattt tgatgtttgg ggccaaggca ccctggtgac ggttagctca      360
```

<210> SEQ ID NO 307
<211> LENGTH: 120
<212> TYPE: PRT
<213> ORGANISM: artificial sequence
<220> FEATURE:
<223> OTHER INFORMATION: synthetic construct

<400> SEQUENCE: 307

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Glu Ser Gly Lys Thr Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Thr His Tyr Ala Arg Tyr Tyr Arg Tyr Phe Asp Val Trp Gly Gln
            100                 105                 110

Gly Thr Leu Val Thr Val Ser Ser
        115                 120
```

<210> SEQ ID NO 308
<211> LENGTH: 372
<212> TYPE: DNA
<213> ORGANISM: artificial sequence
<220> FEATURE:
<223> OTHER INFORMATION: synthetic construct

<400> SEQUENCE: 308

```
caattggtgg aaagcggcgg cggcctggtg caaccgggcg gcagcctgcg tctgagctgc      60
gcggcctccg gatttacctt tagcagctat gcgatgagct gggtgcgcca agccctggg       120 aagggtctcg agtgggtgag cgctattaat ggtactggta tgaagaagta ttatgctgat      180
tctgttaagg gtcgttttac catttcacgt gataattcga aaacaccct gtatctgcaa       240 atgaacagcc tgcgtgcgga agatacggcc gtgtattatt gcgcgcgtgg taagggtaat      300
actcataagc cttatggtta tgttcgttat tttgatgttt ggggccaagg caccctggtg      360
acggttagct ca                                                         372
```

<210> SEQ ID NO 309
<211> LENGTH: 124
<212> TYPE: PRT
<213> ORGANISM: artificial sequence
<220> FEATURE:
<223> OTHER INFORMATION: synthetic construct

<400> SEQUENCE: 309

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Asn Gly Thr Gly Met Lys Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
        115                 120
```

<210> SEQ ID NO 310
<211> LENGTH: 372
<212> TYPE: DNA
<213> ORGANISM: artificial sequence
<220> FEATURE:
<223> OTHER INFORMATION: synthetic construct

<400> SEQUENCE: 310

```
caattggtgg aaagcggcgg cggcctggtg caaccgggcg gcagcctgcg tctgagctgc      60
gcggcctccg gatttacctt tagcagctat gcgatgagct gggtgcgcca agccctgggg     120
aagggtctcg agtgggtgag cgctattaat tataatggtg ctcgtattta ttatgctgat     180
tctgttaagg gtcgttttac catttcacgt gataattcga aaacacccct gtatctgcaa     240
atgaacagcc tgcgtgcgga agatacggcc gtgtattatt gcgcgcgtgg taagggtaat     300
actcataagc cttatggtta tgttcgttat tttgatgttt ggggccaagg caccctggtg     360
acggttagct ca                                                        372
```

<210> SEQ ID NO 311
<211> LENGTH: 124
<212> TYPE: PRT
<213> ORGANISM: artificial sequence
<220> FEATURE:
<223> OTHER INFORMATION: synthetic construct

<400> SEQUENCE: 311

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Asn Tyr Asn Gly Ala Arg Ile Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
```

<210> SEQ ID NO 312
<211> LENGTH: 372
<212> TYPE: DNA
<213> ORGANISM: artificial sequence
<220> FEATURE:
<223> OTHER INFORMATION: synthetic construct

<400> SEQUENCE: 312

```
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgctattaat gctgatggta atcgtaagta ttatgctgat     180
tctgttaagg gtcgttttac catttcacgt gataattcga aaacacccct gtatctgcaa     240
atgaacagcc tgcgtgcgga agatacggcc gtgtattatt gcgcgcgtgg taagggtaat     300
actcataagc cttatggtta tgttcgttat tttgatgttt ggggccaagg caccctggtg     360
acggttagct ca                                                        372
```

<210> SEQ ID NO 313
<211> LENGTH: 124
<212> TYPE: PRT
<213> ORGANISM: artificial sequence
<220> FEATURE:
<223> OTHER INFORMATION: synthetic construct

<400> SEQUENCE: 313

```
Gln Leu Val Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Asn Ala Asp Gly Asn Arg Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
        115                 120
```

<210> SEQ ID NO 314
<211> LENGTH: 372
<212> TYPE: DNA
<213> ORGANISM: artificial sequence
<220> FEATURE:
<223> OTHER INFORMATION: synthetic construct

<400> SEQUENCE: 314

```
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgctattaat gctgatggta atcgtaagta ttatgctgat     180
tctgttaagg gtcgttttac catttcacgt gataattcga aaacacccct gtatctgcaa     240
atgaacagcc tgcgtgcgga agatacggcc gtgtattatt gcgcgcgtgg taagggtaat     300
```

```
actcataagc cttatggtta tgttcgttat tttgatgttt ggggccaagg caccctggtg      360
acggttagct ca                                                         372
```

<210> SEQ ID NO 315
<211> LENGTH: 124
<212> TYPE: PRT
<213> ORGANISM: artificial sequence
<220> FEATURE:
<223> OTHER INFORMATION: synthetic construct

<400> SEQUENCE: 315

```
Gln Leu Val Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Asn Ala Asp Gly Asn Arg Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
        115                 120
```

<210> SEQ ID NO 316
<211> LENGTH: 372
<212> TYPE: DNA
<213> ORGANISM: artificial sequence
<220> FEATURE:
<223> OTHER INFORMATION: synthetic construct

<400> SEQUENCE: 316

```
caattggtgg aaagcggcgg cggcctggtg caaccgggcg gcagcctgcg tctgagctgc      60
gcggcctccg gatttacctt tagcagctat gcgatgagct gggtgcgcca gcccctggg       120 aagggtctcg agtgggtgag cgctattaat gctaatggtt ataagaagta ttatgctgat      180
tctgttaagg gtcgttttac catttcacgt gataattcga aaacacccct gtatctgcaa      240
atgaacagcc tgcgtgcgga agatacggcc gtgtattatt gcgcgcgtgg taagggtaat      300
actcataagc cttatggtta tgttcgttat tttgatgttt ggggccaagg caccctggtg      360
acggttagct ca                                                         372
```

<210> SEQ ID NO 317
<211> LENGTH: 124
<212> TYPE: PRT
<213> ORGANISM: artificial sequence
<220> FEATURE:
<223> OTHER INFORMATION: synthetic construct

<400> SEQUENCE: 317

```
Gln Leu Val Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45
```

Ile Asn Ala Asn Gly Tyr Lys Lys Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
        115                 120

<210> SEQ ID NO 318
<211> LENGTH: 372
<212> TYPE: DNA
<213> ORGANISM: artificial sequence
<220> FEATURE:
<223> OTHER INFORMATION: synthetic construct

<400> SEQUENCE: 318
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgctattaat gctaatggtt ataagaagta ttatgctgat     180
tctgttaagg gtcgttttac catttcacgt gataattcga aaacaccct gtatctgcaa      240 atgaacagcc tgcgtgcgga agatacggcc gtgtattatt gcgcgcgtgg taagggtaat     300
actcataagc cttatggtta tgttcgttat tttgatgttt ggggccaagg caccctggtg     360
acggttagct ca                                                        372

<210> SEQ ID NO 319
<211> LENGTH: 124
<212> TYPE: PRT
<213> ORGANISM: artificial sequence
<220> FEATURE:
<223> OTHER INFORMATION: synthetic construct

<400> SEQUENCE: 319

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Asn Ala Asn Gly Tyr Lys Lys Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Lys Gly Asn Thr His Lys Pro Tyr Gly Tyr Val Arg Tyr Phe Asp
            100                 105                 110

Val Trp Gly Gln Gly Thr Leu Val Thr Val Ser Ser
        115                 120

<210> SEQ ID NO 320
<211> LENGTH: 372
<212> TYPE: DNA
<213> ORGANISM: artificial sequence
<220> FEATURE:

<223> OTHER INFORMATION: synthetic construct

<400> SEQUENCE: 320

```
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgctattaat gctaatggtt ataagaagta ttatgctgat     180
tctgttaagg gtcgttttac catttcacgt gataattcga aaacaccct gtatctgcaa      240
atgaacagcc tgcgtgcgga agatacggcc gtgtattatt gcgcgcgtgg taagggtaat     300
actcataagc cttatggtta tgttcgttat tttgatgttt ggggccaagg caccctggtg     360
acggttagct ca                                                         372
```

<210> SEQ ID NO 321
<211> LENGTH: 124
<212> TYPE: PRT
<213> ORGANISM: artificial sequence
<220> FEATURE:
<223> OTHER INFORMATION: synthetic construct

<400> SEQUENCE: 321

```
Gln Leu Val Glu Ser Gly Gly Gly Leu Val Gln Pro Gly Gly Ser Leu
1               5                   10                  15
Arg Leu Ser Cys Ala Ala Ser Gly Phe Thr Phe Ser Ser Tyr Ala Met
            20                  25                  30
Ser Trp Val Arg Gln Ala Pro Gly Lys Gly Leu Glu Trp Val Ser Ala
        35                  40                  45
Ile Asn Ala Asn Gly Tyr Lys Lys Tyr Tyr Ala Asp Ser Val Lys Gly
    50                  55                  60
Arg Phe Thr Ile Ser Arg Asp Asn Ser Lys Asn Thr Leu Tyr Leu Gln
65                  70                  75                  80
Met Asn Ser Leu Arg Ala Glu Asp Thr Ala Val Tyr Tyr Cys Ala Arg
                85                  90                  95
Gly Lys Gly Asn Thr His Lys Pro Tyr Gly Tyr Val Arg Tyr Phe Asp
            100                 105                 110
Val Trp Gly Gln Gly Thr Leu Val Thr Val Ser Ser
        115                 120
```

<210> SEQ ID NO 322
<211> LENGTH: 366
<212> TYPE: DNA
<213> ORGANISM: artificial sequence
<220> FEATURE:
<223> OTHER INFORMATION: synthetic construct

<400> SEQUENCE: 322

```
caattggtgg aaagcggcgg cggcctggtg caaccgggcg gcagcctgcg tctgagctgc      60
gcggcctccg gatttacctt tagcagctat gcgatgagct gggtgcgcca agcccctggg     120
aagggtctcg agtgggtgag cgctatttct cgttctggtt ctaatattta ttatgctgat     180
tctgttaagg gtcgttttac catttcacgt gataattcga aaacaccct gtatctgcaa      240
atgaacagcc tgcgtgcgga agatacggcc gtgtattatt gcgcgcgtct tctttctcgt     300
ggttataatg gttattatca taagtttgat gtttggggcc aaggcaccct ggtgacggtt     360
agctca                                                                366
```

<210> SEQ ID NO 323
<211> LENGTH: 122
<212> TYPE: PRT

```
<213> ORGANISM: artificial sequence
<220> FEATURE:
<223> OTHER INFORMATION: synthetic construct

<400> SEQUENCE: 323

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Arg Ser Gly Ser Asn Ile Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Leu Ser Arg Gly Tyr Asn Gly Tyr Tyr His Lys Phe Asp Val Trp
            100                 105                 110

Gly Gln Gly Thr Leu Val Thr Val Ser Ser
        115                 120

<210> SEQ ID NO 324
<211> LENGTH: 330
<212> TYPE: DNA
<213> ORGANISM: artificial sequence
<220> FEATURE:
<223> OTHER INFORMATION: synthetic construct

<400> SEQUENCE: 324
gatatcgtgc tgacccagag cccggcgacc ctgagcctgt ctccgggcga acgtgcgacc      60
ctgagctgca gcgagccg gcgtattcat gtttattatc tggcgtggta ccagcagaaa     120
ccaggtcaag caccgcgtct attaatttat ggcgcgagca gccgtgcaac tggggtcccg     180
gcgcgtttta gcggctctgg atccggcacg gattttaccc tgaccattag cagcctggaa     240
cctgaagact ttgcgactta ttattgccag cagacttatg attatcctcc tacctttggc     300
cagggtacga agttgaaat taaacgtacg                                        330

<210> SEQ ID NO 325
<211> LENGTH: 110
<212> TYPE: PRT
<213> ORGANISM: artificial sequence
<220> FEATURE:
<223> OTHER INFORMATION: synthetic construct

<400> SEQUENCE: 325

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Arg Arg Ile His Val Tyr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Thr Tyr Asp Tyr Pro
                85                  90                  95
```

Pro Thr Phe Gly Gln Gly Thr Lys Val Glu Ile Lys Arg Thr
            100                 105                 110

<210> SEQ ID NO 326
<211> LENGTH: 330
<212> TYPE: DNA
<213> ORGANISM: artificial sequence
<220> FEATURE:
<223> OTHER INFORMATION: synthetic construct

<400> SEQUENCE: 326
gatatcgtgc tgacccagag cccggcgacc ctgagcctgt ctccgggcga acgtgcgacc      60
ctgagctgca gagcgagccg gcgtattcat gtttattatc tggcgtggta ccagcagaaa     120
ccaggtcaag caccgcgtct attaatttat ggcgcgagca gccgtgcaac tggggtcccg     180
gcgcgtttta gcggctctgg atccggcacg gattttaccc tgaccattag cagcctggaa     240
cctgaagact ttgcgactta ttattgccag cagacttatg attatcctcc tacctttggc     300
cagggtacga agttgaaat taaacgtacg                                       330

<210> SEQ ID NO 327
<211> LENGTH: 110
<212> TYPE: PRT
<213> ORGANISM: artificial sequence
<220> FEATURE:
<223> OTHER INFORMATION: synthetic construct

<400> SEQUENCE: 327

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Arg Arg Ile His Val Tyr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Thr Tyr Asp Tyr Pro
                85                  90                  95

Pro Thr Phe Gly Gln Gly Thr Lys Val Glu Ile Lys Arg Thr
            100                 105                 110

<210> SEQ ID NO 328
<211> LENGTH: 330
<212> TYPE: DNA
<213> ORGANISM: artificial sequence
<220> FEATURE:
<223> OTHER INFORMATION: synthetic construct

<400> SEQUENCE: 328
gatatcgtgc tgacccagag cccggcgacc ctgagcctgt ctccgggcga acgtgcgacc      60
ctgagctgca gagcgagcca gcgtcttggt cgtctttatc tggcgtggta ccagcagaaa     120
ccaggtcaag caccgcgtct attaatttat ggcgcgagca gccgtgcaac tggggtcccg     180
gcgcgtttta gcggctctgg atccggcacg gattttaccc tgaccattag cagcctggaa     240
cctgaagact ttgcgactta ttattgccag cagacttatg attatcctcc tacctttggc     300
cagggtacga agttgaaat taaacgtacg                                       330

<210> SEQ ID NO 329

```
<211> LENGTH: 110
<212> TYPE: PRT
<213> ORGANISM: artificial sequence
<220> FEATURE:
<223> OTHER INFORMATION: synthetic construct

<400> SEQUENCE: 329

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Leu Gly Arg Leu
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Thr Tyr Asp Tyr Pro
                85                  90                  95

Pro Thr Phe Gly Gln Gly Thr Lys Val Glu Ile Lys Arg Thr
            100                 105                 110

<210> SEQ ID NO 330
<211> LENGTH: 330
<212> TYPE: DNA
<213> ORGANISM: artificial sequence
<220> FEATURE:
<223> OTHER INFORMATION: synthetic construct

<400> SEQUENCE: 330
gatatcgtgc tgacccagag cccggcgacc ctgagcctgt ctccgggcga acgtgcgacc    60
ctgagctgca gcgagccg gcgtattcat gtttattatc tggcgtggta ccagcagaaa    120
ccaggtcaag caccgcgtct attaatttat ggcgcgagca gccgtgcaac tggggtcccg    180
gcgcgtttta gcggctctgg atccggcacg gattttaccc tgaccattag cagcctggaa    240
cctgaagact ttgcgactta ttattgccag cagacttatg attatcctcc tacctttggc    300
cagggtacga aagttgaaat taaacgtacg                                    330

<210> SEQ ID NO 331
<211> LENGTH: 110
<212> TYPE: PRT
<213> ORGANISM: artificial sequence
<220> FEATURE:
<223> OTHER INFORMATION: synthetic construct

<400> SEQUENCE: 331

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Arg Arg Ile His Val Tyr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Thr Tyr Asp Tyr Pro
                85                  90                  95

Pro Thr Phe Gly Gln Gly Thr Lys Val Glu Ile Lys Arg Thr
```

<210> SEQ ID NO 332
<211> LENGTH: 330
<212> TYPE: DNA
<213> ORGANISM: artificial sequence
<220> FEATURE:
<223> OTHER INFORMATION: synthetic construct

<400> SEQUENCE: 332

```
gatatcgtgc tgacccagag cccggcgacc ctgagcctgt ctccgggcga acgtgcgacc    60
ctgagctgca gcgagccg gcgtattcat gtttattatc tggcgtggta ccagcagaaa    120
ccaggtcaag caccgcgtct attaatttat ggcgcgagca gccgtgcaac tggggtcccg    180
gcgcgtttta gcggctctgg atccggcacg gattttaccc tgaccattag cagcctggaa    240
cctgaagact ttgcgactta ttattgccag cagacttatg attatcctcc tacctttggc    300
cagggtacga agttgaaat taaacgtacg                                       330
```

<210> SEQ ID NO 333
<211> LENGTH: 110
<212> TYPE: PRT
<213> ORGANISM: artificial sequence
<220> FEATURE:
<223> OTHER INFORMATION: synthetic construct

<400> SEQUENCE: 333

```
Asp Ile Val Leu Thr Gln Ser Pro Ala Thr Leu Ser Leu Ser Pro Gly
1               5                   10                  15
Glu Arg Ala Thr Leu Ser Cys Arg Ala Ser Arg Arg Ile His Val Tyr
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Val Pro Ala Arg Phe Ser
        50                  55                  60
Gly Ser Gly Ser Gly Thr Asp Phe Thr Leu Thr Ile Ser Ser Leu Glu
65                  70                  75                  80
Pro Glu Asp Phe Ala Thr Tyr Tyr Cys Gln Gln Thr Tyr Asp Tyr Pro
                85                  90                  95
Pro Thr Phe Gly Gln Gly Thr Lys Val Glu Ile Lys Arg Thr
            100                 105                 110
```

<210> SEQ ID NO 334
<211> LENGTH: 330
<212> TYPE: DNA
<213> ORGANISM: artificial sequence
<220> FEATURE:
<223> OTHER INFORMATION: synthetic construct

<400> SEQUENCE: 334

```
gatatcgtgc tgacccagag cccggcgacc ctgagcctgt ctccgggcga acgtgcgacc    60
ctgagctgca gcgagccca gcgtcttggt cgtctttatc tggcgtggta ccagcagaaa    120
ccaggtcaag caccgcgtct attaatttat ggcgcgagca gccgtgcaac tggggtcccg    180
gcgcgtttta gcggctctgg atccggcacg gattttaccc tgaccattag cagcctggaa    240
cctgaagact ttgcgactta ttattgccag cagacttatg attatcctcc tacctttggc    300
cagggtacga agttgaaat taaacgtacg                                       330
```

<210> SEQ ID NO 335
<211> LENGTH: 110

```
<212> TYPE: PRT
<213> ORGANISM: artificial sequence
<220> FEATURE:
<223> OTHER INFORMATION: synthetic construct

<400> SEQUENCE: 335

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Leu Gly Arg Leu
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Thr Tyr Asp Tyr Pro
                85                  90                  95

Pro Thr Phe Gly Gln Gly Thr Lys Val Glu Ile Lys Arg Thr
            100                 105                 110

<210> SEQ ID NO 336
<211> LENGTH: 330
<212> TYPE: DNA
<213> ORGANISM: artificial sequence
<220> FEATURE:
<223> OTHER INFORMATION: synthetic construct

<400> SEQUENCE: 336
gatatcgtgc tgacccagag cccggcgacc ctgagcctgt ctccgggcga acgtgcgacc      60
ctgagctgca gagcgagcca gtttattcag cgtttttatc tggcgtggta ccagcagaaa    120
ccaggtcaag caccgcgtct attaatttat ggcgcgagca gccgtgcaac tggggtcccg    180
gcgcgtttta gcggctctgg atccggcacg gattttaccc tgaccattag cagcctggaa    240
cctgaagact ttgcggttta ttattgccag cagacttata attatcctcc tacctttggc    300
cagggtacga aagttgaaat taaacgtacg                                      330

<210> SEQ ID NO 337
<211> LENGTH: 110
<212> TYPE: PRT
<213> ORGANISM: artificial sequence
<220> FEATURE:
<223> OTHER INFORMATION: synthetic construct

<400> SEQUENCE: 337

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Gln Arg Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Thr Tyr Asn Tyr Pro
                85                  90                  95

Pro Thr Phe Gly Gln Gly Thr Lys Val Glu Ile Lys Arg Thr
            100                 105                 110
```

<210> SEQ ID NO 338
<211> LENGTH: 330
<212> TYPE: DNA
<213> ORGANISM: artificial sequence
<220> FEATURE:
<223> OTHER INFORMATION: synthetic construct

<400> SEQUENCE: 338

```
gatatcgtgc tgacccagag cccggcgacc ctgagcctgt ctccgggcga acgtgcgacc      60
ctgagctgca gagcgagcca gtatgttgat cgtacttatc tggcgtggta ccagcagaaa     120
ccaggtcaag caccgcgtct attaatttat ggcgcgagca gccgtgcaac tggggtcccg     180
gcgcgtttta gcggctctgg atccggcacg gattttaccc tgaccattag cagcctggaa     240
cctgaagact ttgcgactta ttattgccag cagatttatt cttttcctca tacctttggc     300
cagggtacga agttgaaat  taaacgtacg                                       330
```

<210> SEQ ID NO 339
<211> LENGTH: 110
<212> TYPE: PRT
<213> ORGANISM: artificial sequence
<220> FEATURE:
<223> OTHER INFORMATION: synthetic construct

<400> SEQUENCE: 339

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Tyr Val Asp Arg Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Ile Tyr Ser Phe Pro
                85                  90                  95

His Thr Phe Gly Gln Gly Thr Lys Val Glu Ile Lys Arg Thr
            100                 105                 110
```

<210> SEQ ID NO 340
<211> LENGTH: 330
<212> TYPE: DNA
<213> ORGANISM: artificial sequence
<220> FEATURE:
<223> OTHER INFORMATION: synthetic construct

<400> SEQUENCE: 340

```
gatatcgtgc tgacccagag cccggcgacc ctgagcctgt ctccgggcga acgtgcgacc      60
ctgagctgca gagcgagcca gcgtttttt  tataagtatc tggcgtggta ccagcagaaa     120
ccaggtcaag caccgcgtct attaatttct ggttcttcta accgtgcaac tggggtcccg     180
gcgcgtttta gcggctctgg atccggcacg gattttaccc tgaccattag cagcctggaa     240
cctgaagact ttgcggttta ttattgcctt cagctttata atattcctaa tacctttggc     300
cagggtacga agttgaaat  taaacgtacg                                       330
```

<210> SEQ ID NO 341
<211> LENGTH: 110
<212> TYPE: PRT

<213> ORGANISM: artificial sequence
<220> FEATURE:
<223> OTHER INFORMATION: synthetic construct

<400> SEQUENCE: 341

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Phe Phe Tyr Lys
            20                  25                  30

Tyr Leu Ala Trp Tyr Gln Gln Lys Pro Gly Gln Ala Pro Arg Leu Leu
        35                  40                  45

Ile Ser Gly Ser Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Leu Gln Leu Tyr Asn Ile Pro
                85                  90                  95

Asn Thr Phe Gly Gln Gly Thr Lys Val Glu Ile Lys Arg Thr
            100                 105                 110

<210> SEQ ID NO 342
<211> LENGTH: 330
<212> TYPE: DNA
<213> ORGANISM: artificial sequence
<220> FEATURE:
<223> OTHER INFORMATION: synthetic construct

<400> SEQUENCE: 342
gatatcgtgc tgacccagag cccggcgacc ctgagcctgt ctccgggcga acgtgcgacc      60
ctgagctgca gagcgagcca gtatgttgat cgtacttatc tggcgtggta ccagcagaaa     120
ccaggtcaag caccgcgtct attaatttat ggcgcgagca gccgtgcaac tggggtcccg     180
gcgcgtttta gcggctctgg atccggcacg gattttaccc tgaccattag cagcctggaa     240
cctgaagact ttgcgactta ttattgccag cagatttatt cttttcctca tacctttggc     300
cagggtacga agttgaaat taaacgtacg                                       330

<210> SEQ ID NO 343
<211> LENGTH: 110
<212> TYPE: PRT
<213> ORGANISM: artificial sequence
<220> FEATURE:
<223> OTHER INFORMATION: synthetic construct

<400> SEQUENCE: 343

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Tyr Val Asp Arg Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Ile Tyr Ser Phe Pro
                85                  90                  95

His Thr Phe Gly Gln Gly Thr Lys Val Glu Ile Lys Arg Thr
            100                 105                 110

<210> SEQ ID NO 344
<211> LENGTH: 330
<212> TYPE: DNA
<213> ORGANISM: artificial sequence
<220> FEATURE:
<223> OTHER INFORMATION: synthetic construct

<400> SEQUENCE: 344

```
gatatcgtgc tgacccagag cccggcgacc ctgagcctgt ctccgggcga acgtgcgacc    60
ctgagctgca gagcgagcca gtatgttttt cgtcgttatc tggcgtggta ccagcagaaa   120
ccaggtcaag caccgcgtct attaatttct ggttcttcta accgtgcaac tggggtcccg   180
gcgcgtttta gcggctctgg atccggcacg gattttaccc tgaccattag cagcctggaa   240
cctgaagact ttgcggttta ttattgcctt cagctttata atattcctaa tacctttggc   300
cagggtacga agttgaaat taaacgtacg                                     330
```

<210> SEQ ID NO 345
<211> LENGTH: 110
<212> TYPE: PRT
<213> ORGANISM: artificial sequence
<220> FEATURE:
<223> OTHER INFORMATION: synthetic construct

<400> SEQUENCE: 345

```
Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Tyr Val Phe Arg Arg
            20                  25                  30
Tyr Leu Ala Trp Tyr Gln Gln Lys Pro Gly Gln Ala Pro Arg Leu Leu
        35                  40                  45
Ile Ser Gly Ser Ser Asn Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Leu Gln Leu Tyr Asn Ile Pro
                85                  90                  95
Asn Thr Phe Gly Gln Gly Thr Lys Val Glu Ile Lys Arg Thr
            100                 105                 110
```

<210> SEQ ID NO 346
<211> LENGTH: 330
<212> TYPE: DNA
<213> ORGANISM: artificial sequence
<220> FEATURE:
<223> OTHER INFORMATION: synthetic construct

<400> SEQUENCE: 346

```
gatatcgtgc tgacccagag cccggcgacc ctgagcctgt ctccgggcga acgtgcgacc    60
ctgagctgca gagcgagcca gtatgttgat cgtacttatc tggcgtggta ccagcagaaa   120
ccaggtcaag caccgcgtct attaatttat ggcgcgagca gccgtgcaac tggggtcccg   180
gcgcgtttta gcggctctgg atccggcacg gattttaccc tgaccattag cagcctggaa   240
cctgaagact ttgcgactta ttattgccag cagatttatt cttttcctca tacctttggc   300
cagggtacga agttgaaat taaacgtacg                                     330
```

<210> SEQ ID NO 347
<211> LENGTH: 110
<212> TYPE: PRT
<213> ORGANISM: artificial sequence

```
<220> FEATURE:
<223> OTHER INFORMATION: synthetic construct

<400> SEQUENCE: 347

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Tyr Val Asp Arg Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Ile Tyr Ser Phe Pro
                85                  90                  95

His Thr Phe Gly Gln Gly Thr Lys Val Glu Ile Lys Arg Thr
            100                 105                 110

<210> SEQ ID NO 348
<211> LENGTH: 330
<212> TYPE: DNA
<213> ORGANISM: artificial sequence
<220> FEATURE:
<223> OTHER INFORMATION: synthetic construct

<400> SEQUENCE: 348
gatatcgtgc tgacccagag cccggcgacc ctgagcctgt ctccgggcga acgtgcgacc      60
ctgagctgca gcgagcca gcgtctttct cctcgttatc tggcgtggta ccagcagaaa      120
ccaggtcaag caccgcgtct attaatttat ggcgcgagca gccgtgcaac tggggtcccg     180
gcgcgtttta gcggctctgg atccggcacg gatttaccc tgaccattag cagcctggaa      240
cctgaagact ttgcgactta ttattgcctt cagatttata atatgcctat tacctttggc     300
cagggtacga agttgaaat taaacgtacg                                        330

<210> SEQ ID NO 349
<211> LENGTH: 110
<212> TYPE: PRT
<213> ORGANISM: artificial sequence
<220> FEATURE:
<223> OTHER INFORMATION: synthetic construct

<400> SEQUENCE: 349

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Leu Ser Pro Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr
            100                 105                 110
```

<210> SEQ ID NO 350
<211> LENGTH: 330
<212> TYPE: DNA
<213> ORGANISM: artificial sequence
<220> FEATURE:
<223> OTHER INFORMATION: synthetic construct

<400> SEQUENCE: 350

```
gatatcgtgc tgacccagag cccggcgacc ctgagcctgt ctccgggcga acgtgcgacc      60
ctgagctgca gagcgagcca gtatgttttt cgtcgttatc tggcgtggta ccagcagaaa     120
ccaggtcaag caccgcgtct attaatttct ggttcttcta accgtgcaac tggggtcccg     180
gcgcgtttta gcggctctgg atccggcacg gattttaccc tgaccattag cagcctggaa     240
cctgaagact ttgcggttta ttattgcctt cagctttata atattcctaa tacctttggc     300
cagggtacga agttgaaat  taaacgtacg                                      330
```

<210> SEQ ID NO 351
<211> LENGTH: 110
<212> TYPE: PRT
<213> ORGANISM: artificial sequence
<220> FEATURE:
<223> OTHER INFORMATION: synthetic construct

<400> SEQUENCE: 351

Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Tyr Val Phe Arg Arg
            20                  25                  30
Tyr Leu Ala Trp Tyr Gln Gln Lys Pro Gly Gln Ala Pro Arg Leu Leu
        35                  40                  45
Ile Ser Gly Ser Ser Asn Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Leu Gln Leu Tyr Asn Ile Pro
                85                  90                  95
Asn Thr Phe Gly Gln Gly Thr Lys Val Glu Ile Lys Arg Thr
            100                 105                 110

<210> SEQ ID NO 352
<211> LENGTH: 330
<212> TYPE: DNA
<213> ORGANISM: artificial sequence
<220> FEATURE:
<223> OTHER INFORMATION: synthetic construct

<400> SEQUENCE: 352

```
gatatcgtgc tgacccagag cccggcgacc ctgagcctgt ctccgggcga acgtgcgacc      60
ctgagctgca gagcgagcca gcgtgtttct ggtcgttatc tggcgtggta ccagcagaaa     120
ccaggtcaag caccgcgtct attaatttat ggcgcgagca gccgtgcaac tggggtcccg     180
gcgcgtttta gcggctctgg atccggcacg gattttaccc tgaccattag cagcctggaa     240
cctgaagact ttgcgactta ttattgccag cagctttctt cttatcctcc tacctttggc     300
cagggtacga agttgaaat  taaacgtacg                                      330
```

<210> SEQ ID NO 353
<211> LENGTH: 110
<212> TYPE: PRT
<213> ORGANISM: artificial sequence
<220> FEATURE:

<223> OTHER INFORMATION: synthetic construct

<400> SEQUENCE: 353

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Val Ser Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Leu Ser Ser Tyr Pro
                85                  90                  95

Pro Thr Phe Gly Gln Gly Thr Lys Val Glu Ile Lys Arg Thr
            100                 105                 110

<210> SEQ ID NO 354
<211> LENGTH: 39
<212> TYPE: DNA
<213> ORGANISM: artificial sequence
<220> FEATURE:
<223> OTHER INFORMATION: synthetic construct

<400> SEQUENCE: 354
cttactcatt atgctcgtta ttatcgttat tttgatgtt                                  39

<210> SEQ ID NO 355
<211> LENGTH: 13
<212> TYPE: PRT
<213> ORGANISM: artificial sequence
<220> FEATURE:
<223> OTHER INFORMATION: synthetic construct

<400> SEQUENCE: 355

Leu Thr His Tyr Ala Arg Tyr Tyr Arg Tyr Phe Asp Val
1               5                   10

<210> SEQ ID NO 356
<211> LENGTH: 39
<212> TYPE: DNA
<213> ORGANISM: artificial sequence
<220> FEATURE:
<223> OTHER INFORMATION: synthetic construct

<400> SEQUENCE: 356
cttactcatt atgctcgtta ttatcgttat tttgatgtt                                  39

<210> SEQ ID NO 357
<211> LENGTH: 13
<212> TYPE: PRT
<213> ORGANISM: artificial sequence
<220> FEATURE:
<223> OTHER INFORMATION: synthetic construct

<400> SEQUENCE: 357

Leu Thr His Tyr Ala Arg Tyr Tyr Arg Tyr Phe Asp Val
1               5                   10

<210> SEQ ID NO 358
<211> LENGTH: 39
<212> TYPE: DNA
<213> ORGANISM: artificial sequence

```
<220> FEATURE:
<223> OTHER INFORMATION: synthetic construct

<400> SEQUENCE: 358
cttactcatt atgctcgtta ttatcgttat tttgatgtt                              39

<210> SEQ ID NO 359
<211> LENGTH: 13
<212> TYPE: PRT
<213> ORGANISM: artificial sequence
<220> FEATURE:
<223> OTHER INFORMATION: synthetic construct

<400> SEQUENCE: 359

Leu Thr His Tyr Ala Arg Tyr Tyr Arg Tyr Phe Asp Val
1               5                   10

<210> SEQ ID NO 360
<211> LENGTH: 39
<212> TYPE: DNA
<213> ORGANISM: artificial sequence
<220> FEATURE:
<223> OTHER INFORMATION: synthetic construct

<400> SEQUENCE: 360
cttactcatt atgctcgtta ttatcgttat tttgatgtt                              39

<210> SEQ ID NO 361
<211> LENGTH: 13
<212> TYPE: PRT
<213> ORGANISM: artificial sequence
<220> FEATURE:
<223> OTHER INFORMATION: synthetic construct

<400> SEQUENCE: 361

Leu Thr His Tyr Ala Arg Tyr Tyr Arg Tyr Phe Asp Val
1               5                   10

<210> SEQ ID NO 362
<211> LENGTH: 39
<212> TYPE: DNA
<213> ORGANISM: artificial sequence
<220> FEATURE:
<223> OTHER INFORMATION: synthetic construct

<400> SEQUENCE: 362
cttactcatt atgctcgtta ttatcgttat tttgatgtt                              39

<210> SEQ ID NO 363
<211> LENGTH: 13
<212> TYPE: PRT
<213> ORGANISM: artificial sequence
<220> FEATURE:
<223> OTHER INFORMATION: synthetic construct

<400> SEQUENCE: 363

Leu Thr His Tyr Ala Arg Tyr Tyr Arg Tyr Phe Asp Val
1               5                   10

<210> SEQ ID NO 364
<211> LENGTH: 39
<212> TYPE: DNA
<213> ORGANISM: artificial sequence
<220> FEATURE:
<223> OTHER INFORMATION: synthetic construct

<400> SEQUENCE: 364
```

-continued

```
cttactcatt atgctcgtta ttatcgttat tttgatgtt                    39
```

<210> SEQ ID NO 365
<211> LENGTH: 13
<212> TYPE: PRT
<213> ORGANISM: artificial sequence
<220> FEATURE:
<223> OTHER INFORMATION: synthetic construct

<400> SEQUENCE: 365

Leu Thr His Tyr Ala Arg Tyr Tyr Arg Tyr Phe Asp Val
1               5                   10

<210> SEQ ID NO 366
<211> LENGTH: 39
<212> TYPE: DNA
<213> ORGANISM: artificial sequence
<220> FEATURE:
<223> OTHER INFORMATION: synthetic construct

<400> SEQUENCE: 366

```
cttactcatt atgctcgtta ttatcgttat tttgatgtt                    39
```

<210> SEQ ID NO 367
<211> LENGTH: 13
<212> TYPE: PRT
<213> ORGANISM: artificial sequence
<220> FEATURE:
<223> OTHER INFORMATION: synthetic construct

<400> SEQUENCE: 367

Leu Thr His Tyr Ala Arg Tyr Tyr Arg Tyr Phe Asp Val
1               5                   10

<210> SEQ ID NO 368
<211> LENGTH: 51
<212> TYPE: DNA
<213> ORGANISM: artificial sequence
<220> FEATURE:
<223> OTHER INFORMATION: synthetic construct

<400> SEQUENCE: 368

```
ggtaagggta atactcataa gccttatggt tatgttcgtt attttgatgt t       51
```

<210> SEQ ID NO 369
<211> LENGTH: 17
<212> TYPE: PRT
<213> ORGANISM: artificial sequence
<220> FEATURE:
<223> OTHER INFORMATION: synthetic construct

<400> SEQUENCE: 369

Gly Lys Gly Asn Thr His Lys Pro Tyr Gly Tyr Val Arg Tyr Phe Asp
1               5                   10                  15

Val

<210> SEQ ID NO 370
<211> LENGTH: 51
<212> TYPE: DNA
<213> ORGANISM: artificial sequence
<220> FEATURE:
<223> OTHER INFORMATION: synthetic construct

<400> SEQUENCE: 370

```
ggtaagggta atactcataa gccttatggt tatgttcgtt attttgatgt t       51
```

```
<210> SEQ ID NO 371
<211> LENGTH: 17
<212> TYPE: PRT
<213> ORGANISM: artificial sequence
<220> FEATURE:
<223> OTHER INFORMATION: synthetic construct

<400> SEQUENCE: 371

Gly Lys Gly Asn Thr His Lys Pro Tyr Gly Tyr Val Arg Tyr Phe Asp
1               5                   10                  15
Val

<210> SEQ ID NO 372
<211> LENGTH: 51
<212> TYPE: DNA
<213> ORGANISM: artificial sequence
<220> FEATURE:
<223> OTHER INFORMATION: synthetic construct

<400> SEQUENCE: 372 ggtaaggggta atactcataa gccttatggt tatgttcgtt attttgatgt t          51

<210> SEQ ID NO 373
<211> LENGTH: 17
<212> TYPE: PRT
<213> ORGANISM: artificial sequence
<220> FEATURE:
<223> OTHER INFORMATION: synthetic construct

<400> SEQUENCE: 373

Gly Lys Gly Asn Thr His Lys Pro Tyr Gly Tyr Val Arg Tyr Phe Asp
1               5                   10                  15
Val

<210> SEQ ID NO 374
<211> LENGTH: 51
<212> TYPE: DNA
<213> ORGANISM: artificial sequence
<220> FEATURE:
<223> OTHER INFORMATION: synthetic construct

<400> SEQUENCE: 374 ggtaaggggta atactcataa gccttatggt tatgttcgtt attttgatgt t          51

<210> SEQ ID NO 375
<211> LENGTH: 17
<212> TYPE: PRT
<213> ORGANISM: artificial sequence
<220> FEATURE:
<223> OTHER INFORMATION: synthetic construct

<400> SEQUENCE: 375

Gly Lys Gly Asn Thr His Lys Pro Tyr Gly Tyr Val Arg Tyr Phe Asp
1               5                   10                  15
Val

<210> SEQ ID NO 376
<211> LENGTH: 51
<212> TYPE: DNA
<213> ORGANISM: artificial sequence
<220> FEATURE:
<223> OTHER INFORMATION: synthetic construct

<400> SEQUENCE: 376 ggtaaggggta atactcataa gccttatggt tatgttcgtt attttgatgt t          51
```

```
<210> SEQ ID NO 377
<211> LENGTH: 17
<212> TYPE: PRT
<213> ORGANISM: artificial sequence
<220> FEATURE:
<223> OTHER INFORMATION: synthetic construct

<400> SEQUENCE: 377

Gly Lys Gly Asn Thr His Lys Pro Tyr Gly Tyr Val Arg Tyr Phe Asp
1               5                   10                  15

Val

<210> SEQ ID NO 378
<211> LENGTH: 51
<212> TYPE: DNA
<213> ORGANISM: artificial sequence
<220> FEATURE:
<223> OTHER INFORMATION: synthetic construct

<400> SEQUENCE: 378
ggtaagggta atactcataa gccttatggt tatgttcgtt attttgatgt t          51

<210> SEQ ID NO 379
<211> LENGTH: 17
<212> TYPE: PRT
<213> ORGANISM: artificial sequence
<220> FEATURE:
<223> OTHER INFORMATION: synthetic construct

<400> SEQUENCE: 379

Gly Lys Gly Asn Thr His Lys Pro Tyr Gly Tyr Val Arg Tyr Phe Asp
1               5                   10                  15

Val

<210> SEQ ID NO 380
<211> LENGTH: 51
<212> TYPE: DNA
<213> ORGANISM: artificial sequence
<220> FEATURE:
<223> OTHER INFORMATION: synthetic construct

<400> SEQUENCE: 380
ggtaagggta atactcataa gccttatggt tatgttcgtt attttgatgt t          51

<210> SEQ ID NO 381
<211> LENGTH: 17
<212> TYPE: PRT
<213> ORGANISM: artificial sequence
<220> FEATURE:
<223> OTHER INFORMATION: synthetic construct

<400> SEQUENCE: 381

Gly Lys Gly Asn Thr His Lys Pro Tyr Gly Tyr Val Arg Tyr Phe Asp
1               5                   10                  15

Val

<210> SEQ ID NO 382
<211> LENGTH: 45
<212> TYPE: DNA
<213> ORGANISM: artificial sequence
<220> FEATURE:
<223> OTHER INFORMATION: synthetic construct

<400> SEQUENCE: 382
cttctttctc gtggttataa tggttattat cataagtttg atgtt                45
```

<210> SEQ ID NO 383
<211> LENGTH: 15
<212> TYPE: PRT
<213> ORGANISM: artificial sequence
<220> FEATURE:
<223> OTHER INFORMATION: synthetic construct

<400> SEQUENCE: 383

Leu Leu Ser Arg Gly Tyr Asn Gly Tyr Tyr His Lys Phe Asp Val
1               5                   10                  15

<210> SEQ ID NO 384
<211> LENGTH: 24
<212> TYPE: DNA
<213> ORGANISM: artificial sequence
<220> FEATURE:
<223> OTHER INFORMATION: synthetic construct

<400> SEQUENCE: 384
cagcagactt atgattatcc tcct                                          24

<210> SEQ ID NO 385
<211> LENGTH: 8
<212> TYPE: PRT
<213> ORGANISM: artificial sequence
<220> FEATURE:
<223> OTHER INFORMATION: synthetic construct

<400> SEQUENCE: 385

Gln Gln Thr Tyr Asp Tyr Pro Pro
1               5

<210> SEQ ID NO 386
<211> LENGTH: 24
<212> TYPE: DNA
<213> ORGANISM: artificial sequence
<220> FEATURE:
<223> OTHER INFORMATION: synthetic construct

<400> SEQUENCE: 386
cagcagactt atgattatcc tcct                                          24

<210> SEQ ID NO 387
<211> LENGTH: 8
<212> TYPE: PRT
<213> ORGANISM: artificial sequence
<220> FEATURE:
<223> OTHER INFORMATION: synthetic construct

<400> SEQUENCE: 387

Gln Gln Thr Tyr Asp Tyr Pro Pro
1               5

<210> SEQ ID NO 388
<211> LENGTH: 24
<212> TYPE: DNA
<213> ORGANISM: artificial sequence
<220> FEATURE:
<223> OTHER INFORMATION: synthetic construct

<400> SEQUENCE: 388
cagcagactt atgattatcc tcct                                          24

<210> SEQ ID NO 389
<211> LENGTH: 8
<212> TYPE: PRT

```
<213> ORGANISM: artificial sequence
<220> FEATURE:
<223> OTHER INFORMATION: synthetic construct

<400> SEQUENCE: 389

Gln Gln Thr Tyr Asp Tyr Pro Pro
1               5

<210> SEQ ID NO 390
<211> LENGTH: 24
<212> TYPE: DNA
<213> ORGANISM: artificial sequence
<220> FEATURE:
<223> OTHER INFORMATION: synthetic construct

<400> SEQUENCE: 390
cagcagactt atgattatcc tcct                                            24

<210> SEQ ID NO 391
<211> LENGTH: 8
<212> TYPE: PRT
<213> ORGANISM: artificial sequence
<220> FEATURE:
<223> OTHER INFORMATION: synthetic construct

<400> SEQUENCE: 391

Gln Gln Thr Tyr Asp Tyr Pro Pro
1               5

<210> SEQ ID NO 392
<211> LENGTH: 24
<212> TYPE: DNA
<213> ORGANISM: artificial sequence
<220> FEATURE:
<223> OTHER INFORMATION: synthetic construct

<400> SEQUENCE: 392
cagcagactt atgattatcc tcct                                            24

<210> SEQ ID NO 393
<211> LENGTH: 8
<212> TYPE: PRT
<213> ORGANISM: artificial sequence
<220> FEATURE:
<223> OTHER INFORMATION: synthetic construct

<400> SEQUENCE: 393

Gln Gln Thr Tyr Asp Tyr Pro Pro
1               5

<210> SEQ ID NO 394
<211> LENGTH: 24
<212> TYPE: DNA
<213> ORGANISM: artificial sequence
<220> FEATURE:
<223> OTHER INFORMATION: synthetic construct

<400> SEQUENCE: 394
cagcagactt atgattatcc tcct                                            24

<210> SEQ ID NO 395
<211> LENGTH: 8
<212> TYPE: PRT
<213> ORGANISM: artificial sequence
<220> FEATURE:
<223> OTHER INFORMATION: synthetic construct

<400> SEQUENCE: 395
```

Gln Gln Thr Tyr Asp Tyr Pro Pro
1               5

<210> SEQ ID NO 396
<211> LENGTH: 24
<212> TYPE: DNA
<213> ORGANISM: artificial sequence
<220> FEATURE:
<223> OTHER INFORMATION: synthetic construct

<400> SEQUENCE: 396
cagcagactt ataattatcc tcct                                           24

<210> SEQ ID NO 397
<211> LENGTH: 8
<212> TYPE: PRT
<213> ORGANISM: artificial sequence
<220> FEATURE:
<223> OTHER INFORMATION: synthetic construct

<400> SEQUENCE: 397

Gln Gln Thr Tyr Asn Tyr Pro Pro
1               5

<210> SEQ ID NO 398
<211> LENGTH: 24
<212> TYPE: DNA
<213> ORGANISM: artificial sequence
<220> FEATURE:
<223> OTHER INFORMATION: synthetic construct

<400> SEQUENCE: 398
cagcagattt attcttttcc tcat                                           24

<210> SEQ ID NO 399
<211> LENGTH: 8
<212> TYPE: PRT
<213> ORGANISM: artificial sequence
<220> FEATURE:
<223> OTHER INFORMATION: synthetic construct

<400> SEQUENCE: 399

Gln Gln Ile Tyr Ser Phe Pro His
1               5

<210> SEQ ID NO 400
<211> LENGTH: 24
<212> TYPE: DNA
<213> ORGANISM: artificial sequence
<220> FEATURE:
<223> OTHER INFORMATION: synthetic construct

<400> SEQUENCE: 400
cttcagcttt ataatattcc taat                                           24

<210> SEQ ID NO 401
<211> LENGTH: 8
<212> TYPE: PRT
<213> ORGANISM: artificial sequence
<220> FEATURE:
<223> OTHER INFORMATION: synthetic construct

<400> SEQUENCE: 401

Leu Gln Leu Tyr Asn Ile Pro Asn
1               5

```
<210> SEQ ID NO 402
<211> LENGTH: 24
<212> TYPE: DNA
<213> ORGANISM: artificial sequence
<220> FEATURE:
<223> OTHER INFORMATION: synthetic construct

<400> SEQUENCE: 402
cagcagattt attcttttcc tcat                                          24

<210> SEQ ID NO 403
<211> LENGTH: 8
<212> TYPE: PRT
<213> ORGANISM: artificial sequence
<220> FEATURE:
<223> OTHER INFORMATION: synthetic construct

<400> SEQUENCE: 403

Gln Gln Ile Tyr Ser Phe Pro His
1               5

<210> SEQ ID NO 404
<211> LENGTH: 24
<212> TYPE: DNA
<213> ORGANISM: artificial sequence
<220> FEATURE:
<223> OTHER INFORMATION: synthetic construct

<400> SEQUENCE: 404
cttcagcttt ataatattcc taat                                          24

<210> SEQ ID NO 405
<211> LENGTH: 8
<212> TYPE: PRT
<213> ORGANISM: artificial sequence
<220> FEATURE:
<223> OTHER INFORMATION: synthetic construct

<400> SEQUENCE: 405

Leu Gln Leu Tyr Asn Ile Pro Asn
1               5

<210> SEQ ID NO 406
<211> LENGTH: 24
<212> TYPE: DNA
<213> ORGANISM: artificial sequence
<220> FEATURE:
<223> OTHER INFORMATION: synthetic construct

<400> SEQUENCE: 406
cagcagattt attcttttcc tcat                                          24

<210> SEQ ID NO 407
<211> LENGTH: 8
<212> TYPE: PRT
<213> ORGANISM: artificial sequence
<220> FEATURE:
<223> OTHER INFORMATION: synthetic construct

<400> SEQUENCE: 407

Gln Gln Ile Tyr Ser Phe Pro His
1               5

<210> SEQ ID NO 408
<211> LENGTH: 24
<212> TYPE: DNA
<213> ORGANISM: artificial sequence
<220> FEATURE:
```

<223> OTHER INFORMATION: synthetic construct

<400> SEQUENCE: 408
cagcagattt attctttcc tcat                                    24

<210> SEQ ID NO 409
<211> LENGTH: 8
<212> TYPE: PRT
<213> ORGANISM: artificial sequence
<220> FEATURE:
<223> OTHER INFORMATION: synthetic construct

<400> SEQUENCE: 409

Leu Gln Ile Tyr Asn Met Pro Ile
1               5

<210> SEQ ID NO 410
<211> LENGTH: 24
<212> TYPE: DNA
<213> ORGANISM: artificial sequence
<220> FEATURE:
<223> OTHER INFORMATION: synthetic construct

<400> SEQUENCE: 410
cttcagcttt ataatattcc taat                                    24

<210> SEQ ID NO 411
<211> LENGTH: 8
<212> TYPE: PRT
<213> ORGANISM: artificial sequence
<220> FEATURE:
<223> OTHER INFORMATION: synthetic construct

<400> SEQUENCE: 411

Leu Gln Leu Tyr Asn Ile Pro Asn
1               5

<210> SEQ ID NO 412
<211> LENGTH: 24
<212> TYPE: DNA
<213> ORGANISM: artificial sequence
<220> FEATURE:
<223> OTHER INFORMATION: synthetic construct

<400> SEQUENCE: 412
cagcagcttt cttcttatcc tcct                                    24

<210> SEQ ID NO 413
<211> LENGTH: 8
<212> TYPE: PRT
<213> ORGANISM: artificial sequence
<220> FEATURE:
<223> OTHER INFORMATION: synthetic construct

<400> SEQUENCE: 413

Gln Gln Leu Ser Ser Tyr Pro Pro
1               5

<210> SEQ ID NO 414
<211> LENGTH: 52
<212> TYPE: PRT
<213> ORGANISM: artificial sequence
<220> FEATURE:
<223> OTHER INFORMATION: synthetic construct

<400> SEQUENCE: 414

Ile Ser Glu Val Lys Met Asp Ala Glu Phe Arg His Asp Ser Gly Tyr

```
                1               5                  10                  15
Glu Val His His Gln Lys Leu Val Phe Phe Ala Glu Asp Val Gly Ser
                    20                  25                  30

Asn Lys Gly Ala Ile Ile Gly Leu Met Val Gly Gly Val Val Ile Ala
        35                  40                  45

Thr Val Ile Val
    50
```

<210> SEQ ID NO 415
<211> LENGTH: 6
<212> TYPE: PRT
<213> ORGANISM: Artificial
<220> FEATURE:
<223> OTHER INFORMATION: Synthetic Construct

<400> SEQUENCE: 415

```
Ala Glu Phe Arg His Asp
1               5
```

<210> SEQ ID NO 416
<211> LENGTH: 7
<212> TYPE: PRT
<213> ORGANISM: Artificial
<220> FEATURE:
<223> OTHER INFORMATION: Synthetic Construct

<400> SEQUENCE: 416

```
Glu Phe Arg His Asp Ser Gly
1               5
```

<210> SEQ ID NO 417
<211> LENGTH: 5
<212> TYPE: PRT
<213> ORGANISM: Artificial
<220> FEATURE:
<223> OTHER INFORMATION: Synthetic Construct

<400> SEQUENCE: 417

```
Glu Phe Arg His Asp
1               5
```

<210> SEQ ID NO 418
<211> LENGTH: 4
<212> TYPE: PRT
<213> ORGANISM: Artificial
<220> FEATURE:
<223> OTHER INFORMATION: Synthetic Construct

<400> SEQUENCE: 418

```
His Asp Ser Gly
1
```

<210> SEQ ID NO 419
<211> LENGTH: 5
<212> TYPE: PRT
<213> ORGANISM: Artificial
<220> FEATURE:
<223> OTHER INFORMATION: Synthetic Construct

<400> SEQUENCE: 419

```
His His Gln Lys Leu
1               5
```

<210> SEQ ID NO 420
<211> LENGTH: 6
<212> TYPE: PRT

<213> ORGANISM: Artificial
<220> FEATURE:
<223> OTHER INFORMATION: Synthetic Construct

<400> SEQUENCE: 420

Leu Val Phe Phe Ala Glu
1               5

<210> SEQ ID NO 421
<211> LENGTH: 6
<212> TYPE: PRT
<213> ORGANISM: Artificial
<220> FEATURE:
<223> OTHER INFORMATION: Synthetic Construct

<400> SEQUENCE: 421

Val Phe Phe Ala Glu Asp
1               5

<210> SEQ ID NO 422
<211> LENGTH: 4
<212> TYPE: PRT
<213> ORGANISM: Artificial
<220> FEATURE:
<223> OTHER INFORMATION: Synthetic Construct

<400> SEQUENCE: 422

Val Phe Phe Ala
1

<210> SEQ ID NO 423
<211> LENGTH: 6
<212> TYPE: PRT
<213> ORGANISM: Artificial
<220> FEATURE:
<223> OTHER INFORMATION: Synthetic Construct

<400> SEQUENCE: 423

Phe Phe Ala Glu Asp Val
1               5

<210> SEQ ID NO 424
<211> LENGTH: 378
<212> TYPE: DNA
<213> ORGANISM: Artificial
<220> FEATURE:
<223> OTHER INFORMATION: Synthetic Construct

<400> SEQUENCE: 424
caggtggaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcgct attaatgctt ctggtactcg tacttattat     180
gctgattctg ttaagggtcg ttttaccatt tcacgtgata attcgaaaaa cacccctgta     240
ctgcaaatga acagcctgcg tgcggaagat acggccgtgt attattgcgc gcgtggtaag     300
ggtaatactc ataagcctta tggttatgtt cgttattttg atgtttgggg ccaaggcacc     360
ctggtgacgg ttagctca                                                   378

<210> SEQ ID NO 425
<211> LENGTH: 126
<212> TYPE: PRT
<213> ORGANISM: Artificial
<220> FEATURE:
<223> OTHER INFORMATION: Synthetic Construct

```
<400> SEQUENCE: 425

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser
            115                 120                 125
```